US009801932B2

United States Patent
Emery et al.

(10) Patent No.: US 9,801,932 B2
(45) Date of Patent: *Oct. 31, 2017

(54) YERSINIA SPP. POLYPEPTIDES AND METHODS OF USE

(71) Applicant: EPITOPIX, LLC, Willmar, MN (US)

(72) Inventors: Daryll A. Emery, New London, MN (US); Darren E. Straub, New London, MN (US); Laura Wonderling, Des Moines, IA (US)

(73) Assignee: EPITOPIX, LLC, Willmar, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/140,767

(22) Filed: Apr. 28, 2016

(65) Prior Publication Data

US 2016/0228527 A1   Aug. 11, 2016

Related U.S. Application Data

(63) Continuation of application No. 14/933,899, filed on Nov. 5, 2015, now Pat. No. 9,352,029, which is a continuation of application No. 14/793,494, filed on Jul. 7, 2015, now Pat. No. 9,221,899, which is a continuation of application No. 14/048,649, filed on Oct. 8, 2013, now Pat. No. 9,085,613, which is a continuation of application No. 11/336,706, filed on Jan. 20, 2006, now Pat. No. 8,563,004.

(60) Provisional application No. 60/646,106, filed on Jan. 21, 2005.

(51) Int. Cl.
| | | |
|---|---|---|
| A61K 39/02 | (2006.01) | |
| C07K 14/24 | (2006.01) | |
| C07K 16/12 | (2006.01) | |
| A61K 39/00 | (2006.01) | |

(52) U.S. Cl.
CPC ........ *A61K 39/0291* (2013.01); *A61K 39/025* (2013.01); *C07K 14/24* (2013.01); *C07K 16/1228* (2013.01); *A61K 39/00* (2013.01); *A61K 2039/54* (2013.01); *A61K 2039/55* (2013.01); *A61K 2039/552* (2013.01); *A61K 2039/55505* (2013.01); *A61K 2039/55566* (2013.01); *A61K 2039/575* (2013.01)

(58) Field of Classification Search
None
See application file for complete search history.

(56) References Cited

U.S. PATENT DOCUMENTS

| | | | |
|---|---|---|---|
| 5,420,253 A | 5/1995 | Emery | |
| 5,538,733 A | 7/1996 | Emery et al. | |
| 5,830,479 A | 11/1998 | Emery et al. | |
| 5,906,826 A | 5/1999 | Emery et al. | |
| 6,027,736 A | 2/2000 | Emery et al. | |
| 6,248,329 B1 | 6/2001 | Chandrashekar et al. | |
| 6,432,412 B1 | 8/2002 | Emery et al. | |
| 6,610,836 B1 | 8/2003 | Breton et al. | |
| 6,682,754 B2 | 1/2004 | Emery et al. | |
| 8,563,004 B2 | 10/2013 | Emery et al. | |
| 2002/0061569 A1 | 5/2002 | Haselbeck et al. | |
| 2003/0036639 A1 | 2/2003 | Emery et al. | |
| 2003/0064073 A1 | 4/2003 | Emery et al. | |
| 2003/0206922 A1 | 11/2003 | Emery et al. | |
| 2003/0211118 A1 | 11/2003 | Emery et al. | |
| 2004/0197350 A1 | 10/2004 | Emery et al. | |
| 2004/0197869 A1 | 10/2004 | Emery et al. | |
| 2004/0265329 A1 | 12/2004 | Emery et al. | |
| 2005/0037444 A1 | 2/2005 | Meinke et al. | |
| 2005/0095682 A1 | 5/2005 | Emery et al. | |
| 2005/0186217 A1 | 8/2005 | Straub et al. | |
| 2006/0024323 A1 | 2/2006 | Emery et al. | |
| 2006/0083753 A1 | 4/2006 | Straub et al. | |
| 2006/0165718 A1 | 7/2006 | Emery et al. | |
| 2011/0206674 A1 | 8/2011 | Emery et al. | |

FOREIGN PATENT DOCUMENTS

| | | |
|---|---|---|
| JP | 9-505085 | 5/1997 |
| JP | 2013018779 | 1/2013 |
| WO | WO 95/07290 A1 | 3/1995 |
| WO | WO 95/21627 A1 | 8/1995 |
| WO | WO 95/25742 A1 | 9/1995 |
| WO | WO 96/01620 A1 | 1/1996 |
| WO | WO 98/24912 A2 | 6/1998 |
| WO | WO 98/24912 A3 | 6/1998 |
| WO | WO 01/37810 A2 | 5/2001 |
| WO | WO 01/37810 A3 | 5/2001 |
| WO | WO 02/053180 A2 | 7/2002 |
| WO | WO 02/053180 A3 | 7/2002 |
| WO | WO 03/044047 A2 | 5/2003 |
| WO | WO 03/044047 A3 | 5/2003 |
| WO | WO 2004/014419 A1 | 2/2004 |

(Continued)

OTHER PUBLICATIONS

"Alfa Laval Centrifuge Applications" [online]. Dolphin Marine and Industrial Centrifuges, Farmington Hills, MI [retrieved on Mar. 10, 2006]. Retrieved from the Internet:<http://www.dolphinmarine.com/centrifuges_new.php>; 2 pgs.

"Clustalw: Multiple Alignments" [online]. Institut Pasteur, France [retrieved on Mar. 10, 2006]. Retrieved from the Internet:<http://bioweb.pasteur.fr/seqanal/interfaces/clustalw-simple.html; 5 pgs.

"Control Standard Endotoxin" [online]. Associates of Cape Cod, Inc., East Falmouth, MA, Copyright 2004 [retrieved on Mar. 9, 2006]. Retrieved from the Internet:<http://www.acciusa.com/lal/cse.html>; 2 pgs.

"Emulsiflex-C50 Homogenizer" [online]. Avestin Inc., Ottawa, Canada [retrieved on Mar. 9, 2006]. Retrieved from the Internet:<http://www.avestin.com/c50page.html>: 3 pgs.

(Continued)

*Primary Examiner* — Brian J Gangle

(74) *Attorney, Agent, or Firm* — Mueting, Raasch & Gebhardt, PA

(57) ABSTRACT

The present invention provides isolated polypeptides isolatable from a *Yersinia* spp. Also provided by the present invention are compositions that include one or more of the polypeptides, and methods for making and methods for using the polypeptides.

12 Claims, 10 Drawing Sheets

(56) References Cited

FOREIGN PATENT DOCUMENTS

Figure 1:
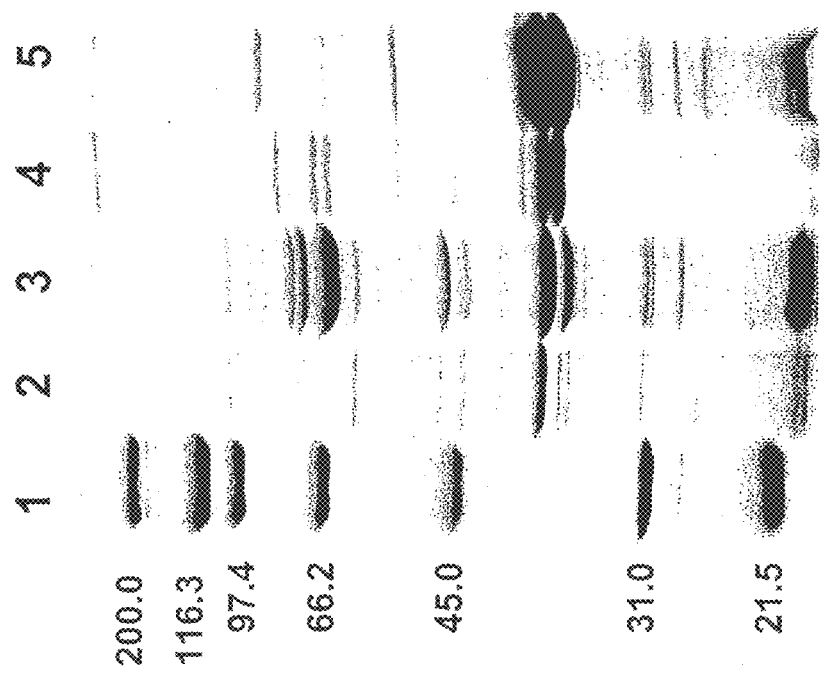
Figure 2:
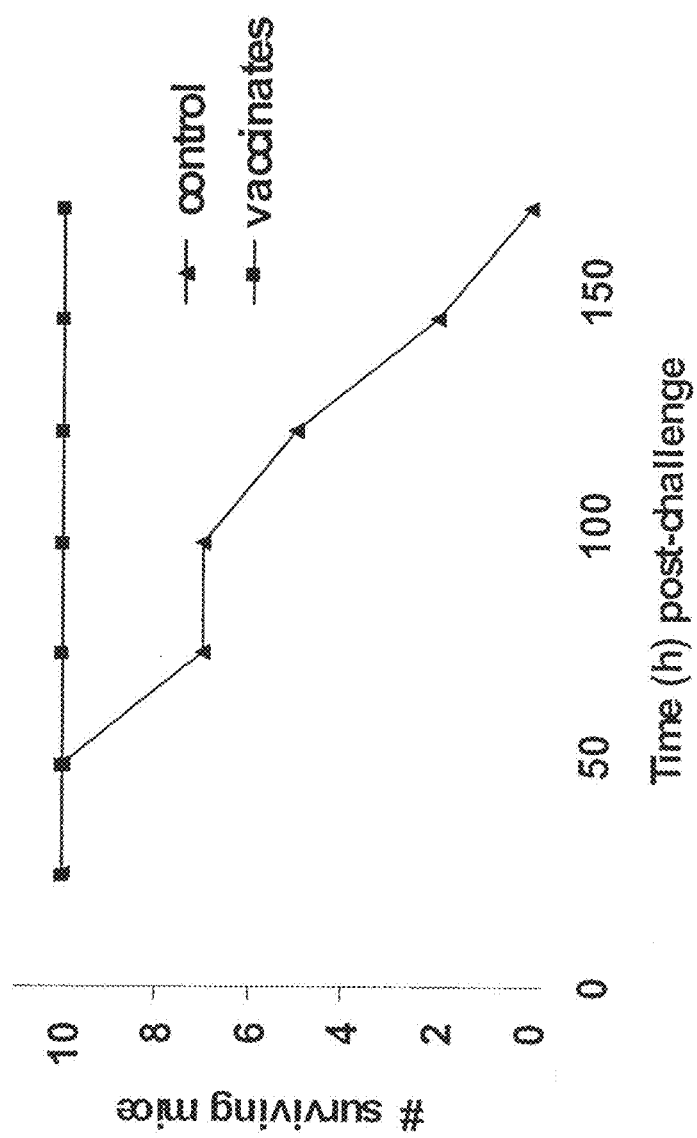

| WO | WO 2005/028665 A2 | 3/2005 |
|---|---|---|
| WO | WO 2005/028665 A3 | 3/2005 |
| WO | WO 2006/011060 A2 | 2/2006 |
| WO | WO 2006/011060 A3 | 2/2006 |
| WO | WO 2006/026373 A1 | 3/2006 |
| WO | WO 2006/079076 A2 | 7/2006 |
| WO | WO 2006/079076 A3 | 7/2006 |
| WO | WO 2006/091517 A2 | 8/2006 |
| WO | WO 2006/113907 A2 | 10/2006 |

OTHER PUBLICATIONS

"Emulsigen Technical Bulletin" [online]. MVP Laboratories, Inc., Omaha, NE, Copyright 2005 [retrieved on Mar. 9, 2006]. Retrieved from the Internet:<http://www.mvplabs.com/adjuvants/Emulsigen%20Final%20Technical%20Bulletin%2012-22-05.pdf>; 2 pgs.

"Endotoxin (10,000 USP Endotoxin Units)" [online]. The United States Pharmacopeial Convention Inc., Rockville, MD, Copyright 2006 [retrieved on Mar. 9, 2006]. Retrieved from the Internet: <http://store.usp.org/OA_HTML/ibeCCtpItmDspRte.jsp?a=b&item=18789>; 1 pg.

"E-Toxate (Technical Bulletin No. 210)" [online]. Sigma Chemical Co., St. Louis, MO, Copyright 2000 [retrieved on Mar. 9, 2006]. Retrieved from the Internet:<http://www.sigmaaldrich.com/sigma/bulletin/21020bul.pdf>; 4 pgs.

"E-Toxate Endotoxin Standard" [online]. Sigma-Aldrich Co., St. Louis, MO, Copyright 2006 [retrieved on Mar. 9, 2006]. Retrieved from the Internet:<http://www.sigmaaldrich.com/catalog/search/ProductDetail/Sigma/E8029>; 2 pgs.

"Large-Scale Continuous Flow Ultracentrifuge Himac CC40" [online]. Hitachi Koki Co., Tokyo, Japan, Copyright 2005 [retrieved on Mar. 9, 2006]. Retrieved from the Internet:<http://www.hitachi-koki.com/himac/products/cc40.htm>; 2 pgs.

"Mascot Peptide Mass Fingerprint Search Engine" [online]. Matrix Science Ltd., Copyright 2005 [retrieved on Mar. 10, 2006]. Retrieved from the Internet:<http://www.matrixscience.com/cgi/search_form.pl?FORMVER=2&SEARCH=PMF>; 1 pg.

"Pyrotell Gel-Clot Formulation" [online]. Associates of Cape Cod, Inc., East Falmouth, MA, Copyright 2004 [retrieved on Mar. 9, 2006]. Retrieved from the Internet:<http://www.acciusa.com/lal/pyrotell.html>; 2 pgs.

"WHO Report on Global Surveillance of Epidemic-Prone Infectious Diseases—Yellow Fever" [online]. World Health Organization, Copyright 2006 [retrieved on Mar. 10, 2006]. Retrieved from the Internet:<http://www.who.int/csr/resources/publications/yellowfev/CSR_ISR_2000_1/en/print.html; 4 pgs.

"Yersinia Enterocolitica" [online]. Sanger Institute, Cambridge, England [retrieved on Mar. 10, 2006]. Retrieved from the Internet:<http://www.sanger.ac.uk/Projects/Y_enterocolitica/>; 2 pgs.

Achtman et al., "*Yersinia pestis*, the cause of plague, is a recently emerged clone of *Yersinia pseudotuberculosis*" *Proc. Natl. Acad. Sci. USA*, Nov. 23, 1999;96(24):14043-14048.

Agbonlahor, "Characteristics of *Yersinia intermedia*-like Bacteria Isolated from Patients with Diarrhea in Nigeria" *J. Clin. Microbiol.*, May 1986;23(5):891-896.

Alpar et al., "Intranasal vaccination against plague, tetanus and diphtheria" *Adv. Drug Deliv. Rev.*, Sep. 23, 2001;51(1-3):173-201.

Al-Tawfiq et al., "An Isogenic Hemoglobin Receptor-Deficient Mutant of *Haemophilus ducreyi* Is Attenuated in the Human Model of Experimental Infection" *J. Infect. Dis.*, Mar. 2000;181(3):1049-1054.

American Type Culture Collection, "ATTC No. 27729," organism: Yersinia enterocolitica; designation: WA [online]; Manassas, VA [retrieved on Mar. 10, 2006]. Retrieved from the Internet:<http://www.atcc.org/common/catalog/numSearch/numResults.cfm?atcNum=27729&CFID=4570103&CFTOKEN=2bbb258c2d347193-E072F7AF-CF26-C682-E10D0712187854BE>; 2 pgs.

Andrews et al., "Bacterial iron homeostasis" *FEMS Microbiol. Rev.*, Jun. 2003;27(2-3):215-237.

Bach et al., "The *Yersinia* high-pathogenicity island is present in different members of the family *Enterobacteriaceae*" *FEMS Microbiol. Lett.*, Feb. 15, 2000;183(2):289-294.

Baumler et al., "Survey on Newly Characterized Iron Uptake Systems of Yersinia enterocolitica" *Zentralbl. Bakteriol.*, Apr. 1993;278(2-3):416-424.

Bearden et al., "Genetic Organization of the Yersiniabactin Biosynthetic Region and Construction of Avirulent Mutants in *Yersinia pestis*" *Infect. Immun.*, May 1997;65(5):1659-1668.

Bearden et al., "The Yfe system of *Yersinia pestis* transports iron and manganese and is required for full virulence of plague" *Mol. Microbiol.*, Apr. 1999;32(2):403-414.

Bleves et al., "How to survive in the host: the *Yersinia* lesson" *Microbes Infect.*, Oct. 2000;2(12):1451-1460.

Blocker et al., "Structure and composition of the *Shigella flexneri* 'needle complex', a part of its type III secretion" *Mol. Microbiol.*, Feb. 2001;39(3):652-663.

Bobrov et al., "Yersiniabactin Production Requires the Thioesterase Domain of HMWP2 and YbtD, a Putative Phosphopantetheinylate Transferase" *Infect. Immun.* Aug. 2002; 70(8):4204-14.

Bosch et al., "Characterization of the *Pasteurella multocida* hgbA Gene Encoding a Hemoglobin-Binding Protein" *Infect. Immun.*, Nov. 2002; 70(11):5955-5964.

Bottone, "*Yersinia enterocolitica*: The Charisma Continues" *Clin. Microbiol. Rev.*, Apr. 1997;10(2):257-276.

Boulianne et al., "Production of functional chimaeric mouse/human antibody" *Nature*, Dec. 13-19, 1984;312(5995):643-646.

Bowie et al., "Deciphering the message in protein sequences: tolerance to amino acid substitutions" *Science*, 1990; 247: 1306-1310.

Boyer et al., "Acquisition of Mn(II) in Addition to Fe(II) Is Required for Full Virulence of *Salmonella enterica* Serovar Typhimurium" *Infect. Immun.*, Nov. 2002; 70(11):6032-6042.

Brem et al., "Functional analysis of yersiniabactin transport genes of *Yersinia enterocolitica*" *Microbiology*, May 2001;147(Pt 5):1115-1127.

Brown et al., "Characterization of Pit, a *Streptococcus pneumoniae* Iron Uptake ABC Transporter" *Infect. Immun.*, Aug. 2002; 70(8):4389-4398.

Brown et al., "Immunization with Components of Two Iron Uptake ABC Transporters Protects Mice against Systemic *Streptococcus pneumoniae* Infection" *Infect. Immun.*, Nov. 2001;69(11):6702-6706.

Bruggemann et al., "Production of human antibody repertoires in transgenic mice" *Curr. Opin. Biotechnol.*, Aug. 1997;8(4):455-458.

Burall et al., "*Proteus mirabilis* Genes That Contribute to Pathogenesis of Urinary Tract Infection: Identification of 25 Signature-Tagged Mutants Attenuated at Least 100-Fold" *Infect. Immun.*, May 2004; 72(5):2922-2938.

Cafferkey et al., "*Yersinia frederiksenii* infection and colonization in hospital staff" *J. Hosp. Infect.*, Jun. 1993;24(2):109-115.

Campoy et al., "Intracellular cyclic AMP concentration is decreased in *Salmonella typhimurium fur* mutants" *Microbiology*, Apr. 2002;148(Pt 4):1039-1048.

Carniel, "The *Yersinia* high-pathogenicity island: an iron-uptake island" *Microbes. Infect.*, Jun. 2001;3(7):561-569.

Carter, et al., "New Strain of *Yersinia enterocolitica* Pathogenic for Rodents," *Applied Microbiology*; Dec. 1973; 26(6):1016-1018.

Carter et al., "Experimental *Yersinia enterocolitica* infection in mice: Kinetics of growth" *Infect. Immun.*, May 1974;9(5): 851-857.

Chain et al., "Insights into the evolution of *Yersinia pestis* through whole-genome comparison with *Yersinia pseudotuberculosis*" *Proc. Natl. Acad. Sci. USA*, Sep. 21, 2004;101(38):13826-13831.

Cohen et al., "Pneumonic Plague in an Untreated Plague-Vaccinated Individual" *JAMA*, Oct. 23, 1967;202(4):365-366.

Collyn et al., "YAPI, a New *Yersinia pseudotuberculosis* Pathogenicity Island" *Infect. Immun.*, Aug. 2004; 72(8):4784-4790.

Confer et al., "Intranasal vaccination of rabbits with *Pasteurella multocida* A:3 outer membranes that express iron-regulated proteins" *Am. J. Vet. Res.*, May 2001; 62(5):697-703.

(56) References Cited

OTHER PUBLICATIONS

Cornelis, "The *Yersinia* Ysc-Yop 'Type III' Weaponry" *Nat. Rev. Mol. Cell. Biol.* Oct. 2002;3(10):742-752.
Database Geneseq [Online], Jul. 29, 2004, "Klebsiella pneumonia polypeptide seqid 14338", XP002640178, retrieved from EBI database accession No. ABO67821.
Database UniProt [Online], Nov. 1, 1996, "SubName: Full=FyuA; Flags: Precursor;", XP002640179, retrieved from EBI database accession No. Q47232.
Database UniProt [Online], Jul. 1, 1993, "RecName: Full=Hemin receptor; Flags: Precursor;", XP002662395, retrieved from EBI database accession No. P31499.
Database UniProt [Online], Nov. 1, 1997, "RecName: Full=Hemin receptor; Flags: Precursor;", XP002662397, retrieved from EBI database accession No. Q56989.
Database Geneseq [Online], Feb. 22, 2007, "*E. coli* O157 immunogenic protein expressed during infection, SEQ ID:165", XP002662399, retrieved from EBI database accession No. AEM19402.
Database EPO Proteins [Online], Nov. 20, 2007, "Sequence 442 from Patent WO2006091517", XP002662400, retrieved from EBI database accession No. CS720636.
Daugherty et al., "Polymerase chain reaction facilitates the cloning, CDR-grafting, and rapid expression of a murine monoclonal antibody directed against the CD18 component of leukocyte integrins" *Nucleic Acids Res.*, May 11, 1991;19(9):2471-2476.
Davis et al., "Pathology of Experimental Pneumonic Plague Produced by Fraction 1-Positive and Fraction 1-Negative *Yersinia pestis* in African Green Monkeys (*Cercopithecus aethiops*)" *Arch. Patho. Lab Med.*, Feb. 1996;120(2):156-163.
de Almeida et al., "Chromosomal irp2 gene in *Yersinia*: distribution, expression, deletion and impact on virulence" *Microb. Pathog.*, Jan. 1993;14(1):9-21.
Di Genaro et al., "Intranasal Immunization with *Yersinia enterocolitica* O:8 Cellular Extract Protects against Local Challenge Infection" *Microbiol. Immunol.*, 1998;42(11):781-788.
Dryla et al., "Identification of a novel iron regulated staphylococcal surface protein with haptoglobin-haemoglobin binding activity" *Mol. Microbiol.*, Jul. 2003;49(1):37-53.
Eitel et al., "The YadA Protein of *Yersinia pseudotuberculosis* Mediates High-Efficiency Uptake into Human Cells under Environmental Conditions in Which Invasin Is Repressed" *Infect. Immun.*, Sep. 2002; 70(9):4880-4891.
Ellis, in Plotkin et al., *Vaccines*, Philadelphia, 1998; 568-575.
Extended European Search Report dated Nov. 17, 2011, in European Patent Application No. 06719369.8, filed Jan. 20, 2006.
Eyles et al., "Generation of protective immune responses to plague by mucosal administration of microsphere coencapsulated recombinant subunits" *J. Control. Release*, Jan. 3, 2000;63(1-2):191-200.
Fantasia et al., "Characterisation of *Yersinia* species isolated from a kennel and from cattle and pig farms" *Vet. Rec.*, May 22, 1993;132(21):532-534.
Fantasia et al., "Isolation of *Yersinia enterocolitica* Biotype 4 Serotype O3 from Canine Sources in Italy" *J. Clin. Microbiol.*, Aug. 1985;22(2):314-315.
Faraldo-Gomez, et al., "Acquisition of Siderophores in Gram-Negative Bacteria" *Nat Rev Mol Cell Biol.*, Feb. 2003; 4(2):105-116.
Farmakis et al., "Pathogenetic aspects of immune deficiency associated with beta-thalassemia" *Med. Sci. Monit.*, Jan. 2003;9(1):RA19-22.
Fernandez et al., "Identification of Specific In Vivo-Induced (ivi) Genes in *Yersinia ruckeri* and Analysis of Ruckerbactin, a Catecholate Siderophore Iron Acquisition System" *Appl. Environ. Microbiol.*, Sep. 2004; 70(9):5199-5207.
Fetherston et al., " Analysis of the Pesticin Receptor from *Yersinia pestis*: Role in Iron-Deficient Growth and Possible Regulation by Its Siderophore" *J. Bacteriol.* Apr. 1995; 177(7):1824-1833.

Friedlander et al., "Relationship Between Virulence and Immunity as Revealed in Recent Studies of the F1 Capsule of *Yersinia pestis*" *Clin. Infect. Dis.*, Oct. 1995;21(Suppl 2):S178-181.
Fukushima et al., "Isolation of *Yersinia* spp. from Bovine Feces" *J. Clin. Microbiol.*, Oct. 1983;18(4):981-982.
Furones et al., "*Yersinia ruckeri*, the causal agent of enteric redmouth disease (ERM) in fish" *Ann. Rev. Fish Dis.*, 1993;3:105-125.
Gasper et al., "Plague (*Yersinia pestis*) in Cats: Description of Experimentally Induced Disease" *J. Med. Entomol.*, Jan. 1993;30(1):20-26.
Gaston et al., "Clinical and Experimental Evidence for Persistent *Yersinia* Infection in Reactive Arthritis" *Arthritis Rheum.*, Oct. 1999;42(10):2239-2242.
Gayraud et al., "Antibiotic Treatment of *Yersinia enterocolitica* Septicemia: A Retrospective Review of 43 Cases" *Clin. Infect. Dis.*, Sep. 1993;17(3):405-410.
Goethe et al., "A novel strategy for protective *Actinobacillus pleuropneumonias* subunit vaccines: detergent extraction of cultures induced by iron restriction" *Vaccine*, Nov. 22, 2001;19(7-8):966-975.
Gong et al., "Characterization of the *Yersinia pestis* Yfu ABC Inorganic Iron Transport System" *Infect. Immun.*, May 2001;67(5):2829-2837.
Greenspan et al., "Defining epitopes: It's not as easy as it seems" *Nature Biotechnology*, 1999; 7: 936-937.
Grosfeld et al., "Effective Protective Immunity to *Yersinia pestis* Infection Conferred by DNA Vaccine Coding for Derivatives of the F1 Capsular Antigen" *Infect. Immun.*, Jan. 2003;71(1):374-383.
Harlow et al., *Antibodies, A Laboratory Manual*, Cold Spring Harbor Laboratory Press, Cold Spring Harbor, NY; Chapter 5 (1988).
Heesemann et al., "Construction of a Mobilizable *Yersinia enterocolitica* Virulence Plasmid" *J. Bacteriol.*, Aug. 1983;155(2):761-767.
Heesemann et al., "Genetically Manipulated Virulence of *Yersinia enterocolitica*" *Infect. Immun.*, Oct. 1984;46(1):105-110.
Henderson et al., "*Vibrio cholerae* Iron Transport Systems: Roles of Heme and Siderophore Iron Transport in Virulence and Identification of a Gene Associated with Multiple Iron Transport Systems" *Infect. Immun.*, Nov. 1994;62(11):5120-5125.
Hinnebusch et al., "Murine toxin of *Yersinia pestis* shows phospholipase D activity but is not required for virulence in mice" *Int. J. Med. Microbiol.*, Oct. 2000;290(4-5):483-487.
Hinnebusch et al., "Role of Yersinia Murine Toxin in Survival of *Yersinia pestis* in the Midgut of the Flea Vector" *Science*, Apr. 26, 2002;296(5568):733-735.
Hoiczyk et al., "Structure and sequence analysis of *Yersinia* YadA and *Moraxella* UspAs reveal a novel class of adhesins," *The Embo Journal*, Oxford University Press, Surrey GB, Nov. 15, 2000, 19(22):5989-5999.
Hoogkamp-Korstanje, "Antibiotics in *Yersinia enterocolitica* infections" *J. Antimicrob. Chemother.*, Jul. 1987;20(1):123-131.
Hornung et al., "The hmu locus of *Yersinia pestis* is essential for utilization of free haemin and haem-protein complexes as iron sources" *Mol. Microbiol.*, May 1996;20(4):725-739.
Horsburgh et al., "PerR Controls Oxidative Stress Resistance and Iron Storage Proteins and Is Required for Virulence in *Staphylococcus aureus*" *Infect. Immun.*, Jun. 2001;69(6):3744-3754.
Hu et al., "Structural Organization of Virulence-Associated Plasmids of *Yersinia pestis*" *J. Bacteriol.*, Oct. 1998;180(19):5192-5202.
Ibrahim et al., "The phylogeny of the genus *Yersinia* based on 16S rDNA sequences" *FEMS Microbiol. Lett.*, Dec. 1, 1993;114(2):173-177.
Igwe et al., "Rational Live Oral Carrier Vaccine Design by Mutating Virulence-Associated Genes of *Yersinia enterocolitica*" *Infect. Immun.*, Oct. 1999;67(10):5500-5507.
Inoue et al., "Three Outbreaks of Yersinia pseudotuberculosis Infection" *Zentralbl Bakteriol Mikrobiol Hyg.* [*B*] , Aug. 1988;186(5-6):504-511.
International Search Report and Written Opinion for PCT application No. PCT/US2006/002474, dated Nov. 21, 2006; 15 pgs.

(56) References Cited

OTHER PUBLICATIONS

Jackson et al., "The Virulence-Enhancing Effect of Iron on Nonpigmented Mutants of Virulent Strains of *Pasteurella pestis*" *Br. J. Exp. Pathol.*, Dec. 1956;37(6):577-583.

Jacobi et al., "Expression Analysis of the Yersiniabactin Receptor Gene fyuA and the Heme Receptor hemR of *Yersinia enterocolitica* In Vitro and In Vivo Using the Reporter Genes for Green Fluorescent Protein and Luciferase" *Infect. Immun.*, Dec. 2001;69(12):7772-7782.

Janakiraman et al., "The putative iron transport system SitABCD encoded on SPI1 is required for full virulence of *Salmonella typhimurium*" *Mol. Microbiol.*, Mar. 2000;35(5):1146-1155.

Jerrett et al., "Yersiniosis in Farmed Deer" *Aust. Vet. J.*, Jan. 1990;67(1):212-214.

Jones et al., "Protection conferred by a fully recombinant sub-unit vaccine against *Yersinia pestis* in male and female mice of four inbred stains" *Vaccine*, Sep. 15, 2000;19(2-3):358-366.

Jones et al., "Replacing the complementarity-determining regions in a human antibody with those from a mouse" *Nature*, May 29-Jun. 4, 1986;321(6069):522-525.

Kageyama et al., "*Yersinia pseudotuberculosis* infection in breeding monkeys: detection and analysis of strain diversity by PCR" *J. Med. Primatol.*, Jun. 2002;31(3):129-135.

Karch et al., "A Genomic Island, Termed High-Pathogenicity Island, Is Present in Certain Non-O157 Shiga Toxin-Producing *Escherichia coli* Clonal Lineages" *Infect. Immun.*, Nov. 1999;67(11):5994-6001.

Karlyshev et al., "Application of High-Density Array-Based Signature-Tagged Mutagenesis to Discover Novel *Yersinia* Virulence-Associated Genes" *Infect. Immun.*, Dec. 2001;69(12):7810-7819.

Kato et al., "Occurrence of *Yersinia enterocolitica* in Wild-Living Birds and Japanese Serows" *Appl. Environ. Microbiol.*, Jan. 1985;49(1):198-200.

Keler et al., "Metachromatic assay for the quantitative determination of bacterial endotoxins" *Anal. Biochem.*, Jul. 1986;156(1):189-193.

Kimbrough et al., "Contribution of *Salmonella typhimurium* type III secretion components to needle complex formation" *Proc. Natl. Acad. Sci. USA*, Sep. 26, 2000;97(20):11008-11013.

Kooi et al., "Characterization of monoclonal antibodies to *Yersinia enterocolitica* iron-regulated proteins," *Canadian Journal of Microbiology*, Canada, 1995; 41(7):562-571.

Kubori et al., "Supramolecular Structure of the *Salmonella typhimurium* Type III Protein Secretion System" *Science*, Apr. 24, 1998;280(5363):602-605.

Leary et al., "Expression of an F1/V fusion protein in attenuated *Salmonella typhimurium* and protection of mice against plague" *Microb. Pathog.*, Sep. 1997;23(3):167-179.

Lenz et al., "*Yersinia enterocolitica* Septicemia During Long-Term Immunosuppressive Treatment" *J. Infect. Dis.*, Dec. 1984;150(6):963.

Lian et al., "Invasiveness of *Yersinia enterocolitica* lacking the virulence plasmid: an in-vivo study" *J. Med. Microbiol.*, Nov. 1987;24(3):219-226.

Likhatskaya et al., "Homology Models of the *Yersinia pseudotuberculosis* and *Yersinia pestis* General Porins and Comparative Analysis of Their Functional and Antigenic Regions" *J. Biomol. Struct. and Dyn.*, 2005; 23(2):163-174.

Lillard et al., "The Haemin Storage (Hms+) Phenotype of *Yersinia pestis* is not Essential for the Pathogenesis of Bubonic Plague in Mammals" *Microbiology*, Jan. 1999; 145(Pt 1):197-209.
Litwin et al., "Role of Catechol Siderophore Synthesis in *Vibrio vulnificus* Virulence" *Infect. Immun*., Jul. 1996;64(7):2834-2838.
LoBuglio et al., "Mouse/human chimeric monoclonal antibody in man: Kinetics and immune response" *Proc. Natl. Acad. Sci. USA*, Jun. 1989;86(11):4220-4224.
Loftus et al., "Clinical Features of Patients with Novel *Yersinia* species" *Dig. Dis. Sci*., Dec. 2002;47(12):2805-2810.
Lonberg et al., "Antigen-specific human antibiotics from mice comprising four distinct genetic modifications" *Nature*, Apr. 28, 1994;368(6474):856-859.
Lonberg et al., "Human Antibodies From Transgenic Mice" *Int. Rev. Immunol*., 1995;13(1):65-93.
Lucier et al., "Iron uptake and iron-repressible polypeptides in Yersinia pestis" Infect. Immun., 1996; 64: 3023-3031.
Meyer et al., "Live, Attenuated *Yersinia pestis* Vaccine: Virulent in Nonhuman Primates, Harmless to Guinea Pigs" *J. Infect. Dis*., May 1974;129,Suppl:S85-S120.
Meyer, "Effectiveness of Live or Killed Plague Vaccines in Man" *Bull. Wld. Hlth. Org*., 1970;42(5):653-666.
Modun et al., "The *Staphylococcus aureus* and *Staphylococcus epidermidis* transferrin-binding proteins are expressed in vivo during infection" *Microbiology*, Apr. 1998;144(Pt 4):1005-1012.
Moore et al., "Hybridization of Deoxyribonucleotide Sequences of *Yersinia enterocolitica* and Other Selected Members of *Enterobacteriaceae*" *Int. J. Syst. Bacteriol*., Oct. 1975;25(4):336-339.
Morrison et al., "Chimeric human antibody molecules: Mouse antigen-binding domains with human constant region domains" *Proc. Natl. Acad. Sci. U.S.A*., Nov. 1984;81(21):6851-6855.
National Center for Biotechnology Information, National Library of Medicine, National Institutes of Health, "BLAST 2 Sequences," Bethesda, MD [retrieved on Mar. 9, 2006]. Retrieved from the Internet:<http://www.ncbi.nlm.nih.gov/BLAST/>; 2 pgs.
Natkin et al., "*Yersinia enterocolitica* and *Yersinia pseudotuberculosis*" *Clin. Lab. Med*., Sep. 1999;19(3):523-536.
Neyt et al., "Insertion of a Yop translocation pore into the macrophage plasma membrane by *Yersinia enterocolitica*: requirement for translocators YopB and YopD, but not LcrG" *Mol. Microbiol*., Sep. 1999;33(5):971-981.
Nikaido et al., "Outer Membrane," In *Escherichia coli and Salmonella typhimurium, Cellular and Molecular Biology*, vol. 1, Neidhardt et al., eds., American Society for Microbiology, Washington, D.C. 1987, pp. 7-22.
Noll et al., "DNA immunization confers systemic, but not mucosal, protection against enteroinvasive bacteria" *Eur. J. Immunol*., Mar. 1999;29(3):986-996.
Noll et al., "Immunity against *Yersinia enterocolitica* by Vaccination with *Yersinia* HSP60 Immunostimulating Complexes or *Yersinia* HSP60 plus Interleukin-12" *Infect. Immun*., Aug. 1996;64(8):2955-2961.
Novagen, *His•Tag GST•Tag Purification and Detection Tools*, 2002; 40 pgs.
Nuorti et al., "A Widespread Outbreak of *Yersinia pseudotuberculosis* O:3 Infection from Iceberg Lettuce" *J. Infect. Dis*., Mar. 1, 2004;189(5):766-774.
Orloski et al., "*Yersinia pestis* infection in three dogs" *J. Am. Vet. Med. Assoc*., Aug. 1, 1995;207(3):316-318.
Pai et al., "Placebo-controlled double-blind evaluation of trimethoprim-sulfamethoxazole treatment of Yersinia enterocolitica gastroenteritis" *J. Pediatr*., Feb. 1984;104(2):308-311.
Panina et al., "Comparative analysis of FUR regulons in gamma-proteobacteria" *Nucleic Acids Res*., Dec. 15, 2001;29(24):5195-5206.
Parkhill et al., "Genome sequence of *Yersinia pestis*, the causative agent of plague" *Nature*, Oct. 4, 2001;413(6855):523-527.
Pattery et al., "Identification and molecular characterization of a novel *Salmonella enteritidis* pathogenicity islet encoding an ABC transporter" *Mol. Microbiol*., Aug. 1999;33(4):791-805.
Pelludat et al., "Transfer of the Core Region Genes of the *Yersinia enterocolitica* WA-C Serotype O:8 High-Pathogenicity Island to *Y. enterocolitica* MRS40, a Strain with Low Levels of Pathogenicity, Confers a Yersiniabactin Biosynthesis Phenotype and Enhanced Mouse Virulence" *Infect. Immun*., Apr. 2002; 70(4):1832-1841.
Perkins et al., "Probability-based protein identification by searching sequence databases using mass spectrometry data" *Electrophoresis*, Dec. 1999;20(18):3551-3567.
Perry et al., "*Yersinia pestis*—etiologic agent of plague" *Clin. Microbiol. Rev*., Jan. 1997;10(1):35-66.
Perry et al., "Yersiniabactin from *Yersinia pestis*: biochemical characterization of the siderophore and its role in iron transport and regulation" *Microbiology*, May 1999;145(Pt 5):1181-1190.
Poelma et al., "*Yersinia enterocolitica* infections in non-human primates" *Acta. Zool. Pathol. Antverp*., Dec. 1977;(69):3-9.

(56) References Cited

OTHER PUBLICATIONS

Poland et al., "Plague," In *CRC Handbook Series in Zoonoses*, Steele et al., eds., CRC Press, Boca Raton, FL 1979, pp. 515-559.
Potter et al., "Protective capacity of the *Pasteurella haemolytica* transferrin-binding proteins TbpA and TbpB in cattle" *Microb. Pathog*., Oct. 1999;27(4):197-206.
Prior et al., "Characterization of the lipopolysaccharide of *Yersinia pestis" Microb. Pathog*., Feb. 2001;30(2):49-57.
Pullen, et al., "Analysis of the *Yersinia pestis* V protein for the presence of linear antibody epitopes"; *Infection and Immunity*, Feb. 1998; 66(2):521-527.
Queen et al., "A humanized antibody that binds to the interleukin 2 receptor" *Proc. Natl. Acad. Sci. USA*, Dec. 1989;86(24):10029-10033.
Rabsch et al., "Role of Receptor Proteins for Enterobactin and 2,3-Dihydroxybenzoylserine in Virulence of *Salmonella enterica" Infect. Immun*., Dec. 2003; 71(12):6953-6961.
Rabsch et al., "The specificity of bacterial siderophore receptors probed by bioassays" *Biol. Metals*, 1991;4(4):244-250.
Rakin et al., "Evidence for Two Evolutionary Lineages of Highly Pathogenic *Yersinia* Species" *J. Bacteriol*., May 1995;177(9):2292-2298.
Rakin et al., "The pesticin receptor of *Yersinia enterocolitica*: a novel virulence factor with dual function" *Mol. Microbiol*., Jul. 1994;13(2):253-263.
Ray et al., "Population-Based Surveillance for *Yersinia enterocolitica* Infections in FoodNet Sites, 1996-1999: Higher Risk of Disease in Infants and Minority Populations" *Clin. Infect. Dis*., Apr. 15, 2004;38(Suppl 3):5181-189.
Reddin et al., "Comparison of the immunological and protective responses elicited by microencapsulated formulations of the F1 antigen from *Yersinia pestis" Vaccine*, May 1998;16(8):761-767.
Reeves, "Role of O-antigen variation in the immune response" *Trends Microbiol*., Oct. 1995;3(10):381-386.
Reissbrodt et al., "Further Differentiation of Enterobacteriaceae by Means of Siderophore-Pattern Analysis" *Zbl. Bakt. Hyg. A*, May 1988;268(3):306-317.
Riechmann et al., "Reshaping human antibodies for therapy" *Nature*, Mar. 24, 1988;332(6162):323-327.
Rossi et al., "Identification and Characterization of the Hemophore-Dependent Heme Acquisition System of *Yersinia pestis" Infect. Immun*., Nov. 2001;69(11):6707-6717.
Russell et al., "A comparison of Plague vaccine, USP and EV76 vaccine induced protection against *Yersinia pestis* in a murine model" *Vaccine*, Nov. 1995;13(16):1551-1556.
Russo et al., "The Siderophore Receptor IroN of Extraintestinal Pathogenic *Escherichia coli* Is a Potential Vaccine Candidate" *Infect. Immun*., Dec. 2003;71(12):7164-7169.
Sabhnani, et al., "Identification of immunodominant epitope of F1 antigen of *Yersinia pestis"; FEMS Immunol. Med. Microbiol*., Feb. 2000; 27(2):155-162.
Sabhnani et al., "Developing subunit immunogens using B and T cell epitopes and their constructs derived from the F1 antigen of *Yersinia pestis* using novel delivery vehicles" *FEMS Immunol. Med. Microbiol*., Oct. 15, 2003;38(3):215-229.
Saken et al., "Molecular Characterization of a Novel Siderophore-Independent Iron Transport System in *Yersinia" Int J Med Microbiol*., Mar. 2000; 290(1):51-60.
Sebastian et al., "The Gonococcal Fur Regulon: Identification of Additional Genes Involved in Major Catabolic, Recombination, and Secretory Pathways" *J. Bacteriol*., Jul. 2002;184(14):3965-3974.
Shayegani et al., "*Yersinia enterocolitica* and Related Species Isolated from Wildlife in New York State" *Appl. Environ. Microbiol*., Sep. 1986;52(3):420-424.
Simonet et al., "Invasin Production by *Yersinia pestis* Is Abolished by Insertion of an IS200-Like Element within the inv Gene" *Infect. Immun*., Jan. 1996;64(1):375-379.
Skurnik et al., "Characterization of the O-antigen gene clusters of *Yersinia pseudotuberculosis* and the cryptic O-antigen gene cluster of *Yersinia pestis* shows that the plague bacillus is most closely related to and has evolved from *Y. pseudotuberculosis* serotype O:1b" *Mol. Microbiol*., Jul. 2000;37(2):316-330.
Skurnik et al., "YadA Mediates Specific Binding of Enteropathogenic *Yersinia enterocolitica* to Human Intestinal Submucosa" *Infect. Immun*., Apr. 1994;62(4):1252-1261.
Slee et al., "Enteritis in cattle due to *Yersinia pseudotuberculosis* infection" *Aust. Vet. J*., Sep. 1988;65(9):271-275.
Slee et al., "Enteritis in sheep and goats due to *Yersinia enterocolitica* infection" *Aust. Vet. J*., Nov. 1990;67(11):396-398.
Slee et al., "Enteritis in sheep, goats and pigs due to *Yersinia pseudotuberculosis* infection" *Aust. Vet. J*., Sep. 1990;67(9):320-322.
Snellings et al., "Complete DNA Sequence of *Yersinia enterocolitica* Serotype 0:8 Low-Calcium-Response Plasmid Reveals a New Virulence Plasmid-Associated Replicon" *Infect. Immun*., Jul. 2001;69(7):4627-4638.
Snyder et al., "Transcriptome of Uropathogenic *Escherichia coli* during Urinary Tract Infection," *Infect. Immun*., Nov. 2004; 72(11):6373-6381.
Sodeinde et al., "A Surface Protease and the Invasive Character of Plague" *Science*, Nov. 6, 1992;258(5084):1004-1007.
Stojiljkovic et al., "Fur Regulon in Gram-negative Bacteria. Identification and Characterization of New Iron-regulated *Escherichia coli* Genes by a Fur Titration Assay" *J. Mol. Biol*., Feb. 18, 1994;236(2):531-545.
Sukhan et al., "Genetic Analysis of Assembly of the *Salmonella enterica* Serovar Typhimurium Type III Secretion-Associated Needle Complex" *J. Bacteriol*., Feb. 2001;183(4):1159-1167.
Swords et al., "Acylation of the Lipooligosaccharide of *Haemophilus influenzae* and Colonization: an htrB Mutation Diminishes the Colonization of Human Airway Epithelial cells" *Infect. Immun*., Aug. 2002; 70(8):4661-4668.
Taccetti et al., "Reactive arthritis triggered by *Yersinia enterocolitica*: a review of 18 pediatric cases" *Clin. Exp. Rheumatol*., Nov.-Dec. 1994;12(6):681-684.
Tatusova et al., "BLAST 2 Sequences, a new tool for comparing protein and nucleotide sequences" *FEMS Microbiol. Lett*., May 15, 1999;174(2):247-250.
Taylor et al., "A transgenic mouse that expresses a diversity of human sequence heavy and light chain immunoglobulins" *Nucleic Acids Res*., Dec. 11, 1992;20(23):6287-6295.
Thompson et al., "CLUSTAL W: improving the sensitivity of progressive multiple sequence alignment through sequence weighting, position-specific gap penalties and weight matrix choice" *Nucleic Acids Res*., Nov. 11, 1994;22(22):4673-4680.
Thompson et al., "Molecular Characterization of the Hemin Uptake Locus (hmu) from *Yersinia pestis* and Analysis of hmu Mutants for Hemin and Hemoprotein Utilization" *Infect. Immun*., Aug. 1999;67(8):3879-3892.
Titball et al., "Plague," In *Vaccines Third Edition*, Plotkin, et al., eds., W.B. Saunders, Philadelphia, PA 1999, pp. 734-742.
Titball et al., "Vaccination against bubonic and pneumonic plague" *Vaccine*, Jul. 20, 2001;19(30):4175-4184.
Torres et al., "TonB-Dependent Systems of Uropathogenic *Escherichia coli*: Aerobactin and Heme Transport and TonB Are Required for Virulence in the Mouse" *Infect. Immun*., Oct. 2001;69(10):6179-6185.
Toyokawa et al., "Large Scale Outbreak of *Yersinia pseudotuberculosis* Serotype 5a Infection at Noheji-machi in Aomori Prefecture" *Kansenshogaku Zasshi*, Jan. 1993;67(1):36-44. (English Language Abstract Included).
Une, "Studies on the Pathogenicity of *Yersinia enterocolitica*. III. Comparative Studies between *Y. enterocolitica* and *Y. pseudotuberculosis" Microbiol. Immunol*., 1977;21(9):505-516.
Verhoeyen et al., "Reshaping Human Antibodies: Grafting an Antilysozyme Activity" *Science*, Mar. 25, 1988;239(4847):1534-1536.
Voet, *Biochemistry, 2nd edition*, 1995; 95.
Visser et al., "Importance of the Ornibactin and Pyochelin Siderophore Transport Systems in *Burkholderia cenocepacia* Lung Infections" *Infect. Immun*., May 2004;72(5):2850-2857.

(56) References Cited

OTHER PUBLICATIONS

Wang et al., "Large-scale isolation of candidate virulence genes of *Pseudomonas aeruginosa* by in vivo selection" *Proc. Natl. Acad. Sci. USA*, Sep. 17, 1996;93(19):10434-10439.

Watson et al., eds., *Endotoxins and Their Detection With the Limulus Amebocyte Lysate Test*, Alan R. Liss, Inc., 150 Fifth Avenue, New York, NY 1982 (Title page, Publication page, and Table of Contents (5 pgs)).

Webb et al., "Immunization with Recombinant Transferrin Binding Protein B Enhances Clearance of Nontypeable *Haemophilus influenzae* from the Rat Lung" *Infect. Immun.*, May 1999;67(5):2138-2144.

Wedege et al., "Immune Responses against Major Outer Membrane Antigens of *Neisseria meningitidis* in Vaccinees and Controls Who Contracted Meningococcal Disease during the Norwegian Serogroup B Protection Trial" *Infect. Immun.*, Jul. 1998;66(7):3223-3231.

Whitby et al., "Transcription of Genes Encoding Iron and Heme Acquisition Proteins of *Haemophilus influenzae* during Acute Otitis Media" *Infect. Immun.*, Nov. 1997;65(11):4696-4700.

Wieser, et al., "A Multiepitope Subunit Vaccine Conveys Protection Against Extraintestinal Pathogenic *Escherichia coli* in Mice," *Infection and Immunity*, Aug. 2010; 78(8):3432-3442.

Williamson et al., "A single dose sub-unit vaccine protects against pneumonic plague" *Vaccine*, Oct. 15, 2000;19(4-5):566-571.

Williamson et al., "Local and systematic immune response to a microencapsulated sub-unit vaccine for plague" *Vaccine*, Dec. 1996;14(17-18):1613-1619.

Williamson, "Plague vaccine research and development" *J. Appl. Microbiol.*, Oct. 2001;91(4):606-608.

Wonderling et al., "A Novel Subunit Vaccine Protects Mice Against *Yersinia* Infection," *Abstracts of the 8th Annual Conference on Vaccine Research*, Baltimore, MD, USA, May 9-11, 2005 [online] May 9, 2005 (May 9, 2005), XP002391065, Abstract No. P66, [retrieved on Jul. 19, 2005]. Retrieved from the Internet:<URL:http://www.nfid.org/conferences/vaccine05/abstracts.pdf>; p. 89. Also included the poster, with attached slides to present each text box as listed on the poster (18 pgs, in color).

Wonderling et al., "A Novel Subunit Vaccine Protects Mice Against *Yersinia* Infection," Poster Presentation at the 8th Annual Conference on Vaccine Research, Baltimore, MD, USA, May 9-11, 2005. Abstract No. P66 retrieved online on Jul. 19, 2005. Retrieved from the Internet:<URL:http://www.nfid.org/conferences/vaccine05/abstracts.pdf>; p. 89, the poster and each text box on the poster in larger type for legibility; 19 pages total.

Yanagawa et al., "Isolation of *Yersinia enterocolitica* and *Yersinia pseudotuberculosis* from Apparently Healthy Dogs and Cats" *Microbiol. Immunol.*, 1978;22(10):643-646.

Zheng, "Isolation of Yersinia enterocolitica from the faeces of diarrhoeic swine" *J. Appl. Bacteriol.*, Jun. 1987;62(6):521-525.

Zhou et al., "Transcriptome analysis of the Mg2+-responsive PhoP regulator in Yersinia pestis" *FEMS Microbiol. Letters*, 2005; 250: 85-95.

Figure 3

SEQ ID NO:1
MTKDPKISVSAALISALFSSPYAFANNDEVHFTAVQISPNSDPDSHVMIFQPEVEAPGGTNALAKGTHS
I
AVGASAEAAERAAVAVGAGSIATGVNSVAIGPLSEALGDSAVTYGAGSTAQKDGVAIGARASTSDTGVA
V
GFNSKVDAKNSVSIGHSSHVAVDHDYSIAIGDRSKTDRKNSVSIGHESLNRQLTHLAAGTKDTDAVNVA
Q
LKKEIEKTQENANKKSAEVLGIANNYTDSKSAETLENARKEAFDLSNDALDMAKKHSNSVARTTLETAE
E
HPNKKSAETLASANVYADSKSSHTLKTANSYTDVTVSNSTKKAIRESNQYTDHKFHQLDNRLDKLDTRV
D
KGLASSAALNSLFQPYGVGKVNFTAGVGGYRSSQALAIGSGYRVNESVALKAGVAYAGSSDVMYNASFN
I
EW

SEQ ID NO:2
MPRSTSDRFRWSPLSLAIACTLSLAVQAADTSSTQTNSKKRIADTMVVTATGNERSSFEAPMMVTVVEA
D
TPTSETATSATDMLRNIPGLTVTGSGRVNGQDVTLRGYGKQGVLTLVDGIRQGTDTGHLNSTFLDPALV
K
RVEIVRGPSALLYGSGALGGVISYETVDAADLLLFGQNSGYRVYSAAATGDHSFGLGASAFGRTDPVDG
I
LSFGTRDIGNIRQSDGFNAPNDETISNVLAKGTWRIDQIQSLSANLRYYNNSALEPKNPQTSAASSTNL
M
TDRSTIQRDAQLKYNIKPLDQEWLNATAQVYYSEVEINARPQGTPEEGRKQTTKGGKLENRTRLFTDSF
A
SHLLTYGTEAYKQEQTPSGATESFPQADIRFGSGWLQDEITLRDLPVSILAGTRYDNYRGSSEGYADVD
A
DKWSSRGAVSVTPTDWLMLFGSYAQAFRAPTMGEMYNDSKHFSMNIWVTPDQLLGTNPNLKPETNETQE
Y
GFGLRFNDLMMAEDDLQFKASYFDTNAKDYISTGVTMDFGFGPGGLYCKNCSTYSTNIDRAKIWGWDAP
M
TYQTQWFNLGLAYNRTRGKNQNTNEWLDTINPDTVTSTLDVPVANSGFAVGWIGTFADRSSRVSSSGTP
Q
AGYGVNDFYVSYKGQEQFKGMTTTVVLGNAFDKGYYGPQGVPQDGRNAKFFVSYQW

SEQ ID NO:3
MNQTISSRAPQKRLAPRLLCVMIGAALGTLSASSWAAAATDSTAENAKKTSATAATAKAEDSKTNDTIT
V
VGAQETFRAGGNDLIPTYLDGQVANGGRIGFLGQQDARNVPFNVIGYTSKMIEDQQANSIADVVKNDAS
V
QNVRGYGNPSQNYPIRGYNLDGDDISFGGLFGVLPRQIVSTSMVERVEVFKGANAFINGISPSGSGVGG
M
INLEPKRAGDTPLTRVTVDYGSASQVGGALDVGRRYGDDDQFGVRVNVLHREGESAIHDQKERTTAVST
G
LDYRGDRARTSLDVGYQKQTIHHMRTDVAIGGATVIPEPPSSTLNYGQSWVYTDMETTFGMLRSEYDVS
Q
NWTVYGSVGASRNEETGQYGAPMLTNNNGDATISRLYVPYVADSVAGLGGIRGHFDTGFITHKVNLGYA
A
NYRTTKSAWNMSGQEDTNIYNPGVIGFPQTVMGSDSQDPQLTSQVRASGLSLSDTLSMMDDKVSLMLGV
R
RQEVTIRNFDSGVPNSAGSLDAMKVTPIYGIMVKPWEKVSLYANHIEALGPGKSAPYQYNGKFVVNAGQ
I
PGIIHSKQNEIGVKFDNQRYGGTLALFEITRPTGMVDPATNVYGFYGEQRNRGIELNVFGEPVFGTRLL
A
SATWLDPKLTKAADSANNGNDAVGVANYQLVFGGEYDIPVVEGLTATGTVVRSGSQYANEANTLKLKPW
T
RLDLGVRYTMPMKDTSLTWRANIENVTNERYWESVEDSGTYIYQGDPRALKLSVSMDF

Figure 3 cont.

```
SEQ ID NO:4
MFSAFIIKRSAILCSLAMFIPLASIADDTIEVTAKAGHEADLPTSGYTATTTKGATKTDQPLILTAQSVS
VVTRQQMDDQNVATVNQALNYTPGVFTGFSGGATRYDTVALRGFHGGDVNNTFLDGLRLLSDGGSYNVLQ
VDPWFLERIDVIKGPSSALYGQSIPGGVVMMTSKRPQFTSEGHFRLTAGNNNTQVAAFDYTDAISEHWAF
RLTGITRNSDTMYDHQREERYAIAPSLLWQPDENTSLLLRANLQKDPSGGYRSAVPADGSIYGQKLSRGF
FDGESNHNVFKRWQQIYSYEFSHKFDDVWSFRQNASYTHSNTQLEQVYQGGWNSDRTLMNRYYSGEDSSL
NAFAVDNQLEADLRTAAVKHKVLLGVDFQKFRNNLRSDSAYATPLNPYTGVSGGSTLYSDYLLTTPGINT
SYLSRRYEQSGVYLQDEMTLDNWHLNLSGRYDRMKTENINNTANSTDERTDNHASGRASLLYSFDSGISP
YVSYSQAITPSLFFDAQQKLLKPMTSEQYEVGIIYQPPGSTSLYSAALYDLTQNDVANRAVPATYYVPAG
KVNSQGLELEARSQISDRLSVIAGYTYNRVKFKDAIDGNDGNTPVLAPSNMASLWAQYEAGYGINVGAGI
RYIGKQWADDANTLRVPSYTLGDASVRADLGTWAASLKGAFVQLNVNNIADKKYVAACYSTSYCYWGAER
SVQATVGYDF

SEQ ID NO:5
MKMTRLYPLALGGLLLPAIANAQTSQQDESTLEVTASKQSSRSASANNVSSTVVSAPELSDAGVTASDKL
PRVLPGLNIENSGNMLFSTISLRGVSSAQDFYNPAVTLYVDGVPQLSTNTIQALTDVQSVELLRGPQGTL
YGKSAQGGIINIVTQQFDSTPRGYIEGGVSSRDSYRSKFNLSGPIQDGLLYGSVTLLRQVDDGDMIRPAT
GSDDLGGTRASIGNVKLRLAPDDQPWEMGFAASRECTRATQDAYVGWNDIKGRKLSLSDGSPDPYMRRCT
DSQTLSGKYTFDDWVFNLISAWQQQHYSRTFPSGSLIVNMPQRWNQDVQELRAATLGDARTVDMVFGLYR
QNTREKLNSAYDMPTMFYLSSTGYTTAETLAAYSDLTWHLTDRFDIGGGVRFSHDKSSTQYHGSMLGNPF
GDQGKSNDDQVLGQLSAGYMLTDDWRVYTRIAQGYKPSGYNIVPTAGLDAKPFVAEKSINYELGTRYETA
DVTLQAATFYTHTKDMQLYSGPVGMQTLSNAGKADATGVELEAKWRFAPGWSWDINGNVIRSEFTNDSEL
YHGNRVPFVPRYGAGSSVNGVIDTRYGALMPRLAVNLVGPHYFDGDNQLRQGTYATLDSSLGWQATERIN
ISVHVDNLFDRRYRTYGYMNGSSAVAQVNMGRTVGINTRIDFF
```

Figure 3 cont.

SEQ ID NO:6
MVTASGFQQRIQDSAASISVVTREQIENKAYTDITDALKDVPGVVVTGGGSRSDISIRGMAAKYTLILVD
GKRVDTRGTRPNSDGSGIEQGWLPFLAAIERIEVVRGPMSSLYGSDAMGGVINVITRKVGKEWHGTVRAD
ATLQEDSKSGDIFQTNAYASGPLIDGLLGLKVSGLLSHRSEDKIVDGYNEQRLRNGAATFTLTPDDKNEF
DFDIGRYVQDRNSTAGRSVALNGKSSDVQYDRNNYAITHHGYYDFGNSTSYVQRDETRNPSREMKSVDNI
FNTQTSFLLDNHTLILGGQYRYEELNDTGNQLASAKDLTKLTRWSWALFAEDEWQMTNDFALTGGVRMDQ
DENYGTHWTPRLYGVWHLAEQWTLKGGVSGGYRSPDLRQATENWGQITGGRGDPAIIIGNANLKPERSIS
QEIGILWDDQEGMNAGVTLFNTDFKDKITEVRRCTDTTGKASGQCMINGASYKFISDRTNVDKAITRGVE
ATFGWDINQEWSLTSNYTFTQSEQKSGQFAGQPLNQMPKRMLNGTLNWQASEALATWVRANYRGKTSEYL
NRTSIGGSTPSYTFVDLGANYQLTKEFRLMGGVYNVLDKRVDIEVNDKVLDGRRYMVGASYDF

SEQ ID NO:7
MTKDFKISVSAALISALFSSPYAFANNDEVHFTAVQISPNSDPDSHVMIFQPEVRAPGGTNALAKGTHSI
AVGASAEAAERAAVAVGAGSIATGVNSVAIGPLSKALGDSAVTYGAGSTAQKDGVAIGARASTSDTGVAV
GFNSKVDAKNSVSIGHSSHVAVDHDYSIAIGDRSKTDRKNSVSIGHESLNRQLTHLAAGTKDTDAVNVAQ
LKKEIEKTQENANKKSAEVLGIANNYTDSKSAETLENARKEAFDLSNDALDMAKKHSNSVARTTLETAEE
HTNKKSAETLASANVYADSKSSHTLKTANSYTDVTVSNSTKKAIRESNQYTDHKFHQLDNRLDKLDTRVD
KGLASSAALNSLFQPYGVGKVNFTAGVGGYRSSQALAIGSGYRVNESVALKACVAYAGSSDVMYNASFNI
EW

SEQ ID NO:8
MKLRVLSLIVPALLVAGSAGAAEIYHKDGNKLDLYGKVDGLHYFSDDKSKDGDQSYMRFGLKGETQISDQ
LTGYGQWEYQANLNRAEDQDQGNFTRLGFAGLKFADYGSLDYGRNYGVLYDVTSWPDVLPEFGGDTYGAD
NFMSQRANGLATYRNTNFFGLVDGLNFALQYQGKNGSPTESRNGRDVKGQNGDGYGMSLSYDLGWGVSAA
AAMSSSKRFTEQNQLLFGNGDRADAYSGGLKYDANNVYLAATYAQTYNLTRFGNFQNNNSGFANKAQNIE
LVAQYQFDFGLRPSVAYLQSKGKDLGNGYGDQDLVQYVDVGATYFFNKNMSTYVDYKINLLDENEFTKNA
GINTDDIVAVGLVYQF

SEQ ID NO:9
MKKNMKLIAITAVLSSVLVLSGCGAMSTAIKKRNLEVKTQMSETIWLEPSSQKTVYLQIKNTSDKNMLGL
APKITKAVQDKGYTVTSSPEDAHYWIQANVLKADKMDLREAEGFLSQGYQGAALGAALGAGITGYNSNSA
GASLGVGLAAGLVGMVADAMVEDINYTMVTDVQISEKTDTPLQTDNVAALKQGTSGYKVQTSTQTGNKRQ
YQTRVVSSANKVNLKFEEAQPVLEDQLAKSIANIL

Figure 3 cont.

SEQ ID NO:10
MAVTNVAELNELVARVKKAQREYANFSQEQVDKIFRAAALAAADAKIPLAKLAVTESGMGIVEDKVIKNH
FASEYIYNAYKDEKTCGILCEDKTFGTITIAEPIGLICGIVPTTNPTSTAIFKALISLKTRNGIIFSPHP
RAKDATNKAADIVLQAAIAAGAPADIIGWIDAPTVELSNQLMHHPDINLILATGGPGMVKAAYSSGKPAI
GVGAGNTPVVVDETADIKRVVASILMSKTFDNGVICASEQSIIVVDSVYDAVRERFASHGGYLLQGKELK
AVQDIILKNGGLNAAIVGQPATKIAEMAGIKVPSNTKILIGEVKVVDESEPFAHEKLSPTLAMYRAKNFE
EAVEKAEKLVEMGGIGHTSCLYTDQDNQTARVKYFGDKMKTARILINTPASQGGIGDLYNFKLAPSLTLG
CGSWGGNSISENVGPKHLINKKTVAKRAENMLWHKLPKSIYFRRGSLPIALEEVATDGAKRAFIVTDRYL
FNNGYADQVTSVLKSHGIETEVFFEVEAAPTLSIVRKGAEQMNSFKPDVIIALGGGSPMDAAKIMWVMYE
HPETHFEELALRFMDIRKRIYKFPKMGVKAKLVAITTTSGTGSEVTPFAVVTDDATGQKYPLADYALTPD
MAIVDANLVMNMPKSLCAFGGLDAVTHALEAYVSVLANEYSDGQALQALKLLKEFLPASYNEGAKNPVAR
ERVHNAATIAGIAFANAFLGVCHSMAHKLGSEFHIPHGLANAMLISNVIRYNANDNPTKQTAFSQYDRPQ
ARRRYAEIADHLGLSAPGDRTAQKIQKLLAWLDEIKAELGIPASIREAGVQEADFLAKVDKLSEDAFDDQ
CTGANPRYPLISELKQILMDTYYGREYVEEFDREEEVAAATAPKAEKKTKK

SEQ ID NO:11
MARKTPIERYRNIGISAHIDAGKTTTTERILFYTGVNHKIGEVHDGAATMDWMEQEQERGITITSAATTC
FWSGMAKQFEPHHVNIIDTPGHVDFTIEVERSMRVLDGAVMVYCAVGGVQPQSETVWRQANKYKVPRIAF
VNKMDRMGANFLRVVGQLKSRLGANPVPLQLAIGAEEKFTGIIDLVKMKAINWNEADQGVTFEYEEIPAD
MAELAAEWHQNLVESAAEASDELMDKYLGGEELTEEEIKKALRQRVLKSEIILVTCGSAFKNKGVQAMLD
AVIEYLPAPTDVESINGILDDGKDTPAVRHSDDKEPFSALAFKIATDPFVGNLTFFRVYSGIVNSGDTVL
NSVKSQRERLGRIVQMHANKREEIKEVHAGDIAAAIGLKDVTTGDTLCDPNNFIILERMEFPEPVISVAV
EPKTKADQEKMGMALGRLAKEDPSFRVWTDEESGQTIIAGMGELHLDILVDRMRREFNVEANVGKPQVAY
RETIRETVKDVEGKHAKQSGGRGQYGHVVIDMSPLPPGGVGYEFVNEIVGGSIPKEFIPAVDKGIQEQLK
SGPLAGYPVVDVKVRLHYGSYHDVDSSELAFKLAGSIAFKEGFKRAKPVLLEPIMKVEVETPEDYMGDVM
GDLNRRRGIIEGMEDTATGKTVRVKVPLSEMFGYATDLRSQTQGRASYSMEFLKYAEAPSNVAKAVIEAR
GK

Figure 3 cont.

SEQ ID NO:12
MTSPFSYTSPVVSVDALKHSIAYKLMFIIGKDPTIATQHDWLNATLFAVRDRMVERWLRSNRAQLSQDVR
QVYYLSMEFLLGRTLSNALLSMGIYDEIEQALDEMGLSLSELLKEENDPGLGNGGLGRLAACFLDSLATL
ALPGRGYGIRYEYGMFSQKIVNGQQMESPDNWLEYGNAWEFPRHNTRYKVRFGGRIQQEGSKIRWLETEE
ILACAYDQIIPGFDTDATNTLRLWSAQASNEINLGKFNQGDYFAAVEDKNHSENVSRVLYPDDSTYSGRE
LRLRQEYFLVSATVQDILNRHWAMHHTFNNLADKIAIHLNDTHPVLSIPEMMRLLIDEHKFTWMDAWDVV
QQVFSYTNHTIMSEALETWPVDMIGKILPRHLQIIFDINDHFLKLVEEQYPDDKELLSRVSVIDENNGRR
IRMAWLAVIASHKVNGVSALHSELMVQSLFADFARIFPNRFCNKTNGVTPRRWLGLANRPLAAVLDDSIG
QTWRTDLSQLSELEKNLDYPSFLLALQKAKLENKKRLAVYIAEKLNIVVNPAALFDVQIKRIHEYKRQLL
NVLHVITRYNRIIDAPDNNWVPRVVIFAGKAASAYYNAKQIIHLINDVAKVINNDPRINRLLKVVFIPNY
SVSLAQLIIPAADLSEQISLAGTEASGTSNMKFALNGALTIGTLDGANVEIRRHVGEENIFIFGNTTEQV
EALRKSGYNPRKYYDEDPELHQVLTQIATGTFSPEEPHRYTNLFDSLVNLGDHYQLLADYRSYVDTQEQV
DALYRNRDEWSRKTLLNIANMGYFSSDRTIKEYADEIWHIKPIRL

SEQ ID NO:13
MKKRFPTLLATLIWTALYSQHTLADLAEQCMLGVPTYDQPLVTGDPNQLPVRINADKTEANYPDNALFTG
NVIVQQGNSTLTANQVELTQVQKPGEVIPLRTVTATGDVNYDDPQIKLKGPKGWSNLNTKDTDMDKGKYQ
MVGRQGRGDADLMKLRDQSRYTILKNGTFTSCLPGDNSWSVVGSEVIHDREEQVVEVWNARFKIGKVPVF
YSPYMQLPVGDKRRSGFLIPNAKFTSNNGFEFLLPYYWNIAPNFDATITPHYMERRGLQWQNEFRYLLAP
GSGTMALDWLPNDRIYTGPDGTDKNATRWLYYWGHSGVMDQVWRFNINYTRVSDPAYFTDLTSQYGSTTD
GYATQIFTAGYANENWNATLSSKQFQVFTAAGNSNAYRAQPQLDMNYYKNDVGPFDMRVYGQAAKFTSVN
PTNPEASRFHIEPTVNLPLSNSWGSINTEAKLLATHYQQDIPASFADNASNPKLEDSVNRVLPQFKVDGK
VVFDRSMDWATGFTQTLEFRAQYLYVFYRNQDDIYIYDTTLMQSDYSGLFRDKTYSGLDRIASANQVSTG
LTSRIYDDARVERFNVSVGQIYYFSRSRTGNTEAIDNSNATGSLVWAGDTFWRINDQLGLKGGAQYDTRL
GSLTLGNAIMEYRKDADRMIQLNYRYASPKYIQAAVPKVYNFDYQQGISQVGTTASWPIADRWAIVGAYY
YDFKAKQFASQLVGLQYNTCCWAVNLGYERKITGWNAQGQTSKYDNKIGFNIELKGLSGGHSLGTAQMLN
SGILFYQSAF

Figure 3 cont.

SEQ ID NO:14
MLRSTSDRFRWSSLSLAIACTLPLATQAADTTTTQTSSKKHSTDTMVVTATGNERSSFEAPMMVTVIEGN
APTSQTAATAADMLRQVPGLTVTGSGRTNGQDVVMRGYGKQGVLTLVDGVRQGTDTGHLNSTFLDPALVK
RIEIVRGPAALLYGSGALGGVIAYETVDAADMLQPGQNSGYRVYSSAATGDRSFGLGASAFGRTDDLDGI
LSFGTRDIGNIRQSNGFNAPNDETISNVLAKGTWQIDSIQSLSANLRYYNNRSAIEPRNPQTSAPSSTNVM
TNRSTIQRDAQLRYNIKPLDQEWLNATAQVYYSEVEINARFQGSAEEGREQTTEGVKLENRTRLFIESPA
SHLLTYGTETYKQEQTPGGATESFPQAKIRFSSGWLQDEITLRDLPVSILAGTRYDNYSGSSDGYADVDA
DKWSSRGAISITPTDWLMLFGSYAQAFRAPTMGEMYNDSKHFAIPIRPGLTLTNYWVPNPNLKPETNETQ
EYGFGLRFSDLLMAEDDLQFKVSYFDTKAKDYISTRVDMQAMTTTSVNIDQAKIWGWDASMSYKPALFNW
DLAYNRTRGKNQNTDEWLDTINPDTVTSIVDVPVANSGFSVGWIGTFANRSSRVSSSTPQAGYGVNDFYV
SYKGQEAFKGMTTTMLLGNVFEKEYYTPQGIPQDGRNVKFFVSYQW

SEQ ID NO:15
MSNKTIAFALVVASSAPVIAADNDNIMVVTASGYEQKIREAAASISVISQNELRQRNYNDLAQALSDVEG
VDVNSSTGKTGGLDISIRGMPSAYTLILVDGIRQNGTSDVTPNGFGAMNTSFMPPLSAIERIEVIRGPMS
TLYGSDAIGGVVNIITKKITRAWASSATLEHTFQENTAFGDSSKFSFYSSGPAVEDQLGLSLRGTIFRRD
ASRVESSNTGVELSRRGPNPVKADNYNLGGKLFWQLNTQSTLWLDGDIANQKYDNSANQLGTIGAREGYE
DTLRYQRRKITLGNDNRLDFGTWNSSLSYNQTENIGRLITNASVPQGSGLAGEKRLLKNTNIILDSKLVA
PLGDNHMVTLGGQYWNAIMKDGIVLANNGDEFAQDAWSLFSEDEWRLLDSLALTYGARYEYQTTFGGHIS
PRAYLVWDAQDNWTVKGGVSTGYKTFTLAQLHNGISGVTGQGTITTIGNPKLEPESSVNTEVGVYYENET
GFGANVTLFHNRFRNKINSVSIDNTTSTYTNVGKAITQGIEVASTIPLWSDDWMLGINYTFTDSEQKDGN
NKGARLTNTPKNMVNARLNWNINEQLSTWLKAEYRSKTARFTQNYANLSAANKVVYNNLGSEFKPFSVLN
LGVAYKVTKDVTLNGAVNRLLDKDFTRTHIFAVGNGTTTAGDYFTSSQSTAGYVVPGRNYWVSVRVNF

Figure 3 cont.

SEQ ID NO:16
MKMTRLYPLALGGLLLPAIANAQTSQQDESTLVVTASKQSSRSASANNVSSTVVSAPELSDAGVTASDKL
PRVLPGLNIENSGNMLFSTISLRGVSSAQDFYNPAVTLYVDGVPQLSTNTIQALTDVQSVELLKGPQGTL
YGKSAQGGIINIVTQQPDSTPRGYIEGGVSSRDSYRSKFNLSGPIQDGLLYCSVTLLRQVDDGDMINPAT
GSDDLGGTRASIGNVKLKLAFDDQPWEMGFAASRECTRATQDAYVGWNDIKGRKLSISDGSPDPYMRRCT
DSQTLSGRYTTDDWVFNLISAWQQQHYSRTFPSGSLIVNMPQRWNQDVQELRAATLGDARTVDMVFGLYR
QNTREKLNSAYDMPTMPYLSSTGYTTAETLAAYSDLTWHLTDRFDIGGGVRFSRDKSSTQYHGSMLGNPF
GDQGKSNDDQVLGQLSAGYMLTDDWRVYTRVAQGYKPSGYNIVPTAGLDAKPFVAEKSINYELGTRYETA
DVTLQAATFYTHTKDMQLYSGPVRMQTLSNAGKADATGVELEARWRFAPGWSWDINGRVIRSEFTNDSEL
YHGNRVPFVPRYGAGSSVNGVIDTRYGALMPRLAVNLVGFHYFDSDNQLRQGTYATLDSSLGWQATERMN
ISVYVDNLFDRRYRTYGYMNGSSAVAQVNMGRTVGINFRIDPF

SEQ ID NO:17
MAAKDVKFGNDARIKMLRGVNILADAVKVTLGPKGRNVVLDKSFGSPTITKDGVSVAREIELEDKFENMG
AQMVKEVASKANDAAGDGTTTATVLAQSIITEGLKAVAAGMNPMDLKRGIDKAVIAAVEELKKLSVPCSD
SKAIAQVGTISANSDSTVGELIAQAMEKVGKEGVITVEEGSGLQDELDVVEGMQFDRGYLSPYFINKPET
GSIELESPFILLADKKISNIREMLPVLEAVAKAGKPLLIIAEDVEGEALATLVVNTMRGIVKVAAVKAPG
FGDRRKAMLQDIATLTAGTVISEEIGLELEKTTLEDLGQAKRVVINKDTTTIIDGVGDEAAIQGRVAQIR
QQIEDATSDYDKEKLQERVAKLAGGVAVIKVGAATEVEMKEKKARVEDALHATRAAVEEGVVAGGGVALI
RAAHAIAGLKGDNEDQNVGIKVALRAMESPLRQIVVNAGEEASVIANKVKAGEGSFGYNAYTEEYGDMIA
MGILDPTKVTRSALQYAASIAGLMITTECMVTDLPRDDKGADMGAGMGGMGGMGGMM

SEQ ID NO:18
MQMKKLLFLLIGLSLAGFSTMSQAENLLQVYKQARDSNFDLRKAAADRDAAYERINEVRSELLPQLGLSA
GYTHANGFRDASNSFDSNATSGSLKLTQTIFDMSKWRALTLQEKAAGIQDVTFQTSEQQLLLNTATAYFN
VLRAIDSLSYTEAQKQSVYRQLDQTTQRFNVGLVAITDVQNARASYDTVLAAEVAARNNLDRALESIRQI
TGVYYPELASLRVERLKTQRPDAVNNLLKEAEKRNLSLLSARLSQDLAREQIKSAETGYMFTVDLTASSI
TNTRYSGSTPSSQQVNNDSGQNQIGVQFSLFLYSGEATNSAVKQAQYNFVGASELLESAHRNMVQTLRS
SFNNISASISSINAYQQVVISNQSSLDAMEAGYQVGTETILDVLTATTNLYQSKQQLADAKYNYLINQLN
IKSALGTINMNDLMALNAVLDKPVPTSAAALAFENTTRQFVTTFRAQ

Figure 3 cont.

SEQ ID NO:19
MSKEKFERTKPHVNVGTIGHVDHGKTTLTAAITTVLAKTYGGSARAFDQIDNAPEEKARGITINTSHVEY
DTPARHYAHVDCPGHADYVKNMITGAAQMDGAILVVAATDGPMPQTREHILLGRQVGVPYIIVFMNKCDM
VDDEELLELVEMEVRELLSAYDFPGDDLPVVRGSALKALEGEAEWEAKIIELAGYLDSYIPEPERAIDKP
FLLPIEDVFSISGRGTVVTGRVERGIVKVGEEVEIVGIKDTVKSTCTGVEMFRKLLDEGRAGENVGVLLR
GIKREDIERGQVLAKPGSIKPHTTFESEVYILSKDEGGRHTPFFKGYRPQFYFRTTDVTGTIELPEGVEM
VMPGDNINMIVTLIHPIAMDDGLRFAIREGGRTVGAGVVAKVIA

SEQ ID NO:20
MKLRVLSFIIPALLVAGSASAAEIYNKDGNKLDLYGKIDGLHYFSDNKNLDGDQSYMRFGLKGETQITDQ
LTGYGQWEYQVNLNKAENEDGNHDSFTRVGFAGLKFADYGSLDYGRNYGVLYDVTSWTDVLPEFGGDTYG
ADNFLSQRGNGMLTYRNTNFFGLVDGLNFALQYQGKNGSSSEFNNGRGVADQNGDGYGMSLSYDLGWGVS
ASAAMASSLRTTAQNDLQYGQGKRANAYTGGLKYDANNVYLAANYTQTYNLTRFGDFSNRSSDAAFGFAD
KAHNIEVVAQYQFDFGLRPSVAYLQSKGKDIGIYGDQDLLKYVDIGATYFFNKNMSTYVDYKINLLDKND
FTKNARINTDDIVAVGMVYQF

SEQ ID NO:21
MYNIDYNSFRSVKGFNRRVRFLVMHYTAFNFKDSIDALTGPSVSAHYLVPDPTEQTYIDAGFKDMRIFNL
VDENERAWHAGVSYWDGRNNLNDTAIGIETVNLATDNDGVFTFPPYNVTQIAAIKALASNILYRFPDITP
VNVVGHSDIAPGRKSDPGAAFPWKALYDAGIGAWYDDETKQRYLDQFLCSLPSKNDIISKLKRYGYDTSG
AVSEVGYNQLIRAFQLHFRPCNYDGIPDAETVAILYALVDKYKP

SEQ ID NO:22
MRKLLSGGLLLLLAGCSSSDHRNSNELIDRGTYQIDTHYPSVAKNERVRFLVLHYTAVGDAESLRLLTQG
EVSAHYLIPTHPKKAGGKAIALQLVPEAQRAWHAGVSSWQGRNNLNDTSIGIEIVNLGFTEKMLGRTWYP
YNESQIELIEQLTKDIVQRYNISPSDVVAHSDIAPLRKSDPGPLFPWKRLAEKGVGAWPDDATVAKYIGG
RDKKGAASVAVIQQALAAYGYKIPQNGQLDTETRQVIKAFQMHFRPQDFSGVPDVETEAIALALVEKYRT
LST

SEQ ID NO:23
MVTVLGIVITIWMVFMNKFLLVSSLIACLSIASVNVYAEGESSISIGYAQSRVEEDGYKLDKNPRGFNLK
YRYEFNNDWGVIGSFAQTRRGFEESVDGFKLIDGDFKYYSVTAGPVFRINEYVSLYGLLGAGHGKAKFSS
IPGQSESRSKTSLAYGAGLQFNPHPNFVIDASYEYSKLDDVKVGTWMLGAGYRF

SEQUENCE LISTING

```
<160> NUMBER OF SEQ ID NOS: 451

<210> SEQ ID NO 1
<211> LENGTH: 422
<212> TYPE: PRT
<213> ORGANISM: Yersinia enterocolitica

<400> SEQUENCE: 1

Met Thr Lys Asp Phe Lys Ile Ser Val Ser Ala Ala Leu Ile Ser Ala
1               5                   10                  15

Leu Phe Ser Ser Pro Tyr Ala Phe Ala Asn Asn Asp Glu Val His Phe
            20                  25                  30

Thr Ala Val Gln Ile Ser Pro Asn Ser Asp Pro Asp Ser His Val Met
        35                  40                  45
```

```
Ile Phe Gln Pro Glu Val Arg Ala Pro Gly Gly Thr Asn Ala Leu Ala
 50                  55                  60

Lys Gly Thr His Ser Ile Ala Val Gly Ala Ser Ala Glu Ala Ala Glu
 65                  70                  75                  80

Arg Ala Ala Val Ala Val Gly Ala Gly Ser Ile Ala Thr Gly Val Asn
                 85                  90                  95

Ser Val Ala Ile Gly Pro Leu Ser Lys Ala Leu Gly Asp Ser Ala Val
                100                 105                 110

Thr Tyr Gly Ala Gly Ser Thr Ala Gln Lys Asp Gly Val Ala Ile Gly
            115                 120                 125

Ala Arg Ala Ser Thr Ser Asp Thr Gly Val Ala Val Gly Phe Asn Ser
130                 135                 140

Lys Val Asp Ala Lys Asn Ser Val Ser Ile Gly His Ser Ser His Val
145                 150                 155                 160

Ala Val Asp His Asp Tyr Ser Ile Ala Ile Gly Asp Arg Ser Lys Thr
                165                 170                 175

Asp Arg Lys Asn Ser Val Ser Ile Gly His Glu Ser Leu Asn Arg Gln
            180                 185                 190

Leu Thr His Leu Ala Ala Gly Thr Lys Asp Thr Asp Ala Val Asn Val
        195                 200                 205

Ala Gln Leu Lys Lys Glu Ile Glu Lys Thr Gln Glu Asn Ala Asn Lys
210                 215                 220

Lys Ser Ala Glu Val Leu Gly Ile Ala Asn Asn Tyr Thr Asp Ser Lys
225                 230                 235                 240

Ser Ala Glu Thr Leu Glu Asn Ala Arg Lys Glu Ala Phe Asp Leu Ser
                245                 250                 255

Asn Asp Ala Leu Asp Met Ala Lys Lys His Ser Asn Ser Val Ala Arg
            260                 265                 270

Thr Thr Leu Glu Thr Ala Glu His Thr Asn Lys Lys Ser Ala Glu
        275                 280                 285

Thr Leu Ala Ser Ala Asn Val Tyr Ala Asp Ser Lys Ser Ser His Thr
        290                 295                 300

Leu Lys Thr Ala Asn Ser Tyr Thr Asp Val Thr Val Ser Asn Ser Thr
305                 310                 315                 320

Lys Lys Ala Ile Arg Glu Ser Asn Gln Tyr Thr Asp His Lys Phe His
                325                 330                 335

Gln Leu Asp Asn Arg Leu Asp Lys Leu Asp Thr Arg Val Asp Lys Gly
            340                 345                 350

Leu Ala Ser Ser Ala Ala Leu Asn Ser Leu Phe Gln Pro Tyr Gly Val
        355                 360                 365

Gly Lys Val Asn Phe Thr Ala Gly Val Gly Gly Tyr Arg Ser Ser Gln
        370                 375                 380

Ala Leu Ala Ile Gly Ser Gly Tyr Arg Val Asn Glu Ser Val Ala Leu
385                 390                 395                 400

Lys Ala Gly Val Ala Tyr Ala Gly Ser Ser Asp Val Met Tyr Asn Ala
                405                 410                 415

Ser Phe Asn Ile Glu Trp
                420

<210> SEQ ID NO 2
<211> LENGTH: 686
<212> TYPE: PRT
<213> ORGANISM: Yersinia enterocolitica

<400> SEQUENCE: 2
```

-continued

```
Met Pro Arg Ser Thr Ser Asp Arg Phe Arg Trp Ser Pro Leu Ser Leu
1               5                   10                  15

Ala Ile Ala Cys Thr Leu Ser Leu Ala Val Gln Ala Ala Asp Thr Ser
            20                  25                  30

Ser Thr Gln Thr Asn Ser Lys Lys Arg Ile Ala Asp Thr Met Val Val
        35                  40                  45

Thr Ala Thr Gly Asn Glu Arg Ser Ser Phe Glu Ala Pro Met Met Val
    50                  55                  60

Thr Val Val Glu Ala Asp Thr Pro Thr Ser Glu Thr Ala Thr Ser Ala
65                  70                  75                  80

Thr Asp Met Leu Arg Asn Ile Pro Gly Leu Thr Val Thr Gly Ser Gly
                85                  90                  95

Arg Val Asn Gly Gln Asp Val Thr Leu Arg Gly Tyr Gly Lys Gln Gly
            100                 105                 110

Val Leu Thr Leu Val Asp Gly Ile Arg Gln Gly Thr Asp Thr Gly His
        115                 120                 125

Leu Asn Ser Thr Phe Leu Asp Pro Ala Leu Val Lys Arg Val Glu Ile
    130                 135                 140

Val Arg Gly Pro Ser Ala Leu Leu Tyr Gly Ser Gly Ala Leu Gly Gly
145                 150                 155                 160

Val Ile Ser Tyr Glu Thr Val Asp Ala Ala Asp Leu Leu Pro Gly
                165                 170                 175

Gln Asn Ser Gly Tyr Arg Val Tyr Ser Ala Ala Thr Gly Asp His
            180                 185                 190

Ser Phe Gly Leu Gly Ala Ser Ala Phe Gly Arg Thr Asp Asp Val Asp
        195                 200                 205

Gly Ile Leu Ser Phe Gly Thr Arg Asp Ile Gly Asn Ile Arg Gln Ser
    210                 215                 220

Asp Gly Phe Asn Ala Pro Asn Asp Glu Thr Ile Ser Asn Val Leu Ala
225                 230                 235                 240

Lys Gly Thr Trp Arg Ile Asp Gln Ile Gln Ser Leu Ser Ala Asn Leu
                245                 250                 255

Arg Tyr Tyr Asn Asn Ser Ala Leu Glu Pro Lys Asn Pro Gln Thr Ser
            260                 265                 270

Ala Ala Ser Ser Thr Asn Leu Met Thr Asp Arg Ser Thr Ile Gln Arg
        275                 280                 285

Asp Ala Gln Leu Lys Tyr Asn Ile Lys Pro Leu Asp Gln Glu Trp Leu
    290                 295                 300

Asn Ala Thr Ala Gln Val Tyr Tyr Ser Glu Val Glu Ile Asn Ala Arg
305                 310                 315                 320

Pro Gln Gly Thr Pro Glu Glu Gly Arg Lys Gln Thr Thr Lys Gly Gly
                325                 330                 335

Lys Leu Glu Asn Arg Thr Arg Leu Phe Thr Asp Ser Phe Ala Ser His
            340                 345                 350

Leu Leu Thr Tyr Gly Thr Glu Ala Tyr Lys Gln Glu Gln Thr Pro Ser
        355                 360                 365

Gly Ala Thr Glu Ser Phe Pro Gln Ala Asp Ile Arg Phe Gly Ser Gly
    370                 375                 380

Trp Leu Gln Asp Glu Ile Thr Leu Arg Asp Leu Pro Val Ser Ile Leu
385                 390                 395                 400

Ala Gly Thr Arg Tyr Asp Asn Tyr Arg Gly Ser Ser Glu Gly Tyr Ala
                405                 410                 415
```

-continued

```
Asp Val Asp Ala Asp Lys Trp Ser Ser Arg Gly Ala Val Ser Val Thr
            420                 425                 430

Pro Thr Asp Trp Leu Met Leu Phe Gly Ser Tyr Ala Gln Ala Phe Arg
        435                 440                 445

Ala Pro Thr Met Gly Glu Met Tyr Asn Asp Ser Lys His Phe Ser Met
    450                 455                 460

Asn Ile Trp Val Thr Pro Asp Gln Leu Leu Gly Thr Asn Pro Asn Leu
465                 470                 475                 480

Lys Pro Glu Thr Asn Glu Thr Gln Glu Tyr Gly Phe Gly Leu Arg Phe
                485                 490                 495

Asn Asp Leu Met Met Ala Glu Asp Asp Leu Gln Phe Lys Ala Ser Tyr
            500                 505                 510

Phe Asp Thr Asn Ala Lys Asp Tyr Ile Ser Thr Gly Val Thr Met Asp
        515                 520                 525

Phe Gly Phe Gly Pro Gly Gly Leu Tyr Cys Lys Asn Cys Ser Thr Tyr
    530                 535                 540

Ser Thr Asn Ile Asp Arg Ala Lys Ile Trp Gly Trp Asp Ala Thr Met
545                 550                 555                 560

Thr Tyr Gln Thr Gln Trp Phe Asn Leu Gly Leu Ala Tyr Asn Arg Thr
                565                 570                 575

Arg Gly Lys Asn Gln Asn Thr Asn Glu Trp Leu Asp Thr Ile Asn Pro
            580                 585                 590

Asp Thr Val Thr Ser Thr Leu Asp Val Pro Val Ala Asn Ser Gly Phe
        595                 600                 605

Ala Val Gly Trp Ile Gly Thr Phe Ala Asp Arg Ser Ser Arg Val Ser
    610                 615                 620

Ser Ser Gly Thr Pro Gln Ala Gly Tyr Gly Val Asn Asp Phe Tyr Val
625                 630                 635                 640

Ser Tyr Lys Gly Gln Glu Gln Phe Lys Gly Met Thr Thr Thr Val Val
                645                 650                 655

Leu Gly Asn Ala Phe Asp Lys Gly Tyr Tyr Gly Pro Gln Gly Val Pro
            660                 665                 670

Gln Asp Gly Arg Asn Ala Lys Phe Phe Val Ser Tyr Gln Trp
        675                 680                 685

<210> SEQ ID NO 3
<211> LENGTH: 758
<212> TYPE: PRT
<213> ORGANISM: Yersinia enterocolitica

<400> SEQUENCE: 3

Met Asn Gln Thr Ile Ser Ser Arg Ala Pro Gln Lys Arg Leu Ala Pro
1               5                   10                  15

Arg Leu Leu Cys Val Met Ile Gly Ala Ala Leu Gly Thr Leu Ser Ala
            20                  25                  30

Ser Ser Trp Ala Ala Ala Ala Thr Asp Ser Thr Ala Glu Asn Ala Lys
        35                  40                  45

Lys Thr Ser Ala Thr Ala Ala Thr Ala Lys Ala Glu Asp Ser Lys Thr
    50                  55                  60

Asn Asp Thr Ile Thr Val Val Gly Ala Gln Glu Thr Phe Arg Ala Gly
65                  70                  75                  80

Gly Asn Asp Leu Ile Pro Thr Tyr Leu Asp Gly Gln Val Ala Asn Gly
                85                  90                  95

Gly Arg Ile Gly Phe Leu Gly Gln Gln Asp Ala Arg Asn Val Pro Phe
            100                 105                 110
```

```
Asn Val Ile Gly Tyr Thr Ser Lys Met Ile Glu Asp Gln Gln Ala Asn
            115                 120                 125

Ser Ile Ala Asp Val Val Lys Asn Asp Ala Ser Val Gln Asn Val Arg
        130                 135                 140

Gly Tyr Gly Asn Pro Ser Gln Asn Tyr Arg Ile Arg Gly Tyr Asn Leu
145                 150                 155                 160

Asp Gly Asp Ile Ser Phe Gly Gly Leu Phe Gly Val Leu Pro Arg
                165                 170                 175

Gln Ile Val Ser Thr Ser Met Val Glu Arg Val Glu Val Phe Lys Gly
                180                 185                 190

Ala Asn Ala Phe Ile Asn Gly Ile Ser Pro Ser Gly Ser Gly Val Gly
            195                 200                 205

Gly Met Ile Asn Leu Glu Pro Lys Arg Ala Gly Asp Thr Pro Leu Thr
        210                 215                 220

Arg Val Thr Val Asp Tyr Gly Ser Ala Ser Gln Val Gly Gly Ala Leu
225                 230                 235                 240

Asp Val Gly Arg Arg Tyr Gly Asp Asp Gln Phe Gly Val Arg Val
                245                 250                 255

Asn Val Leu His Arg Glu Gly Glu Ser Ala Ile His Asp Gln Lys Glu
                260                 265                 270

Arg Thr Thr Ala Val Ser Thr Gly Leu Asp Tyr Arg Gly Asp Arg Ala
        275                 280                 285

Arg Thr Ser Leu Asp Val Gly Tyr Gln Lys Gln Thr Ile His His Met
        290                 295                 300

Arg Thr Asp Val Ala Ile Gly Gly Ala Thr Val Ile Pro Glu Pro Pro
305                 310                 315                 320

Ser Ser Thr Leu Asn Tyr Gly Gln Ser Trp Val Tyr Thr Asp Met Glu
                325                 330                 335

Thr Thr Phe Gly Met Leu Arg Ser Glu Tyr Asp Val Ser Gln Asn Trp
                340                 345                 350

Thr Val Tyr Gly Ser Val Gly Ala Ser Arg Asn Glu Glu Thr Gly Gln
        355                 360                 365

Tyr Gly Ala Pro Met Leu Thr Asn Asn Gly Asp Ala Thr Ile Ser
370                 375                 380

Arg Leu Tyr Val Pro Tyr Val Ala Asp Ser Val Ala Gly Leu Gly Gly
385                 390                 395                 400

Ile Arg Gly His Phe Asp Thr Gly Pro Ile Thr His Lys Val Asn Leu
                405                 410                 415

Gly Tyr Ala Ala Asn Tyr Arg Thr Thr Lys Ser Ala Trp Asn Met Ser
                420                 425                 430

Gly Gln Glu Asp Thr Asn Ile Tyr Asn Pro Gly Val Ile Gly Phe Pro
        435                 440                 445

Gln Thr Val Met Gly Ser Asp Ser Gln Asp Pro Gln Leu Thr Ser Gln
450                 455                 460

Val Arg Ala Ser Gly Leu Ser Leu Ser Asp Thr Leu Ser Met Met Asp
465                 470                 475                 480

Asp Lys Val Ser Leu Met Leu Gly Val Arg Arg Gln Glu Val Thr Ile
                485                 490                 495

Arg Asn Phe Asp Ser Gly Val Pro Asn Ser Ala Gly Ser Leu Asp Ala
                500                 505                 510

Met Lys Val Thr Pro Ile Tyr Gly Ile Met Val Lys Pro Trp Glu Lys
                515                 520                 525
```

```
Val Ser Leu Tyr Ala Asn His Ile Glu Ala Leu Gly Pro Gly Lys Ser
            530                 535                 540

Ala Pro Tyr Gln Tyr Asn Gly Lys Pro Val Val Asn Ala Gly Gln Ile
545                 550                 555                 560

Pro Gly Ile Ile His Ser Lys Gln Asn Glu Ile Gly Val Lys Phe Asp
                565                 570                 575

Asn Gln Arg Tyr Gly Gly Thr Leu Ala Leu Phe Glu Ile Thr Arg Pro
            580                 585                 590

Thr Gly Met Val Asp Pro Ala Thr Asn Val Tyr Gly Phe Tyr Gly Glu
            595                 600                 605

Gln Arg Asn Arg Gly Ile Glu Leu Asn Val Phe Gly Glu Pro Val Phe
610                 615                 620

Gly Thr Arg Leu Leu Ala Ser Ala Thr Trp Leu Asp Pro Lys Leu Thr
625                 630                 635                 640

Lys Ala Ala Asp Ser Ala Asn Asn Gly Asn Asp Ala Val Gly Val Ala
                645                 650                 655

Asn Tyr Gln Leu Val Phe Gly Gly Glu Tyr Asp Ile Pro Val Val Glu
            660                 665                 670

Gly Leu Thr Ala Thr Gly Thr Val Val Arg Ser Gly Ser Gln Tyr Ala
675                 680                 685

Asn Glu Ala Asn Thr Leu Lys Leu Lys Pro Trp Thr Arg Leu Asp Leu
690                 695                 700

Gly Val Arg Tyr Thr Met Pro Met Lys Asp Thr Ser Leu Thr Trp Arg
705                 710                 715                 720

Ala Asn Ile Glu Asn Val Thr Asn Glu Arg Tyr Trp Glu Ser Val Glu
                725                 730                 735

Asp Ser Gly Thr Tyr Ile Tyr Gln Gly Asp Pro Arg Ala Leu Lys Leu
            740                 745                 750

Ser Val Ser Met Asp Phe
            755

<210> SEQ ID NO 4
<211> LENGTH: 710
<212> TYPE: PRT
<213> ORGANISM: Yersinia enterocolitica

<400> SEQUENCE: 4

Met Phe Ser Ala Phe Ile Ile Lys Arg Ser Ala Ile Leu Cys Ser Leu
1               5                   10                  15

Ala Met Phe Ile Pro Leu Ala Ser Ile Ala Asp Asp Thr Ile Glu Val
            20                  25                  30

Thr Ala Lys Ala Gly His Glu Ala Asp Leu Pro Thr Ser Gly Tyr Thr
            35                  40                  45

Ala Thr Thr Thr Lys Gly Ala Thr Lys Thr Asp Gln Pro Leu Ile Leu
50                  55                  60

Thr Ala Gln Ser Val Ser Val Val Thr Arg Gln Gln Met Asp Asp Gln
65                  70                  75                  80

Asn Val Ala Thr Val Asn Gln Ala Leu Asn Tyr Thr Pro Gly Val Phe
                85                  90                  95

Thr Gly Phe Ser Gly Gly Ala Thr Arg Tyr Asp Thr Val Ala Leu Arg
            100                 105                 110

Gly Phe His Gly Gly Asp Val Asn Asn Thr Phe Leu Asp Gly Leu Arg
            115                 120                 125

Leu Leu Ser Asp Gly Gly Ser Tyr Asn Val Leu Gln Val Asp Pro Trp
130                 135                 140
```

```
Phe Leu Glu Arg Ile Asp Val Ile Lys Gly Pro Ser Ala Leu Tyr
145                 150                 155                 160

Gly Gln Ser Ile Pro Gly Gly Val Val Met Met Thr Ser Lys Arg Pro
            165                 170                 175

Gln Phe Thr Ser Glu Gly His Phe Arg Leu Thr Ala Gly Asn Asn Asn
            180                 185                 190

Thr Gln Val Ala Ala Phe Asp Tyr Thr Asp Ala Ile Ser Glu His Trp
            195                 200                 205

Ala Phe Arg Leu Thr Gly Ile Thr Arg Asn Ser Asp Thr Met Tyr Asp
210                 215                 220

His Gln Arg Glu Glu Arg Tyr Ala Ile Ala Pro Ser Leu Leu Trp Gln
225                 230                 235                 240

Pro Asp Glu Asn Thr Ser Leu Leu Arg Ala Asn Leu Gln Lys Asp
            245                 250                 255

Pro Ser Gly Gly Tyr His Ser Ala Val Pro Ala Asp Gly Ser Ile Tyr
            260                 265                 270

Gly Gln Lys Leu Ser Arg Gly Phe Phe Asp Gly Glu Ser Asn His Asn
            275                 280                 285

Val Phe Lys Arg Trp Gln Gln Ile Tyr Ser Tyr Glu Phe Ser His Lys
290                 295                 300

Phe Asp Asp Val Trp Ser Phe Arg Gln Asn Ala Ser Tyr Thr His Ser
305                 310                 315                 320

Asn Thr Gln Leu Glu Gln Val Tyr Gln Gly Gly Trp Asn Ser Asp Arg
            325                 330                 335

Thr Leu Met Asn Arg Tyr Tyr Ser Gly Glu Asp Ser Ser Leu Asn Ala
            340                 345                 350

Phe Ala Val Asp Asn Gln Leu Glu Ala Asp Leu Arg Thr Ala Ala Val
            355                 360                 365

Lys His Lys Val Leu Leu Gly Val Asp Phe Gln Lys Phe Arg Asn Asn
370                 375                 380

Leu Arg Ser Asp Ser Ala Tyr Ala Thr Pro Leu Asn Pro Tyr Thr Gly
385                 390                 395                 400

Val Ser Gly Gly Ser Thr Leu Tyr Ser Asp Tyr Leu Leu Thr Thr Pro
            405                 410                 415

Gly Ile Asn Thr Ser Tyr Leu Ser Arg Arg Tyr Glu Gln Ser Gly Val
            420                 425                 430

Tyr Leu Gln Asp Glu Met Thr Leu Asp Asn Trp His Leu Asn Leu Ser
            435                 440                 445

Gly Arg Tyr Asp Arg Met Lys Thr Glu Asn Ile Asn Asn Thr Ala Asn
            450                 455                 460

Ser Thr Asp Glu Arg Thr Asp Asn His Ala Ser Gly Arg Ala Ser Leu
465                 470                 475                 480

Leu Tyr Ser Phe Asp Ser Gly Ile Ser Pro Tyr Val Ser Tyr Ser Gln
            485                 490                 495

Ala Ile Thr Pro Ser Leu Phe Pro Asp Ala Gln Gln Lys Leu Leu Lys
            500                 505                 510

Pro Met Thr Ser Glu Gln Tyr Glu Val Gly Ile Ile Tyr Gln Pro Pro
            515                 520                 525

Gly Ser Thr Ser Leu Tyr Ser Ala Ala Leu Tyr Asp Leu Thr Gln Asn
            530                 535                 540

Asp Val Ala Asn Arg Ala Val Pro Ala Thr Tyr Tyr Val Pro Ala Gly
545                 550                 555                 560
```

```
Lys Val Asn Ser Gln Gly Leu Glu Leu Glu Ala Arg Ser Gln Ile Ser
                565                 570                 575

Asp Arg Leu Ser Val Ile Ala Gly Tyr Thr Tyr Asn Arg Val Lys Phe
            580                 585                 590

Lys Asp Ala Ile Asp Gly Asn Asp Gly Asn Thr Pro Val Leu Ala Pro
        595                 600                 605

Ser Asn Met Ala Ser Leu Trp Ala Gln Tyr Glu Ala Gly Tyr Gly Ile
    610                 615                 620

Asn Val Gly Ala Gly Ile Arg Tyr Ile Gly Lys Gln Trp Ala Asp Asp
625                 630                 635                 640

Ala Asn Thr Leu Arg Val Pro Ser Tyr Thr Leu Gly Asp Ala Ser Val
                645                 650                 655

Arg Ala Asp Leu Gly Thr Trp Ala Ala Ser Leu Lys Gly Ala Phe Val
            660                 665                 670

Gln Leu Asn Val Asn Asn Ile Ala Asp Lys Lys Tyr Val Ala Ala Cys
        675                 680                 685

Tyr Ser Thr Ser Tyr Cys Tyr Trp Gly Ala Glu Arg Ser Val Gln Ala
    690                 695                 700

Thr Val Gly Tyr Asp Phe
705                 710

<210> SEQ ID NO 5
<211> LENGTH: 673
<212> TYPE: PRT
<213> ORGANISM: Yersinia enterocolitica

<400> SEQUENCE: 5

Met Lys Met Thr Arg Leu Tyr Pro Leu Ala Leu Gly Gly Leu Leu Leu
1               5                   10                  15

Pro Ala Ile Ala Asn Ala Gln Thr Ser Gln Gln Asp Glu Ser Thr Leu
            20                  25                  30

Glu Val Thr Ala Ser Lys Gln Ser Ser Arg Ser Ala Ser Ala Asn Asn
        35                  40                  45

Val Ser Ser Thr Val Val Ser Ala Pro Glu Leu Ser Asp Ala Gly Val
    50                  55                  60

Thr Ala Ser Asp Lys Leu Pro Arg Val Leu Pro Gly Leu Asn Ile Glu
65                  70                  75                  80

Asn Ser Gly Asn Met Leu Phe Ser Thr Ile Ser Leu Arg Gly Val Ser
                85                  90                  95

Ser Ala Gln Asp Phe Tyr Asn Pro Ala Val Thr Leu Tyr Val Asp Gly
            100                 105                 110

Val Pro Gln Leu Ser Thr Asn Thr Ile Gln Ala Leu Thr Asp Val Gln
        115                 120                 125

Ser Val Glu Leu Leu Arg Gly Pro Gln Gly Thr Leu Tyr Gly Lys Ser
    130                 135                 140

Ala Gln Gly Gly Ile Ile Asn Ile Val Thr Gln Gln Pro Asp Ser Thr
145                 150                 155                 160

Pro Arg Gly Tyr Ile Glu Gly Gly Val Ser Ser Arg Asp Ser Tyr Arg
                165                 170                 175

Ser Lys Phe Asn Leu Ser Gly Pro Ile Gln Asp Gly Leu Leu Tyr Gly
            180                 185                 190

Ser Val Thr Leu Leu Arg Gln Val Asp Asp Gly Asp Met Ile Asn Pro
        195                 200                 205

Ala Thr Gly Ser Asp Asp Leu Gly Gly Thr Arg Ala Ser Ile Gly Asn
    210                 215                 220
```

```
Val Lys Leu Arg Leu Ala Pro Asp Asp Gln Pro Trp Glu Met Gly Phe
225                 230                 235                 240

Ala Ala Ser Arg Glu Cys Thr Arg Ala Thr Gln Asp Ala Tyr Val Gly
            245                 250                 255

Trp Asn Asp Ile Lys Gly Arg Lys Leu Ser Leu Ser Asp Gly Ser Pro
        260                 265                 270

Asp Pro Tyr Met Arg Arg Cys Thr Asp Ser Gln Thr Leu Ser Gly Lys
    275                 280                 285

Tyr Thr Thr Asp Asp Trp Val Phe Asn Leu Ile Ser Ala Trp Gln Gln
290                 295                 300

Gln His Tyr Ser Arg Thr Phe Pro Ser Gly Ser Leu Ile Val Asn Met
305                 310                 315                 320

Pro Gln Arg Trp Asn Gln Asp Val Gln Glu Leu Arg Ala Ala Thr Leu
            325                 330                 335

Gly Asp Ala Arg Thr Val Asp Met Val Phe Gly Leu Tyr Arg Gln Asn
        340                 345                 350

Thr Arg Glu Lys Leu Asn Ser Ala Tyr Asp Met Pro Thr Met Pro Tyr
    355                 360                 365

Leu Ser Ser Thr Gly Tyr Thr Thr Ala Glu Thr Leu Ala Ala Tyr Ser
370                 375                 380

Asp Leu Thr Trp His Leu Thr Asp Arg Phe Asp Ile Gly Gly Gly Val
385                 390                 395                 400

Arg Phe Ser His Asp Lys Ser Ser Thr Gln Tyr His Gly Ser Met Leu
            405                 410                 415

Gly Asn Pro Phe Gly Asp Gln Gly Lys Ser Asn Asp Gln Val Leu
        420                 425                 430

Gly Gln Leu Ser Ala Gly Tyr Met Leu Thr Asp Trp Arg Val Tyr
    435                 440                 445

Thr Arg Ile Ala Gln Gly Tyr Lys Pro Ser Gly Tyr Asn Ile Val Pro
450                 455                 460

Thr Ala Gly Leu Asp Ala Lys Pro Phe Val Ala Glu Lys Ser Ile Asn
465                 470                 475                 480

Tyr Glu Leu Gly Thr Arg Tyr Glu Thr Ala Asp Val Thr Leu Gln Ala
            485                 490                 495

Ala Thr Phe Tyr Thr His Thr Lys Asp Met Gln Leu Tyr Ser Gly Pro
        500                 505                 510

Val Gly Met Gln Thr Leu Ser Asn Ala Gly Lys Ala Asp Ala Thr Gly
    515                 520                 525

Val Glu Leu Glu Ala Lys Trp Arg Phe Ala Pro Gly Trp Ser Trp Asp
530                 535                 540

Ile Asn Gly Asn Val Ile Arg Ser Glu Phe Thr Asn Asp Ser Glu Leu
545                 550                 555                 560

Tyr His Gly Asn Arg Val Pro Phe Val Pro Arg Tyr Gly Ala Gly Ser
            565                 570                 575

Ser Val Asn Gly Val Ile Asp Thr Arg Tyr Gly Ala Leu Met Pro Arg
        580                 585                 590

Leu Ala Val Asn Leu Val Gly Pro His Tyr Phe Asp Gly Asp Asn Gln
    595                 600                 605

Leu Arg Gln Gly Thr Tyr Ala Thr Leu Asp Ser Ser Leu Gly Trp Gln
610                 615                 620

Ala Thr Glu Arg Ile Asn Ile Ser Val His Val Asp Asn Leu Phe Asp
625                 630                 635                 640
```

```
Arg Arg Tyr Arg Thr Tyr Gly Tyr Met Asn Gly Ser Ser Ala Val Ala
            645                 650                 655

Gln Val Asn Met Gly Arg Thr Val Gly Ile Asn Thr Arg Ile Asp Phe
            660                 665                 670

Phe

<210> SEQ ID NO 6
<211> LENGTH: 623
<212> TYPE: PRT
<213> ORGANISM: Yersinia bercovieri

<400> SEQUENCE: 6

Met Val Thr Ala Ser Gly Phe Gln Gln Arg Ile Gln Asp Ser Ala Ala
1               5                   10                  15

Ser Ile Ser Val Val Thr Arg Glu Gln Ile Glu Asn Lys Ala Tyr Thr
            20                  25                  30

Asp Ile Thr Asp Ala Leu Lys Asp Val Pro Gly Val Val Thr Gly
            35                  40                  45

Gly Gly Ser His Ser Asp Ile Ser Ile Arg Gly Met Ala Ala Lys Tyr
        50                  55                  60

Thr Leu Ile Leu Val Asp Gly Lys Arg Val Asp Thr Arg Gly Thr Arg
65                  70                  75                  80

Pro Asn Ser Asp Gly Ser Gly Ile Glu Gln Gly Trp Leu Pro Pro Leu
                85                  90                  95

Ala Ala Ile Glu Arg Ile Glu Val Val Arg Gly Pro Met Ser Ser Leu
            100                 105                 110

Tyr Gly Ser Asp Ala Met Gly Gly Val Ile Asn Val Ile Thr Arg Lys
            115                 120                 125

Val Gly Lys Glu Trp His Gly Thr Val Arg Ala Asp Ala Thr Leu Gln
    130                 135                 140

Glu Asp Ser Lys Ser Gly Asp Ile Phe Gln Thr Asn Ala Tyr Ala Ser
145                 150                 155                 160

Gly Pro Leu Ile Asp Gly Leu Leu Gly Leu Lys Val Ser Gly Leu Leu
                165                 170                 175

Ser His Arg Ser Glu Asp Lys Ile Val Asp Gly Tyr Asn Glu Gln Arg
            180                 185                 190

Leu Arg Asn Gly Ala Ala Thr Phe Thr Leu Thr Pro Asp Asp Lys Asn
            195                 200                 205

Glu Phe Asp Phe Asp Ile Gly His Tyr Val Gln Asp Arg Asn Ser Thr
    210                 215                 220

Ala Gly Arg Ser Val Ala Leu Asn Gly Lys Ser Ser Asp Val Gln Tyr
225                 230                 235                 240

Asp Arg Asn Asn Tyr Ala Ile Thr His His Gly Tyr Tyr Asp Phe Gly
                245                 250                 255

Asn Ser Thr Ser Tyr Val Gln Arg Asp Glu Thr Arg Asn Pro Ser Arg
            260                 265                 270

Glu Met Lys Ser Val Asp Asn Ile Phe Asn Thr Gln Thr Ser Phe Leu
    275                 280                 285

Leu Asp Asn His Thr Leu Ile Leu Gly Gly Gln Tyr Arg Tyr Glu Glu
    290                 295                 300

Leu Asn Asp Thr Gly Asn Gln Leu Ala Ser Ala Lys Asp Leu Thr Lys
305                 310                 315                 320

Leu Thr Arg Trp Ser Trp Ala Leu Phe Ala Glu Asp Glu Trp Gln Met
                325                 330                 335
```

-continued

```
Thr Asn Asp Phe Ala Leu Thr Gly Gly Val Arg Met Asp Gln Asp Glu
            340                 345                 350

Asn Tyr Gly Thr His Trp Thr Pro Arg Leu Tyr Gly Val Trp His Leu
        355                 360                 365

Ala Glu Gln Trp Thr Leu Lys Gly Gly Val Ser Gly Gly Tyr Arg Ser
    370                 375                 380

Pro Asp Leu Arg Gln Ala Thr Glu Asn Trp Gly Gln Ile Thr Gly Gly
385                 390                 395                 400

Arg Gly Asp Pro Ala Ile Ile Ile Gly Asn Ala Asn Leu Lys Pro Glu
                405                 410                 415

Arg Ser Ile Ser Gln Glu Ile Gly Ile Leu Trp Asp Asp Gln Glu Gly
            420                 425                 430

Met Asn Ala Gly Val Thr Leu Phe Asn Thr Asp Phe Lys Asp Lys Ile
        435                 440                 445

Thr Glu Val Arg Arg Cys Thr Asp Thr Thr Gly Lys Ala Ser Gly Gln
    450                 455                 460

Cys Met Ile Asn Gly Ala Ser Tyr Lys Phe Ile Ser Asp Arg Thr Asn
465                 470                 475                 480

Val Asp Lys Ala Ile Thr Arg Gly Val Glu Ala Thr Phe Gly Trp Asp
                485                 490                 495

Ile Asn Gln Glu Trp Ser Leu Thr Ser Asn Tyr Thr Phe Thr Gln Ser
            500                 505                 510

Glu Gln Lys Ser Gly Gln Phe Ala Gly Gln Pro Leu Asn Gln Met Pro
        515                 520                 525

Lys His Met Leu Asn Gly Thr Leu Asn Trp Gln Ala Ser Glu Ala Leu
    530                 535                 540

Ala Thr Trp Val Arg Ala Asn Tyr Arg Gly Lys Thr Ser Glu Tyr Leu
545                 550                 555                 560

Asn Arg Thr Ser Ile Gly Gly Ser Thr Pro Ser Tyr Thr Phe Val Asp
                565                 570                 575

Leu Gly Ala Asn Tyr Gln Leu Thr Lys Glu Phe Arg Leu Met Gly Gly
            580                 585                 590

Val Tyr Asn Val Leu Asp Lys Arg Val Asp Ile Glu Val Asn Asp Lys
        595                 600                 605

Val Leu Asp Gly Arg Arg Tyr Met Val Gly Ala Ser Tyr Asp Phe
    610                 615                 620

<210> SEQ ID NO 7
<211> LENGTH: 422
<212> TYPE: PRT
<213> ORGANISM: Yersinia enterocolitica

<400> SEQUENCE: 7

Met Thr Lys Asp Phe Lys Ile Ser Val Ser Ala Ala Leu Ile Ser Ala
1               5                   10                  15

Leu Phe Ser Ser Pro Tyr Ala Phe Ala Asn Asn Asp Glu Val His Phe
            20                  25                  30

Thr Ala Val Gln Ile Ser Pro Asn Ser Asp Pro Asp Ser His Val Met
        35                  40                  45

Ile Phe Gln Pro Glu Val Arg Ala Pro Gly Gly Thr Asn Ala Leu Ala
    50                  55                  60

Lys Gly Thr His Ser Ile Ala Val Gly Ala Ser Ala Glu Ala Ala Glu
65                  70                  75                  80

Arg Ala Ala Val Ala Val Gly Ala Gly Ser Ile Ala Thr Gly Val Asn
                85                  90                  95
```

Ser Val Ala Ile Gly Pro Leu Ser Lys Ala Leu Gly Asp Ser Ala Val
                100                 105                 110

Thr Tyr Gly Ala Gly Ser Thr Ala Gln Lys Asp Gly Val Ala Ile Gly
            115                 120                 125

Ala Arg Ala Ser Thr Ser Asp Thr Gly Val Ala Val Gly Phe Asn Ser
130                 135                 140

Lys Val Asp Ala Lys Asn Ser Val Ser Ile Gly His Ser Ser His Val
145                 150                 155                 160

Ala Val Asp His Asp Tyr Ser Ile Ala Ile Gly Asp Arg Ser Lys Thr
                165                 170                 175

Asp Arg Lys Asn Ser Val Ser Ile Gly His Glu Ser Leu Asn Arg Gln
            180                 185                 190

Leu Thr His Leu Ala Ala Gly Thr Lys Asp Thr Asp Ala Val Asn Val
        195                 200                 205

Ala Gln Leu Lys Lys Glu Ile Glu Lys Thr Gln Glu Asn Ala Asn Lys
210                 215                 220

Lys Ser Ala Glu Val Leu Gly Ile Ala Asn Asn Tyr Thr Asp Ser Lys
225                 230                 235                 240

Ser Ala Glu Thr Leu Glu Asn Ala Arg Lys Glu Ala Phe Asp Leu Ser
                245                 250                 255

Asn Asp Ala Leu Asp Met Ala Lys Lys His Ser Asn Ser Val Ala Arg
            260                 265                 270

Thr Thr Leu Glu Thr Ala Glu Glu His Thr Asn Lys Lys Ser Ala Glu
        275                 280                 285

Thr Leu Ala Ser Ala Asn Val Tyr Ala Asp Ser Lys Ser Ser His Thr
290                 295                 300

Leu Lys Thr Ala Asn Ser Tyr Thr Asp Val Thr Val Ser Asn Ser Thr
305                 310                 315                 320

Lys Lys Ala Ile Arg Glu Ser Asn Gln Tyr Thr Asp His Lys Phe His
                325                 330                 335

Gln Leu Asp Asn Arg Leu Asp Lys Leu Asp Thr Arg Val Asp Lys Gly
            340                 345                 350

Leu Ala Ser Ser Ala Ala Leu Asn Ser Leu Phe Gln Pro Tyr Gly Val
        355                 360                 365

Gly Lys Val Asn Phe Thr Ala Gly Val Gly Gly Tyr Arg Ser Ser Gln
370                 375                 380

Ala Leu Ala Ile Gly Ser Gly Tyr Arg Val Asn Glu Ser Val Ala Leu
385                 390                 395                 400

Lys Ala Gly Val Ala Tyr Ala Gly Ser Ser Asp Val Met Tyr Asn Ala
                405                 410                 415

Ser Phe Asn Ile Glu Trp
            420

<210> SEQ ID NO 8
<211> LENGTH: 366
<212> TYPE: PRT
<213> ORGANISM: Yersinia bercovieri

<400> SEQUENCE: 8

Met Lys Leu Arg Val Leu Ser Leu Leu Val Pro Ala Leu Leu Val Ala
1               5                   10                  15

Gly Ser Ala Gly Ala Ala Glu Ile Tyr His Lys Asp Gly Asn Lys Leu
            20                  25                  30

Asp Leu Tyr Gly Lys Val Asp Gly Leu His Tyr Phe Ser Asp Asp Lys

```
        35                  40                  45

Ser Lys Asp Gly Asp Gln Ser Tyr Met Arg Phe Gly Leu Lys Gly Glu
    50                  55                  60

Thr Gln Ile Ser Asp Gln Leu Thr Gly Tyr Gly Gln Trp Glu Tyr Gln
65                  70                  75                  80

Ala Asn Leu Asn Lys Ala Glu Asp Gln Asp Gln Gly Asn Phe Thr Arg
                85                  90                  95

Leu Gly Phe Ala Gly Leu Lys Phe Ala Asp Tyr Gly Ser Leu Asp Tyr
            100                 105                 110

Gly Arg Asn Tyr Gly Val Leu Tyr Asp Val Thr Ser Trp Thr Asp Val
        115                 120                 125

Leu Pro Glu Phe Gly Gly Asp Thr Tyr Gly Ala Asp Asn Phe Met Ser
    130                 135                 140

Gln Arg Ala Asn Gly Leu Ala Thr Tyr Arg Asn Thr Asn Phe Phe Gly
145                 150                 155                 160

Leu Val Asp Gly Leu Asn Phe Ala Leu Gln Tyr Gln Gly Lys Asn Gly
                165                 170                 175

Ser Pro Thr Glu Ser Asn Asn Gly Arg Asp Val Lys Gly Gln Asn Gly
            180                 185                 190

Asp Gly Tyr Gly Met Ser Leu Ser Tyr Asp Leu Gly Trp Gly Val Ser
        195                 200                 205

Ala Ala Ala Ala Met Ser Ser Ser Lys Arg Thr Thr Glu Gln Asn Gln
    210                 215                 220

Leu Leu Phe Gly Asn Gly Asp Arg Ala Asp Ala Tyr Ser Gly Gly Leu
225                 230                 235                 240

Lys Tyr Asp Ala Asn Asn Val Tyr Leu Ala Ala Thr Tyr Ala Gln Thr
                245                 250                 255

Tyr Asn Leu Thr Arg Phe Gly Asn Phe Gln Asn Asn Asn Ser Gly Phe
            260                 265                 270

Ala Asn Lys Ala Gln Asn Ile Glu Leu Val Ala Gln Tyr Gln Phe Asp
        275                 280                 285

Phe Gly Leu Arg Pro Ser Val Ala Tyr Leu Gln Ser Lys Gly Lys Asp
    290                 295                 300

Leu Gly Asn Gly Tyr Gly Asp Gln Asp Leu Val Gln Tyr Val Asp Val
305                 310                 315                 320

Gly Ala Thr Tyr Phe Phe Asn Lys Asn Met Ser Thr Tyr Val Asp Tyr
                325                 330                 335

Lys Ile Asn Leu Leu Asp Glu Asn Glu Phe Thr Lys Asn Ala Gly Ile
            340                 345                 350

Asn Thr Asp Asp Ile Val Ala Val Gly Leu Val Tyr Gln Phe
        355                 360                 365

<210> SEQ ID NO 9
<211> LENGTH: 245
<212> TYPE: PRT
<213> ORGANISM: Yersinia enterocolitica

<400> SEQUENCE: 9

Met Lys Lys Asn Met Lys Leu Ile Ala Ile Thr Ala Val Leu Ser Ser
1               5                   10                  15

Val Leu Val Leu Ser Gly Cys Gly Ala Met Ser Thr Ala Ile Lys Lys
            20                  25                  30

Arg Asn Leu Glu Val Lys Thr Gln Met Ser Glu Thr Ile Trp Leu Glu
        35                  40                  45
```

```
Pro Ser Ser Gln Lys Thr Val Tyr Leu Gln Ile Lys Asn Thr Ser Asp
    50                  55                  60

Lys Asn Met Leu Gly Leu Ala Pro Lys Ile Thr Lys Ala Val Gln Asp
65                  70                  75                  80

Lys Gly Tyr Thr Val Thr Ser Ser Pro Glu Asp Ala His Tyr Trp Ile
                85                  90                  95

Gln Ala Asn Val Leu Lys Ala Asp Lys Met Asp Leu Arg Glu Ala Glu
            100                 105                 110

Gly Phe Leu Ser Gln Gly Tyr Gln Gly Ala Ala Leu Gly Ala Ala Leu
        115                 120                 125

Gly Ala Gly Ile Thr Gly Tyr Asn Ser Asn Ser Ala Gly Ala Ser Leu
    130                 135                 140

Gly Val Gly Leu Ala Ala Gly Leu Val Gly Met Val Ala Asp Ala Met
145                 150                 155                 160

Val Glu Asp Ile Asn Tyr Thr Met Val Thr Asp Val Gln Ile Ser Glu
                165                 170                 175

Lys Thr Asp Thr Pro Leu Gln Thr Asp Asn Val Ala Ala Leu Lys Gln
            180                 185                 190

Gly Thr Ser Gly Tyr Lys Val Gln Thr Ser Thr Gln Thr Gly Asn Lys
        195                 200                 205

His Gln Tyr Gln Thr Arg Val Val Ser Ser Ala Asn Lys Val Asn Leu
    210                 215                 220

Lys Phe Glu Glu Ala Gln Pro Val Leu Glu Asp Gln Leu Ala Lys Ser
225                 230                 235                 240

Ile Ala Asn Ile Leu
            245

<210> SEQ ID NO 10
<211> LENGTH: 891
<212> TYPE: PRT
<213> ORGANISM: Yersinia pestis

<400> SEQUENCE: 10

Met Ala Val Thr Asn Val Ala Glu Leu Asn Glu Leu Val Ala Arg Val
1               5                   10                  15

Lys Lys Ala Gln Arg Glu Tyr Ala Asn Phe Ser Gln Glu Gln Val Asp
                20                  25                  30

Lys Ile Phe Arg Ala Ala Ala Leu Ala Ala Ala Asp Ala Arg Ile Pro
            35                  40                  45

Leu Ala Lys Leu Ala Val Thr Glu Ser Gly Met Gly Ile Val Glu Asp
        50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Ile Leu Cys Glu Asp Lys Thr Phe Gly
                85                  90                  95

Thr Ile Thr Ile Ala Glu Pro Ile Gly Leu Ile Cys Gly Ile Val Pro
            100                 105                 110

Thr Thr Asn Pro Thr Ser Thr Ala Ile Phe Lys Ala Leu Ile Ser Leu
        115                 120                 125

Lys Thr Arg Asn Gly Ile Ile Phe Ser Pro His Pro Arg Ala Lys Asp
    130                 135                 140

Ala Thr Asn Lys Ala Ala Asp Ile Val Leu Gln Ala Ile Ala Ala
145                 150                 155                 160

Gly Ala Pro Ala Asp Ile Ile Gly Trp Ile Asp Ala Pro Thr Val Glu
                165                 170                 175
```

```
Leu Ser Asn Gln Leu Met His His Pro Asp Ile Asn Leu Ile Leu Ala
            180                 185                 190

Thr Gly Gly Pro Gly Met Val Lys Ala Ala Tyr Ser Ser Gly Lys Pro
            195                 200                 205

Ala Ile Gly Val Gly Ala Gly Asn Thr Pro Val Val Val Asp Glu Thr
210                 215                 220

Ala Asp Ile Lys Arg Val Val Ala Ser Ile Leu Met Ser Lys Thr Phe
225                 230                 235                 240

Asp Asn Gly Val Ile Cys Ala Ser Glu Gln Ser Ile Ile Val Val Asp
                245                 250                 255

Ser Val Tyr Asp Ala Val Arg Glu Arg Phe Ala Ser His Gly Gly Tyr
            260                 265                 270

Leu Leu Gln Gly Lys Glu Leu Lys Ala Val Gln Asp Ile Ile Leu Lys
            275                 280                 285

Asn Gly Gly Leu Asn Ala Ala Ile Val Gly Gln Pro Ala Thr Lys Ile
            290                 295                 300

Ala Glu Met Ala Gly Ile Lys Val Pro Ser Asn Thr Lys Ile Leu Ile
305                 310                 315                 320

Gly Glu Val Lys Val Val Asp Glu Ser Glu Pro Phe Ala His Glu Lys
                325                 330                 335

Leu Ser Pro Thr Leu Ala Met Tyr Arg Ala Lys Asn Phe Glu Glu Ala
            340                 345                 350

Val Glu Lys Ala Glu Lys Leu Val Glu Met Gly Gly Ile Gly His Thr
            355                 360                 365

Ser Cys Leu Tyr Thr Asp Gln Asp Asn Gln Thr Ala Arg Val Lys Tyr
            370                 375                 380

Phe Gly Asp Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Lys Thr Val Ala Lys Arg Ala
            435                 440                 445

Glu Asn Met Leu Trp His Lys Leu Pro Lys Ser Ile Tyr Phe Arg Arg
            450                 455                 460

Gly Ser Leu Pro Ile Ala Leu Glu Glu Val Ala Thr Asp Gly Ala Lys
465                 470                 475                 480

Arg Ala Phe Ile Val Thr Asp Arg Tyr Leu Phe Asn Asn Gly Tyr Ala
                485                 490                 495

Asp Gln Val Thr Ser Val Leu Lys Ser His Gly Ile Glu Thr Glu Val
            500                 505                 510

Phe Phe Glu Val Glu Ala Ala Pro Thr Leu Ser Ile Val Arg Lys Gly
            515                 520                 525

Ala Glu Gln Met Asn Ser Phe Lys Pro Asp Val Ile Ile Ala Leu Gly
            530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Leu
            580                 585                 590
```

Val Ala Ile Thr Thr Thr Ser Gly Thr Gly Ser Glu Val Thr Pro Phe
            595                 600                 605

Ala Val Val Thr Asp Asp Ala Thr Gly Gln Lys Tyr Pro Leu Ala Asp
610                 615                 620

Tyr Ala Leu Thr Pro Asp Met Ala Ile Val Asp Ala Asn Leu Val Met
625                 630                 635                 640

Asn Met Pro Lys Ser Leu Cys Ala Phe Gly Gly Leu Asp Ala Val Thr
                645                 650                 655

His Ala Leu Glu Ala Tyr Val Ser Val Leu Ala Asn Glu Tyr Ser Asp
            660                 665                 670

Gly Gln Ala Leu Gln Ala Leu Lys Leu Leu Lys Glu Phe Leu Pro Ala
        675                 680                 685

Ser Tyr Asn Glu Gly Ala Lys Asn Pro Val Ala Arg Glu Arg Val His
    690                 695                 700

Asn Ala Ala Thr Ile Ala Gly Ile Ala Phe Ala Asn Ala Phe Leu Gly
705                 710                 715                 720

Val Cys His Ser Met Ala His Lys Leu Gly Ser Glu Phe His Ile Pro
                725                 730                 735

His Gly Leu Ala Asn Ala Met Leu Ile Ser Asn Val Ile Arg Tyr Asn
            740                 745                 750

Ala Asn Asp Asn Pro Thr Lys Gln Thr Ala Phe Ser Gln Tyr Asp Arg
        755                 760                 765

Pro Gln Ala Arg Arg Arg Tyr Ala Glu Ile Ala Asp His Leu Gly Leu
    770                 775                 780

Ser Ala Pro Gly Asp Arg Thr Ala Gln Lys Ile Gln Lys Leu Leu Ala
785                 790                 795                 800

Trp Leu Asp Glu Ile Lys Ala Glu Leu Gly Ile Pro Ala Ser Ile Arg
                805                 810                 815

Glu Ala Gly Val Gln Glu Ala Asp Phe Leu Ala Lys Val Asp Lys Leu
            820                 825                 830

Ser Glu Asp Ala Phe Asp Asp Gln Cys Thr Gly Ala Asn Pro Arg Tyr
        835                 840                 845

Pro Leu Ile Ser Glu Leu Lys Gln Ile Leu Met Asp Thr Tyr Tyr Gly
    850                 855                 860

Arg Glu Tyr Val Glu Glu Phe Asp Arg Glu Glu Val Ala Ala Ala
865                 870                 875                 880

Thr Ala Pro Lys Ala Glu Lys Lys Thr Lys Lys
                885                 890

<210> SEQ ID NO 11
<211> LENGTH: 702
<212> TYPE: PRT
<213> ORGANISM: Yersinia pseudotuberculosis

<400> SEQUENCE: 11

Met Ala Arg Lys Thr Pro Ile Glu Arg Tyr Arg Asn Ile Gly Ile Ser
1               5                   10                  15

Ala His Ile Asp Ala Gly Lys Thr Thr Thr Glu Arg Ile Leu Phe
            20                  25                  30

Tyr Thr Gly Val Asn His Lys Ile Gly Glu Val His Asp Gly Ala Ala
        35                  40                  45

Thr Met Asp Trp Met Glu Gln Glu Gln Glu Arg Gly Ile Thr Ile Thr
    50                  55                  60

Ser Ala Ala Thr Thr Cys Phe Trp Ser Gly Met Ala Lys Gln Phe Glu
65                  70                  75                  80

-continued

```
Pro His His Val Asn Ile Ile Asp Thr Pro Gly His Val Asp Phe Thr
                85                  90                  95
Ile Glu Val Glu Arg Ser Met Arg Val Leu Asp Gly Ala Val Met Val
            100                 105                 110
Tyr Cys Ala Val Gly Gly Val Gln Pro Gln Ser Glu Thr Val Trp Arg
        115                 120                 125
Gln Ala Asn Lys Tyr Lys Val Pro Arg Ile Ala Phe Val Asn Lys Met
    130                 135                 140
Asp Arg Met Gly Ala Asn Phe Leu Arg Val Val Gly Gln Leu Lys Ser
145                 150                 155                 160
Arg Leu Gly Ala Asn Pro Val Pro Leu Gln Leu Ala Ile Gly Ala Glu
                165                 170                 175
Glu Lys Phe Thr Gly Ile Ile Asp Leu Val Lys Met Lys Ala Ile Asn
            180                 185                 190
Trp Asn Glu Ala Asp Gln Gly Val Thr Phe Glu Tyr Glu Glu Ile Pro
        195                 200                 205
Ala Asp Met Ala Glu Leu Ala Ala Glu Trp His Gln Asn Leu Val Glu
    210                 215                 220
Ser Ala Glu Ala Ser Asp Glu Leu Met Asp Lys Tyr Leu Gly Gly
225                 230                 235                 240
Glu Glu Leu Thr Glu Glu Ile Lys Lys Ala Leu Arg Gln Arg Val
                245                 250                 255
Leu Lys Ser Glu Ile Ile Leu Val Thr Cys Gly Ser Ala Phe Lys Asn
            260                 265                 270
Lys Gly Val Gln Ala Met Leu Asp Ala Val Ile Glu Tyr Leu Pro Ala
        275                 280                 285
Pro Thr Asp Val Glu Ser Ile Asn Gly Ile Leu Asp Asp Gly Lys Asp
    290                 295                 300
Thr Pro Ala Val Arg His Ser Asp Asp Lys Glu Pro Phe Ser Ala Leu
305                 310                 315                 320
Ala Phe Lys Ile Ala Thr Asp Pro Phe Val Gly Asn Leu Thr Phe Phe
                325                 330                 335
Arg Val Tyr Ser Gly Ile Val Asn Ser Gly Asp Thr Val Leu Asn Ser
            340                 345                 350
Val Lys Ser Gln Arg Glu Arg Leu Gly Arg Ile Val Gln Met His Ala
        355                 360                 365
Asn Lys Arg Glu Glu Ile Lys Glu Val His Ala Gly Asp Ile Ala Ala
    370                 375                 380
Ala Ile Gly Leu Lys Asp Val Thr Thr Gly Asp Thr Leu Cys Asp Pro
385                 390                 395                 400
Asn Asn Pro Ile Ile Leu Glu Arg Met Glu Phe Pro Glu Pro Val Ile
                405                 410                 415
Ser Val Ala Val Glu Pro Lys Thr Lys Ala Asp Gln Glu Lys Met Gly
            420                 425                 430
Met Ala Leu Gly Arg Leu Ala Lys Glu Asp Pro Ser Phe Arg Val Trp
        435                 440                 445
Thr Asp Glu Glu Ser Gly Gln Thr Ile Ile Ala Gly Met Gly Glu Leu
    450                 455                 460
His Leu Asp Ile Leu Val Asp Arg Met Arg Arg Glu Phe Asn Val Glu
465                 470                 475                 480
Ala Asn Val Gly Lys Pro Gln Val Ala Tyr Arg Glu Thr Ile Arg Glu
                485                 490                 495
```

```
Thr Val Lys Asp Val Glu Gly Lys His Ala Lys Gln Ser Gly Gly Arg
            500                 505                 510

Gly Gln Tyr Gly His Val Val Ile Asp Met Ser Pro Leu Pro Pro Gly
        515                 520                 525

Gly Val Gly Tyr Glu Phe Val Asn Glu Ile Val Gly Gly Ser Ile Pro
    530                 535                 540

Lys Glu Phe Ile Pro Ala Val Asp Lys Gly Ile Gln Glu Gln Leu Lys
545                 550                 555                 560

Ser Gly Pro Leu Ala Gly Tyr Pro Val Val Asp Val Lys Val Arg Leu
                565                 570                 575

His Tyr Gly Ser Tyr His Asp Val Asp Ser Ser Glu Leu Ala Phe Lys
            580                 585                 590

Leu Ala Gly Ser Ile Ala Phe Lys Glu Gly Phe Lys Arg Ala Lys Pro
        595                 600                 605

Val Leu Leu Glu Pro Ile Met Lys Val Glu Val Glu Thr Pro Glu Asp
    610                 615                 620

Tyr Met Gly Asp Val Met Gly Asp Leu Asn Arg Arg Arg Gly Ile Ile
625                 630                 635                 640

Glu Gly Met Glu Asp Thr Ala Thr Gly Lys Thr Val Arg Val Lys Val
                645                 650                 655

Pro Leu Ser Glu Met Phe Gly Tyr Ala Thr Asp Leu Arg Ser Gln Thr
            660                 665                 670

Gln Gly Arg Ala Ser Tyr Ser Met Glu Phe Leu Glu Tyr Ala Glu Ala
        675                 680                 685

Pro Ser Asn Val Ala Lys Ala Val Ile Glu Ala Arg Gly Lys
    690                 695                 700

<210> SEQ ID NO 12
<211> LENGTH: 815
<212> TYPE: PRT
<213> ORGANISM: Yersinia pestis

<400> SEQUENCE: 12

Met Thr Ser Pro Phe Ser Tyr Thr Ser Pro Val Val Ser Val Asp Ala
1               5                   10                  15

Leu Lys His Ser Ile Ala Tyr Lys Leu Met Phe Ile Ile Gly Lys Asp
            20                  25                  30

Pro Thr Ile Ala Thr Gln His Asp Trp Leu Asn Ala Thr Leu Phe Ala
        35                  40                  45

Val Arg Asp Arg Met Val Glu Arg Trp Leu Arg Ser Asn Arg Ala Gln
    50                  55                  60

Leu Ser Gln Asp Val Arg Gln Val Tyr Tyr Leu Ser Met Glu Phe Leu
65                  70                  75                  80

Leu Gly Arg Thr Leu Ser Asn Ala Leu Leu Ser Met Gly Ile Tyr Asp
                85                  90                  95

Glu Ile Glu Gln Ala Leu Asp Glu Met Gly Leu Ser Leu Ser Glu Leu
            100                 105                 110

Leu Lys Glu Glu Asn Asp Pro Gly Leu Gly Asn Gly Gly Leu Gly Arg
        115                 120                 125

Leu Ala Ala Cys Phe Leu Asp Ser Leu Ala Thr Leu Ala Leu Pro Gly
    130                 135                 140

Arg Gly Tyr Gly Ile Arg Tyr Glu Tyr Gly Met Phe Ser Gln Lys Ile
145                 150                 155                 160

Val Asn Gly Gln Gln Met Glu Ser Pro Asp Asn Trp Leu Glu Tyr Gly
                165                 170                 175
```

```
Asn Ala Trp Glu Phe Pro Arg His Asn Thr Arg Tyr Lys Val Arg Phe
            180                 185                 190

Gly Gly Arg Ile Gln Gln Gly Ser Lys Ile Arg Trp Leu Glu Thr
        195                 200                 205

Glu Glu Ile Leu Ala Cys Ala Tyr Asp Gln Ile Pro Gly Phe Asp
    210                 215                 220

Thr Asp Ala Thr Asn Thr Leu Arg Leu Trp Ser Ala Gln Ala Ser Asn
225                 230                 235                 240

Glu Ile Asn Leu Gly Lys Phe Asn Gln Gly Asp Tyr Phe Ala Ala Val
                245                 250                 255

Glu Asp Lys Asn His Ser Glu Asn Val Ser Arg Val Leu Tyr Pro Asp
            260                 265                 270

Asp Ser Thr Tyr Ser Gly Arg Glu Leu Arg Leu Arg Gln Glu Tyr Phe
        275                 280                 285

Leu Val Ser Ala Thr Val Gln Asp Ile Leu Asn Arg His Trp Ala Met
    290                 295                 300

His His Thr Phe Asn Asn Leu Ala Asp Lys Ile Ala Ile His Leu Asn
305                 310                 315                 320

Asp Thr His Pro Val Leu Ser Ile Pro Glu Met Met Arg Leu Leu Ile
                325                 330                 335

Asp Glu His Lys Phe Thr Trp Met Asp Ala Trp Asp Val Val Gln Gln
            340                 345                 350

Val Phe Ser Tyr Thr Asn His Thr Leu Met Ser Glu Ala Leu Glu Thr
        355                 360                 365

Trp Pro Val Asp Met Ile Gly Lys Ile Leu Pro Arg His Leu Gln Ile
    370                 375                 380

Ile Phe Asp Ile Asn Asp His Phe Leu Lys Leu Val Glu Glu Gln Tyr
385                 390                 395                 400

Pro Asp Asp Lys Glu Leu Leu Ser Arg Val Ser Val Ile Asp Glu Asn
                405                 410                 415

Asn Gly Arg Arg Ile Arg Met Ala Trp Leu Ala Val Ile Ala Ser His
            420                 425                 430

Lys Val Asn Gly Val Ser Ala Leu His Ser Glu Leu Met Val Gln Ser
        435                 440                 445

Leu Phe Ala Asp Phe Ala Arg Ile Phe Pro Asn Arg Phe Cys Asn Lys
    450                 455                 460

Thr Asn Gly Val Thr Pro Arg Arg Trp Leu Gly Leu Ala Asn Arg Pro
465                 470                 475                 480

Leu Ala Ala Val Leu Asp Asp Ser Ile Gly Gln Thr Trp Arg Thr Asp
                485                 490                 495

Leu Ser Gln Leu Ser Glu Leu Glu Lys Asn Leu Asp Tyr Pro Ser Phe
            500                 505                 510

Leu Leu Ala Leu Gln Lys Ala Lys Leu Glu Asn Lys Lys Arg Leu Ala
        515                 520                 525

Val Tyr Ile Ala Glu Lys Leu Asn Ile Val Val Asn Pro Ala Ala Leu
    530                 535                 540

Phe Asp Val Gln Ile Lys Arg Ile His Glu Tyr Lys Arg Gln Leu Leu
545                 550                 555                 560

Asn Val Leu His Val Ile Thr Arg Tyr Asn Arg Ile Ile Asp Ala Pro
                565                 570                 575

Asp Asn Asn Trp Val Pro Arg Val Ile Phe Ala Gly Lys Ala Ala
            580                 585                 590
```

Ser Ala Tyr Tyr Asn Ala Lys Gln Ile Ile His Leu Ile Asn Asp Val
            595                 600                 605

Ala Lys Val Ile Asn Asn Asp Pro Arg Ile Asn Asn Leu Leu Lys Val
610                 615                 620

Val Phe Ile Pro Asn Tyr Ser Val Ser Leu Ala Gln Leu Ile Ile Pro
625                 630                 635                 640

Ala Ala Asp Leu Ser Glu Gln Ile Ser Leu Ala Gly Thr Glu Ala Ser
            645                 650                 655

Gly Thr Ser Asn Met Lys Phe Ala Leu Asn Gly Ala Leu Thr Ile Gly
            660                 665                 670

Thr Leu Asp Gly Ala Asn Val Glu Ile Arg Glu His Val Gly Glu Glu
            675                 680                 685

Asn Ile Phe Ile Phe Gly Asn Thr Thr Glu Gln Val Glu Ala Leu Arg
690                 695                 700

Lys Ser Gly Tyr Asn Pro Arg Lys Tyr Tyr Asp Glu Asp Pro Glu Leu
705                 710                 715                 720

His Gln Val Leu Thr Gln Ile Ala Thr Gly Thr Phe Ser Pro Glu Glu
            725                 730                 735

Pro His Arg Tyr Thr Asn Leu Phe Asp Ser Leu Val Asn Leu Gly Asp
            740                 745                 750

His Tyr Gln Leu Leu Ala Asp Tyr Arg Ser Tyr Val Asp Thr Gln Glu
            755                 760                 765

Gln Val Asp Ala Leu Tyr Arg Asn Arg Asp Glu Trp Ser Arg Lys Thr
            770                 775                 780

Leu Leu Asn Ile Ala Asn Met Gly Tyr Phe Ser Ser Asp Arg Thr Ile
785                 790                 795                 800

Lys Glu Tyr Ala Asp Glu Ile Trp His Ile Lys Pro Ile Arg Leu
            805                 810                 815

<210> SEQ ID NO 13
<211> LENGTH: 780
<212> TYPE: PRT
<213> ORGANISM: Yersinia pestis

<400> SEQUENCE: 13

Met Lys Lys Arg Phe Pro Thr Leu Leu Ala Thr Leu Ile Trp Thr Ala
1               5                   10                  15

Leu Tyr Ser Gln His Thr Leu Ala Asp Leu Ala Glu Gln Cys Met Leu
            20                  25                  30

Gly Val Pro Thr Tyr Asp Gln Pro Leu Val Thr Gly Asp Pro Asn Gln
        35                  40                  45

Leu Pro Val Arg Ile Asn Ala Asp Lys Thr Glu Ala Asn Tyr Pro Asp
50                  55                  60

Asn Ala Leu Phe Thr Gly Asn Val Ile Val Gln Gly Asn Ser Thr
65                  70                  75                  80

Leu Thr Ala Asn Gln Val Glu Leu Thr Gln Val Gln Lys Pro Gly Glu
            85                  90                  95

Val Ile Pro Leu Arg Thr Val Thr Ala Thr Gly Asp Val Asn Tyr Asp
            100                 105                 110

Asp Pro Gln Ile Lys Leu Lys Gly Pro Lys Gly Trp Ser Asn Leu Asn
        115                 120                 125

Thr Lys Asp Thr Asp Met Asp Lys Gly Lys Tyr Gln Met Val Gly Arg
130                 135                 140

Gln Gly Arg Gly Asp Ala Asp Leu Met Lys Leu Arg Asp Gln Ser Arg
145                 150                 155                 160

```
Tyr Thr Ile Leu Lys Asn Gly Thr Phe Thr Ser Cys Leu Pro Gly Asp
                165                 170                 175

Asn Ser Trp Ser Val Val Gly Ser Glu Val Ile His Asp Arg Glu Glu
            180                 185                 190

Gln Val Val Glu Val Trp Asn Ala Arg Phe Lys Ile Gly Lys Val Pro
        195                 200                 205

Val Phe Tyr Ser Pro Tyr Met Gln Leu Pro Val Gly Asp Lys Arg Arg
    210                 215                 220

Ser Gly Phe Leu Ile Pro Asn Ala Lys Phe Thr Ser Asn Asn Gly Phe
225                 230                 235                 240

Glu Phe Leu Leu Pro Tyr Tyr Trp Asn Ile Ala Pro Asn Phe Asp Ala
                245                 250                 255

Thr Ile Thr Pro His Tyr Met Glu Arg Arg Gly Leu Gln Trp Gln Asn
            260                 265                 270

Glu Phe Arg Tyr Leu Leu Ala Pro Gly Ser Gly Thr Met Ala Leu Asp
        275                 280                 285

Trp Leu Pro Asn Asp Arg Ile Tyr Thr Gly Pro Asp Gly Thr Asp Lys
    290                 295                 300

Asn Ala Thr Arg Trp Leu Tyr Tyr Trp Gly His Ser Gly Val Met Asp
305                 310                 315                 320

Gln Val Trp Arg Phe Asn Ile Asn Tyr Thr Arg Val Ser Asp Pro Ala
                325                 330                 335

Tyr Phe Thr Asp Leu Thr Ser Gln Tyr Gly Ser Thr Thr Asp Gly Tyr
            340                 345                 350

Ala Thr Gln Ile Phe Thr Ala Gly Tyr Ala Asn Glu Asn Trp Asn Ala
        355                 360                 365

Thr Leu Ser Ser Lys Gln Phe Gln Val Phe Thr Ala Ala Gly Asn Ser
    370                 375                 380

Asn Ala Tyr Arg Ala Gln Pro Gln Leu Asp Met Asn Tyr Tyr Lys Asn
385                 390                 395                 400

Asp Val Gly Pro Phe Asp Met His Val Tyr Gly Gln Ala Ala Lys Phe
                405                 410                 415

Thr Ser Val Asn Pro Thr Asn Pro Glu Ala Ser Arg Phe His Ile Glu
            420                 425                 430

Pro Thr Val Asn Leu Pro Leu Ser Asn Ser Trp Gly Ser Ile Asn Thr
        435                 440                 445

Glu Ala Lys Leu Leu Ala Thr His Tyr Gln Gln Asp Ile Pro Ala Ser
    450                 455                 460

Phe Ala Asp Asn Ala Ser Asn Pro Lys Leu Lys Asp Ser Val Asn Arg
465                 470                 475                 480

Val Leu Pro Gln Phe Lys Val Asp Gly Lys Val Val Phe Asp Arg Ser
                485                 490                 495

Met Asp Trp Ala Thr Gly Phe Thr Gln Thr Leu Glu Pro Arg Ala Gln
            500                 505                 510

Tyr Leu Tyr Val Pro Tyr Arg Asn Gln Asp Asp Ile Tyr Ile Tyr Asp
        515                 520                 525

Thr Thr Leu Met Gln Ser Asp Tyr Ser Gly Leu Phe Arg Asp Arg Thr
    530                 535                 540

Tyr Ser Gly Leu Asp Arg Ile Ala Ser Ala Asn Gln Val Ser Thr Gly
545                 550                 555                 560

Leu Thr Ser Arg Ile Tyr Asp Asp Ala Arg Val Glu Arg Phe Asn Val
                565                 570                 575
```

-continued

```
Ser Val Gly Gln Ile Tyr Tyr Phe Ser Arg Ser Arg Thr Gly Asn Thr
            580                 585                 590

Glu Ala Ile Asp Asn Ser Asn Ala Thr Gly Ser Leu Val Trp Ala Gly
        595                 600                 605

Asp Thr Phe Trp Arg Ile Asn Asp Gln Leu Gly Leu Lys Gly Gly Ala
    610                 615                 620

Gln Tyr Asp Thr Arg Leu Gly Ser Leu Thr Leu Gly Asn Ala Ile Met
625                 630                 635                 640

Glu Tyr Arg Lys Asp Ala Asp Arg Met Ile Gln Leu Asn Tyr Arg Tyr
                645                 650                 655

Ala Ser Pro Lys Tyr Ile Gln Ala Ala Val Pro Lys Val Tyr Asn Pro
            660                 665                 670

Asp Tyr Gln Gln Gly Ile Ser Gln Val Gly Thr Thr Ala Ser Trp Pro
        675                 680                 685

Ile Ala Asp Arg Trp Ala Ile Val Gly Ala Tyr Tyr Tyr Asp Thr Lys
    690                 695                 700

Ala Lys Gln Pro Ala Ser Gln Leu Val Gly Leu Gln Tyr Asn Thr Cys
705                 710                 715                 720

Cys Trp Ala Val Asn Leu Gly Tyr Glu Arg Lys Ile Thr Gly Trp Asn
                725                 730                 735

Ala Gln Gly Gln Thr Ser Lys Tyr Asp Asn Lys Ile Gly Phe Asn Ile
            740                 745                 750

Glu Leu Arg Gly Leu Ser Gly His Ser Leu Gly Thr Ala Gln Met
        755                 760                 765

Leu Asn Ser Gly Ile Leu Pro Tyr Gln Ser Ala Phe
    770                 775                 780

<210> SEQ ID NO 14
<211> LENGTH: 676
<212> TYPE: PRT
<213> ORGANISM: Yersinia pestis

<400> SEQUENCE: 14

Met Leu Arg Ser Thr Ser Asp Arg Phe Arg Trp Ser Ser Leu Ser Leu
1               5                   10                  15

Ala Ile Ala Cys Thr Leu Pro Leu Ala Thr Gln Ala Ala Asp Thr Thr
            20                  25                  30

Thr Thr Gln Thr Ser Ser Lys Lys His Ser Thr Asp Thr Met Val Val
        35                  40                  45

Thr Ala Thr Gly Asn Glu Arg Ser Ser Phe Glu Ala Pro Met Met Val
    50                  55                  60

Thr Val Ile Glu Gly Asn Ala Pro Thr Ser Gln Thr Ala Ala Thr Ala
65                  70                  75                  80

Ala Asp Met Leu Arg Gln Val Pro Gly Leu Thr Val Thr Gly Ser Gly
                85                  90                  95

Arg Thr Asn Gly Gln Asp Val Val Met Arg Gly Tyr Gly Lys Gln Gly
            100                 105                 110

Val Leu Thr Leu Val Asp Gly Val Arg Gln Gly Thr Asp Thr Gly His
        115                 120                 125

Leu Asn Ser Thr Phe Leu Asp Pro Ala Leu Val Lys Arg Ile Glu Ile
    130                 135                 140

Val Arg Gly Pro Ala Ala Leu Leu Tyr Gly Ser Gly Ala Leu Gly Gly
145                 150                 155                 160

Val Ile Ala Tyr Glu Thr Val Asp Ala Ala Asp Met Leu Gln Pro Gly
                165                 170                 175
```

```
Gln Asn Ser Gly Tyr Arg Val Tyr Ser Ser Ala Ala Thr Gly Asp His
                180                 185                 190

Ser Phe Gly Leu Gly Ala Ser Ala Phe Gly Arg Thr Asp Asp Leu Asp
            195                 200                 205

Gly Ile Leu Ser Phe Gly Thr Arg Asp Ile Gly Asn Ile Arg Gln Ser
        210                 215                 220

Asn Gly Phe Asn Ala Pro Asn Asp Glu Thr Ile Ser Asn Val Leu Ala
225                 230                 235                 240

Lys Gly Thr Trp Gln Ile Asp Ser Ile Gln Ser Leu Ser Ala Asn Leu
                245                 250                 255

Arg Tyr Tyr Asn Asn Ser Ala Ile Glu Pro Lys Asn Pro Gln Thr Ser
                260                 265                 270

Ala Pro Ser Ser Thr Asn Val Met Thr Asn Arg Ser Thr Ile Gln Arg
            275                 280                 285

Asp Ala Gln Leu Arg Tyr Asn Ile Lys Pro Leu Asp Gln Glu Trp Leu
        290                 295                 300

Asn Ala Thr Ala Gln Val Tyr Tyr Ser Glu Val Glu Ile Asn Ala Arg
305                 310                 315                 320

Pro Gln Gly Ser Ala Glu Glu Gly Arg Glu Gln Thr Thr Glu Gly Val
                325                 330                 335

Lys Leu Glu Asn Arg Thr Arg Leu Phe Ile Glu Ser Pro Ala Ser His
                340                 345                 350

Leu Leu Thr Tyr Gly Thr Glu Thr Tyr Lys Gln Glu Gln Thr Pro Gly
            355                 360                 365

Gly Ala Thr Glu Ser Phe Pro Gln Ala Lys Ile Arg Phe Ser Ser Gly
        370                 375                 380

Trp Leu Gln Asp Glu Ile Thr Leu Arg Asp Leu Pro Val Ser Ile Leu
385                 390                 395                 400

Ala Gly Thr Arg Tyr Asp Asn Tyr Ser Gly Ser Ser Asp Gly Tyr Ala
                405                 410                 415

Asp Val Asp Ala Asp Lys Trp Ser Ser Arg Gly Ala Ile Ser Ile Thr
                420                 425                 430

Pro Thr Asp Trp Leu Met Leu Phe Gly Ser Tyr Ala Gln Ala Phe Arg
            435                 440                 445

Ala Pro Thr Met Gly Glu Met Tyr Asn Asp Ser Lys His Phe Ala Ile
450                 455                 460

Pro Ile Arg Pro Gly Leu Thr Leu Thr Asn Tyr Trp Val Pro Asn Pro
465                 470                 475                 480

Asn Leu Lys Pro Glu Thr Asn Glu Thr Gln Glu Tyr Gly Phe Gly Leu
                485                 490                 495

Arg Phe Asp Leu Leu Met Ala Glu Asp Asp Leu Gln Phe Lys Val
            500                 505                 510

Ser Tyr Phe Asp Thr Lys Ala Lys Asp Tyr Ile Ser Thr Arg Val Asp
        515                 520                 525

Met Gln Ala Met Thr Thr Thr Ser Val Asn Ile Asp Gln Ala Lys Ile
                530                 535                 540

Trp Gly Trp Asp Ala Ser Met Ser Tyr Lys Thr Ala Leu Phe Asn Trp
545                 550                 555                 560

Asp Leu Ala Tyr Asn Arg Thr Arg Gly Lys Asn Gln Asn Thr Asp Glu
                565                 570                 575

Trp Leu Asp Thr Ile Asn Pro Asp Thr Val Thr Ser Ile Val Asp Val
            580                 585                 590
```

```
Pro Val Ala Asn Ser Gly Phe Ser Val Gly Trp Ile Gly Thr Phe Ala
            595                 600                 605

Asn Arg Ser Ser Arg Val Ser Ser Ser Thr Pro Gln Ala Gly Tyr Gly
610                 615                 620

Val Asn Asp Phe Tyr Val Ser Tyr Lys Gly Gln Glu Ala Phe Lys Gly
625                 630                 635                 640

Met Thr Thr Thr Met Leu Leu Gly Asn Val Phe Glu Lys Glu Tyr Tyr
                645                 650                 655

Thr Pro Gln Gly Ile Pro Gln Asp Gly Arg Asn Val Lys Phe Phe Val
            660                 665                 670

Ser Tyr Gln Trp
        675

<210> SEQ ID NO 15
<211> LENGTH: 698
<212> TYPE: PRT
<213> ORGANISM: Yersinia pseudotuberculosis

<400> SEQUENCE: 15

Met Ser Asn Lys Thr Ile Ala Phe Ala Leu Val Val Ala Ser Ser Ala
1               5                   10                  15

Pro Val Ile Ala Ala Asp Asn Asp Asn Ile Met Val Val Thr Ala Ser
            20                  25                  30

Gly Tyr Glu Gln Lys Ile Arg Glu Ala Ala Ser Ile Ser Val Ile
        35                  40                  45

Ser Gln Asn Glu Leu Arg Gln Arg Asn Tyr Asn Asp Leu Ala Gln Ala
    50                  55                  60

Leu Ser Asp Val Glu Gly Val Asp Val Asn Ser Ser Thr Gly Lys Thr
65                  70                  75                  80

Gly Gly Leu Asp Ile Ser Ile Arg Gly Met Pro Ser Ala Tyr Thr Leu
                85                  90                  95

Ile Leu Val Asp Gly Ile Arg Gln Asn Gly Thr Ser Asp Val Thr Pro
            100                 105                 110

Asn Gly Phe Gly Ala Met Asn Thr Ser Phe Met Pro Pro Leu Ser Ala
        115                 120                 125

Ile Glu Arg Ile Glu Val Ile Arg Gly Pro Met Ser Thr Leu Tyr Gly
    130                 135                 140

Ser Asp Ala Ile Gly Gly Val Val Asn Ile Ile Thr Lys Lys Ile Thr
145                 150                 155                 160

Lys Ala Trp Ala Ser Ser Ala Thr Leu Glu His Thr Phe Gln Glu Asn
                165                 170                 175

Thr Ala Phe Gly Asp Ser Ser Lys Phe Ser Phe Tyr Ser Ser Gly Pro
            180                 185                 190

Ala Val Glu Asp Gln Leu Gly Leu Ser Leu Arg Gly Thr Ile Phe Arg
        195                 200                 205

Arg Asp Ala Ser Arg Val Glu Ser Ser Asn Thr Gly Val Glu Leu Ser
    210                 215                 220

Arg Arg Gly Pro Asn Pro Val Lys Ala Asp Asn Tyr Asn Leu Gly Gly
225                 230                 235                 240

Lys Leu Phe Trp Gln Leu Asn Thr Gln Ser Thr Leu Trp Leu Asp Gly
                245                 250                 255

Asp Ile Ala Asn Gln Lys Tyr Asp Asn Ser Ala Asn Gln Leu Gly Thr
            260                 265                 270

Ile Gly Ala Arg Gly Gly Tyr Glu Asp Thr Leu Arg Tyr Gln Arg Arg
        275                 280                 285
```

```
Lys Ile Thr Leu Gly Asn Asp Asn Arg Leu Asp Phe Gly Thr Trp Asn
    290                 295                 300
Ser Ser Leu Ser Tyr Asn Gln Thr Glu Asn Ile Gly Arg Leu Ile Thr
305                 310                 315                 320
Asn Ala Ser Val Pro Gln Gly Ser Gly Leu Ala Gly Glu Lys Arg Leu
                325                 330                 335
Leu Lys Asn Thr Asn Ile Ile Leu Asp Ser Lys Leu Val Ala Pro Leu
            340                 345                 350
Gly Asp Asn His Met Val Thr Leu Gly Gly Gln Tyr Trp Asn Ala Ile
        355                 360                 365
Met Lys Asp Gly Ile Val Leu Ala Asn Asn Gly Asp Glu Phe Ala Gln
    370                 375                 380
Asp Ala Trp Ser Leu Phe Ser Glu Asp Glu Trp Arg Leu Leu Asp Ser
385                 390                 395                 400
Leu Ala Leu Thr Tyr Gly Ala Arg Tyr Glu Tyr Gln Thr Thr Phe Gly
                405                 410                 415
Gly His Ile Ser Pro Arg Ala Tyr Leu Val Trp Asp Ala Gln Asp Asn
            420                 425                 430
Trp Thr Val Lys Gly Gly Val Ser Thr Gly Tyr Lys Thr Pro Thr Leu
        435                 440                 445
Ala Gln Leu His Asn Gly Ile Ser Gly Val Thr Gly Gln Gly Thr Ile
    450                 455                 460
Thr Thr Ile Gly Asn Pro Lys Leu Glu Pro Glu Ser Ser Val Asn Thr
465                 470                 475                 480
Glu Val Gly Val Tyr Tyr Glu Asn Glu Thr Gly Phe Gly Ala Asn Val
                485                 490                 495
Thr Leu Phe His Asn Arg Phe Arg Asn Lys Ile Asn Ser Val Ser Ile
            500                 505                 510
Asp Asn Thr Thr Ser Thr Tyr Thr Asn Val Gly Lys Ala Ile Thr Gln
        515                 520                 525
Gly Ile Glu Val Ala Ser Thr Ile Pro Leu Trp Ser Asp Asp Trp Met
    530                 535                 540
Leu Gly Ile Asn Tyr Thr Phe Thr Asp Ser Glu Gln Lys Asp Gly Asn
545                 550                 555                 560
Asn Lys Gly Ala Arg Leu Thr Asn Thr Pro Lys Asn Met Val Asn Ala
                565                 570                 575
Arg Leu Asn Trp Asn Ile Asn Glu Gln Leu Ser Thr Trp Leu Lys Ala
            580                 585                 590
Glu Tyr Arg Ser Lys Thr Ala Arg Phe Thr Gln Asn Tyr Ala Asn Leu
        595                 600                 605
Ser Ala Ala Asn Lys Val Val Tyr Asn Asn Leu Gly Ser Glu Phe Lys
    610                 615                 620
Pro Phe Ser Val Leu Asn Leu Gly Val Ala Tyr Lys Val Thr Lys Asp
625                 630                 635                 640
Val Thr Leu Asn Gly Ala Val Asn Asn Leu Leu Asp Lys Asp Phe Thr
                645                 650                 655
Arg Thr His Ile Phe Ala Val Gly Asn Gly Thr Thr Thr Ala Gly Asp
            660                 665                 670
Tyr Phe Thr Ser Ser Gln Ser Thr Ala Gly Tyr Val Val Pro Gly Arg
        675                 680                 685
Asn Tyr Trp Val Ser Val Asn Val Asn Phe
    690                 695
```

<210> SEQ ID NO 16
<211> LENGTH: 673
<212> TYPE: PRT
<213> ORGANISM: Yersinia pestis

<400> SEQUENCE: 16

Met Lys Met Thr Arg Leu Tyr Pro Leu Ala Leu Gly Gly Leu Leu Leu
1               5                   10                  15

Pro Ala Ile Ala Asn Ala Gln Thr Ser Gln Gln Asp Glu Ser Thr Leu
            20                  25                  30

Val Val Thr Ala Ser Lys Gln Ser Ser Arg Ser Ala Ser Ala Asn Asn
        35                  40                  45

Val Ser Ser Thr Val Val Ser Ala Pro Glu Leu Ser Asp Ala Gly Val
50                  55                  60

Thr Ala Ser Asp Lys Leu Pro Arg Val Leu Pro Gly Leu Asn Ile Glu
65                  70                  75                  80

Asn Ser Gly Asn Met Leu Phe Ser Thr Ile Ser Leu Arg Gly Val Ser
                85                  90                  95

Ser Ala Gln Asp Phe Tyr Asn Pro Ala Val Thr Leu Tyr Val Asp Gly
            100                 105                 110

Val Pro Gln Leu Ser Thr Asn Thr Ile Gln Ala Leu Thr Asp Val Gln
        115                 120                 125

Ser Val Glu Leu Leu Arg Gly Pro Gln Gly Thr Leu Tyr Gly Lys Ser
130                 135                 140

Ala Gln Gly Gly Ile Ile Asn Ile Val Thr Gln Gln Pro Asp Ser Thr
145                 150                 155                 160

Pro Arg Gly Tyr Ile Glu Gly Gly Val Ser Ser Arg Asp Ser Tyr Arg
                165                 170                 175

Ser Lys Phe Asn Leu Ser Gly Pro Ile Gln Asp Gly Leu Leu Tyr Gly
            180                 185                 190

Ser Val Thr Leu Leu Arg Gln Val Asp Asp Gly Asp Met Ile Asn Pro
        195                 200                 205

Ala Thr Gly Ser Asp Asp Leu Gly Gly Thr Arg Ala Ser Ile Gly Asn
210                 215                 220

Val Lys Leu Arg Leu Ala Pro Asp Asp Gln Pro Trp Glu Met Gly Phe
225                 230                 235                 240

Ala Ala Ser Arg Glu Cys Thr Arg Ala Thr Gln Asp Ala Tyr Val Gly
                245                 250                 255

Trp Asn Asp Ile Lys Gly Arg Lys Leu Ser Ile Ser Asp Gly Ser Pro
            260                 265                 270

Asp Pro Tyr Met Arg Arg Cys Thr Asp Ser Gln Thr Leu Ser Gly Lys
        275                 280                 285

Tyr Thr Thr Asp Asp Trp Val Phe Asn Leu Ile Ser Ala Trp Gln Gln
290                 295                 300

Gln His Tyr Ser Arg Thr Phe Pro Ser Gly Ser Leu Ile Val Asn Met
305                 310                 315                 320

Pro Gln Arg Trp Asn Gln Asp Val Gln Glu Leu Arg Ala Ala Thr Leu
                325                 330                 335

Gly Asp Ala Arg Thr Val Asp Met Val Phe Gly Leu Tyr Arg Gln Asn
            340                 345                 350

Thr Arg Glu Lys Leu Asn Ser Ala Tyr Asp Met Pro Thr Met Pro Tyr
        355                 360                 365

Leu Ser Ser Thr Gly Tyr Thr Thr Ala Glu Thr Leu Ala Ala Tyr Ser
370                 375                 380

-continued

```
Asp Leu Thr Trp His Leu Thr Asp Arg Phe Asp Ile Gly Gly Gly Val
385                 390                 395                 400

Arg Phe Ser His Asp Lys Ser Thr Gln Tyr His Gly Ser Met Leu
            405                 410                 415

Gly Asn Pro Phe Gly Asp Gln Gly Lys Ser Asn Asp Asp Gln Val Leu
            420                 425                 430

Gly Gln Leu Ser Ala Gly Tyr Met Leu Thr Asp Asp Trp Arg Val Tyr
            435                 440                 445

Thr Arg Val Ala Gln Gly Tyr Lys Pro Ser Gly Tyr Asn Ile Val Pro
        450                 455                 460

Thr Ala Gly Leu Asp Ala Lys Pro Phe Val Ala Glu Lys Ser Ile Asn
465                 470                 475                 480

Tyr Glu Leu Gly Thr Arg Tyr Glu Thr Ala Asp Val Thr Leu Gln Ala
                485                 490                 495

Ala Thr Phe Tyr Thr His Thr Lys Asp Met Gln Leu Tyr Ser Gly Pro
            500                 505                 510

Val Arg Met Gln Thr Leu Ser Asn Ala Gly Lys Ala Asp Ala Thr Gly
            515                 520                 525

Val Glu Leu Glu Ala Lys Trp Arg Phe Ala Pro Gly Trp Ser Trp Asp
        530                 535                 540

Ile Asn Gly Asn Val Ile Arg Ser Glu Phe Thr Asn Asp Ser Glu Leu
545                 550                 555                 560

Tyr His Gly Asn Arg Val Pro Phe Val Pro Arg Tyr Gly Ala Gly Ser
                565                 570                 575

Ser Val Asn Gly Val Ile Asp Thr Arg Tyr Gly Ala Leu Met Pro Arg
            580                 585                 590

Leu Ala Val Asn Leu Val Gly Pro His Tyr Phe Asp Gly Asp Asn Gln
            595                 600                 605

Leu Arg Gln Gly Thr Tyr Ala Thr Leu Asp Ser Ser Leu Gly Trp Gln
        610                 615                 620

Ala Thr Glu Arg Met Asn Ile Ser Val Tyr Val Asp Asn Leu Phe Asp
625                 630                 635                 640

Arg Arg Tyr Arg Thr Tyr Gly Tyr Met Asn Gly Ser Ser Ala Val Ala
                645                 650                 655

Gln Val Asn Met Gly Arg Thr Val Gly Ile Asn Thr Arg Ile Asp Phe
            660                 665                 670

Phe
```

<210> SEQ ID NO 17
<211> LENGTH: 548
<212> TYPE: PRT
<213> ORGANISM: Yersinia pseudotuberculosis

<400> SEQUENCE: 17

```
Met Ala Ala Lys Asp Val Lys Phe Gly Asn Asp Ala Arg Ile Lys Met
1               5                   10                  15

Leu Arg Gly Val Asn Ile Leu Ala Asp Ala Val Lys Val Thr Leu Gly
            20                  25                  30

Pro Lys Gly Arg Asn Val Val Leu Asp Lys Ser Phe Gly Ser Pro Thr
        35                  40                  45

Ile Thr Lys Asp Gly Val Ser Val Ala Arg Glu Ile Glu Leu Glu Asp
    50                  55                  60

Lys Phe Glu Asn Met Gly Ala Gln Met Val Lys Glu Val Ala Ser Lys
65                  70                  75                  80
```

-continued

```
Ala Asn Asp Ala Ala Gly Asp Gly Thr Thr Thr Ala Thr Val Leu Ala
                85                  90                  95

Gln Ser Ile Ile Thr Glu Gly Leu Lys Ala Val Ala Ala Gly Met Asn
            100                 105                 110

Pro Met Asp Leu Lys Arg Gly Ile Asp Lys Ala Val Ile Ala Ala Val
        115                 120                 125

Glu Glu Leu Lys Lys Leu Ser Val Pro Cys Ser Asp Ser Lys Ala Ile
    130                 135                 140

Ala Gln Val Gly Thr Ile Ser Ala Asn Ser Asp Ser Thr Val Gly Glu
145                 150                 155                 160

Leu Ile Ala Gln Ala Met Glu Lys Val Gly Lys Glu Gly Val Ile Thr
                165                 170                 175

Val Glu Glu Gly Ser Gly Leu Gln Asp Glu Leu Asp Val Val Glu Gly
            180                 185                 190

Met Gln Phe Asp Arg Gly Tyr Leu Ser Pro Tyr Phe Ile Asn Lys Pro
        195                 200                 205

Glu Thr Gly Ser Ile Glu Leu Glu Ser Pro Phe Ile Leu Leu Ala Asp
    210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255

Glu Ala Leu Ala Thr Leu Val Val Asn Thr Met Arg Gly Ile Val Lys
            260                 265                 270

Val Ala Ala Val Lys Ala Pro Gly Phe Gly Asp Arg Arg Lys Ala Met
        275                 280                 285

Leu Gln Asp Ile Ala Thr Leu Thr Ala Gly Thr Val Ile Ser Glu Glu
    290                 295                 300

Ile Gly Leu Glu Leu Glu Lys Thr Thr Leu Glu Asp Leu Gly Gln Ala
305                 310                 315                 320

Lys Arg Val Val Ile Asn Lys Asp Thr Thr Ile Ile Ile Asp Gly Val
                325                 330                 335

Gly Asp Glu Ala Ala Ile Gln Gly Arg Val Ala Gln Ile Arg Gln Gln
            340                 345                 350

Ile Glu Asp Ala Thr Ser Asp Tyr Asp Lys Glu Lys Leu Gln Glu Arg
        355                 360                 365

Val Ala Lys Leu Ala Gly Gly Val Ala Val Ile Lys Val Gly Ala Ala
    370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Val Val Ala Gly Gly Gly
                405                 410                 415

Val Ala Leu Ile Arg Ala Ala His Ala Ile Ala Gly Leu Lys Gly Asp
            420                 425                 430

Asn Glu Asp Gln Asn Val Gly Ile Lys Val Ala Leu Arg Ala Met Glu
        435                 440                 445

Ser Pro Leu Arg Gln Ile Val Val Asn Ala Gly Glu Glu Ala Ser Val
    450                 455                 460

Ile Ala Asn Lys Val Lys Ala Gly Glu Gly Ser Phe Gly Tyr Asn Ala
465                 470                 475                 480

Tyr Thr Glu Glu Tyr Gly Asp Met Ile Ala Met Gly Ile Leu Asp Pro
                485                 490                 495
```

```
Thr Lys Val Thr Arg Ser Ala Leu Gln Tyr Ala Ala Ser Ile Ala Gly
            500                 505                 510

Leu Met Ile Thr Thr Glu Cys Met Val Thr Asp Leu Pro Arg Asp Asp
            515                 520                 525

Lys Gly Ala Asp Met Gly Ala Gly Gly Met Gly Gly Met Gly Gly Met
530                 535                 540

Gly Gly Met Met
545

<210> SEQ ID NO 18
<211> LENGTH: 467
<212> TYPE: PRT
<213> ORGANISM: Yersinia pestis

<400> SEQUENCE: 18

Met Gln Met Lys Lys Leu Leu Pro Leu Leu Ile Gly Leu Ser Leu Ala
1               5                   10                  15

Gly Phe Ser Thr Met Ser Gln Ala Glu Asn Leu Leu Gln Val Tyr Lys
            20                  25                  30

Gln Ala Arg Asp Ser Asn Pro Asp Leu Arg Lys Ala Ala Ala Asp Arg
        35                  40                  45

Asp Ala Ala Tyr Glu Lys Ile Asn Glu Val Arg Ser Pro Leu Leu Pro
    50                  55                  60

Gln Leu Gly Leu Ser Ala Gly Tyr Thr His Ala Asn Gly Phe Arg Asp
65                  70                  75                  80

Ala Ser Asn Ser Pro Asp Ser Asn Ala Thr Ser Gly Ser Leu Lys Leu
                85                  90                  95

Thr Gln Thr Ile Phe Asp Met Ser Lys Trp Arg Ala Leu Thr Leu Gln
            100                 105                 110

Glu Lys Ala Ala Gly Ile Gln Asp Val Thr Phe Gln Thr Ser Glu Gln
        115                 120                 125

Gln Leu Ile Leu Asn Thr Ala Thr Ala Tyr Phe Asn Val Leu Arg Ala
    130                 135                 140

Ile Asp Ser Leu Ser Tyr Thr Glu Ala Gln Lys Gln Ser Val Tyr Arg
145                 150                 155                 160

Gln Leu Asp Gln Thr Thr Gln Arg Phe Asn Val Gly Leu Val Ala Ile
                165                 170                 175

Thr Asp Val Gln Asn Ala Arg Ala Ser Tyr Asp Thr Val Leu Ala Ala
            180                 185                 190

Glu Val Ala Ala Arg Asn Asn Leu Asp Asn Ala Leu Glu Ser Leu Arg
        195                 200                 205

Gln Ile Thr Gly Val Tyr Tyr Pro Glu Leu Ala Ser Leu Asn Val Glu
    210                 215                 220

Arg Leu Lys Thr Gln Arg Pro Asp Ala Val Asn Leu Leu Lys Glu
225                 230                 235                 240

Ala Glu Lys Arg Asn Leu Ser Leu Leu Ser Ala Arg Leu Ser Gln Asp
                245                 250                 255

Leu Ala Arg Glu Gln Ile Lys Ser Ala Glu Thr Gly Tyr Met Pro Thr
            260                 265                 270

Val Asp Leu Thr Ala Ser Ser Ile Thr Asn Thr Arg Tyr Ser Gly
        275                 280                 285

Gly Thr Pro Ser Ser Gln Gln Val Asn Asn Asp Ser Gly Gln Asn Gln
    290                 295                 300

Ile Gly Val Gln Phe Ser Leu Pro Leu Tyr Ser Gly Gly Ala Thr Asn
305                 310                 315                 320
```

```
Ser Ala Val Lys Gln Ala Gln Tyr Asn Phe Val Gly Ala Ser Glu Leu
            325                 330                 335

Leu Glu Ser Ala His Arg Asn Met Val Gln Thr Leu Arg Ser Ser Phe
        340                 345                 350

Asn Asn Ile Ser Ala Ser Ile Ser Ser Ile Asn Ala Tyr Gln Gln Val
            355                 360                 365

Val Ile Ser Asn Gln Ser Ser Leu Asp Ala Met Glu Ala Gly Tyr Gln
        370                 375                 380

Val Gly Thr Arg Thr Ile Leu Asp Val Leu Thr Ala Thr Thr Asn Leu
385                 390                 395                 400

Tyr Gln Ser Lys Gln Gln Leu Ala Asp Ala Arg Tyr Asn Tyr Leu Ile
            405                 410                 415

Asn Gln Leu Asn Ile Lys Ser Ala Leu Gly Thr Leu Asn Met Asn Asp
        420                 425                 430

Leu Met Ala Leu Asn Ala Val Leu Asp Lys Pro Val Pro Thr Ser Ala
            435                 440                 445

Ala Ala Leu Ala Pro Glu Asn Thr Thr Arg Gln Thr Val Thr Thr Pro
    450                 455                 460

Arg Ala Gln
465

<210> SEQ ID NO 19
<211> LENGTH: 394
<212> TYPE: PRT
<213> ORGANISM: Yersinia pseudotuberculosis

<400> SEQUENCE: 19

Met Ser Lys Glu Lys Phe Glu Arg Thr Lys Pro His Val Asn Val Gly
1               5                   10                  15

Thr Ile Gly His Val Asp His Gly Lys Thr Thr Leu Thr Ala Ala Ile
            20                  25                  30

Thr Thr Val Leu Ala Lys Thr Tyr Gly Gly Ser Ala Arg Ala Phe Asp
        35                  40                  45

Gln Ile Asp Asn Ala Pro Glu Glu Lys Ala Arg Gly Ile Thr Ile Asn
    50                  55                  60

Thr Ser His Val Glu Tyr Asp Thr Pro Ala Arg His Tyr Ala His Val
65                  70                  75                  80

Asp Cys Pro Gly His Ala Asp Tyr Val Lys Asn Met Ile Thr Gly Ala
            85                  90                  95

Ala Gln Met Asp Gly Ala Ile Leu Val Val Ala Ala Thr Asp Gly Pro
        100                 105                 110

Met Pro Gln Thr Arg Glu His Ile Leu Leu Gly Arg Gln Val Gly Val
    115                 120                 125

Pro Tyr Ile Ile Val Phe Met Asn Lys Cys Asp Met Val Asp Asp Glu
130                 135                 140

Glu Leu Leu Glu Leu Val Glu Met Glu Val Arg Glu Leu Leu Ser Ala
145                 150                 155                 160

Tyr Asp Phe Pro Gly Asp Asp Leu Pro Val Val Arg Gly Ser Ala Leu
            165                 170                 175

Lys Ala Leu Glu Gly Glu Ala Glu Trp Glu Ala Lys Ile Ile Glu Leu
        180                 185                 190

Ala Gly Tyr Leu Asp Ser Tyr Ile Pro Glu Pro Glu Arg Ala Ile Asp
    195                 200                 205

Lys Pro Phe Leu Leu Pro Ile Glu Asp Val Phe Ser Ile Ser Gly Arg
```

```
                        210                 215                 220
Gly Thr Val Val Thr Gly Arg Val Glu Arg Gly Ile Val Lys Val Gly
225                 230                 235                 240

Glu Glu Val Glu Ile Val Gly Ile Lys Asp Thr Val Lys Ser Thr Cys
                245                 250                 255

Thr Gly Val Glu Met Phe Arg Lys Leu Leu Asp Glu Gly Arg Ala Gly
            260                 265                 270

Glu Asn Val Gly Val Leu Leu Arg Gly Ile Lys Arg Glu Asp Ile Glu
        275                 280                 285

Arg Gly Gln Val Leu Ala Lys Pro Gly Ser Ile Lys Pro His Thr Thr
    290                 295                 300

Phe Glu Ser Glu Val Tyr Ile Leu Ser Lys Asp Glu Gly Gly Arg His
305                 310                 315                 320

Thr Pro Phe Phe Lys Gly Tyr Arg Pro Gln Phe Tyr Phe Arg Thr Thr
                325                 330                 335

Asp Val Thr Gly Thr Ile Glu Leu Pro Glu Gly Val Glu Met Val Met
            340                 345                 350

Pro Gly Asp Asn Ile Asn Met Ile Val Thr Leu Ile His Pro Ile Ala
        355                 360                 365

Met Asp Asp Gly Leu Arg Phe Ala Ile Arg Glu Gly Arg Thr Val
370                 375                 380

Gly Ala Gly Val Val Ala Lys Val Ile Ala
385                 390

<210> SEQ ID NO 20
<211> LENGTH: 371
<212> TYPE: PRT
<213> ORGANISM: Yersinia pestis

<400> SEQUENCE: 20

Met Lys Leu Arg Val Leu Ser Phe Ile Ile Pro Ala Leu Leu Val Ala
1               5                   10                  15

Gly Ser Ala Ser Ala Ala Glu Ile Tyr Asn Lys Asp Gly Asn Lys Leu
            20                  25                  30

Asp Leu Tyr Gly Lys Ile Asp Gly Leu His Tyr Phe Ser Asp Asn Lys
        35                  40                  45

Asn Leu Asp Gly Asp Gln Ser Tyr Met Arg Phe Gly Leu Lys Gly Glu
    50                  55                  60

Thr Gln Ile Thr Asp Gln Leu Thr Gly Tyr Gly Gln Trp Glu Tyr Gln
65                  70                  75                  80

Val Asn Leu Asn Lys Ala Glu Asn Glu Gly Asn His Asp Ser Phe
                85                  90                  95

Thr Arg Val Gly Phe Ala Gly Leu Lys Phe Ala Asp Tyr Gly Ser Leu
            100                 105                 110

Asp Tyr Gly Arg Asn Tyr Gly Val Leu Tyr Asp Val Thr Ser Trp Thr
        115                 120                 125

Asp Val Leu Pro Glu Phe Gly Gly Asp Thr Tyr Gly Ala Asp Asn Phe
    130                 135                 140

Leu Ser Gln Arg Gly Asn Gly Met Leu Thr Tyr Arg Asn Thr Asn Phe
145                 150                 155                 160

Phe Gly Leu Val Asp Gly Leu Asn Phe Ala Leu Gln Tyr Gln Gly Lys
                165                 170                 175

Asn Gly Ser Ser Ser Glu Thr Asn Asn Gly Arg Gly Val Ala Asp Gln
            180                 185                 190
```

```
Asn Gly Asp Gly Tyr Gly Met Ser Leu Ser Tyr Asp Leu Gly Trp Gly
            195                 200                 205

Val Ser Ala Ser Ala Ala Met Ala Ser Ser Leu Arg Thr Thr Ala Gln
    210                 215                 220

Asn Asp Leu Gln Tyr Gly Gln Gly Lys Arg Ala Asn Ala Tyr Thr Gly
225                 230                 235                 240

Gly Leu Lys Tyr Asp Ala Asn Asn Val Tyr Leu Ala Ala Asn Tyr Thr
                245                 250                 255

Gln Thr Tyr Asn Leu Thr Arg Phe Gly Asp Phe Ser Asn Arg Ser Ser
            260                 265                 270

Asp Ala Ala Phe Gly Phe Ala Asp Lys Ala His Asn Ile Glu Val Val
        275                 280                 285

Ala Gln Tyr Gln Phe Asp Phe Gly Leu Arg Pro Ser Val Ala Tyr Leu
    290                 295                 300

Gln Ser Lys Gly Lys Asp Ile Gly Ile Tyr Gly Asp Gln Asp Leu Leu
305                 310                 315                 320

Lys Tyr Val Asp Ile Gly Ala Thr Tyr Phe Phe Asn Lys Asn Met Ser
                325                 330                 335

Thr Tyr Val Asp Tyr Lys Ile Asn Leu Leu Asp Lys Asn Asp Phe Thr
            340                 345                 350

Lys Asn Ala Arg Ile Asn Thr Asp Asp Ile Val Ala Val Gly Met Val
        355                 360                 365

Tyr Gln Phe
    370

<210> SEQ ID NO 21
<211> LENGTH: 254
<212> TYPE: PRT
<213> ORGANISM: Yersinia pestis

<400> SEQUENCE: 21

Met Tyr Asn Ile Asp Tyr Asn Ser Phe Arg Ser Val Lys Gly Phe Asn
1               5                   10                  15

Arg Arg Val Arg Phe Leu Val Met His Tyr Thr Ala Phe Asn Phe Lys
            20                  25                  30

Asp Ser Ile Asp Ala Leu Thr Gly Pro Ser Val Ser Ala His Tyr Leu
        35                  40                  45

Val Pro Asp Pro Thr Glu Gln Thr Tyr Ile Asp Ala Gly Phe Lys Asp
    50                  55                  60

Met Arg Ile Phe Asn Leu Val Asp Glu Asn Glu Arg Ala Trp His Ala
65                  70                  75                  80

Gly Val Ser Tyr Trp Asp Gly Arg Asn Asn Leu Asn Asp Thr Ala Ile
                85                  90                  95

Gly Ile Glu Thr Val Asn Leu Ala Thr Asp Asn Asp Gly Val Phe Thr
            100                 105                 110

Phe Pro Pro Tyr Asn Val Thr Gln Ile Ala Ala Ile Lys Ala Leu Ala
        115                 120                 125

Ser Asn Ile Leu Tyr Arg Phe Pro Asp Ile Thr Pro Val Asn Val Val
    130                 135                 140

Gly His Ser Asp Ile Ala Pro Gly Arg Lys Ser Asp Pro Gly Ala Ala
145                 150                 155                 160

Phe Pro Trp Lys Ala Leu Tyr Asp Ala Gly Ile Gly Ala Trp Tyr Asp
                165                 170                 175

Asp Glu Thr Lys Gln Arg Tyr Leu Asp Gln Phe Leu Cys Ser Leu Pro
            180                 185                 190
```

```
Ser Lys Asn Asp Ile Ile Ser Lys Leu Lys Arg Tyr Gly Tyr Asp Thr
        195                 200                 205

Ser Gly Ala Val Ser Glu Val Gly Tyr Asn Gln Leu Ile Arg Ala Phe
    210                 215                 220

Gln Leu His Phe Arg Pro Cys Asn Tyr Asp Gly Ile Pro Asp Ala Glu
225                 230                 235                 240

Thr Val Ala Ile Leu Tyr Ala Leu Val Asp Lys Tyr Lys Pro
                245                 250

<210> SEQ ID NO 22
<211> LENGTH: 283
<212> TYPE: PRT
<213> ORGANISM: Yersinia pestis

<400> SEQUENCE: 22

Met Arg Lys Leu Leu Ser Gly Gly Leu Leu Leu Leu Leu Ala Gly Cys
1               5                   10                  15

Ser Ser Ser Asp His Arg Asn Ser Asn Glu Leu Ile Asp Arg Gly Thr
            20                  25                  30

Tyr Gln Ile Asp Thr His Tyr Pro Ser Val Ala Lys Asn Glu Arg Val
        35                  40                  45

Arg Phe Leu Val Leu His Tyr Thr Ala Val Gly Asp Ala Glu Ser Leu
    50                  55                  60

Arg Leu Leu Thr Gln Gly Glu Val Ser Ala His Tyr Leu Ile Pro Thr
65                  70                  75                  80

His Pro Lys Lys Ala Gly Gly Lys Ala Ile Ala Leu Gln Leu Val Pro
                85                  90                  95

Glu Ala Gln Arg Ala Trp His Ala Gly Val Ser Ser Trp Gln Gly Arg
            100                 105                 110

Asn Asn Leu Asn Asp Thr Ser Ile Gly Ile Glu Ile Val Asn Leu Gly
        115                 120                 125

Phe Thr Glu Lys Met Leu Gly Arg Thr Trp Tyr Pro Tyr Asn Glu Ser
    130                 135                 140

Gln Ile Glu Leu Ile Glu Gln Leu Thr Lys Asp Ile Val Gln Arg Tyr
145                 150                 155                 160

Asn Ile Ser Pro Ser Asp Val Val Ala His Ser Asp Ile Ala Pro Leu
                165                 170                 175

Arg Lys Ser Asp Pro Gly Pro Leu Phe Pro Trp Lys Arg Leu Ala Glu
            180                 185                 190

Lys Gly Val Gly Ala Trp Pro Asp Asp Ala Thr Val Ala Lys Tyr Ile
        195                 200                 205

Gly Gly Arg Asp Lys Lys Gly Ala Ala Ser Val Ala Val Ile Gln Gln
    210                 215                 220

Ala Leu Ala Ala Tyr Gly Tyr Lys Ile Pro Gln Asn Gly Gln Leu Asp
225                 230                 235                 240

Thr Glu Thr Arg Gln Val Ile Lys Ala Phe Gln Met His Phe Arg Pro
                245                 250                 255

Gln Asp Phe Ser Gly Val Pro Asp Val Glu Thr Glu Ala Ile Ala Leu
            260                 265                 270

Ala Leu Val Glu Lys Tyr Arg Thr Leu Ser Thr
        275                 280

<210> SEQ ID NO 23
<211> LENGTH: 194
<212> TYPE: PRT
```

-continued

<213> ORGANISM: Yersinia pestis

<400> SEQUENCE: 23

Met Val Thr Val Leu Gly Ile Val Ile Thr Ile Trp Met Val Phe Met
1               5                   10                  15

Asn Lys Thr Leu Leu Val Ser Ser Leu Ile Ala Cys Leu Ser Ile Ala
            20                  25                  30

Ser Val Asn Val Tyr Ala Glu Gly Glu Ser Ser Ile Ser Ile Gly Tyr
        35                  40                  45

Ala Gln Ser Arg Val Lys Glu Asp Gly Tyr Lys Leu Asp Lys Asn Pro
    50                  55                  60

Arg Gly Phe Asn Leu Lys Tyr Arg Tyr Glu Phe Asn Asn Asp Trp Gly
65                  70                  75                  80

Val Ile Gly Ser Phe Ala Gln Thr Arg Arg Gly Phe Glu Glu Ser Val
                85                  90                  95

Asp Gly Phe Lys Leu Ile Asp Gly Asp Phe Lys Tyr Tyr Ser Val Thr
            100                 105                 110

Ala Gly Pro Val Phe Arg Ile Asn Glu Tyr Val Ser Leu Tyr Gly Leu
        115                 120                 125

Leu Gly Ala Gly His Gly Lys Ala Lys Phe Ser Ser Ile Phe Gly Gln
    130                 135                 140

Ser Glu Ser Arg Ser Lys Thr Ser Leu Ala Tyr Gly Ala Gly Leu Gln
145                 150                 155                 160

Phe Asn Pro His Pro Asn Phe Val Ile Asp Ala Ser Tyr Glu Tyr Ser
                165                 170                 175

Lys Leu Asp Asp Val Lys Val Gly Thr Trp Met Leu Gly Ala Gly Tyr
            180                 185                 190

Arg Phe

<210> SEQ ID NO 24
<211> LENGTH: 7
<212> TYPE: PRT
<213> ORGANISM: Yersinia enterocolitica

<400> SEQUENCE: 24

Phe His Gln Leu Asp Asn Arg
1               5

<210> SEQ ID NO 25
<211> LENGTH: 11
<212> TYPE: PRT
<213> ORGANISM: Yersinia enterocolitica

<400> SEQUENCE: 25

Val Asn Phe Thr Ala Gly Val Gly Gly Tyr Arg
1               5                   10

<210> SEQ ID NO 26
<211> LENGTH: 12
<212> TYPE: PRT
<213> ORGANISM: Yersinia enterocolitica

<400> SEQUENCE: 26

Asn Ser Val Ser Ile Gly His Glu Ser Leu Asn Arg
1               5                   10

<210> SEQ ID NO 27
<211> LENGTH: 15
<212> TYPE: PRT

<213> ORGANISM: Yersinia enterocolitica

<400> SEQUENCE: 27

Ala Ser Thr Ser Asp Thr Gly Val Ala Val Gly Phe Asn Ser Lys
1 5 10 15

<210> SEQ ID NO 28
<211> LENGTH: 15
<212> TYPE: PRT
<213> ORGANISM: Yersinia enterocolitica

<400> SEQUENCE: 28

Ser Ala Glu Thr Leu Ala Ser Ala Asn Val Tyr Ala Asp Ser Lys
1 5 10 15

<210> SEQ ID NO 29
<211> LENGTH: 14
<212> TYPE: PRT
<213> ORGANISM: Yersinia enterocolitica
<220> FEATURE:
<221> NAME/KEY: MOD_RES
<222> LOCATION: (12)..(12)
<223> OTHER INFORMATION: Oxidized Met

<400> SEQUENCE: 29

Glu Ala Phe Asp Leu Ser Asn Asp Ala Leu Asp Met Ala Lys
1 5 10

<210> SEQ ID NO 30
<211> LENGTH: 15
<212> TYPE: PRT
<213> ORGANISM: Yersinia enterocolitica

<400> SEQUENCE: 30

Ser Ala Glu Val Leu Gly Ile Ala Asn Asn Tyr Thr Asp Ser Lys
1 5 10 15

<210> SEQ ID NO 31
<211> LENGTH: 17
<212> TYPE: PRT
<213> ORGANISM: Yersinia enterocolitica

<400> SEQUENCE: 31

Ala Leu Gly Asp Ser Ala Val Thr Tyr Gly Ala Gly Ser Thr Ala Gln
1 5 10 15

Lys

<210> SEQ ID NO 32
<211> LENGTH: 15
<212> TYPE: PRT
<213> ORGANISM: Yersinia enterocolitica
<220> FEATURE:
<221> NAME/KEY: MOD_RES
<222> LOCATION: (12)..(12)
<223> OTHER INFORMATION: Oxidized Met

<400> SEQUENCE: 32

Glu Ala Phe Asp Leu Ser Asn Asp Ala Leu Asp Met Ala Lys Lys
1 5 10 15

<210> SEQ ID NO 33
<211> LENGTH: 24
<212> TYPE: PRT
<213> ORGANISM: Yersinia enterocolitica

<400> SEQUENCE: 33

```
Ala Ala Val Ala Val Gly Ala Gly Ser Ile Ala Thr Gly Val Asn Ser
1               5                   10                  15

Val Ala Ile Gly Pro Leu Ser Lys
            20
```

<210> SEQ ID NO 34
<211> LENGTH: 6
<212> TYPE: PRT
<213> ORGANISM: Yersinia enterocolitica

<400> SEQUENCE: 34

```
Asp Ile Gly Asn Ile Arg
1               5
```

<210> SEQ ID NO 35
<211> LENGTH: 7
<212> TYPE: PRT
<213> ORGANISM: Yersinia enterocolitica

<400> SEQUENCE: 35

```
Phe Phe Val Ser Tyr Gln Trp
1               5
```

<210> SEQ ID NO 36
<211> LENGTH: 9
<212> TYPE: PRT
<213> ORGANISM: Yersinia enterocolitica

<400> SEQUENCE: 36

```
Val Asn Gly Gln Asp Val Thr Leu Arg
1               5
```

<210> SEQ ID NO 37
<211> LENGTH: 9
<212> TYPE: PRT
<213> ORGANISM: Yersinia enterocolitica

<400> SEQUENCE: 37

```
Ala Ser Tyr Phe Asp Thr Asn Ala Lys
1               5
```

<210> SEQ ID NO 38
<211> LENGTH: 11
<212> TYPE: PRT
<213> ORGANISM: Yersinia enterocolitica

<400> SEQUENCE: 38

```
Asp Leu Pro Val Ser Ile Leu Ala Gly Thr Arg
1               5                   10
```

<210> SEQ ID NO 39
<211> LENGTH: 11
<212> TYPE: PRT
<213> ORGANISM: Yersinia enterocolitica

<400> SEQUENCE: 39

```
Gln Gly Val Leu Thr Leu Val Asp Gly Ile Arg
1               5                   10
```

<210> SEQ ID NO 40
<211> LENGTH: 12
<212> TYPE: PRT
<213> ORGAN

<400> SEQUENCE: 40

Asn Ile Pro Gly Leu Thr Val Thr Gly Ser Gly Arg
1               5                   10

<210> SEQ ID NO 41
<211> LENGTH: 10
<212> TYPE: PRT
<213> ORGANISM: Yersinia enterocolitica

<400> SEQUENCE: 41

Tyr Tyr Asn Asn Ser Ala Leu Glu Pro Lys
1               5                   10

<210> SEQ ID NO 42
<211> LENGTH: 12
<212> TYPE: PRT
<213> ORGANISM: Yersinia enterocolitica

<400> SEQUENCE: 42

Ala Pro Thr Met Gly Glu Met Tyr Asn Asp Ser Lys
1               5                   10

<210> SEQ ID NO 43
<211> LENGTH: 12
<212> TYPE: PRT
<213> ORGANISM: Yersinia enterocolitica

<400> SEQUENCE: 43

Ile Asp Gln Ile Gln Ser Leu Ser Ala Asn Leu Arg
1               5                   10

<210> SEQ ID NO 44
<211> LENGTH: 13
<212> TYPE: PRT
<213> ORGANISM: Yersinia enterocolitica

<400> SEQUENCE: 44

Thr Asp Asp Val Asp Gly Ile Leu Ser Phe Gly Thr Arg
1               5                   10

<210> SEQ ID NO 45
<211> LENGTH: 14
<212> TYPE: PRT
<213> ORGANISM: Yersinia enterocolitica

<400> SEQUENCE: 45

Gly Met Thr Thr Thr Val Val Leu Gly Asn Ala Phe Asp Lys
1               5                   10

<210> SEQ ID NO 46
<211> LENGTH: 14
<212> TYPE: PRT
<213> ORGANISM: Yersinia enterocolitica

<400> SEQUENCE: 46

Ile Ala Asp Thr Met Val Val Thr Ala Thr Gly Asn Glu Arg
1               5                   10

<210> SEQ ID NO 47
<211> LENGTH: 13
<212> TYPE: PRT
<213> ORGANISM: Yersinia enterocolitica

<400> SEQUENCE: 47

```
Phe Gly Ser Gly Trp Leu Gln Asp Glu Ile Thr Leu Arg
1               5                   10
```

<210> SEQ ID NO 48
<211> LENGTH: 16
<212> TYPE: PRT
<213> ORGANISM: Yersinia enterocolitica

<400> SEQUENCE: 48

```
Asn Pro Gln Thr Ser Ala Ala Ser Ser Thr Asn Leu Met Thr Asp Arg
1               5                   10                  15
```

<210> SEQ ID NO 49
<211> LENGTH: 14
<212> TYPE: PRT
<213> ORGANISM: Yersinia enterocolitica

<400> SEQUENCE: 49

```
Phe Asn Asp Leu Met Met Ala Glu Asp Asp Leu Gln Phe Lys
1               5                   10
```

<210> SEQ ID NO 50
<211> LENGTH: 17
<212> TYPE: PRT
<213> ORGANISM: Yersinia enterocolitica

<400> SEQUENCE: 50

```
Gly Ser Ser Glu Gly Tyr Ala Asp Val Asp Ala Asp Lys Trp Ser Ser
1               5                   10                  15

Arg
```

<210> SEQ ID NO 51
<211> LENGTH: 18
<212> TYPE: PRT
<213> ORGANISM: Yersinia enterocolitica

<400> SEQUENCE: 51

```
Gln Glu Gln Thr Pro Ser Gly Ala Thr Glu Ser Phe Pro Gln Ala Asp
1               5                   10                  15

Ile Arg
```

<210> SEQ ID NO 52
<211> LENGTH: 19
<212> TYPE: PRT
<213> ORGANISM: Yersinia enterocolitica

<400> SEQUENCE: 52

```
Gln Gly Thr Asp Thr Gly His Leu Asn Ser Thr Phe Leu Asp Pro Ala
1               5                   10                  15

Leu Val Lys
```

<210> SEQ ID NO 53
<211> LENGTH: 19
<212> TYPE: PRT
<213> ORGANISM: Yersinia enterocolitica

<400> SEQUENCE: 53

```
Gln Ser Asp Gly Phe Asn Ala Pro Asn Asp Glu Thr Ile Ser Asn Val
1               5                   10                  15

Leu Ala Lys
```

<210> SEQ ID NO 54

<211> LENGTH: 21
<212> TYPE: PRT
<213> ORGANISM: Yersinia enterocolitica

<400> SEQUENCE: 54

Val Tyr Ser Ala Ala Ala Thr Gly Asp His Ser Phe Gly Leu Gly Ala
1               5                   10                  15

Ser Ala Phe Gly Arg
            20

<210> SEQ ID NO 55
<211> LENGTH: 19
<212> TYPE: PRT
<213> ORGANISM: Yersinia enterocolitica

<400> SEQUENCE: 55

Leu Phe Thr Asp Ser Phe Ala Ser His Leu Leu Thr Tyr Gly Thr Glu
1               5                   10                  15

Ala Tyr Lys

<210> SEQ ID NO 56
<211> LENGTH: 21
<212> TYPE: PRT
<213> ORGANISM: Yersinia enterocolitica

<400> SEQUENCE: 56

Val Ser Ser Ser Gly Thr Pro Gln Ala Gly Tyr Gly Val Asn Asp Phe
1               5                   10                  15

Tyr Val Ser Tyr Lys
            20

<210> SEQ ID NO 57
<211> LENGTH: 22
<212> TYPE: PRT
<213> ORGANISM: Yersinia enterocolitica

<400> SEQUENCE: 57

Gly Ala Val Ser Val Thr Pro Thr Asp Trp Leu Met Leu Phe Gly Ser
1               5                   10                  15

Tyr Ala Gln Ala Phe Arg
            20

<210> SEQ ID NO 58
<211> LENGTH: 30
<212> TYPE: PRT
<213> ORGANISM: Yersinia enterocolitica

<400> SEQUENCE: 58

Ser Ser Phe Glu Ala Pro Met Met Val Thr Val Val Glu Ala Asp Thr
1               5                   10                  15

Pro Thr Ser Glu Thr Ala Thr Ser Ala Thr Asp Met Leu Arg
            20                  25                  30

<210> SEQ ID NO 59
<211> LENGTH: 9
<212> TYPE: PRT
<213> ORGANISM: Yersinia enterocolitica

<400> SEQUENCE: 59

Asn Asp Ala Ser Val Gln Asn Val Arg
1               5

<210> SEQ ID NO 60
<211> LENGTH: 10
<212> TYPE: PRT
<213> ORGANISM: Yersinia enterocolitica

<400> SEQUENCE: 60

Ile Gly Phe Leu Gly Gln Gln Asp Ala Arg
1 5 10

<210> SEQ ID NO 61
<211> LENGTH: 10
<212> TYPE: PRT
<213> ORGANISM: Yersinia enterocolitica

<400> SEQUENCE: 61

Val Asn Leu Gly Tyr Ala Ala Asn Tyr Arg
1 5 10

<210> SEQ ID NO 62
<211> LENGTH: 10
<212> TYPE: PRT
<213> ORGANISM: Yersinia enterocolitica

<400> SEQUENCE: 62

Gly Tyr Gly Asn Pro Ser Gln Asn Tyr Arg
1 5 10

<210> SEQ ID NO 63
<211> LENGTH: 10
<212> TYPE: PRT
<213> ORGANISM: Yersinia enterocolitica

<400> SEQUENCE: 63

Tyr Gly Asp Asp Asp Gln Phe Gly Val Arg
1 5 10

<210> SEQ ID NO 64
<211> LENGTH: 11
<212> TYPE: PRT
<213> ORGANISM: Yersinia enterocolitica

<400> SEQUENCE: 64

Gly His Phe Asp Thr Gly Pro Ile Thr His Lys
1 5 10

<210> SEQ ID NO 65
<211> LENGTH: 11
<212> TYPE: PRT
<213> ORGANISM: Yersinia enterocolitica

<400> SEQUENCE: 65

Leu Leu Ala Ser Ala Thr Trp Leu Asp Pro Lys
1 5 10

<210> SEQ ID NO 66
<211> LENGTH: 12
<212> TYPE: PRT
<213> ORGANISM: Yersinia enterocolitica

<400> SEQUENCE: 66

Asn Val Pro Phe Asn Val Ile Gly Tyr Thr Ser Lys
1 5 10

<210> SEQ ID NO 67
<211> LENGTH: 12

<212> TYPE: PRT
<213> ORGANISM: Yersinia enterocolitica

<400> SEQUENCE: 67

Leu Lys Pro Trp Thr Arg Leu Asp Leu Gly Val Arg
1 5 10

<210> SEQ ID NO 68
<211> LENGTH: 15
<212> TYPE: PRT
<213> ORGANISM: Yersinia enterocolitica

<400> SEQUENCE: 68

Val Ser Leu Tyr Ala Asn His Ile Glu Ala Leu Gly Pro Gly Lys
1 5 10 15

<210> SEQ ID NO 69
<211> LENGTH: 15
<212> TYPE: PRT
<213> ORGANISM: Yersinia enterocolitica

<400> SEQUENCE: 69

Gly Ile Glu Leu Asn Val Phe Gly Glu Pro Val Phe Gly Thr Arg
1 5 10 15

<210> SEQ ID NO 70
<211> LENGTH: 15
<212> TYPE: PRT
<213> ORGANISM: Yersinia enterocolitica

<400> SEQUENCE: 70

Thr Asn Asp Thr Ile Thr Val Val Gly Ala Gln Glu Thr Phe Arg
1 5 10 15

<210> SEQ ID NO 71
<211> LENGTH: 14
<212> TYPE: PRT
<213> ORGANISM: Yersinia enterocolitica

<400> SEQUENCE: 71

Val Thr Pro Ile Tyr Gly Ile Met Val Lys Pro Trp Glu Lys
1 5 10

<210> SEQ ID NO 72
<211> LENGTH: 17
<212> TYPE: PRT
<213> ORGANISM: Yersinia enterocolitica

<400> SEQUENCE: 72

Asn Phe Asp Ser Gly Val Pro Asn Ser Ala Gly Ser Leu Asp Ala Met
1 5 10 15

Lys

<210> SEQ ID NO 73
<211> LENGTH: 17
<212> TYPE: PRT
<213> ORGANISM: Yersinia enterocolitica

<400> SEQUENCE: 73

Leu Tyr Val Pro Tyr Val Ala Asp Ser Val Ala Gly Leu Gly Gly Ile
1 5 10 15

Arg

-continued

```
<210> SEQ ID NO 74
<211> LENGTH: 19
<212> TYPE: PRT
<213> ORGANISM: Yersinia enterocolitica

<400> SEQUENCE: 74

Val Thr Val Asp Tyr Gly Ser Ala Ser Gln Val Gly Gly Ala Leu Asp
1               5                   10                  15

Val Gly Arg

<210> SEQ ID NO 75
<211> LENGTH: 20
<212> TYPE: PRT
<213> ORGANISM: Yersinia enterocolitica

<400> SEQUENCE: 75

Ala Gly Gly Asn Asp Leu Ile Pro Thr Tyr Leu Asp Gly Gln Val Ala
1               5                   10                  15

Asn Gly Gly Arg
            20

<210> SEQ ID NO 76
<211> LENGTH: 19
<212> TYPE: PRT
<213> ORGANISM: Yersinia enterocolitica

<400> SEQUENCE: 76

Ser Glu Tyr Asp Val Ser Gln Asn Trp Thr Val Tyr Gly Ser Val Gly
1               5                   10                  15

Ala Ser Arg

<210> SEQ ID NO 77
<211> LENGTH: 20
<212> TYPE: PRT
<213> ORGANISM: Yersinia enterocolitica

<400> SEQUENCE: 77

Gly Tyr Asn Leu Asp Gly Asp Asp Ile Ser Phe Gly Gly Leu Phe Gly
1               5                   10                  15

Val Leu Pro Arg
            20

<210> SEQ ID NO 78
<211> LENGTH: 19
<212> TYPE: PRT
<213> ORGANISM: Yersinia enterocolitica

<400> SEQUENCE: 78

Ser Gly Ser Gln Tyr Ala Asn Glu Ala Asn Thr Leu Lys Leu Lys Pro
1               5                   10                  15

Trp Thr Arg

<210> SEQ ID NO 79
<211> LENGTH: 25
<212> TYPE: PRT
<213> ORGANISM: Yersinia enterocolitica

<400> SEQUENCE: 79

Gly Ala Asn Ala Phe Ile Asn Gly Ile Ser Pro Ser Gly Ser Gly Val
1               5                   10                  15

Gly Gly Met Ile Asn Leu Glu Pro Lys
            20                  25
```

<210> SEQ ID NO 80
<211> LENGTH: 23
<212> TYPE: PRT
<213> ORGANISM: Yersinia enterocolitica

<400> SEQUENCE: 80

Asn Glu Glu Thr Gly Gln Tyr Gly Ala Pro Met Leu Thr Asn Asn Asn
1 5 10 15

Gly Asp Ala Thr Ile Ser Arg
20

<210> SEQ ID NO 81
<211> LENGTH: 24
<212> TYPE: PRT
<213> ORGANISM: Yersinia enterocolitica

<400> SEQUENCE: 81

Ser Ala Pro Tyr Gln Tyr Asn Gly Lys Pro Val Val Asn Ala Gly Gln
1 5 10 15

Ile Pro Gly Ile Ile His Ser Lys
20

<210> SEQ ID NO 82
<211> LENGTH: 31
<212> TYPE: PRT
<213> ORGANISM: Yersinia enterocolitica

<400> SEQUENCE: 82

Tyr Gly Gly Thr Leu Ala Leu Phe Glu Ile Thr Arg Pro Thr Gly Met
1 5 10 15

Val Asp Pro Ala Thr Asn Val Tyr Gly Phe Tyr Gly Glu Gln Arg
20 25 30

<210> SEQ ID NO 83
<211> LENGTH: 7
<212> TYPE: PRT
<213> ORGANISM: Yersinia enterocolitica

<400> SEQUENCE: 83

Tyr Asp Thr Val Ala Leu Arg
1 5

<210> SEQ ID NO 84
<211> LENGTH: 9
<212> TYPE: PRT
<213> ORGANISM: Yersinia enterocolitica

<400> SEQUENCE: 84

Val Leu Leu Gly Val Asp Phe Gln Lys
1 5

<210> SEQ ID NO 85
<211> LENGTH: 8
<212> TYPE: PRT
<213> ORGANISM: Yersinia enterocolitica

<400> SEQUENCE: 85

Phe Asp Asp Val Trp Ser Phe Arg
1 5

<210> SEQ ID NO 86
<211> LENGTH: 10

```
<212> TYPE: PRT
<213> ORGANISM: Yersinia enterocolitica

<400> SEQUENCE: 86

Ser Val Gln Ala Thr Val Gly Tyr Asp Phe
1 5 10

<210> SEQ ID NO 87
<211> LENGTH: 11
<212> TYPE: PRT
<213> ORGANISM: Yersinia enterocolitica

<400> SEQUENCE: 87

Ala Asp Leu Gly Thr Trp Ala Ala Ser Leu Lys
1 5 10

<210> SEQ ID NO 88
<211> LENGTH: 10
<212> TYPE: PRT
<213> ORGANISM: Yersinia enterocolitica

<400> SEQUENCE: 88

Gln Trp Ala Asp Asp Ala Asn Thr Leu Arg
1 5 10

<210> SEQ ID NO 89
<211> LENGTH: 11
<212> TYPE: PRT
<213> ORGANISM: Yersinia enterocolitica

<400> SEQUENCE: 89

Val Asn Ser Gln Gly Leu Glu Leu Glu Ala Arg
1 5 10

<210> SEQ ID NO 90
<211> LENGTH: 12
<212> TYPE: PRT
<213> ORGANISM: Yersinia enterocolitica

<400> SEQUENCE: 90

Ala Val Pro Ala Thr Tyr Tyr Val Pro Ala Gly Lys
1 5 10

<210> SEQ ID NO 91
<211> LENGTH: 11
<212> TYPE: PRT
<213> ORGANISM: Yersinia enterocolitica

<400> SEQUENCE: 91

Leu Ser Val Ile Ala Gly Tyr Thr Tyr Asn Arg
1 5 10

<210> SEQ ID NO 92
<211> LENGTH: 12
<212> TYPE: PRT
<213> ORGANISM: Yersinia enterocolitica

<400> SEQUENCE: 92

Val Pro Ser Tyr Thr Leu Gly Asp Ala Ser Val Arg
1 5 10

<210> SEQ ID NO 93
<211> LENGTH: 11
<212> TYPE: PRT
<213> ORGANISM: Yersinia enterocolitica

```
<400> SEQUENCE: 93

Arg Pro Gln Phe Thr Ser Glu Gly His Phe Arg
1               5                   10

<210> SEQ ID NO 94
<211> LENGTH: 13
<212> TYPE: PRT
<213> ORGANISM: Yersinia enterocolitica

<400> SEQUENCE: 94

Gly Phe Phe Asp Gly Glu Ser Asn His Asn Val Phe Lys
1               5                   10

<210> SEQ ID NO 95
<211> LENGTH: 14
<212> TYPE: PRT
<213> ORGANISM: Yersinia enterocolitica

<400> SEQUENCE: 95

Gly Ala Phe Val Gln Leu Asn Val Asn Asn Ile Ala Asp Lys
1               5                   10

<210> SEQ ID NO 96
<211> LENGTH: 12
<212> TYPE: PRT
<213> ORGANISM: Yersinia enterocolitica

<400> SEQUENCE: 96

Trp Gln Gln Ile Tyr Ser Tyr Glu Phe Ser His Lys
1               5                   10

<210> SEQ ID NO 97
<211> LENGTH: 14
<212> TYPE: PRT
<213> ORGANISM: Yersinia enterocolitica

<400> SEQUENCE: 97

Gly Phe Phe Asp Gly Glu Ser Asn His Asn Val Phe Lys Arg
1               5                   10

<210> SEQ ID NO 98
<211> LENGTH: 16
<212> TYPE: PRT
<213> ORGANISM: Yersinia enterocolitica

<400> SEQUENCE: 98

Gly Phe His Gly Gly Asp Val Asn Asn Thr Phe Leu Asp Gly Leu Arg
1               5                   10                  15

<210> SEQ ID NO 99
<211> LENGTH: 13
<212> TYPE: PRT
<213> ORGANISM: Yersinia enterocolitica

<400> SEQUENCE: 99

Arg Trp Gln Gln Ile Tyr Ser Tyr Glu Phe Ser His Lys
1               5                   10

<210> SEQ ID NO 100
<211> LENGTH: 18
<212> TYPE: PRT
<213> ORGANISM: Yersinia enterocolitica

<400> SEQUENCE: 100
```

Ala Gly His Glu Ala Asp Leu Pro Thr Ser Gly Tyr Thr Ala Thr Thr
1               5                   10                  15

Thr Lys

<210> SEQ ID NO 101
<211> LENGTH: 17
<212> TYPE: PRT
<213> ORGANISM: Yersinia enterocolitica

<400> SEQUENCE: 101

Thr Asp Gln Pro Leu Ile Leu Thr Ala Gln Ser Val Ser Val Val Thr
1               5                   10                  15

Arg

<210> SEQ ID NO 102
<211> LENGTH: 20
<212> TYPE: PRT
<213> ORGANISM: Yersinia enterocolitica

<400> SEQUENCE: 102

Asp Pro Ser Gly Gly Tyr His Ser Ala Val Pro Ala Asp Gly Ser Ile
1               5                   10                  15

Tyr Gly Gln Lys
            20

<210> SEQ ID NO 103
<211> LENGTH: 21
<212> TYPE: PRT
<213> ORGANISM: Yersinia enterocolitica

<400> SEQUENCE: 103

Gly Pro Ser Ser Ala Leu Tyr Gly Gln Ser Ile Pro Gly Gly Val Val
1               5                   10                  15

Met Met Thr Ser Lys
            20

<210> SEQ ID NO 104
<211> LENGTH: 18
<212> TYPE: PRT
<213> ORGANISM: Yersinia enterocolitica

<400> SEQUENCE: 104

Lys Tyr Val Ala Ala Cys Tyr Ser Thr Ser Tyr Cys Tyr Trp Gly Ala
1               5                   10                  15

Glu Arg

<210> SEQ ID NO 105
<211> LENGTH: 20
<212> TYPE: PRT
<213> ORGANISM: Yersinia enterocolitica

<400> SEQUENCE: 105

Tyr Ala Ile Ala Pro Ser Leu Leu Trp Gln Pro Asp Glu Asn Thr Ser
1               5                   10                  15

Leu Leu Leu Arg
            20

<210> SEQ ID NO 106
<211> LENGTH: 20
<212> TYPE: PRT
<213> ORGANISM: Yersinia enterocolitica

```
<400> SEQUENCE: 106

Leu Leu Ser Asp Gly Gly Ser Tyr Asn Val Leu Gln Val Asp Pro Trp
1               5                   10                  15

Phe Leu Glu Arg
            20

<210> SEQ ID NO 107
<211> LENGTH: 24
<212> TYPE: PRT
<213> ORGANISM: Yersinia enterocolitica

<400> SEQUENCE: 107

Gln Asn Ala Ser Tyr Thr His Ser Asn Thr Gln Leu Glu Gln Val Tyr
1               5                   10                  15

Gln Gly Gly Trp Asn Ser Asp Arg
            20

<210> SEQ ID NO 108
<211> LENGTH: 26
<212> TYPE: PRT
<213> ORGANISM: Yersinia enterocolitica

<400> SEQUENCE: 108

Leu Thr Ala Gly Asn Asn Asn Thr Gln Val Ala Ala Phe Asp Tyr Thr
1               5                   10                  15

Asp Ala Ile Ser Glu His Trp Ala Phe Arg
            20                  25

<210> SEQ ID NO 109
<211> LENGTH: 25
<212> TYPE: PRT
<213> ORGANISM: Yersinia enterocolitica

<400> SEQUENCE: 109

Arg Tyr Glu Gln Ser Gly Val Tyr Leu Gln Asp Glu Met Thr Leu Asp
1               5                   10                  15

Asn Trp His Leu Asn Leu Ser Gly Arg
            20                  25

<210> SEQ ID NO 110
<211> LENGTH: 31
<212> TYPE: PRT
<213> ORGANISM: Yersinia enterocolitica

<400> SEQUENCE: 110

Gln Gln Met Asp Asp Gln Asn Val Ala Thr Val Asn Gln Ala Leu Asn
1               5                   10                  15

Tyr Thr Pro Gly Val Phe Thr Gly Phe Ser Gly Gly Ala Thr Arg
            20                  25                  30

<210> SEQ ID NO 111
<211> LENGTH: 6
<212> TYPE: PRT
<213> ORGANISM: Yersinia enterocolitica

<400> SEQUENCE: 111

Val Pro Phe Val Pro Arg
1               5

<210> SEQ ID NO 112
<211> LENGTH: 7
```

<212> TYPE: PRT
<213> ORGANISM: Yersinia enterocolitica

<400> SEQUENCE: 112

Thr Val Gly Ile Asn Thr Arg
1 5

<210> SEQ ID NO 113
<211> LENGTH: 7
<212> TYPE: PRT
<213> ORGANISM: Yersinia enterocolitica

<400> SEQUENCE: 113

Tyr Gly Ala Leu Met Pro Arg
1 5

<210> SEQ ID NO 114
<211> LENGTH: 8
<212> TYPE: PRT
<213> ORGANISM: Yersinia enterocolitica

<400> SEQUENCE: 114

Phe Asp Ile Gly Gly Gly Val Arg
1 5

<210> SEQ ID NO 115
<211> LENGTH: 9
<212> TYPE: PRT
<213> ORGANISM: Yersinia enterocolitica

<400> SEQUENCE: 115

Gly Pro Gln Gly Thr Leu Tyr Gly Lys
1 5

<210> SEQ ID NO 116
<211> LENGTH: 10
<212> TYPE: PRT
<213> ORGANISM: Yersinia enterocolitica

<400> SEQUENCE: 116

Gly Tyr Ile Glu Gly Gly Val Ser Ser Arg
1 5 10

<210> SEQ ID NO 117
<211> LENGTH: 9
<212> TYPE: PRT
<213> ORGANISM: Yersinia enterocolitica

<400> SEQUENCE: 117

Ser Ile Asn Tyr Glu Leu Gly Thr Arg
1 5

<210> SEQ ID NO 118
<211> LENGTH: 9
<212> TYPE: PRT
<213> ORGANISM: Yersinia enterocolitica

<400> SEQUENCE: 118

Trp Asn Gln Asp Val Gln Glu Leu Arg
1 5

<210> SEQ ID NO 119
<211> LENGTH: 10
<212> TYPE: PRT
<213> ORGANISM: Yersinia enterocolitica

<400> SEQUENCE: 119

Thr Val Asp Met Val Phe Gly Leu Tyr Arg
1               5                   10

<210> SEQ ID NO 120
<211> LENGTH: 14
<212> TYPE: PRT
<213> ORGANISM: Yersinia enterocolitica

<400> SEQUENCE: 120

Tyr Gly Ala Gly Ser Ser Val Asn Gly Val Ile Asp Thr Arg
1               5                   10

<210> SEQ ID NO 121
<211> LENGTH: 13
<212> TYPE: PRT
<213> ORGANISM: Yersinia enterocolitica

<400> SEQUENCE: 121

Leu Ser Leu Ser Asp Gly Ser Pro Asp Pro Tyr Met Arg
1 5 10

<210> SEQ ID NO 122
<211> LENGTH: 13
<212> TYPE: PRT
<213> ORGANISM: Yersinia enterocolitica

<400> SEQUENCE: 122

Ala Thr Gln Asp Ala Tyr Val Gly Trp Asn Asp Ile Lys
1 5 10

<210> SEQ ID NO 123
<211> LENGTH: 13
<212> TYPE: PRT
<213> ORGANISM: Yersinia enterocolitica

<400> SEQUENCE: 123

Ile Asn Ile Ser Val His Val Asp Asn Leu Phe Asp Arg
1 5 10

<210> SEQ ID NO 124
<211> LENGTH: 14
<212> TYPE: PRT
<213> ORGANISM: Yersinia enterocolitica

<400> SEQUENCE: 124

Thr Phe Pro Ser Gly Ser Leu Ile Val Asn Met Pro Gln Arg
1 5 10

<210> SEQ ID NO 125
<211> LENGTH: 14
<212> TYPE: PRT
<213> ORGANISM: Yersinia enterocolitica

<400> SEQUENCE: 125

Lys Leu Ser Leu Ser Asp Gly Ser Pro Asp Pro Tyr Met Arg
1 5 10

<210> SEQ ID NO 126
<211> LENGTH: 14
<212> TYPE: PRT
<213> ORGANISM: Yersinia enterocolitica

<400> SEQUENCE: 126

```
Ser Glu Phe Thr Asn Asp Ser Glu Leu Tyr His Gly Asn Arg
1               5                   10
```

<210> SEQ ID NO 127
<211> LENGTH: 15
<212> TYPE: PRT
<213> ORGANISM: Yersinia enterocolitica

<400> SEQUENCE: 127

```
Phe Ala Pro Gly Trp Ser Trp Asp Ile Asn Gly Asn Val Ile Arg
1               5                   10                  15
```

<210> SEQ ID NO 128
<211> LENGTH: 16
<212> TYPE: PRT
<213> ORGANISM: Yersinia enterocolitica

<400> SEQUENCE: 128

```
Leu Ala Pro Asp Asp Gln Pro Trp Glu Met Gly Phe Ala Ala Ser Arg
1               5                   10                  15
```

<210> SEQ ID NO 129
<211> LENGTH: 18
<212> TYPE: PRT
<213> ORGANISM: Yersinia enterocolitica

<400> SEQUENCE: 129

```
Thr Tyr Gly Tyr Met Asn Gly Ser Ser Ala Val Ala Gln Val Asn Met
1               5                   10                  15

Gly Arg
```

<210> SEQ ID NO 130
<211> LENGTH: 19
<212> TYPE: PRT
<213> ORGANISM: Yersinia enterocolitica

<400> SEQUENCE: 130

```
Ser Ala Gln Gly Gly Ile Ile Asn Ile Val Thr Gln Gln Pro Asp Ser
1               5                   10                  15

Thr Pro Arg
```

<210> SEQ ID NO 131
<211> LENGTH: 18
<212> TYPE: PRT
<213> ORGANISM: Yersinia enterocolitica

<400> SEQUENCE: 131

```
Gln Gly Thr Tyr Ala Thr Leu Asp Ser Ser Leu Gly Trp Gln Ala Thr
1               5                   10                  15

Glu Arg
```

<210> SEQ ID NO 132
<211> LENGTH: 19
<212> TYPE: PRT
<213> ORGANISM: Yersinia enterocolitica

<400> SEQUENCE: 132

```
Asp Met Gln Leu Tyr Ser Gly Pro Val Gly Met Gln Thr Leu Ser Asn
1               5                   10                  15

Ala Gly Lys
```

<210> SEQ ID NO 133
<211> LENGTH: 19
<212> TYPE: PRT
<213> ORGANISM: Yersinia enterocolitica

<400> SEQUENCE: 133

Ser Ser Thr Gln Tyr His Gly Ser Met Leu Gly Asn Pro Phe Gly Asp
1               5                   10                  15

Gln Gly Lys

<210> SEQ ID NO 134
<211> LENGTH: 18
<212> TYPE: PRT
<213> ORGANISM: Yersinia enterocolitica

<400> SEQUENCE: 134

Leu Ala Val Asn Leu Val Gly Pro His Tyr Phe Asp Gly Asp Asn Gln
1               5                   10                  15

Leu Arg

<210> SEQ ID NO 135
<211> LENGTH: 18
<212> TYPE: PRT
<213> ORGANISM: Yersinia enterocolitica

<400> SEQUENCE: 135

Leu Arg Leu Ala Pro Asp Asp Gln Pro Trp Glu Met Gly Phe Ala Ala
1               5                   10                  15

Ser Arg

<210> SEQ ID NO 136
<211> LENGTH: 21
<212> TYPE: PRT
<213> ORGANISM: Yersinia enterocolitica

<400> SEQUENCE: 136

Gln Val Asp Asp Gly Asp Met Ile Asn Pro Ala Thr Gly Ser Asp Asp
1               5                   10                  15

Leu Gly Gly Thr Arg
            20

<210> SEQ ID NO 137
<211> LENGTH: 20
<212> TYPE: PRT
<213> ORGANISM: Yersinia enterocolitica

<400> SEQUENCE: 137

Phe Asn Leu Ser Gly Pro Ile Gln Asp Gly Leu Leu Tyr Gly Ser Val
1               5                   10                  15

Thr Leu Leu Arg
            20

<210> SEQ ID NO 138
<211> LENGTH: 21
<212> TYPE: PRT
<213> ORGANISM: Yersinia enterocolitica

<400> SEQUENCE: 138

Val Leu Pro Gly Leu Asn Ile Glu Asn Ser Gly Asn Met Leu Phe Ser
1               5                   10                  15

Thr Ile Ser Leu Arg
            20

<210> SEQ ID NO 139
<211> LENGTH: 20
<212> TYPE: PRT
<213> ORGANISM: Yersinia enterocolitica

<400> SEQUENCE: 139

Ser Glu Phe Thr Asn Asp Ser Glu Leu Tyr His Gly Asn Arg Val Pro
1               5                   10                  15

Phe Val Pro Arg
            20

<210> SEQ ID NO 140
<211> LENGTH: 22
<212> TYPE: PRT
<213> ORGANISM: Yersinia enterocolitica

<400> SEQUENCE: 140

Ser Lys Phe Asn Leu Ser Gly Pro Ile Gln Asp Gly Leu Leu Tyr Gly
1               5                   10                  15

Ser Val Thr Leu Leu Arg
            20

<210> SEQ ID NO 141
<211> LENGTH: 21
<212> TYPE: PRT
<213> ORGANISM: Yersinia enterocolitica

<400> SEQUENCE: 141

Ser Asn Asp Asp Gln Val Leu Gly Gln Leu Ser Ala Gly Tyr Met Leu
1               5                   10                  15

Thr Asp Asp Trp Arg
            20

<210> SEQ ID NO 142
<211> LENGTH: 27
<212> TYPE: PRT
<213> ORGANISM: Yersinia enterocolitica

<400> SEQUENCE: 142

Ser Ala Ser Ala Asn Asn Val Ser Ser Thr Val Val Ser Ala Pro Glu
1               5                   10                  15

Leu Ser Asp Ala Gly Val Thr Ala Ser Asp Lys
            20                  25

<210> SEQ ID NO 143
<211> LENGTH: 21
<212> TYPE: PRT
<213> ORGANISM: Yersinia enterocolitica

<400> SEQUENCE: 143

Tyr Thr Thr Asp Asp Trp Val Phe Asn Leu Ile Ser Ala Trp Gln Gln
1               5                   10                  15

Gln His Tyr Ser Arg
            20

<210> SEQ ID NO 144
<211> LENGTH: 27
<212> TYPE: PRT
<213> ORGANISM: Yersinia enterocolitica

<400> SEQUENCE: 144

-continued

Ile Ala Gln Gly Tyr Lys Pro Ser Gly Tyr Asn Ile Val Pro Thr Ala
1               5                   10                  15

Gly Leu Asp Ala Lys Pro Phe Val Ala Glu Lys
            20                  25

<210> SEQ ID NO 145
<211> LENGTH: 30
<212> TYPE: PRT
<213> ORGANISM: Yersinia enterocolitica

<400> SEQUENCE: 145

Ser Ala Ser Ala Asn Asn Val Ser Ser Thr Val Ser Ala Pro Glu
1               5                   10                  15

Leu Ser Asp Ala Gly Val Thr Ala Ser Asp Lys Leu Pro Arg
            20                  25                  30

<210> SEQ ID NO 146
<211> LENGTH: 8
<212> TYPE: PRT
<213> ORGANISM: Yersinia enterocolitica

<400> SEQUENCE: 146

Val Ser Gly Leu Leu Ser His Arg
1               5

<210> SEQ ID NO 147
<211> LENGTH: 7
<212> TYPE: PRT
<213> ORGANISM: Yersinia enterocolitica

<400> SEQUENCE: 147

Thr Ser Glu Tyr Leu Asn Arg
1               5

<210> SEQ ID NO 148
<211> LENGTH: 7
<212> TYPE: PRT
<213> ORGANISM: Yersinia enterocolitica

<400> SEQUENCE: 148

Glu Trp His Gly Thr Val Arg
1               5

<210> SEQ ID NO 149
<211> LENGTH: 9
<212> TYPE: PRT
<213> ORGANISM: Yersinia enterocolitica

<400> SEQUENCE: 149

Tyr Thr Leu Ile Leu Val Asp Gly Lys
1               5

<210> SEQ ID NO 150
<211> LENGTH: 9
<212> TYPE: PRT
<213> ORGANISM: Yersinia enterocolitica

<400> SEQUENCE: 150

Arg Val Asp Ile Glu Val Asn Asp Lys
1               5

<210> SEQ ID NO 151
<211> LENGTH: 10
<212> TYPE: PRT

<213> ORGANISM: Yersinia enterocolitica

<400> SEQUENCE: 151

Val Gly Lys Glu Trp His Gly Thr Val Arg
1 5 10

<210> SEQ ID NO 152
<211> LENGTH: 10
<212> TYPE: PRT
<213> ORGANISM: Yersinia enterocolitica

<400> SEQUENCE: 152

Tyr Thr Leu Ile Leu Val Asp Gly Lys Arg
1 5 10

<210> SEQ ID NO 153
<211> LENGTH: 11
<212> TYPE: PRT
<213> ORGANISM: Yersinia enterocolitica

<400> SEQUENCE: 153

Leu Met Gly Gly Val Tyr Asn Val Leu Asp Lys
1 5 10

<210> SEQ ID NO 154
<211> LENGTH: 13
<212> TYPE: PRT
<213> ORGANISM: Yersinia enterocolitica

<400> SEQUENCE: 154

Ile Gln Asp Ser Ala Ala Ser Ile Ser Val Val Thr Arg
1 5 10

<210> SEQ ID NO 155
<211> LENGTH: 14
<212> TYPE: PRT
<213> ORGANISM: Yersinia enterocolitica

<400> SEQUENCE: 155

Met Asp Gln Asp Glu Asn Tyr Gly Thr His Trp Thr Pro Arg
1 5 10

<210> SEQ ID NO 156
<211> LENGTH: 14
<212> TYPE: PRT
<213> ORGANISM: Yersinia enterocolitica

<400> SEQUENCE: 156

Asn Glu Phe Asp Phe Asp Ile Gly His Tyr Val Gln Asp Arg
1 5 10

<210> SEQ ID NO 157
<211> LENGTH: 19
<212> TYPE: PRT
<213> ORGANISM: Yersinia enterocolitica

<400> SEQUENCE: 157

Asp Val Pro Gly Val Val Val Thr Gly Gly Gly Ser His Ser Asp Ile
1 5 10 15

Ser Ile Arg

<210> SEQ ID NO 158
<211> LENGTH: 24
<212> TYPE: PRT

<213> ORGANISM: Yersinia enterocolitica

<400> SEQUENCE: 158

```
Gly Thr Arg Pro Asn Ser Asp Gly Ser Gly Ile Glu Gln Gly Trp Leu
1               5                   10                  15

Pro Pro Leu Ala Ala Ile Glu Arg
            20
```

<210> SEQ ID NO 159
<211> LENGTH: 22
<212> TYPE: PRT
<213> ORGANISM: Yersinia enterocolitica

<400> SEQUENCE: 159

```
Asn Asn Tyr Ala Ile Thr His His Gly Tyr Tyr Asp Phe Gly Asn Ser
1               5                   10                  15

Thr Ser Tyr Val Gln Arg
            20
```

<210> SEQ ID NO 160
<211> LENGTH: 29
<212> TYPE: PRT
<213> ORGANISM: Yersinia enterocolitica

<400> SEQUENCE: 160

```
Ala Tyr Thr Asp Ile Thr Asp Ala Leu Lys Asp Val Pro Gly Val Val
1               5                   10                  15

Val Thr Gly Gly Gly Ser His Ser Asp Ile Ser Ile Arg
            20                  25
```

<210> SEQ ID NO 161
<211> LENGTH: 27
<212> TYPE: PRT
<213> ORGANISM: Yersinia enterocolitica

<400> SEQUENCE: 161

```
Asn Gly Ala Ala Thr Phe Thr Leu Thr Pro Asp Asp Lys Asn Glu Phe
1               5                   10                  15

Asp Phe Asp Ile Gly His Tyr Val Gln Asp Arg
            20                  25
```

<210> SEQ ID NO 162
<211> LENGTH: 11
<212> TYPE: PRT
<213> ORGANISM: Yersinia enterocolitica

<400> SEQUENCE: 162

```
Val Asn Phe Thr Ala Gly Val Gly Gly Tyr Arg
1               5                   10
```

<210> SEQ ID NO 163
<211> LENGTH: 12
<212> TYPE: PRT
<213> ORGANISM: Yersinia enterocolitica

<400> SEQUENCE: 163

```
Ser Ser Gln Ala Leu Ala Ile Gly Ser Gly Tyr Arg
1               5                   10
```

<210> SEQ ID NO 164
<211> LENGTH: 12
<212> TYPE: PRT
<213> ORGANISM: Yersinia enterocolitica

<400> SEQUENCE: 164

Asn Ser Val Ser Ile Gly His Glu Ser Leu Asn Arg
1               5                   10

<210> SEQ ID NO 165
<211> LENGTH: 15
<212> TYPE: PRT
<213> ORGANISM: Yersinia enterocolitica

<400> SEQUENCE: 165

Ala Ser Thr Ser Asp Thr Gly Val Ala Val Gly Phe Asn Ser Lys
1               5                   10                  15

<210> SEQ ID NO 166
<211> LENGTH: 13
<212> TYPE: PRT
<213> ORGANISM: Yersinia enterocolitica

<400> SEQUENCE: 166

Thr Thr Leu Glu Thr Ala Glu Glu His Thr Asn Lys Lys
1               5                   10

<210> SEQ ID NO 167
<211> LENGTH: 15
<212> TYPE: PRT
<213> ORGANISM: Yersinia enterocolitica

<400> SEQUENCE: 167

Ser Ala Glu Thr Leu Ala Ser Ala Asn Val Tyr Ala Asp Ser Lys
1               5                   10                  15

<210> SEQ ID NO 168
<211> LENGTH: 15
<212> TYPE: PRT
<213> ORGANISM: Yersinia enterocolitica

<400> SEQUENCE: 168

Ser Ala Glu Val Leu Gly Ile Ala Asn Asn Tyr Thr Asp Ser Lys
1               5                   10                  15

<210> SEQ ID NO 169
<211> LENGTH: 17
<212> TYPE: PRT
<213> ORGANISM: Yersinia enterocolitica

<400> SEQUENCE: 169

Ala Leu Gly Asp Ser Ala Val Thr Tyr Gly Ala Gly Ser Thr Ala Gln
1               5                   10                  15

Lys

<210> SEQ ID NO 170
<211> LENGTH: 7
<212> TYPE: PRT
<213> ORGANISM: Yersinia enterocolitica

<400> SEQUENCE: 170

Leu Gly Phe Ala Gly Leu Lys
1               5

<210> SEQ ID NO 171
<211> LENGTH: 9
<212> TYPE: PRT
<213> ORGANISM: Yersinia enterocolitica

<400> SEQUENCE: 171

Ala Asp Ala Tyr Ser Gly Gly Leu Lys
1               5

<210> SEQ ID NO 172
<211> LENGTH: 8
<212> TYPE: PRT
<213> ORGANISM: Yersinia enterocolitica

<400> SEQUENCE: 172

Asp Gly Asp Gln Ser Tyr Met Arg
1               5

<210> SEQ ID NO 173
<211> LENGTH: 10
<212> TYPE: PRT
<213> ORGANISM: Yersinia enterocolitica

<400> SEQUENCE: 173

Asp Gly Asn Lys Leu Asp Leu Tyr Gly Lys
1               5                   10

<210> SEQ ID NO 174
<211> LENGTH: 11
<212> TYPE: PRT
<213> ORGANISM: Yersinia enterocolitica

<400> SEQUENCE: 174

Ala Glu Asp Gln Asp Gln Gly Asn Phe Thr Arg
1               5                   10

<210> SEQ ID NO 175
<211> LENGTH: 11
<212> TYPE: PRT
<213> ORGANISM: Yersinia enterocolitica

<400> SEQUENCE: 175

Val Asp Gly Leu His Tyr Phe Ser Asp Asp Lys
1               5                   10

<210> SEQ ID NO 176
<211> LENGTH: 11
<212> TYPE: PRT
<213> ORGANISM: Yersinia enterocolitica

<400> SEQUENCE: 176

Ile Asn Leu Leu Asp Glu Asn Glu Phe Thr Lys
1               5                   10

<210> SEQ ID NO 177
<211> LENGTH: 13
<212> TYPE: PRT
<213> ORGANISM: Yersinia enterocolitica

<400> SEQUENCE: 177

Val Asp Gly Leu His Tyr Phe Ser Asp Asp Lys Ser Lys
1               5                   10

<210> SEQ ID NO 178
<211> LENGTH: 18
<212> TYPE: PRT
<213> ORGANISM: Yersinia enterocolitica

<400> SEQUENCE: 178

```
Asn Ala Gly Ile Asn Thr Asp Asp Ile Val Ala Val Gly Leu Val Tyr
1               5                   10                  15

Gln Phe

<210> SEQ ID NO 179
<211> LENGTH: 20
<212> TYPE: PRT
<213> ORGANISM: Yersinia enterocolitica

<400> SEQUENCE: 179

Asn Thr Asn Phe Phe Gly Leu Val Asp Gly Leu Asn Phe Ala Leu Gln
1               5                   10                  15

Tyr Gln Gly Lys
            20

<210> SEQ ID NO 180
<211> LENGTH: 20
<212> TYPE: PRT
<213> ORGANISM: Yersinia enterocolitica

<400> SEQUENCE: 180

Tyr Asp Ala Asn Asn Val Tyr Leu Ala Ala Thr Tyr Ala Gln Thr Tyr
1               5                   10                  15

Asn Leu Thr Arg
            20

<210> SEQ ID NO 181
<211> LENGTH: 23
<212> TYPE: PRT
<213> ORGANISM: Yersinia enterocolitica

<400> SEQUENCE: 181

Gly Glu Thr Gln Ile Ser Asp Gln Leu Thr Gly Tyr Gly Gln Trp Glu
1               5                   10                  15

Tyr Gln Ala Asn Leu Asn Lys
            20

<210> SEQ ID NO 182
<211> LENGTH: 26
<212> TYPE: PRT
<213> ORGANISM: Yersinia enterocolitica

<400> SEQUENCE: 182

Ala Gln Asn Ile Glu Leu Val Ala Gln Tyr Gln Phe Asp Phe Gly Leu
1               5                   10                  15

Arg Pro Ser Val Ala Tyr Leu Gln Ser Lys
            20                  25

<210> SEQ ID NO 183
<211> LENGTH: 27
<212> TYPE: PRT
<213> ORGANISM: Yersinia enterocolitica

<400> SEQUENCE: 183

Phe Gly Leu Lys Gly Glu Thr Gln Ile Ser Asp Gln Leu Thr Gly Tyr
1               5                   10                  15

Gly Gln Trp Glu Tyr Gln Ala Asn Leu Asn Lys
            20                  25

<210> SEQ ID NO 184
<211> LENGTH: 7
```

<212> TYPE: PRT
<213> ORGANISM: Yersinia enterocolitica

<400> SEQUENCE: 184

Thr Val Tyr Leu Gln Ile Lys
1               5

<210> SEQ ID NO 185
<211> LENGTH: 13
<212> TYPE: PRT
<213> ORGANISM: Yersinia enterocolitica
<220> FEATURE:
<221> NAME/KEY: MOD_RES
<222> LOCATION: (7)..(7)
<223> OTHER INFORMATION: Oxidized Met

<400> SEQUENCE: 185

Asn Thr Ser Asp Lys Asn Met Leu Gly Leu Ala Pro Lys
1               5                   10

<210> SEQ ID NO 186
<211> LENGTH: 14
<212> TYPE: PRT
<213> ORGANISM: Yersinia enterocolitica

<400> SEQUENCE: 186

Phe Glu Glu Ala Gln Pro Val Leu Glu Asp Gln Leu Ala Lys
1               5                   10

<210> SEQ ID NO 187
<211> LENGTH: 15
<212> TYPE: PRT
<213> ORGANISM: Yersinia enterocolitica
<220> FEATURE:
<221> NAME/KEY: MOD_RES
<222> LOCATION: (3)..(3)
<223> OTHER INFORMATION: Oxidized Met

<400> SEQUENCE: 187

Thr Gln Met Ser Glu Thr Ile Trp Leu Glu Pro Ser Ser Gln Lys
1               5                   10                  15

<210> SEQ ID NO 188
<211> LENGTH: 16
<212> TYPE: PRT
<213> ORGANISM: Yersinia enterocolitica

<400> SEQUENCE: 188

Val Gln Thr Ser Thr Gln Thr Gly Asn Lys His Gln Tyr Gln Thr Arg
1               5                   10                  15

<210> SEQ ID NO 189
<211> LENGTH: 18
<212> TYPE: PRT
<213> ORGANISM: Yersinia enterocolitica

<400> SEQUENCE: 189

Val Asn Leu Lys Phe Glu Glu Ala Gln Pro Val Leu Glu Asp Gln Leu
1               5                   10                  15

Ala Lys

<210> SEQ ID NO 190
<211> LENGTH: 21
<212> TYPE: PRT
<213> ORGANISM: Yersinia enterocolitica

```
<400> SEQUENCE: 190

Gly Tyr Thr Val Thr Ser Ser Pro Glu Asp Ala His Tyr Trp Ile Gln
1               5                   10                  15

Ala Asn Val Leu Lys
            20

<210> SEQ ID NO 191
<211> LENGTH: 6
<212> TYPE: PRT
<213> ORGANISM: Yersinia pestis

<400> SEQUENCE: 191

Ala Leu Ile Ser Leu Lys
1               5

<210> SEQ ID NO 192
<211> LENGTH: 5
<212> TYPE: PRT
<213> ORGANISM: Yersinia pestis

<400> SEQUENCE: 192

Ser Ile Tyr Phe Arg
1               5

<210> SEQ ID NO 193
<211> LENGTH: 7
<212> TYPE: PRT
<213> ORGANISM: Yersinia pestis

<400> SEQUENCE: 193

Ile Leu Ile Gly Glu Val Lys
1               5

<210> SEQ ID NO 194
<211> LENGTH: 7
<212> TYPE: PRT
<213> ORGANISM: Yersinia pestis

<400> SEQUENCE: 194

Asn Pro Val Ala Arg Glu Arg
1               5

<210> SEQ ID NO 195
<211> LENGTH: 8
<212> TYPE: PRT
<213> ORGANISM: Yersinia pestis

<400> SEQUENCE: 195

Ala Val Gln Asp Ile Ile Leu Lys
1               5

<210> SEQ ID NO 196
<211> LENGTH: 8
<212> TYPE: PRT
<213> ORGANISM: Yersinia pestis

<400> SEQUENCE: 196

Tyr Pro Leu Ile Ser Glu Leu Lys
1               5

<210> SEQ ID NO 197
<211> LENGTH: 10
<212> TYPE: PRT
<213> ORGANISM: Yersinia pestis
```

<400> SEQUENCE: 197

Asn Gly Ile Ile Phe Ser Pro His Pro Arg
1               5                   10

<210> SEQ ID NO 198
<211> LENGTH: 12
<212> TYPE: PRT
<213> ORGANISM: Yersinia pestis

<400> SEQUENCE: 198

Glu Ala Gly Val Gln Glu Ala Asp Phe Leu Ala Lys
1               5                   10

<210> SEQ ID NO 199
<211> LENGTH: 11
<212> TYPE: PRT
<213> ORGANISM: Yersinia pestis

<400> SEQUENCE: 199

Asn Phe Glu Glu Ala Val Glu Lys Ala Glu Lys
1               5                   10

<210> SEQ ID NO 200
<211> LENGTH: 12
<212> TYPE: PRT
<213> ORGANISM: Yersinia pestis

<400> SEQUENCE: 200

Val Val Asp Glu Ser Glu Pro Phe Ala His Glu Lys
1               5                   10

<210> SEQ ID NO 201
<211> LENGTH: 15
<212> TYPE: PRT
<213> ORGANISM: Yersinia pestis

<400> SEQUENCE: 201

Asn Gly Gly Leu Asn Ala Ala Ile Val Gly Gln Pro Ala Thr Lys
1               5                   10                  15

<210> SEQ ID NO 202
<211> LENGTH: 15
<212> TYPE: PRT
<213> ORGANISM: Yersinia pestis

<400> SEQUENCE: 202

Ala Ala Ala Leu Ala Ala Ala Asp Ala Arg Ile Pro Leu Ala Lys
1               5                   10                  15

<210> SEQ ID NO 203
<211> LENGTH: 14
<212> TYPE: PRT
<213> ORGANISM: Yersinia pestis

<400> SEQUENCE: 203

Ala Val Thr Asn Val Ala Glu Leu Asn Glu Leu Val Ala Arg
1               5                   10

<210> SEQ ID NO 204
<211> LENGTH: 13
<212> TYPE: PRT
<213> ORGANISM: Yersinia pestis

<400> SEQUENCE: 204

```
Gln Thr Ala Phe Ser Gln Tyr Asp Arg Pro Gln Ala Arg
1               5                   10
```

<210> SEQ ID NO 205
<211> LENGTH: 15
<212> TYPE: PRT
<213> ORGANISM: Yersinia pestis

<400> SEQUENCE: 205

```
Leu Leu Lys Glu Phe Leu Pro Ala Ser Tyr Asn Glu Gly Ala Lys
1               5                   10                  15
```

<210> SEQ ID NO 206
<211> LENGTH: 16
<212> TYPE: PRT
<213> ORGANISM: Yersinia pestis

<400> SEQUENCE: 206

```
Tyr Ala Glu Ile Ala Asp His Leu Gly Leu Ser Ala Pro Gly Asp Arg
1               5                   10                  15
```

<210> SEQ ID NO 207
<211> LENGTH: 17
<212> TYPE: PRT
<213> ORGANISM: Yersinia pestis

<400> SEQUENCE: 207

```
Gly Ser Leu Pro Ile Ala Leu Glu Glu Val Ala Thr Asp Gly Ala Lys
1               5                   10                  15

Arg
```

<210> SEQ ID NO 208
<211> LENGTH: 15
<212> TYPE: PRT
<213> ORGANISM: Yersinia pestis

<400> SEQUENCE: 208

```
Glu Tyr Ala Asn Phe Ser Gln Glu Gln Val Asp Lys Ile Phe Arg
1               5                   10                  15
```

<210> SEQ ID NO 209
<211> LENGTH: 16
<212> TYPE: PRT
<213> ORGANISM: Yersinia pestis

<400> SEQUENCE: 209

```
Asn His Phe Ala Ser Glu Tyr Ile Tyr Asn Ala Tyr Lys Asp Glu Lys
1               5                   10                  15
```

<210> SEQ ID NO 210
<211> LENGTH: 19
<212> TYPE: PRT
<213> ORGANISM: Yersinia pestis

<400> SEQUENCE: 210

```
Ile Leu Ile Asn Thr Pro Ala Ser Gln Gly Gly Ile Gly Asp Leu Tyr
1               5                   10                  15

Asn Phe Lys
```

<210> SEQ ID NO 211
<211> LENGTH: 19
<212> TYPE: PRT
<213> ORGANISM: Yersinia pestis

<400> SEQUENCE: 211

Glu Tyr Val Glu Glu Phe Asp Arg Glu Glu Val Ala Ala Ala Thr
1               5                   10                  15

Ala Pro Lys

<210> SEQ ID NO 212
<211> LENGTH: 22
<212> TYPE: PRT
<213> ORGANISM: Yersinia pestis

<400> SEQUENCE: 212

Tyr Asn Ala Asn Asp Asn Pro Thr Lys Gln Thr Ala Phe Ser Gln Tyr
1               5                   10                  15

Asp Arg Pro Gln Ala Arg
            20

<210> SEQ ID NO 213
<211> LENGTH: 29
<212> TYPE: PRT
<213> ORGANISM: Yersinia pestis

<400> SEQUENCE: 213

Ala Ala Tyr Ser Ser Gly Lys Pro Ala Ile Gly Val Gly Ala Gly Asn
1               5                   10                  15

Thr Pro Val Val Val Asp Glu Thr Ala Asp Ile Lys Arg
            20                  25

<210> SEQ ID NO 214
<211> LENGTH: 10
<212> TYPE: PRT
<213> ORGANISM: Yersinia pestis

<400> SEQUENCE: 214

Ile Leu Phe Tyr Thr Gly Val Asn His Lys
1               5                   10

<210> SEQ ID NO 215
<211> LENGTH: 14
<212> TYPE: PRT
<213> ORGANISM: Yersinia pestis

<400> SEQUENCE: 215

Tyr Arg Asn Ile Gly Ile Ser Ala His Ile Asp Ala Gly Lys
1               5                   10

<210> SEQ ID NO 216
<211> LENGTH: 14
<212> TYPE: PRT
<213> ORGANISM: Yersinia pestis

<400> SEQUENCE: 216

His Ser Asp Asp Lys Glu Pro Phe Ser Ala Leu Ala Phe Lys
1               5                   10

<210> SEQ ID NO 217
<211> LENGTH: 14
<212> TYPE: PRT
<213> ORGANISM: Yersinia pestis

<400> SEQUENCE: 217

Ile Ala Thr Asp Pro Phe Val Gly Asn Leu Thr Phe Phe Arg
1               5                   10

<210> SEQ ID NO 218
<211> LENGTH: 14
<212> TYPE: PRT
<213> ORGANISM: Yersinia pestis

<400> SEQUENCE: 218

Tyr Leu Gly Gly Glu Glu Leu Thr Glu Glu Glu Ile Lys Lys
1               5                   10

<210> SEQ ID NO 219
<211> LENGTH: 15
<212> TYPE: PRT
<213> ORGANISM: Yersinia pestis

<400> SEQUENCE: 219

Met Glu Phe Pro Glu Pro Val Ile Ser Val Ala Val Glu Pro Lys
1               5                   10                  15

<210> SEQ ID NO 220
<211> LENGTH: 15
<212> TYPE: PRT
<213> ORGANISM: Yersinia pestis

<400> SEQUENCE: 220

Glu Phe Ile Pro Ala Val Asp Lys Gly Ile Gln Glu Gln Leu Lys
1               5                   10                  15

<210> SEQ ID NO 221
<211> LENGTH: 17
<212> TYPE: PRT
<213> ORGANISM: Yersinia pestis

<400> SEQUENCE: 221

Leu Gly Ala Asn Pro Val Pro Leu Gln Leu Ala Ile Gly Ala Glu Glu
1               5                   10                  15

Lys

<210> SEQ ID NO 222
<211> LENGTH: 17
<212> TYPE: PRT
<213> ORGANISM: Yersinia pestis

<400> SEQUENCE: 222

Val Tyr Ser Gly Ile Val Asn Ser Gly Asp Thr Val Leu Asn Ser Val
1               5                   10                  15

Lys

<210> SEQ ID NO 223
<211> LENGTH: 16
<212> TYPE: PRT
<213> ORGANISM: Yersinia pestis

<400> SEQUENCE: 223

Glu Phe Asn Val Glu Ala Asn Val Gly Lys Pro Gln Val Ala Tyr Arg
1               5                   10                  15

<210> SEQ ID NO 224
<211> LENGTH: 18
<212> TYPE: PRT
<213> ORGANISM: Yersinia pestis

<400> SEQUENCE: 224

```
Glu Glu Ile Lys Glu Val His Ala Gly Asp Ile Ala Ala Ala Ile Gly
1               5                   10                  15
Leu Lys

<210> SEQ ID NO 225
<211> LENGTH: 17
<212> TYPE: PRT
<213> ORGANISM: Yersinia pestis

<400> SEQUENCE: 225

Leu His Tyr Gly Ser Tyr His Asp Val Asp Ser Ser Glu Leu Ala Phe
1               5                   10                  15
Lys

<210> SEQ ID NO 226
<211> LENGTH: 20
<212> TYPE: PRT
<213> ORGANISM: Yersinia pestis

<400> SEQUENCE: 226

Val Tyr Ser Gly Ile Val Asn Ser Gly Asp Thr Val Leu Asn Ser Val
1               5                   10                  15
Lys Ser Gln Arg
            20

<210> SEQ ID NO 227
<211> LENGTH: 7
<212> TYPE: PRT
<213> ORGANISM: Yersinia pestis

<400> SEQUENCE: 227

Asn Arg Asp Glu Trp Ser Arg
1               5

<210> SEQ ID NO 228
<211> LENGTH: 9
<212> TYPE: PRT
<213> ORGANISM: Yersinia pestis
<220> FEATURE:
<221> NAME/KEY: MOD_RES
<222> LOCATION: (5)..(5)
<223> OTHER INFORMATION: Oxidized Met

<400> SEQUENCE: 228

Tyr Glu Tyr Gly Met Phe Ser Gln Lys
1               5

<210> SEQ ID NO 229
<211> LENGTH: 11
<212> TYPE: PRT
<213> ORGANISM: Yersinia pestis

<400> SEQUENCE: 229

Val Ser Val Ile Asp Glu Asn Asn Gly Arg Arg
1               5                   10

<210> SEQ ID NO 230
<211> LENGTH: 12
<212> TYPE: PRT
<213> ORGANISM: Yersinia pestis

<400> SEQUENCE: 230

Val Leu Tyr Pro Asp Asp Ser Thr Tyr Ser Gly Arg
1               5                   10
```

<210> SEQ ID NO 231
<211> LENGTH: 14
<212> TYPE: PRT
<213> ORGANISM: Yersinia pestis

<400> SEQUENCE: 231

Glu Glu Asn Asp Pro Gly Leu Gly Asn Gly Gly Leu Gly Arg
1               5                   10

<210> SEQ ID NO 232
<211> LENGTH: 12
<212> TYPE: PRT
<213> ORGANISM: Yersinia pestis

<400> SEQUENCE: 232

Ile Ile Asp Ala Pro Asp Asn Asn Trp Val Pro Arg
1               5                   10

<210> SEQ ID NO 233
<211> LENGTH: 13
<212> TYPE: PRT
<213> ORGANISM: Yersinia pestis

<400> SEQUENCE: 233

Asn Leu Asp Tyr Pro Ser Phe Leu Leu Ala Leu Gln Lys
1               5                   10

<210> SEQ ID NO 234
<211> LENGTH: 13
<212> TYPE: PRT
<213> ORGANISM: Yersinia pestis

<400> SEQUENCE: 234

Glu Tyr Ala Asp Glu Ile Trp His Ile Lys Pro Ile Arg
1               5                   10

<210> SEQ ID NO 235
<211> LENGTH: 14
<212> TYPE: PRT
<213> ORGANISM: Yersinia pestis

<400> SEQUENCE: 235

Ser Tyr Val Asp Thr Gln Glu Gln Val Asp Ala Leu Tyr Arg
1               5                   10

<210> SEQ ID NO 236
<211> LENGTH: 14
<212> TYPE: PRT
<213> ORGANISM: Yersinia pestis
<220> FEATURE:
<221> NAME/KEY: MOD_RES
<222> LOCATION: (10)..(10)
<223> OTHER INFORMATION: Oxidized Met

<400> SEQUENCE: 236

Gly Tyr Gly Ile Arg Tyr Glu Tyr Gly Met Phe Ser Gln Lys
1               5                   10

<210> SEQ ID NO 237
<211> LENGTH: 15
<212> TYPE: PRT
<213> ORGANISM: Yersinia pestis
<220> FEATURE:
<221> NAME/KEY: MOD_RES
<222> LOCATION: (8)..(8)

```
<223> OTHER INFORMATION: Oxidized Met

<400> SEQUENCE: 237

Thr Leu Leu Asn Ile Ala Asn Met Gly Tyr Phe Ser Ser Asp Arg
1               5                   10                  15

<210> SEQ ID NO 238
<211> LENGTH: 17
<212> TYPE: PRT
<213> ORGANISM: Yersinia pestis

<400> SEQUENCE: 238

Thr

```
<211> LENGTH: 8
<212> TYPE: PRT
<213> ORGANISM: Yersinia pestis

<400> SEQUENCE: 243

Tyr Ile Gln Ala Ala Val Pro Lys
1               5

<210> SEQ ID NO 244
<211> LENGTH: 7
<212> TYPE: PRT
<213> ORGANISM: Yersinia pestis

<400> SEQUENCE: 244

Phe Asn Ile Asn Tyr Thr Arg
1               5

<210> SEQ ID NO 245
<211> LENGTH: 9
<212> TYPE: PRT
<213> ORGANISM: Yersinia pestis

<400> SEQUENCE: 245

Ser Gly Phe Leu Ile Pro Asn Ala Lys
1               5

<210> SEQ ID NO 246
<211> LENGTH: 8
<212> TYPE: PRT
<213> ORGANISM: Yersinia pestis

<400> SEQUENCE: 246

Ile Gly Phe Asn Ile Glu Leu Arg
1               5

<210> SEQ ID NO 247
<211> LENGTH: 9
<212> TYPE: PRT
<213> ORGANISM: Yersinia pestis

<400> SEQUENCE: 247

Ala Gln Tyr Leu Tyr Val Pro Tyr Arg
1               5

<210> SEQ ID NO 248
<211> LENGTH: 9
<212> TYPE: PRT
<213> ORGANISM: Yersinia pestis

<400> SEQUENCE: 248

Gly Leu Gln Trp Gln Asn Glu Phe Arg
1               5

<210> SEQ ID NO 249
<211> LENGTH: 12
<212> TYPE: PRT
<213> ORGANISM: Yersinia pestis

<400> SEQUENCE: 249

Ile Thr Gly Trp Asn Ala Gln Gly Gln Thr Ser Lys
1               5                   10

<210> SEQ ID NO 250
<211> LENGTH: 10
<212> TYPE: PRT
```

<213> ORGANISM: Yersinia pestis

<400> SEQUENCE: 250

Arg Gly Leu Gln Trp Gln Asn Glu Phe Arg
1               5                   10

<210> SEQ ID NO 251
<211> LENGTH: 11
<212> TYPE: PRT
<213> ORGANISM: Yersinia pestis

<400> SEQUENCE: 251

Glu Glu Gln Val Val Glu Val Trp Asn Ala Arg
1               5                   10

<210> SEQ ID NO 252
<211> LENGTH: 14
<212> TYPE: PRT
<213> ORGANISM: Yersinia pestis

<400> SEQUENCE: 252

Ile Ala Ser Ala Asn Gln Val Ser Thr Gly Leu Thr Ser Arg
1               5                   10

<210> SEQ ID NO 253
<211> LENGTH: 13
<212> TYPE: PRT
<213> ORGANISM: Yersinia pestis

<400> SEQUENCE: 253

Phe Thr Ser Val Asn Pro Thr Asn Pro Glu Ala Ser Arg
1               5                   10

<210> SEQ ID NO 254
<211> LENGTH: 14
<212> TYPE: PRT
<213> ORGANISM: Yersinia pestis

<400> SEQUENCE: 254

Ile Tyr Thr Gly Pro Asp Gly Thr Asp Lys Asn Ala Thr Arg
1               5                   10

<210> SEQ ID NO 255
<211> LENGTH: 13
<212> TYPE: PRT
<213> ORGANISM: Yersinia pestis

<400> SEQUENCE: 255

Phe Asn Val Ser Val Gly Gln Ile Tyr Tyr Phe Ser Arg
1               5                   10

<210> SEQ ID NO 256
<211> LENGTH: 15
<212> TYPE: PRT
<213> ORGANISM: Yersinia pestis

<400> SEQUENCE: 256

Gln Phe Gln Val Phe Thr Ala Ala Gly Asn Ser Asn Ala Tyr Arg
1               5                   10                  15

<210> SEQ ID NO 257
<211> LENGTH: 16
<212> TYPE: PRT
<213> ORGANISM: Yersinia pestis -continued

<400> SEQUENCE: 257

Thr Val Thr Ala Thr Gly Asp Val Asn Tyr Asp Asp Pro Gln Ile Lys
1               5                   10                  15

<210> SEQ ID NO 258
<211> LENGTH: 22
<212> TYPE: PRT
<213> ORGANISM: Yersinia pestis

<400> SEQUENCE: 258

Leu Leu Ala Thr His Tyr Gln Gln Asp Ile Pro Ala Ser Phe Ala Asp
1               5                   10                  15

Asn Ala Ser Asn Pro Lys
            20

<210> SEQ ID NO 259
<211> LENGTH: 24
<212> TYPE: PRT
<213> ORGANISM: Yersinia pestis

<400> SEQUENCE: 259

Val Tyr Asn Pro Asp Tyr Gln Gln Gly Ile Ser Gln Val Gly Thr Thr
1               5                   10                  15

Ala Ser Trp Pro Ile Ala Asp Arg
            20

<210> SEQ ID NO 260
<211> LENGTH: 6
<212> TYPE: PRT
<213> ORGANISM: Yersinia pestis

<400> SEQUENCE: 260

Asp Ile Gly Asn Ile Arg
1               5

<210> SEQ ID NO 261
<211> LENGTH: 6
<212> TYPE: PRT
<213> ORGANISM: Yersinia pestis

<400> SEQUENCE: 261

Arg Ile Glu Ile Val Arg
1               5

<210> SEQ ID NO 262
<211> LENGTH: 7
<212> TYPE: PRT
<213> ORGANISM: Yersinia pestis

<400> SEQUENCE: 262

Val Ser Tyr Phe Asp Thr Lys
1               5

<210> SEQ ID NO 263
<211> LENGTH: 8
<212> TYPE: PRT
<213> ORGANISM: Yersinia pestis

<400> SEQUENCE: 263

Ala Lys Asp Tyr Ile Ser Thr Arg
1               5

<210> SEQ ID NO 264

```
<211> LENGTH: 11
<212> TYPE: PRT
<213> ORGANISM: Yersinia pestis

<400> SEQUENCE: 264

Asp Leu Pro Val Ser Ile Leu Ala Gly Thr Arg
1               5                   10

<210> SEQ ID NO 265
<211> LENGTH: 11
<212> TYPE: PRT
<213> ORGANISM: Yersinia pestis

<400> SEQUENCE: 265

Gln Gly Val Leu Thr Leu Val Asp Gly Val Arg
1               5                   10

<210> SEQ ID NO 266
<211> LENGTH: 12
<212> TYPE: PRT
<213> ORGANISM: Yersinia pestis

<400> SEQUENCE: 266

Gln Val Pro Gly Leu Thr Val Thr Gly Ser Gly Arg
1               5                   10

<210> SEQ ID NO 267
<211> LENGTH: 10
<212> TYPE: PRT
<213> ORGANISM: Yersinia pestis

<400> SEQUENCE: 267

Tyr Tyr Asn Asn Ser Ala Ile Glu Pro Lys
1               5                   10

<210> SEQ ID NO 268
<211> LENGTH: 12
<212> TYPE: PRT
<213> ORGANISM: Yersinia pestis

<400> SEQUENCE: 268

Glu Gln Thr Thr Glu Gly Val Lys Leu Glu Asn Arg
1               5                   10

<210> SEQ ID NO 269
<211> LENGTH: 13
<212> TYPE: PRT
<213> ORGANISM: Yersinia pestis

<400> SEQUENCE: 269

Thr Asp Asp Leu Asp Gly Ile Leu Ser Phe Gly Thr Arg
1               5                   10

<210> SEQ ID NO 270
<211> LENGTH: 12
<212> TYPE: PRT
<213> ORGANISM: Yersinia pestis

<400> SEQUENCE: 270

Thr Ala Leu Phe Asn Trp Asp Leu Ala Tyr Asn Arg
1               5                   10

<210> SEQ ID NO 271
<211> LENGTH: 13
<212> TYPE: PRT
```

<213> ORGANISM: Yersinia pestis

<400> SEQUENCE: 271

Glu Tyr Tyr Thr Pro Gln Gly Ile Pro Gln Asp Gly Arg
1               5                   10

<210> SEQ ID NO 272
<211> LENGTH: 13
<212> TYPE: PRT
<213> ORGANISM: Yersinia pestis

<400> SEQUENCE: 272

Phe Ser Ser Gly Trp Leu Gln Asp Glu Ile Thr Leu Arg
1               5                   10

<210> SEQ ID NO 273
<211> LENGTH: 15
<212> TYPE: PRT
<213> ORGANISM: Yersinia pestis

<400> SEQUENCE: 273

His Ser Thr Asp Thr Met Val Val Thr Ala Thr Gly Asn Glu Arg
1               5                   10                  15

<210> SEQ ID NO 274
<211> LENGTH: 16
<212> TYPE: PRT
<213> ORGANISM: Yersinia pestis

<400> SEQUENCE: 274

Gln Glu Gln Thr Pro Gly Gly Ala Thr Glu Ser Phe Pro Gln Ala Lys
1               5                   10                  15

<210> SEQ ID NO 275
<211> LENGTH: 16
<212> TYPE: PRT
<213> ORGANISM: Yersinia pestis

<400> SEQUENCE: 275

Lys His Ser Thr Asp Thr Met Val Val Thr Ala Thr Gly Asn Glu Arg
1               5                   10                  15

<210> SEQ ID NO 276
<211> LENGTH: 16
<212> TYPE: PRT
<213> ORGANISM: Yersinia pestis

<400> SEQUENCE: 276

Gly Thr Trp Gln Ile Asp Ser Ile Gln Ser Leu Ser Ala Asn Leu Arg
1               5                   10                  15

<210> SEQ ID NO 277
<211> LENGTH: 15
<212> TYPE: PRT
<213> ORGANISM: Yersinia pestis

<400> SEQUENCE: 277

Ile Arg Phe Ser Ser Gly Trp Leu Gln Asp Glu Ile Thr Leu Arg
1               5                   10                  15

<210> SEQ ID NO 278
<211> LENGTH: 17
<212> TYPE: PRT
<213> ORGANISM: Yersinia pestis

<400> SEQUENCE: 278

Val Asp Met Gln Ala Met Thr Thr Thr Ser Val Asn Ile Asp Gln Ala
1               5                   10                  15

Lys

<210> SEQ ID NO 279
<211> LENGTH: 18
<212> TYPE: PRT
<213> ORGANISM: Yersinia pestis

<400> SEQUENCE: 279

Tyr Asp Asn Tyr Ser Gly Ser Ser Asp Gly Tyr Ala Asp Val Asp Ala
1               5                   10                  15

Asp Lys

<210> SEQ ID NO 280
<211> LENGTH: 19
<212> TYPE: PRT
<213> ORGANISM: Yersinia pestis

<400> SEQUENCE: 280

Gln Gly Thr Asp Thr Gly His Leu Asn Ser Thr Phe Leu Asp Pro Ala
1               5                   10                  15

Leu Val Lys

<210> SEQ ID NO 281
<211> LENGTH: 19
<212> TYPE: PRT
<213> ORGANISM: Yersinia pestis

<400> SEQUENCE: 281

Gln Ser Asn Gly Phe Asn Ala Pro Asn Asp Glu Thr Ile Ser Asn Val
1               5                   10                  15

Leu Ala Lys

<210> SEQ ID NO 282
<211> LENGTH: 21
<212> TYPE: PRT
<213> ORGANISM: Yersinia pestis

<400> SEQUENCE: 282

Val Tyr Ser Ser Ala Ala Thr Gly Asp His Ser Phe Gly Leu Gly Ala
1               5                   10                  15

Ser Ala Phe Gly Arg
            20

<210> SEQ ID NO 283
<211> LENGTH: 20
<212> TYPE: PRT
<213> ORGANISM: Yersinia pestis

<400> SEQUENCE: 283

Val Ser Ser Ser Thr Pro Gln Ala Gly Tyr Gly Val Asn Asp Phe Tyr
1               5                   10                  15

Val Ser Tyr Lys
            20

<210> SEQ ID NO 284
<211> LENGTH: 19
<212> TYPE: PRT
<213> ORGANISM: Yersinia pestis

<400> SEQUENCE: 284

Leu Phe Ile Glu Ser Pro Ala Ser His Leu Leu Thr Tyr Gly Thr Glu
1               5                   10                  15

Thr Tyr Lys

<210> SEQ ID NO 285
<211> LENGTH: 21
<212> TYPE: PRT
<213> ORGANISM: Yersinia pestis

<400> SEQUENCE: 285

Thr Arg Leu Phe Ile Glu Ser Pro Ala Ser His Leu Leu Thr Tyr Gly
1               5                   10                  15

Thr Glu Thr Tyr Lys
            20

<210> SEQ ID NO 286
<211> LENGTH: 22
<212> TYPE: PRT
<213> ORGANISM: Yersinia pestis

<400> SEQUENCE: 286

Tyr Asp Asn Tyr Ser Gly Ser Ser Asp Gly Tyr Ala Asp Val Asp Ala
1               5                   10                  15

Asp Lys Trp Ser Ser Arg
            20

<210> SEQ ID NO 287
<211> LENGTH: 26
<212> TYPE: PRT
<213> ORGANISM: Yersinia pestis

<400> SEQUENCE: 287

Val Ser Ser Ser Thr Pro Gln Ala Gly Tyr Gly Val Asn Asp Phe Tyr
1               5                   10                  15

Val Ser Tyr Lys Gly Gln Glu Ala Phe Lys
            20                  25

<210> SEQ ID NO 288
<211> LENGTH: 5
<212> TYPE: PRT
<213> ORGANISM: Yersinia pestis

<400> SEQUENCE: 288

Ile Glu Val Ile Arg
1               5

<210> SEQ ID NO 289
<211> LENGTH: 6
<212> TYPE: PRT
<213> ORGANISM: Yersinia pestis

<400> SEQUENCE: 289

Gly Thr Ile Phe Arg Arg
1               5

<210> SEQ ID NO 290
<211> LENGTH: 8
<212> TYPE: PRT
<213> ORGANISM: Yersinia pestis

<400> SEQUENCE: 290

```
Gly Gly Tyr Glu Asp Thr Leu Arg
1               5

<210> SEQ ID NO 291
<211> LENGTH: 9
<212> TYPE: PRT
<213> ORGANISM: Yersinia pestis

<400> SEQUENCE: 291

Thr Gly Gly Leu Asp Ile Ser Ile Arg
1               5

<210> SEQ ID NO 292
<211> LENGTH: 12
<212> TYPE: PRT
<213> ORGANISM: Yersinia pestis

<400> SEQUENCE: 292

Leu Leu Asp Ser Leu Ala Leu Thr Tyr Gly Ala Arg
1               5                   10

<210> SEQ ID NO 293
<211> LENGTH: 12
<212> TYPE: PRT
<213> ORGANISM: Yersinia pestis

<400> SEQUENCE: 293

Leu Leu Lys Asn Thr Asn Ile Ile Leu Asp Ser Lys
1               5                   10

<210> SEQ ID NO 294
<211> LENGTH: 13
<212> TYPE: PRT
<213> ORGANISM: Yersinia pestis

<400> SEQUENCE: 294

Phe Thr Gln Asn Tyr Ala Asn Leu Ser Ala Ala Asn Lys
1               5                   10

<210> SEQ ID NO 295
<211> LENGTH: 14
<212> TYPE: PRT
<213> ORGANISM: Yersinia pestis

<400> SEQUENCE: 295

Tyr Asp Asn Ser Ala Asn Gln Leu Gly Thr Ile Gly Ala Arg
1               5                   10

<210> SEQ ID NO 296
<211> LENGTH: 15
<212> TYPE: PRT
<213> ORGANISM: Yersinia pestis

<400> SEQUENCE: 296

Glu Ala Ala Ala Ser Ile Ser Val Ile Ser Gln Asn Glu Leu Arg
1               5                   10                  15

<210> SEQ ID NO 297
<211> LENGTH: 15
<212> TYPE: PRT
<213> ORGANISM: Yersinia pestis

<400> SEQUENCE: 297

Gly Met Pro Ser Ala Tyr Thr Leu Ile Leu Val Asp Gly Ile Arg
```

<210> SEQ ID NO 298
<211> LENGTH: 17
<212> TYPE: PRT
<213> ORGANISM: Yersinia pestis

<400> SEQUENCE: 298

Leu Ile Thr Asn Ala Ser Val Pro Gln Gly Ser Gly Leu Ala Gly Glu
1               5                   10                  15
Lys

<210> SEQ ID NO 299
<211> LENGTH: 14
<212> TYPE: PRT
<213> ORGANISM: Yersinia pestis

<400> SEQUENCE: 299

Tyr Glu Tyr Gln Thr Thr Phe Gly Gly His Ile Ser Pro Arg
1               5                   10

<210> SEQ ID NO 300
<211> LENGTH: 16
<212> TYPE: PRT
<213> ORGANISM: Yersinia pestis

<400> SEQUENCE: 300

Asp Ala Ser Arg Val Glu Ser Ser Asn Thr Gly Val Glu Leu Ser Arg
1               5                   10                  15

<210> SEQ ID NO 301
<211> LENGTH: 14
<212> TYPE: PRT
<213> ORGANISM: Yersinia pestis

<400> SEQUENCE: 301

Ala Tyr Leu Val Trp Asp Ala Gln Asp Asn Trp Thr Val Lys
1               5                   10

<210> SEQ ID NO 302
<211> LENGTH: 14
<212> TYPE: PRT
<213> ORGANISM: Yersinia pestis

<400> SEQUENCE: 302

Leu Asn Trp Asn Ile Asn Glu Gln Leu Ser Thr Trp Leu Lys
1               5                   10

<210> SEQ ID NO 303
<211> LENGTH: 18
<212> TYPE: PRT
<213> ORGANISM: Yersinia pestis

<400> SEQUENCE: 303

Leu Ile Thr Asn Ala Ser Val Pro Gln Gly Ser Gly Leu Ala Gly Glu
1               5                   10                  15
Lys Arg

<210> SEQ ID NO 304
<211> LENGTH: 18
<212> TYPE: PRT
<213> ORGANISM: Yersinia pestis

<400> SEQUENCE: 304

```
Ile Asn Ser Val Ser Ile Asp Asn Thr Thr Ser Thr Tyr Thr Asn Val
1               5                   10                  15

Gly Lys

<210> SEQ ID NO 305
<211> LENGTH: 18
<212> TYPE: PRT
<213> ORGANISM: Yersinia pestis

<400> SEQUENCE: 305

Asp Val Thr Leu Asn Gly Ala Val Asn Leu Leu Asp Lys Asp Phe
1               5                   10                  15

Thr Arg

<210> SEQ ID NO 306
<211> LENGTH: 19
<212> TYPE: PRT
<213> ORGANISM: Yersinia pestis

<400> SEQUENCE: 306

Phe Ser Phe Tyr Ser Ser Gly Pro Ala Val Glu Asp Gln Leu Gly Leu
1               5                   10                  15

Ser Leu Arg

<210> SEQ ID NO 307
<211> LENGTH: 20
<212> TYPE: PRT
<213> ORGANISM: Yersinia pestis

<400> SEQUENCE: 307

Asn Lys Ile Asn Ser Val Ser Ile Asp Asn Thr Thr Ser Thr Tyr Thr
1               5                   10                  15

Asn Val Gly Lys
            20

<210> SEQ ID NO 308
<211> LENGTH: 20
<212> TYPE: PRT
<213> ORGANISM: Yersinia pestis

<400> SEQUENCE: 308

Leu Asp Phe Gly Thr Trp Asn Ser Ser Leu Ser Tyr Asn Gln Thr Glu
1               5                   10                  15

Asn Ile Gly Arg
            20

<210> SEQ ID NO 309
<211> LENGTH: 23
<212> TYPE: PRT
<213> ORGANISM: Yersinia pestis

<400> SEQUENCE: 309

Asn Tyr Asn Asp Leu Ala Gln Ala Leu Ser Asp Val Glu Gly Val Asp
1               5                   10                  15

Val Asn Ser Ser Thr Gly Lys
            20

<210> SEQ ID NO 310
<211> LENGTH: 23
<212> TYPE: PRT
<213> ORGANISM: Yersinia pestis
```

<400> SEQUENCE: 310

Ala Trp Ala Ser Ser Ala Thr Leu Glu His Thr Phe Gln Glu Asn Thr
1               5                   10                  15

Ala Phe Gly Asp Ser Ser Lys
            20

<210> SEQ ID NO 311
<211> LENGTH: 23
<212> TYPE: PRT
<213> ORGANISM: Yersinia pestis

<400> SEQUENCE: 311

Val Val Tyr Asn Asn Leu Gly Ser Glu Phe Lys Pro Phe Ser Val Leu
1               5                   10                  15

Asn Leu Gly Val Ala Tyr Lys
            20

<210> SEQ ID NO 312
<211> LENGTH: 23
<212> TYPE: PRT
<213> ORGANISM: Yersinia pestis

<400> SEQUENCE: 312

Val Val Tyr Asn Asn Leu Gly Ser Glu Phe Lys Pro Phe Ser Val Leu
1               5                   10                  15

Asn Leu Gly Val Ala Tyr Lys
            20

<210> SEQ ID NO 313
<211> LENGTH: 27
<212> TYPE: PRT
<213> ORGANISM: Yersinia pestis

<400> SEQUENCE: 313

Thr Pro Thr Leu Ala Gln Leu His Asn Gly Ile Ser Gly Val Thr Gly
1               5                   10                  15

Gln Gly Thr Ile Thr Thr Ile Gly Asn Pro Lys
            20                  25

<210> SEQ ID NO 314
<211> LENGTH: 26
<212> TYPE: PRT
<213> ORGANISM: Yersinia pestis

<400> SEQUENCE: 314

Asp Gly Ile Val Leu Ala Asn Asn Gly Asp Glu Phe Ala Gln Asp Ala
1               5                   10                  15

Trp Ser Leu Phe Ser Glu Asp Glu Trp Arg
            20                  25

<210> SEQ ID NO 315
<211> LENGTH: 31
<212> TYPE: PRT
<213> ORGANISM: Yersinia pestis

<400> SEQUENCE: 315

Thr His Ile Phe Ala Val Gly Asn Gly Thr Thr Thr Ala Gly Asp Tyr
1               5                   10                  15

Phe Thr Ser Ser Gln Ser Thr Ala Gly Tyr Val Val Pro Gly Arg
            20                  25                  30

-continued

<210> SEQ ID NO 316
<211> LENGTH: 28
<212> TYPE: PRT
<213> ORGANISM: Yersinia pestis

<400> SEQUENCE: 316

Ile Thr Leu Gly Asn Asp Asn Arg Leu Asp Phe Gly Thr Trp Asn Ser
1               5                   10                  15

Ser Leu Ser Tyr Asn Gln Thr Glu Asn Ile Gly Arg
            20                  25

<210> SEQ ID NO 317
<211> LENGTH: 35
<212> TYPE: PRT
<213> ORGANISM: Yersinia pestis

<400> SEQUENCE: 317

Gly Gly Val Ser Thr Gly Tyr Lys Thr Pro Thr Leu Ala Gln Leu His
1               5                   10                  15

Asn Gly Ile Ser Gly Val Thr Gly Gln Gly Thr Ile Thr Thr Ile Gly
            20                  25                  30

Asn Pro Lys
        35

<210> SEQ ID NO 318
<211> LENGTH: 31
<212> TYPE: PRT
<213> ORGANISM: Yersinia pestis

<400> SEQUENCE: 318

Leu Glu Pro Glu Ser Ser Val Asn Thr Glu Val Gly Val Tyr Tyr Glu
1               5                   10                  15

Asn Glu Thr Gly Phe Gly Ala Asn Val Thr Leu Phe His Asn Arg
            20                  25                  30

<210> SEQ ID NO 319
<211> LENGTH: 6
<212> TYPE: PRT
<213> ORGANISM: Yersinia pestis

<400> SEQUENCE: 319

Val Pro Phe Val Pro Arg
1               5

<210> SEQ ID NO 320
<211> LENGTH: 7
<212> TYPE: PRT
<213> ORGANISM: Yersinia pestis

<400> SEQUENCE: 320

Thr Val Gly Ile Asn Thr Arg
1               5

<210> SEQ ID NO 321
<211> LENGTH: 8
<212> TYPE: PRT
<213> ORGANISM: Yersinia pestis

<400> SEQUENCE: 321

Ala Ala Thr Leu Gly Asp Ala Arg
1               5

<210> SEQ ID NO 322
<211> LENGTH: 7
<212> TYPE: PRT
<213> ORGANISM: Yersinia pestis

<400> SEQUENCE: 322

Tyr Gly Ala Leu Met Pro Arg
1 5

<210> SEQ ID NO 323
<211> LENGTH: 9
<212> TYPE: PRT
<213> ORGANISM: Yersinia pestis

<400> SEQUENCE: 323

Gly Pro Gln Gly Thr Leu Tyr Gly Lys
1 5

<210> SEQ ID NO 324
<211> LENGTH: 10
<212> TYPE: PRT
<213> ORGANISM: Yersinia pestis

<400> SEQUENCE: 324

Gly Tyr Ile Glu Gly Gly Val Ser Ser Arg
1 5 10

<210> SEQ ID NO 325
<211> LENGTH: 9
<212> TYPE: PRT
<213> ORGANISM: Yersinia pestis

<400> SEQUENCE: 325

Ser Ile Asn Tyr Glu Leu Gly Thr Arg
1 5

<210> SEQ ID NO 326
<211> LENGTH: 11
<212> TYPE: PRT
<213> ORGANISM: Yersinia pestis

<400> SEQUENCE: 326

Ala Asp Ala Thr Gly Val Glu Leu Glu Ala Lys
1 5 10

<210> SEQ ID NO 327
<211> LENGTH: 10
<212> TYPE: PRT
<213> ORGANISM: Yersinia pestis

<400> SEQUENCE: 327

Asp Met Gln Leu Tyr Ser Gly Pro Val Arg
1 5 10

<210> SEQ ID NO 328
<211> LENGTH: 9
<212> TYPE: PRT
<213> ORGANISM: Yersinia pestis

<400> SEQUENCE: 328

Trp Asn Gln Asp Val Gln Glu Leu Arg
1 5

<210> SEQ ID NO 329
<211> LENGTH: 10

```
<212> TYPE: PRT
<213> ORGANISM: Yersinia pestis

<400> SEQUENCE: 329

Thr Val Asp Met Val Phe Gly Leu Tyr Arg
1               5                   10

<210> SEQ ID NO 330
<211> LENGTH: 11
<212> TYPE: PRT
<213> ORGANISM: Yersinia pestis

<400> SEQUENCE: 330

Thr Val Gly Ile Asn Thr Arg Ile Asp Phe Phe
1               5                   10

<210> SEQ ID NO 331
<211> LENGTH: 14
<212> TYPE: PRT
<213> ORGANISM: Yersinia pestis

<400> SEQUENCE: 331

Tyr Gly Ala Gly Ser Ser Val Asn Gly Val Ile Asp Thr Arg
1               5                   10

<210> SEQ ID NO 332
<211> LENGTH: 13
<212> TYPE: PRT
<213> ORGANISM: Yersinia pestis

<400> SEQUENCE: 332

Ala Asp Ala Thr Gly Val Glu Leu Glu Ala Lys Trp Arg
1               5                   10

<210> SEQ ID NO 333
<211> LENGTH: 13
<212> TYPE: PRT
<213> ORGANISM: Yersinia pestis

<400> SEQUENCE: 333

Ala Thr Gln Asp Ala Tyr Val Gly Trp Asn Asp Ile Lys
1               5                   10

<210> SEQ ID NO 334
<211> LENGTH: 14
<212> TYPE: PRT
<213> ORGANISM: Yersinia pestis

<400> SEQUENCE: 334

Thr Phe Pro Ser Gly Ser Leu Ile Val Asn Met Pro Gln Arg
1               5                   10

<210> SEQ ID NO 335
<211> LENGTH: 14
<212> TYPE: PRT
<213> ORGANISM: Yersinia pestis

<400> SEQUENCE: 335

Ser Glu Phe Thr Asn Asp Ser Glu Leu Tyr His Gly Asn Arg
1               5                   10

<210> SEQ ID NO 336
<211> LENGTH: 15
<212> TYPE: PRT
<213> ORGANISM: Yersinia pestis
```

<400> SEQUENCE: 336

Ala Thr Gln Asp Ala Tyr Val Gly Trp Asn Asp Ile Lys Gly Arg
1               5                   10                  15

<210> SEQ ID NO 337
<211> LENGTH: 15
<212> TYPE: PRT
<213> ORGANISM: Yersinia pestis

<400> SEQUENCE: 337

Phe Ala Pro Gly Trp Ser Trp Asp Ile Asn Gly Asn Val Ile Arg
1               5                   10                  15

<210> SEQ ID NO 338
<211> LENGTH: 16
<212> TYPE: PRT
<213> ORGANISM: Yersinia pestis

<400> SEQUENCE: 338

Leu Ala Pro Asp Asp Gln Pro Trp Glu Met Gly Phe Ala Ala Ser Arg
1               5                   10                  15

<210> SEQ ID NO 339
<211> LENGTH: 18
<212> TYPE: PRT
<213> ORGANISM: Yersinia pestis

<400> SEQUENCE: 339

Thr Tyr Gly Tyr Met Asn Gly Ser Ser Ala Val Ala Gln Val Asn Met
1               5                   10                  15

Gly Arg

<210> SEQ ID NO 340
<211> LENGTH: 17
<212> TYPE: PRT
<213> ORGANISM: Yersinia pestis

<400> SEQUENCE: 340

Glu Cys Thr Arg Ala Thr Gln Asp Ala Tyr Val Gly Trp Asn Asp Ile
1               5                   10                  15

Lys

<210> SEQ ID NO 341
<211> LENGTH: 19
<212> TYPE: PRT
<213> ORGANISM: Yersinia pestis

<400> SEQUENCE: 341

Ser Ala Gln Gly Gly Ile Ile Asn Ile Val Thr Gln Gln Pro Asp Ser
1               5                   10                  15

Thr Pro Arg

<210> SEQ ID NO 342
<211> LENGTH: 19
<212> TYPE: PRT
<213> ORGANISM: Yersinia pestis

<400> SEQUENCE: 342

Ser Ser Thr Gln Tyr His Gly Ser Met Leu Gly Asn Pro Phe Gly Asp
1               5                   10                  15

Gln Gly Lys

<210> SEQ ID NO 343
<211> LENGTH: 18
<212> TYPE: PRT
<213> ORGANISM: Yersinia pestis

<400> SEQUENCE: 343

Leu Ala Val Asn Leu Val Gly Pro His Tyr Phe Asp Gly Asp Asn Gln
1               5                   10                  15

Leu Arg

<210> SEQ ID NO 344
<211> LENGTH: 18
<212> TYPE: PRT
<213> ORGANISM: Yersinia pestis

<400> SEQUENCE: 344

Tyr Glu Thr Ala Asp Val Thr Leu Gln Ala Ala Thr Phe Tyr Thr His
1               5                   10                  15

Thr Lys

<210> SEQ ID NO 345
<211> LENGTH: 20
<212> TYPE: PRT
<213> ORGANISM: Yersinia pestis

<400> SEQUENCE: 345

Phe Asn Leu Ser Gly Pro Ile Gln Asp Gly Leu Leu Tyr Gly Ser Val
1               5                   10                  15

Thr Leu Leu Arg
            20

<210> SEQ ID NO 346
<211> LENGTH: 20
<212> TYPE: PRT
<213> ORGANISM: Yersinia pestis

<400> SEQUENCE: 346

Ser Glu Phe Thr Asn Asp Ser Glu Leu Tyr His Gly Asn Arg Val Pro
1               5                   10                  15

Phe Val Pro Arg
            20

<210> SEQ ID NO 347
<211> LENGTH: 22
<212> TYPE: PRT
<213> ORGANISM: Yersinia pestis

<400> SEQUENCE: 347

Ser Lys Phe Asn Leu Ser Gly Pro Ile Gln Asp Gly Leu Leu Tyr Gly
1               5                   10                  15

Ser Val Thr Leu Leu Arg
            20

<210> SEQ ID NO 348
<211> LENGTH: 27
<212> TYPE: PRT
<213> ORGANISM: Yersinia pestis

<400> SEQUENCE: 348

Val Ala Gln Gly Tyr Lys Pro Ser Gly Tyr Asn Ile Val Pro Thr Ala
1               5                   10                  15

Gly Leu Asp Ala Lys Pro Phe Val Ala Glu Lys
            20                  25

<210> SEQ ID NO 349
<211> LENGTH: 30
<212> TYPE: PRT
<213> ORGANISM: Yersinia pestis

<400> SEQUENCE: 349

Ser Ala Ser Ala Asn Asn Val Ser Ser Thr Val Val Ser Ala Pro Glu
1               5                   10                  15

Leu Ser Asp Ala Gly Val Thr Ala Ser Asp Lys Leu Pro Arg
            20                  25                  30

<210> SEQ ID NO 350
<211> LENGTH: 9
<212> TYPE: PRT
<213> ORGANISM: Yersinia pestis

<400> SEQUENCE: 350

Val Glu Asp Ala Leu His Ala Thr Arg
1               5

<210> SEQ ID NO 351
<211> LENGTH: 12
<212> TYPE: PRT
<213> ORGANISM: Yersinia pestis

<400> SEQUENCE: 351

Val Ala Ala Val Lys Ala Pro Gly Phe Gly Asp Arg
1               5                   10

<210> SEQ ID NO 352
<211> LENGTH: 11
<212> TYPE: PRT
<213> ORGANISM: Yersinia pestis

<400> SEQUENCE: 352

Thr Thr Leu Glu Asp Leu Gly Gln Ala Lys Arg
1               5                   10

<210> SEQ ID NO 353
<211> LENGTH: 11
<212> TYPE: PRT
<213> ORGANISM: Yersinia pestis

<400> SEQUENCE: 353

Ala Arg Val Glu Asp Ala Leu His Ala Thr Arg
1               5                   10

<210> SEQ ID NO 354
<211> LENGTH: 12
<212> TYPE: PRT
<213> ORGANISM: Yersinia pestis

<400> SEQUENCE: 354

Val Gly Ala Ala Thr Glu Val Glu Met Lys Glu Lys
1               5                   10

<210> SEQ ID NO 355
<211> LENGTH: 17
<212> TYPE: PRT
<213> ORGANISM: Yersinia pestis -continued

```
<400> SEQUENCE: 355

Ala Ala Val Glu Glu Gly Val Val Ala Gly Gly Gly Val Ala Leu Ile
1               5                   10                  15

Arg

<210> SEQ ID NO 356
<211> LENGTH: 15
<212> TYPE: PRT
<213> ORGANISM: Yersinia pestis

<400> SEQUENCE: 356

Asn Val Val Leu Asp Lys Ser Phe Gly Ser Pro Thr Ile Thr Lys
1               5                   10                  15

<210> SEQ ID NO 357
<211> LENGTH: 16
<212> TYPE: PRT
<213> ORGANISM: Yersinia pestis

<400> SEQUENCE: 357

Ser Phe Gly Ser Pro Thr Ile Thr Lys Asp Gly Val Ser Val Ala Arg
1               5                   10                  15

<210> SEQ ID NO 358
<211> LENGTH: 14
<212> TYPE: PRT
<213> ORGANISM: Yersinia pestis

<400> SEQUENCE: 358

Gln Gln Ile Glu Asp Ala Thr Ser Asp Tyr Asp Lys Glu Lys
1               5                   10

<210> SEQ ID NO 359
<211> LENGTH: 20
<212> TYPE: PRT
<213> ORGANISM: Yersinia pestis

<400> SEQUENCE: 359

Ala Ala His Ala Ile Ala Gly Leu Lys Gly Asp Asn Glu Asp Gln Asn
1               5                   10                  15

Val Gly Ile Lys
            20

<210> SEQ ID NO 360
<211> LENGTH: 23
<212> TYPE: PRT
<213> ORGANISM: Yersinia pestis

<400> SEQUENCE: 360

Val Val Ile Asn Lys Asp Thr Thr Ile Ile Asp Gly Val Gly Asp
1               5                   10                  15

Glu Ala Ala Ile Gln Gly Arg
            20

<210> SEQ ID NO 361
<211> LENGTH: 8
<212> TYPE: PRT
<213> ORGANISM: Yersinia pestis

<400> SEQUENCE: 361

Asn Leu Ser Leu Leu Ser Ala Arg
1               5
```

<210> SEQ ID NO 362
<211> LENGTH: 9
<212> TYPE: PRT
<213> ORGANISM: Yersinia pestis

<400> SEQUENCE: 362

Gln Thr Val Thr Thr Pro Arg Ala Gln
1               5

<210> SEQ ID NO 363
<211> LENGTH: 11
<212> TYPE: PRT
<213> ORGANISM: Yersinia pestis

<400> SEQUENCE: 363

Ala Ala Ala Asp Arg Asp Ala Ala Tyr Glu Lys
1               5                   10

<210> SEQ ID NO 364
<211> LENGTH: 11
<212> TYPE: PRT
<213> ORGANISM: Yersinia pestis

<400> SEQUENCE: 364

Asn Asn Leu Asp Asn Ala Leu Glu Ser Leu Arg
1               5                   10

<210> SEQ ID NO 365
<211> LENGTH: 11
<212> TYPE: PRT
<213> ORGANISM: Yersinia pestis

<400> SEQUENCE: 365

Leu Ser Gln Asp Leu Ala Arg Glu Gln Ile Lys
1               5                   10

<210> SEQ ID NO 366
<211> LENGTH: 11
<212> TYPE: PRT
<213> ORGANISM: Yersinia pestis

<400> SEQUENCE: 366

Asp Ala Ala Tyr Glu Lys Ile Asn Glu Val Arg
1               5                   10

<210> SEQ ID NO 367
<211> LENGTH: 12
<212> TYPE: PRT
<213> ORGANISM: Yersinia pestis

<400> SEQUENCE: 367

Ala Ile Asp Ser Leu Ser Tyr Thr Glu Ala Gln Lys
1               5                   10

<210> SEQ ID NO 368
<211> LENGTH: 12
<212> TYPE: PRT
<213> ORGANISM: Yersinia pestis

<400> SEQUENCE: 368

Thr Gln Arg Pro Asp Ala Val Asn Asn Leu Leu Lys
1               5                   10

<210> SEQ ID NO 369

```
<211> LENGTH: 11
<212> TYPE: PRT
<213> ORGANISM: Yersinia pestis

<400> SEQUENCE: 369

Tyr Asn Tyr Leu Ile Asn Gln Leu Asn Ile Lys
1               5                   10

<210> SEQ ID NO 370
<211> LENGTH: 14
<212> TYPE: PRT
<213> ORGANISM: Yersinia pestis

<400> SEQUENCE: 370

Ala Ser Tyr Asp Thr Val Leu Ala Ala Glu Val Ala Ala Arg
1               5                   10

<210> SEQ ID NO 371
<211> LENGTH: 14
<212> TYPE: PRT
<213> ORGANISM: Yersinia pestis

<400> SEQUENCE: 371

Leu Lys Thr Gln Arg Pro Asp Ala Val Asn Asn Leu Leu Lys
1               5                   10

<210> SEQ ID NO 372
<211> LENGTH: 15
<212> TYPE: PRT
<213> ORGANISM: Yersinia pestis

<400> SEQUENCE: 372

Phe Asn Val Gly Leu Val Ala Ile Thr Asp Val Gln Asn Ala Arg
1               5                   10                  15

<210> SEQ ID NO 373
<211> LENGTH: 16
<212> TYPE: PRT
<213> ORGANISM: Yersinia pestis

<400> SEQUENCE: 373

Thr Ile Leu Asp Val Leu Thr Ala Thr Thr Asn Leu Tyr Gln Ser Lys
1               5                   10                  15

<210> SEQ ID NO 374
<211> LENGTH: 17
<212> TYPE: PRT
<213> ORGANISM: Yersinia pestis

<400> SEQUENCE: 374

Gln Ile Thr Gly Val Tyr Tyr Pro Glu Leu Ala Ser Leu Asn Val Glu
1               5                   10                  15

Arg

<210> SEQ ID NO 375
<211> LENGTH: 17
<212> TYPE: PRT
<213> ORGANISM: Yersinia pestis

<400> SEQUENCE: 375

Ala Ile Asp Ser Leu Ser Tyr Thr Glu Ala Gln Lys Gln Ser Val Tyr
1               5                   10                  15

Arg
```

-continued

<210> SEQ ID NO 376
<211> LENGTH: 18
<212> TYPE: PRT
<213> ORGANISM: Yersinia pestis

<400> SEQUENCE: 376

Gln Ala Gln Tyr Asn Phe Val Gly Ala Ser Glu Leu Leu Glu Ser Ala
1               5                   10                  15

His Arg

<210> SEQ ID NO 377
<211> LENGTH: 20
<212> TYPE: PRT
<213> ORGANISM: Yersinia pestis

<400> SEQUENCE: 377

Ser Pro Leu Leu Pro Gln Leu Gly Leu Ser Ala Gly Tyr Thr His Ala
1               5                   10                  15

Asn Gly Phe Arg
            20

<210> SEQ ID NO 378
<211> LENGTH: 18
<212> TYPE: PRT
<213> ORGANISM: Yersinia pestis

<400> SEQUENCE: 378

Gln Gln Leu Ala Asp Ala Arg Tyr Asn Tyr Leu Ile Asn Gln Leu Asn
1               5                   10                  15

Ile Lys

<210> SEQ ID NO 379
<211> LENGTH: 25
<212> TYPE: PRT
<213> ORGANISM: Yersinia pestis

<400> SEQUENCE: 379

Ile Asn Glu Val Arg Ser Pro Leu Leu Pro Gln Leu Gly Leu Ser Ala
1               5                   10                  15

Gly Tyr Thr His Ala Asn Gly Phe Arg
            20                  25

<210> SEQ ID NO 380
<211> LENGTH: 6
<212> TYPE: PRT
<213> ORGANISM: Yersinia pestis

<400> SEQUENCE: 380

His Thr Pro Phe Phe Lys
1               5

<210> SEQ ID NO 381
<211> LENGTH: 7
<212> TYPE: PRT
<213> ORGANISM: Yersinia pestis

<400> SEQUENCE: 381

Glu His Ile Leu Leu Gly Arg
1               5

<210> SEQ ID NO 382
<211> LENGTH: 8

```
<212> TYPE: PRT
<213> ORGANISM: Yersinia pestis

<400> SEQUENCE: 382

Phe Ala Ile Arg Glu Gly Gly Arg
1               5

<210> SEQ ID NO 383
<211> LENGTH: 10
<212> TYPE: PRT
<213> ORGANISM: Yersinia pestis

<400> SEQUENCE: 383

Ala Gly Glu Asn Val Gly Val Leu Leu Arg
1               5                   10

<210> SEQ ID NO 384
<211> LENGTH: 10
<212> TYPE: PRT
<213> ORGANISM: Yersinia pestis

<400> SEQUENCE: 384

Gly Thr Val Val Thr Gly Arg Val Glu Arg
1               5                   10

<210> SEQ ID NO 385
<211> LENGTH: 13
<212> TYPE: PRT
<213> ORGANISM: Yersinia pestis

<400> SEQUENCE: 385

Glu Gly Gly Arg Thr Val Gly Ala Gly Val Val Ala Lys
1               5                   10

<210> SEQ ID NO 386
<211> LENGTH: 11
<212> TYPE: PRT
<213> ORGANISM: Yersinia pestis

<400> SEQUENCE: 386

Ala Leu Glu Gly Glu Ala Glu Trp Glu Ala Lys
1               5                   10

<210> SEQ ID NO 387
<211> LENGTH: 9
<212> TYPE: PRT
<213> ORGANISM: Yersinia pestis

<400> SEQUENCE: 387

Gly Tyr Arg Pro Gln Phe Tyr Phe Arg
1               5

<210> SEQ ID NO 388
<211> LENGTH: 11
<212> TYPE: PRT
<213> ORGANISM: Yersinia pestis

<400> SEQUENCE: 388

Asp Glu Gly Gly Arg His Thr Pro Phe Phe Lys
1               5                   10

<210> SEQ ID NO 389
<211> LENGTH: 12
<212> TYPE: PRT
<213> ORGANISM: Yersinia pestis
```

<400> SEQUENCE: 389

Ala Phe Asp Gln Ile Asp Asn Ala Pro Glu Glu Lys
1               5                   10

<210> SEQ ID NO 390
<211> LENGTH: 14
<212> TYPE: PRT
<213> ORGANISM: Yersinia pestis

<400> SEQUENCE: 390

Ala Phe Asp Gln Ile Asp Asn Ala Pro Glu Glu Lys Ala Arg
1               5                   10

<210> SEQ ID NO 391
<211> LENGTH: 15
<212> TYPE: PRT
<213> ORGANISM: Yersinia pestis

<400> SEQUENCE: 391

Val Gly Glu Glu Val Glu Ile Val Gly Ile Lys Asp Thr Val Lys
1               5                   10                  15

<210> SEQ ID NO 392
<211> LENGTH: 16
<212> TYPE: PRT
<213> ORGANISM: Yersinia pestis

<400> SEQUENCE: 392

Leu Leu Asp Glu Gly Arg Ala Gly Glu Asn Val Gly Val Leu Leu Arg
1               5                   10                  15

<210> SEQ ID NO 393
<211> LENGTH: 16
<212> TYPE: PRT
<213> ORGANISM: Yersinia pestis

<400> SEQUENCE: 393

Gly Ile Thr Ile Asn Thr Ser His Val Glu Tyr Asp Thr Pro Ala Arg
1               5                   10                  15

<210> SEQ ID NO 394
<211> LENGTH: 17
<212> TYPE: PRT
<213> ORGANISM: Yersinia pestis

<400> SEQUENCE: 394

Thr Lys Pro His Val Asn Val Gly Thr Ile Gly His Val Asp His Gly
1               5                   10                  15

Lys

<210> SEQ ID NO 395
<211> LENGTH: 17
<212> TYPE: PRT
<213> ORGANISM: Yersinia pestis

<400> SEQUENCE: 395

Glu Leu Leu Ser Ala Tyr Asp Phe Pro Gly Asp Asp Leu Pro Val Val
1               5                   10                  15

Arg

<210> SEQ ID NO 396
<211> LENGTH: 17

```
<212> TYPE: PRT
<213> ORGANISM: Yersinia pestis

<400> SEQUENCE: 396

Ile Ile Glu Leu Ala Gly Tyr Leu Asp Ser Tyr Ile Pro Glu Pro Glu
1               5                   10                  15

Arg

<210> SEQ ID NO 397
<211> LENGTH: 18
<212> TYPE: PRT
<213> ORGANISM: Yersinia pestis

<400> SEQUENCE: 397

Ala Arg Gly Ile Thr Ile Asn Thr Ser His Val Glu Tyr Asp Thr Pro
1               5                   10                  15

Ala Arg

<210> SEQ ID NO 398
<211> LENGTH: 7
<212> TYPE: PRT
<213> ORGANISM: Yersinia pestis

<400> SEQUENCE: 398

Val Gly Phe Ala Gly Leu Lys
1               5

<210> SEQ ID NO 399
<211> LENGTH: 9
<212> TYPE: PRT
<213> ORGANISM: Yersinia pestis

<400> SEQUENCE: 399

Ala Asn Ala Tyr Thr Gly Gly Leu Lys
1               5

<210> SEQ ID NO 400
<211> LENGTH: 8
<212> TYPE: PRT
<213> ORGANISM: Yersinia pestis

<400> SEQUENCE: 400

Gly Asn Gly Met Leu Thr Tyr Arg
1               5

<210> SEQ ID NO 401
<211> LENGTH: 10
<212> TYPE: PRT
<213> ORGANISM: Yersinia pestis

<400> SEQUENCE: 401

Arg Ala Asn Ala Tyr Thr Gly Gly Leu Lys
1               5                   10

<210> SEQ ID NO 402
<211> LENGTH: 11
<212> TYPE: PRT
<213> ORGANISM: Yersinia pestis

<400> SEQUENCE: 402

Ser Ser Asp Ala Ala Phe Gly Phe Ala Asp Lys
1               5                   10
```

```
<210> SEQ ID NO 403
<211> LENGTH: 9
<212> TYPE: PRT
<213> ORGANISM: Yersinia pestis

<400> SEQUENCE: 403

Asn Met Ser Thr Tyr Val Asp Tyr Lys
1               5

<210> SEQ ID NO 404
<211> LENGTH: 11
<212> TYPE: PRT
<213> ORGANISM: Yersinia pestis

<400> SEQUENCE: 404

Asn Gly Ser Ser Ser Glu Thr Asn Asn Gly Arg
1               5                   10

<210> SEQ ID NO 405
<211> LENGTH: 10
<212> TYPE: PRT
<213> ORGANISM: Yersinia pestis

<400> SEQUENCE: 405

Asn Leu Asp Gly Asp Gln Ser Tyr Met Arg
1               5                   10

<210> SEQ ID NO 406
<211> LENGTH: 11
<212> TYPE: PRT
<213> ORGANISM: Yersinia pestis

<400> SEQUENCE: 406

Phe Ala Asp Tyr Gly Ser Leu Asp Tyr Gly Arg
1               5                   10

<210> SEQ ID NO 407
<211> LENGTH: 11
<212> TYPE: PRT
<213> ORGANISM: Yersinia pestis

<400> SEQUENCE: 407

Ile Asp Gly Leu His Tyr Phe Ser Asp Asn Lys
1               5                   10

<210> SEQ ID NO 408
<211> LENGTH: 11
<212> TYPE: PRT
<213> ORGANISM: Yersinia pestis

<400> SEQUENCE: 408

Ile Asn Leu Leu Asp Lys Asn Asp Phe Thr Lys
1               5                   10

<210> SEQ ID NO 409
<211> LENGTH: 13
<212> TYPE: PRT
<213> ORGANISM: Yersinia pestis

<400> SEQUENCE: 409

Thr Thr Ala Gln Asn Asp Leu Gln Tyr Gly Gln Gly Lys
1               5                   10

<210> SEQ ID NO 410
<211> LENGTH: 12
```

```
<212> TYPE: PRT
<213> ORGANISM: Yersinia pestis

<400> SEQUENCE: 410

Tyr Val Asp Ile Gly Ala Thr Tyr Phe Phe Asn Lys
1               5                   10

<210> SEQ ID NO 411
<211> LENGTH: 13
<212> TYPE: PRT
<213> ORGANISM: Yersinia pestis

<400> SEQUENCE: 411

Ala Glu Asn Glu Asp Gly Asn His Asp Ser Phe Thr Arg
1               5                   10

<210> SEQ ID NO 412
<211> LENGTH: 14
<212> TYPE: PRT
<213> ORGANISM: Yersinia pestis

<400> SEQUENCE: 412

Gly Lys Asp Ile Gly Ile Tyr Gly Asp Gln Asp Leu Leu Lys
1               5                   10

<210> SEQ ID NO 413
<211> LENGTH: 14
<212> TYPE: PRT
<213> ORGANISM: Yersinia pestis

<400> SEQUENCE: 413

Thr Thr Ala Gln Asn Asp Leu Gln Tyr Gly Gln Gly Lys Arg
1               5                   10

<210> SEQ ID NO 414
<211> LENGTH: 20
<212> TYPE: PRT
<213> ORGANISM: Yersinia pestis

<400> SEQUENCE: 414

Asn Thr Asn Phe Phe Gly Leu Val Asp Gly Leu Asn Phe Ala Leu Gln
1               5                   10                  15

Tyr Gln Gly Lys
            20

<210> SEQ ID NO 415
<211> LENGTH: 20
<212> TYPE: PRT
<213> ORGANISM: Yersinia pestis

<400> SEQUENCE: 415

Tyr Asp Ala Asn Asn Val Tyr Leu Ala Ala Asn Tyr Thr Gln Thr Tyr
1               5                   10                  15

Asn Leu Thr Arg
            20

<210> SEQ ID NO 416
<211> LENGTH: 21
<212> TYPE: PRT
<213> ORGANISM: Yersinia pestis

<400> SEQUENCE: 416

Ile Asp Gly Leu His Tyr Phe Ser Asp Asn Lys Asn Leu Asp Gly Asp
1               5                   10                  15
```

Gln Ser Tyr Met Arg
            20

<210> SEQ ID NO 417
<211> LENGTH: 23
<212> TYPE: PRT
<213> ORGANISM: Yersinia pestis

<400> SEQUENCE: 417

Gly Glu Thr Gln Ile Thr Asp Gln Leu Thr Gly Tyr Gly Gln Trp Glu
1 5 10 15

Tyr Gln Val Asn Leu Asn Lys
20

<210> SEQ ID NO 418
<211> LENGTH: 26
<212> TYPE: PRT
<213> ORGANISM: Yersinia pestis

<400> SEQUENCE: 418

Ala His Asn Ile Glu Val Val Ala Gln Tyr Gln Phe Asp Phe Gly Leu
1 5 10 15

Arg Pro Ser Val Ala Tyr Leu Gln Ser Lys
20 25

<210> SEQ ID NO 419
<211> LENGTH: 33
<212> TYPE: PRT
<213> ORGANISM: Yersinia pestis

<400> SEQUENCE: 419

Gly Val Ala Asp Gln Asn Gly Asp Gly Tyr Gly Met Ser Leu Ser Tyr
1 5 10 15

Asp Leu Gly Trp Gly Val Ser Ala Ser Ala Ala Met Ala Ser Ser Leu
20 25 30

Arg

<210> SEQ ID NO 420
<211> LENGTH: 9
<212> TYPE: PRT
<213> ORGANISM: Yersinia pestis

<400> SEQUENCE: 420

Ala Leu Ala Ser Asn Ile Leu Tyr Arg
1 5

<210> SEQ ID NO 421
<211> LENGTH: 10
<212> TYPE: PRT
<213> ORGANISM: Yersinia pestis

<400> SEQUENCE: 421

Ser Asp Pro Gly Ala Ala Phe Pro Trp Lys
1 5 10

<210> SEQ ID NO 422
<211> LENGTH: 11
<212> TYPE: PRT
<213> ORGANISM: Yersinia pestis

<400> SEQUENCE: 422

Lys Ser Asp Pro Gly Ala Ala Phe Pro Trp Lys

```
<210> SEQ ID NO 423
<211> LENGTH: 10
<212> TYPE: PRT
<213> ORGANISM: Yersinia pestis

<400> SEQUENCE: 423

Ile Phe Asn Leu Val Asp Glu Asn Glu Arg
1               5                   10

<210> SEQ ID NO 424
<211> LENGTH: 10
<212> TYPE: PRT
<213> ORGANISM: Yersinia pestis

<400> SEQUENCE: 424

Met Tyr Asn Ile Asp Tyr Asn Ser Phe Arg
1               5                   10

<210> SEQ ID NO 425
<211> LENGTH: 12
<212> TYPE: PRT
<213> ORGANISM: Yersinia pestis

<400> SEQUENCE: 425

Ala Trp His Ala Gly Val Ser Tyr Trp Asp Gly Arg
1               5                   10

<210> SEQ ID NO 426
<211> LENGTH: 16
<212> TYPE: PRT
<213> ORGANISM: Yersinia pestis

<400> SEQUENCE: 426

Ala Leu Tyr Asp Ala Gly Ile Gly Ala Trp Tyr Asp Asp Glu Thr Lys
1               5                   10                  15

<210> SEQ ID NO 427
<211> LENGTH: 19
<212> TYPE: PRT
<213> ORGANISM: Yersinia pestis

<400> SEQUENCE: 427

Phe Pro Asp Ile Thr Pro Val Asn Val Val Gly His Ser Asp Ile Ala
1               5                   10                  15

Pro Gly Arg

<210> SEQ ID NO 428
<211> LENGTH: 19
<212> TYPE: PRT
<213> ORGANISM: Yersinia pestis

<400> SEQUENCE: 428

Tyr Gly Tyr Asp Thr Ser Gly Ala Val Ser Glu Val Gly Tyr Asn Gln
1               5                   10                  15

Leu Ile Arg

<210> SEQ ID NO 429
<211> LENGTH: 20
<212> TYPE: PRT
<213> ORGANISM: Yersinia pestis

<400> SEQUENCE: 429
```

```
Phe Pro Asp Ile Thr Pro Val Asn Val Gly His Ser Asp Ile Ala
1               5                   10                  15

Pro Gly Arg Lys
            20

<210> SEQ ID NO 430
<211> LENGTH: 10
<212> TYPE: PRT
<213> ORGANISM: Yersinia pestis

<400> SEQUENCE: 430

Ser Asp Pro Gly Pro Leu Phe Pro Trp Lys
1               5                   10

<210> SEQ ID NO 431
<211> LENGTH: 11
<212> TYPE: PRT
<213> ORGANISM: Yersinia pestis

<400> SEQUENCE: 431

Ser Asp Pro Gly Pro Leu Phe Pro Trp Lys Arg
1               5                   10

<210> SEQ ID NO 432
<211> LENGTH: 12
<212> TYPE: PRT
<213> ORGANISM: Yersinia pestis

<400> SEQUENCE: 432

Ala Ile Ala Leu Gln Leu Val Pro Glu Ala Gln Arg
1               5                   10

<210> SEQ ID NO 433
<211> LENGTH: 12
<212> TYPE: PRT
<213> ORGANISM: Yersinia pestis

<400> SEQUENCE: 433

Ala Trp His Ala Gly Val Ser Ser Trp Gln Gly Arg
1               5                   10

<210> SEQ ID NO 434
<211> LENGTH: 12
<212> TYPE: PRT
<213> ORGANISM: Yersinia pestis

<400> SEQUENCE: 434

Ile Pro Gln Asn Gly Gln Leu Asp Thr Glu Thr Arg
1               5                   10

<210> SEQ ID NO 435
<211> LENGTH: 14
<212> TYPE: PRT
<213> ORGANISM: Yersinia pestis

<400> SEQUENCE: 435

Gly Thr Tyr Gln Ile Asp Thr His Tyr Pro Ser Val Ala Lys
1               5                   10

<210> SEQ ID NO 436
<211> LENGTH: 18
<212> TYPE: PRT
<213> ORGANISM: Yersinia pestis
```

-continued

<400> SEQUENCE: 436

Gly Ala Ala Ser Val Ala Val Ile Gln Gln Ala Leu Ala Ala Tyr Gly
1               5                   10                  15

Tyr Lys

<210> SEQ ID NO 437
<211> LENGTH: 16
<212> TYPE: PRT
<213> ORGANISM: Yersinia pestis

<400> SEQUENCE: 437

Phe Leu Val Leu His Tyr Thr Ala Val Gly Asp Ala Glu Ser Leu Arg
1               5                   10                  15

<210> SEQ ID NO 438
<211> LENGTH: 18
<212> TYPE: PRT
<213> ORGANISM: Yersinia pestis

<400> SEQUENCE: 438

Tyr Asn Ile Ser Pro Ser Asp Val Val Ala His Ser Asp Ile Ala Pro
1               5                   10                  15

Leu Arg

<210> SEQ ID NO 439
<211> LENGTH: 20
<212> TYPE: PRT
<213> ORGANISM: Yersinia pestis

<400> SEQUENCE: 439

Asn Asn Leu Asn Asp Thr Ser Ile Gly Ile Glu Ile Val Asn Leu Gly
1               5                   10                  15

Phe Thr Glu Lys
            20

<210> SEQ ID NO 440
<211> LENGTH: 24
<212> TYPE: PRT
<213> ORGANISM: Yersinia pestis

<400> SEQUENCE: 440

Ala Ile Ala Leu Gln Leu Val Pro Glu Ala Gln Arg Ala Trp His Ala
1               5                   10                  15

Gly Val Ser Ser Trp Gln Gly Arg
            20

<210> SEQ ID NO 441
<211> LENGTH: 7
<212> TYPE: PRT
<213> ORGANISM: Yersinia pestis

<400> SEQUENCE: 441

Leu Ile Asp Gly Asp Phe Lys
1               5

<210> SEQ ID NO 442
<211> LENGTH: 10
<212> TYPE: PRT
<213> ORGANISM: Yersinia pestis

<400> SEQUENCE: 442

Gly Phe Glu Glu Ser Val Asp Gly Phe Lys

```
1               5                   10

<210> SEQ ID NO 443
<211> LENGTH: 11
<212> TYPE: PRT
<213> ORGANISM: Yersinia pestis

<400> SEQUENCE: 443

Val Gly Thr Trp Met Leu Gly Ala Gly Tyr Arg
1               5                   10

<210> SEQ ID NO 444
<211> LENGTH: 11
<212> TYPE: PRT
<213> ORGANISM: Yersinia pestis

<400> SEQUENCE: 444

Phe Ser Ser Ile Phe Gly Gln Ser Glu Ser Arg
1               5                   10

<210> SEQ ID NO 445
<211> LENGTH: 11
<212> TYPE: PRT
<213> ORGANISM: Yersinia pestis

<400> SEQUENCE: 445

Tyr Tyr Ser Val Thr Ala Gly Pro Val Phe Arg
1               5                   10

<210> SEQ ID NO 446
<211> LENGTH: 11
<212> TYPE: PRT
<213> ORGANISM: Yersinia pestis

<400> SEQUENCE: 446

Arg Gly Phe Glu Glu Ser Val Asp Gly Phe Lys
1               5                   10

<210> SEQ ID NO 447
<211> LENGTH: 12
<212> TYPE: PRT
<213> ORGANISM: Yersinia pestis

<400> SEQUENCE: 447

Val Gly Thr Trp Met Leu Gly Ala Gly Tyr Arg Phe
1               5                   10

<210> SEQ ID NO 448
<211> LENGTH: 17
<212> TYPE: PRT
<213> ORGANISM: Yersinia pestis

<400> SEQUENCE: 448

Ile Asn Glu Tyr Val Ser Leu Tyr Gly Leu Leu Gly Ala Gly His Gly
1               5                   10                  15

Lys

<210> SEQ ID NO 449
<211> LENGTH: 17
<212> TYPE: PRT
<213> ORGANISM: Yersinia pestis

<400> SEQUENCE: 449

Tyr Glu Phe Asn Asn Asp Trp Gly Val Ile Gly Ser Phe Ala Gln Thr
```

```
1               5                  10                 15
Arg

<210> SEQ ID NO 450
<211> LENGTH: 27
<212> TYPE: PRT
<213> ORGANISM: Yersinia pestis

<400> SEQUENCE: 450

Thr Ser Leu Ala Tyr Gly Ala Gly Leu Gln Phe Asn Pro His Pro Asn
1               5                  10                 15

Phe Val Ile Asp Ala Ser Tyr Glu Tyr Ser Lys
            20                  25

<210> SEQ ID NO 451
<211> LENGTH: 17
<212> TYPE: PRT
<213> ORGANISM: Yersinia pestis

<400> SEQUENCE: 451

Ile Arg Glu Ala Ala Ala Ser Ile Ser Val Ile Ser Gln Asn Glu Leu
1               5                  10                 15

Arg
```

YERSINIA SPP. POLYPEPTIDES AND METHODS OF USE

CONTINUING APPLICATION DATA

This application is a continuation patent application of U.S. patent application Ser. No. 14/933,899 filed on Nov. 5, 2015; which is a continuation patent application of U.S. patent application Ser. No. 14/793,494, filed on Jul. 7, 2015, now U.S. Pat. No. 9,221,899; which is a continuation patent application of U.S. patent application Ser. No. 14/048,649, filed on Oct. 8, 2013, now U.S. Pat. No. 9,085,613; which is a continuation patent application of U.S. patent application Ser. No. 11/336,706, filed on Jan. 20, 2006, now U.S. Pat. No. 8,563,004; which claims the benefit of U.S. Provisional Application No. 60/646,106, filed Jan. 21, 2005, each of which is incorporated herein by reference.

SEQUENCE LISTING

This application contains a Sequence Listing electronically submitted via EFS-Web to the United States Patent and Trademark Office as an ASCII text filed entitled "29300410108_SequenceListing_ST25.txt" having a size of 195 kilobytes and created on Apr. 27, 2016. Due to the electronic filing of the Sequence Listing, the electronically submitted Sequence Listing serves as both the paper copy required by 37 CFR §1.821(c) and the CRF required by §1.821(e). The information contained in the Sequence Listing is incorporated by reference herein.

BACKGROUND

There are three *Yersinia* species that are pathogenic to humans: *Y. pestis, Y. pseudotuberculosis*, and *Y. enterocolitica. Y. pestis* is the causative agent of plague, while *Y. pseudotuberculosis* and specific pathogenic serovars of *Y. enterocolitica* cause gastrointestinal illnesses. Other species of *Yersinia*, including *Y. rohdei, Y. aldovae, Y. bercovieri, Y. frederiksenii, Y. intermedia, Y. kristensenii*, and *Y. moolaretti*, are considered *enterocolitica*-like opportunist pathogens with the ability to cause diarrheal illness in susceptible individuals (Agbonlahor, J Clin Microbiol, 23, 891-6, (1986), Cafferkey, et al., J Hosp Infect, 24, 109-15, (1993), Loftus, et al., Dig Dis Sci, 47, 2805-10, (2002)). The *Yersinia* can also infect other animal species causing a range of illnesses. Most wild and domestic species of mammals are prone to infections with the enteropathogens *Y. enterocolitica* and *Y. pseduotuberculosis*, although most of these infections are subclinical and such animals usually serve only as asymptomatic carriers of the pathogens for transmission to humans (Fantasia, et al., J Clin Microbiol, 22, 314-5, (1985), Fantasia, et al., Vet Rec, 132, 532-4, (1993), Fukushima. et al., J Clin Microbiol, 18, 981-2, (1983), Kageyama, et al., J Med Primatol, 31, 129-35, (2002), Kato, et al., Appl Environ Microbiol, 49, 198-200, (1985), Poelma, et al., Acta Zool Pathol Antverp, 3-9, (1977), Shayegani, et al., Appl Environ Microbiol, 52, 420-4, (1986), Yanagawa, et al., Microbiol Immunol, 22, 643-6, (1978).). However, there are reports that the enteropathogenic *Yersinia* have been associated with diarrheal illness and general malaise in domestic animals such as sheep, cattle, goats, pigs, dogs, birds and farmed deer (Jerrett, I. V., et al., Aust Vet J, 67, 212-4, (1990). Slee, K. J., et al., Aust Vet J, 65, 271-5, (1988), Slee, K. J. and C. Button, Aust Vet J, 67, 396-8, (1990), Slee, K. J. and C. Button, Aust Vet J, 67, 320-2, (1990), Zheng, X. B., J Appl Bacteriol, 62, 521-5, (1987)).

*Y. pestis* can cause disease in a variety of rodent species as well as nonhuman primates (Davis, K. J., et al., Arch Pathol Lab Med, 120, 156-63, (1996), Meyer, K. F., et al., J Infect Dis, 129, Suppl:S85-12, (1974). *Y. pestis* is also associated with potentially severe infections in domestic cats (Gasper, P. W., et al., J Med Entomol, 30, 20-6, (1993)) and a few cases of *Y. pestis* infection have been reported in dogs (Orloski, K. A. and M. Eidson, J Am Vet Med Assoc, 207, 316-8, (1995)). In addition, *Yersinia ruckeri* is a pathogen of fish, causing redmouth disease in salmonids (Furones, M. D., et al., Ann. Rev. Fish Dis., 3, 105-125, (1993)).

Plague is undoubtedly one of the most devastating acute infectious disease in the recorded history of man, estimated to have killed 100 to 200 million people worldwide (Perry, R. D. and J. D. Fetherston, Clin Microbiol Rev, 10, 35-66, (1997)). In recent years plague outbreaks have been relatively uncommon in the U.S. and other industrialized countries, although endemic foci exist in all continents except Australia. Worldwide surveys indicated 2000 to 5000 annual cases of plague reported in the last several years, although epidemiologists suspect that many human cases of plague are unreported. *Y. pseudotuberculosis* outbreaks are fairly rare, and have occurred primarily in Finland, Japan, and the former Soviet Union (Inoue, M., et al., Zentralbl Bakteriol Mikrobiol Hyg [B], 186, 504-511, (1988), Nuorti, J. P., et al., J Infect Dis, 189, 766-774, (2004), Rodina, L. V., et al., Zh Mikrobiol Epidemiol Immunobiol, 116-118, (1998), Toyokawa, Y., et al., Kansenshogaku Zasshi, 67, 36-44, (1993)). Most *Y. pseudotuberculosis* infections are assumed to be transmitted by the oral-fecal route; however, a vehicle of transmission has not been identified in many cases. In the United States, infections by *Y. enterocolitica* are more common than those with *Y. pseudotuberculosis*, and are typically associated with the consumption of contaminated pork products (Ray, S. M., et al., Clin Infect Dis, 38 Suppl 3. S181-189, (2004)). The incidence of human disease caused by the *Y. enterocolitica* in the U.S. is difficult to determine, simply because infections associated with this organism are typically self-limiting and insufficient detection techniques have limited the ability to correctly diagnose the causative agent. However, FoodNet surveillance for 1996-1999 estimated approximately 1 case of *Y. enterocolitica* infection per 100,000 in the United States (Ray, S. M., et al., Clin Infect Dis, 38 Suppl 3, S181-189, (2004)).

Plague is an infectious disease of animals and humans having both enzootic and epizootic components of transmission. The most naturally occurring means of transmission is from an infected rodent reservoir to fleas, which serve as natural vectors for transmission to humans. However, human-to-human transmission can also occur by direct contact or respiratory inhalation of contaminated droplets (Pneumonic form). Nevertheless, in natural infections *Y. pestis* typically enter humans by a subcutaneous route into the bloodstream, where they travel to the lymph nodes and begin to multiply. Clinical manifestations of plague include large swollen masses near the lymph nodes, referred to as bubos. Occasionally, *Y. pestis* multiplies rapidly in the bloodstream, inducing septicemia with an accompanying general malaise that includes fever, headache, chills, and occasionally gastrointestinal disturbances. These symptoms are often misdiagnosed early, and antibiotic therapy may therefore be administered too late for effective intervention. Septicemic infection by *Y. pestis* has a 50% fatality rate (Perry, R. D. and J. D. Fetherston, Clin Microbiol Rev, 10, 35-66, (1997)), and can lead to pulmonary infection. The pneumonic form of plague is extremely infectious by the aerosol route and is characterized by a rapid onset of disease and a mortality rate close to 100%. Therefore, although antibiotic therapies are available and effective if administered early, the rapid onset of pneumonic plague and the misdiagnosis of septicemic plague are major obstacles in treatment of the disease.

*Y. enterocolitica* and *Y. pseudotuberculosis* are considered enteropathogens since most human infections are transmitted by the fecal-oral route and are limited to the gastrointestinal tract. In a normal host, *Y. enterocolitica* causes a diarrheal illness, which may be accompanied by fever and lower quadrant pain that mimics appendicitis. *Y. pseudotuberculosis* typically does not cause diarrheal illness, and is more likely to cause mesenteric lymphadenitis which can be misdiagnosed as appendicitis. Following ingestion, both organisms attach to the intestinal lymphoid tissues and traverse the mucosal layer, where they can subsequently multiply in the mesenteric lymph nodes and migrate to the spleen and liver (Lian, C. J., et al., J Med Microbiol, 24, 219-226, (1987), Une, T., Microbiol Immunol, 21, 505-516, (1977)). *Y. pseudotuberculosis* and some serotypes of *Y. enterocolitica* can also spread to the vascular system and cause fatal cases of septicemia (Bottone, E. J., Clin. Microbiol. Rev., 10, 257-276, (1997), Lenz, T., et al., J Infect Dis, 150, 963, (1984)), although these more invasive infections are typically limited to susceptible individuals. *Y. enterocolitica* has also been associated with septicemia following blood transfusions; in these cases, the blood supply was contaminated with the organism, which can survive and grow at refrigeration temperatures (Natkin, J. B., KG, Clin Lab Med, 19, 523-536, (1999)). Furthermore, intestinal *Yersinia* infections can lead to delayed sequelae such as reactive arthritis and thyroiditis (Bottone, E. J., Clin. Microbiol. Rev., 10, 257-276, (1997), Gaston, J. S., et al., Arthritis Rheum., 42, 2239-2242, (1999), Taccetti, G., et al., Clin Exp Rheumatol, 12, 681-684, (1994)). Antibiotic therapy has not been demonstrated to reduce the severity or duration of gastrointestinal illness caused by these two pathogens (Hoogkamp-Korstanje, J., J Antimicrob Chemother, 20, 123, (1987), Pai, C. H., et al., J Pediatr, 104, 308-11, (1984)). However, a susceptible host is typically treated with antibiotics to prevent more serious clinical manifestations of disease. Septicemia caused by either of these enteropathogens is also generally treated with antibiotics, and such therapies are frequently successful against *Y. enterocolitica* (Gayraud, M., et al., Clin Infect Dis, 17, 405-10, (1993)). In contrast, antibiotic therapy has traditionally been less effective in patients where septicemia is caused by *Y. pseudotuberculosis*, and the mortality rate associated with *Y. pseudotuberculosis* septicemia is approximately 75% (Natkin, J. B., KG, Clin Lab Med, 19, 523-536, (1999)).

Although natural infection by *Y. pestis* is rare in this country, there is fear that the organism will become a bioterrorism agent. As a tool of deliberate mass infection, the *Y. pestis* organism is a prime candidate due to several characteristics. First, the organism is highly infectious when spread by aerosol, a convenient method of mass dissemination. Second, there is a high mortality rate associated with *Y. pestis* infection if left untreated, and the pneumonic form of plague is distinguished by a rapid onset of symptoms that may be recognized too late for an effective intervention. Finally, *Y. pestis* has a well-defined genetic system, thus antibiotic-resistant strains are relatively easy to engineer.

Several plague vaccines with varying levels of efficacy and safety have been investigated. One of the earliest vaccines consisted of killed whole cells (KWC) of *Y. pestis*; this type of vaccine was first used in the late 1890's and confers protection against the bubonic form of plague. However, there is evidence that KWC immunizations offer little protection against pneumonic plague (Cohen, R. J. and J. L. Stockard, JAMA, 202, 365-366, (1967), Meyer, K. F., Bull World Health Organ, 42, 653-666, (1970)), and an additional drawback to these vaccines is that multiple injections over several months are required for protective immunity. An attenuated strain of *Y. pestis*, strain EV76, has been studied as a live vaccine for plague. In mouse studies, this vaccine has been shown to protect against both subcutaneous and inhalation challenges and requires as few as one dose for protection (Russell, P., et al., Vaccine, 13, 155-1556, (1995)). However, strain EV76 is not fully avirulent, causing death in approximately 1% of vaccinated mice (Russell, P., et al., Vaccine, 13, 1551-1556, (1995)). Interestingly, there have been several unsuccessful attempts to create an avirulent strain of *Y. pestis* suitable for use as a live vaccine (Titball, R. W. and E. D. Williamson, Vaccine, 19, 4175-4184, (2001)).

Subunit vaccines are considered to be the most promising type of vaccine for safe and effective prevention of plague, primarily because there is no fear of adverse effects in a human host. Several surface proteins associated with *Yersinia* virulence were tested for their immunogenicity; all of these proteins induced an antibody response but only the F1 capsule and the secreted V antigen elicited good protection against challenge (Titball, R. W. and E; D. Williamson, Vaccine, 19, 4175-4184, (2001)). Both F1 and V antigen provide protection as individual antigens in animal models, although the combination of the two antigens provides superior protection. Many recent studies have tested F1/V vaccines formulated with alternative adjuvants in an attempt to find the best delivery system for the F1 and V antigens (Alpar, H. O., et al., Adv. Drug Deliv. Rev., 51, 173-201, (2001), Byles, J. E., et al., J Control Release, 63, 191-200, (2000), Jones, S. M., et al., Vaccine, 19, 358-366, (2001), Reddin, K. M., et al., Vaccine, 16, 761-767, (1998), Williamson, E. D., et al., Vaccine, 19, 566-571, (2000). Williamson, E. D., et al., Vaccine, 14, 1613-9, (1996)).

Other innovative strategies have used attenuated *Salmonella* strains as vaccine carriers for *Y. pestis* antigens. When a *Salmonella* aroA mutant expressing an F1/V fusion protein was used as a vaccine strain, 86% of mice survived a subsequent lethal challenge dose of *Y. pestis* (Leary, S. E., et al., Microb Pathog, 23, 167-179, (1997)). Similarly, a vaccine consisting of a DNA plasmid bearing a gene encoding truncated-F1 capsule provided 80 to 100% protection in different mouse strains (Grosfeld, H., et al., Infect Immun, 71, 374-383, (2003)). In addition, a group of investigators mapped the B- and T-cell epitopes of the F1 antigen and utilized the immunoreactive peptides in vaccine formulations (Sabhnani, L, et al., FEMS Immunol Med Microbiol, 38, 215-29, (2003)). Their results indicated that a mixture of epitopic peptides protected 83% of mice against a lethal dose of *Y. pestis*.

In contrast to the extensive search for protective plague vaccines, very little research efforts have been focused on preventing infections by the enteropathogenic *Yersinia* species. However, a few studies have demonstrated promising results. For example, attenuated *Y. enterocolitica* strains administered orally to mice displayed protective effects, reducing the bacterial load in the spleen and liver following oral challenge (Igwe, E. I., et al., Infect Immun, 67, 5500-5507, (1999)). However, these strains were engineered primarily as live oral vaccine carriers, and no further testing of these strains for prevention of yersiniosis has been reported. Two subunit vaccines were demonstrated as effective in animal models of infection. The first consisted of cellular extracts from *Y. enterocolitica* and was administered intranasally to mice. The immunized mice demonstrated enhanced clearance of an intranasal challenge dose of *Y. enterocolitica* from the lungs (Di Genaro, M. S., et al., Microbiol. Immunol., 42, 781-788, (1998)). A second subunit vaccine was formulated using a heat shock protein HSP60 from *Y. enterocolitica* adjuvanted with interleukin-12 (Noll, A. and Autenriethlb, Infect Immun, 64, 2955-2961, (1996)). Immunizations with this vaccine resulted in significantly fewer bacteria in mouse spleens following challenge, illustrating a protective effect. Additional work utilized a vaccine consisting of DNA encoding the *Y. enterocolitica* HSP60 in intramuscular immunizations in mice (Noll, A., et al., Eur J Immunol, 29, 986-996, (1999)). This study demonstrated that hsp60 mRNA was present in various host tissues following immunization, but protection against *Y. enterocolitica* challenge was limited to the spleen and no protection was observed in the intestinal mucosa.

The similarities and differences between the diseases caused by the pathogenic *Yersinia* species have been the focus of much research in the past decade. This is partly due to several observations that suggest the pathogenic *Yersinia* provide a useful model of pathogen evolution. First, DNA hybridization studies and recent genomic comparisons of fully sequenced *Y. pestis* and *Y. pseudotuberculosis* strains have indicated that these two pathogens are highly related (Chain, P. S., et al., Proc. Natl. Acad. Sci. USA, 101, 13826-13831, (2004), Ibrahim, A., et al., FEMS Microbiol Lett, 114, 173-177, (1993)), and it has been estimated that *Y. pestis* evolved from *Y. pseudotuberculosis* as recently as 1,500 to 20,000 years ago (Achtman, M., et al., Proc. Natl. Acad. Sci. USA, 96, 14043-14048, (1999)). However, despite their close evolutionary relationship, *Y. pseudotuberculosis* and *Y. pestis* cause very different diseases in humans. Furthermore, partial sequencing and 16s RNA hybridization studies suggested that *Y. enterocolitica* is more distantly related to the other pathogenic species of this genus (Ibrahim, A., et al., FEMS Microbiol Lett, 114, 173-177, (1993), Moore, R. L. and R. R. Brubaker, Int J Syst Bacteriol, 25, 336-339, (1975)), although *Y. enterocolitica* causes gastrointestinal infections similar to those observed with *Y. pseudotuberculosis*. Recent research has thus been focused on the virulence genes of the three pathogenic *Yersinia* species in an attempt to elucidate the different mechanisms they employ to cause disease. Mouse models have been particularly instructive in studying *Yersinia* pathogenesis, since all three species cause similar diseases in mice when injected intravenously, and more natural infections can be effectively simulated through oral and pneumonic challenge routes in mice.

A few virulence factors are unique to *Y. pestis*. These include proteins encoded on the *Y. pestis* plasmids pPCP and pMT, plasmids that are not found in *Y. enterocolitica* or *Y. pseudotuberculosis*. The pPCP plasmid encodes the plasminogen activator, a protein involved in rapid dissemination of bacteria into mammalian host tissues following subcutaneous injection (Sodeinde, O. A., et al., Science, 258, 1004-1007, (1992)). The pMT plasmid harbors at least two genes that aid in the infection of non-human hosts. The pMT-encoded caf1 gene is required for assembly of the F1 capsule, a factor that inhibits phagocytosis in the murine host but is not required for virulence in primates (Friedlander, A. M., et al., Clin. Infect. Dis., 21 Suppl 2, S178-181, (1995)). The murine toxin is also encoded on the pMT plasmid, and is believed to promote survival in the flea although it is not a required virulence factor in murine hosts (Hinnebusch, B. J., et al., Science, 296, 733-735, (2002), Hinnebusch, J., et al., Int J Med Microbiol, 290, 483-487, (2000)). Other differences between the species are the structures of the lipopolysaccharide (LPS) molecules produced by the yersiniae. Both *Y. enterocolitica* and *Y. pseudotuberculosis* express variable O-antigen side chains, which have been theorized to enhance survival in the gastrointestinal tract (Reeves, P., Trends Microbiol., 3, 381-386, (1995)) and may inhibit complement-mediated lysis during invasive disease (Karlyshev, A. V., et al., Infect Immun, 69, 7810-7819, (2001)). In contrast, *Y. pestis* has a rough LPS phenotype with no O-specific side chains due to mutations in several O-antigen biosynthesis genes (Prior, J. G., et al., Microb. Pathog., 30, 48-57, (2001), Skurnik, M. P., A; Ervela, E. Mol Microbiol, 37, 316-330, (2000)).

Interestingly, genomic sequencing projects revealed that several virulence genes present in all three pathogenic *Yersinia* species have acquired mutations in *Y. pestis* that rendered them non-functional (Chain, P. S., et al., Proc. Natl. Acad. Sci. USA, 101, 13826-13831, (2004), Parkhill, J., et al., Nature, 413, 523-527, (2001)). Some of these encode invasin proteins that function during intestinal invasion in the enteropathogenic *Y. enterocolitica* and *Y. pseudotuberculosis* species, a host niche not colonized by *Y. pestis* (Simonet, M., et al., Infect Immun, 64, 375-379, (1996)). Other genes with lost function in *Y. pestis* include those involved in intermediary metabolism, and these functional losses are theorized to be part of the evolution of *Y. pestis* into an obligate parasitic species with the inability to survive outside the host (Parkhill, J., et al., Nature, 413, 523-527, (2001)). Research on the pathogenesis of *Yersinia* has largely been focused on the 70 kb virulence plasmid that is found in all pathogenic species of *Yersinia*. The sequence of this plasmid, called pYV in *Y. pseudotuberculosis* and pathogenic *Y. enterocolitica* and pCD1 in *Y. pestis*, is remarkably conserved between *Y. pseudotuberculosis* and *Y. pestis* (Chain, P. S., et al., Proc. Nat). Acad. Sci. USA, 101, 13826-13831, (2004)). Accordingly, the more distantly-related *Y. enterocolitica* species harbors a more divergent pYV plasmid, but the virulence gene sequences are highly conserved among all three species (Hu, P., et al., J Bacteriol, 180, 5192-5202, (1998), Snellings, N. J., et al., Infect Immun, 69, 4627-38, (2001)). Focus on this plasmid began when experiments determined that the pYV plasmid is absolutely required for virulence of *Yersinia*, although the plasmid alone cannot restore virulence to specific avirulent strains suggesting that non-pVY genes are also involved in pathogenesis (Heesemann, J., et al., Infect Immun, 46, 105-110, (1984), Heesemann, J. and R. Laufs, J Bacteriol, 155.761-767, (1983)). A large locus on this plasmid encodes the Ysc-Yop system, a type III secretion system and its associated effector proteins. This system was the first example of a type 11 secretion apparatus, now identified in many animal and plant microbial pathogens (for review, see Cornelis, G. R., Nat. Rev. Mol. Cell. Biol., 3, 742-752, (2002)). The *Yersinia* Yop-Ysc secretion system includes "injectisome" proteins, translocator effector proteins, and Yop effector proteins. Electron microscopy and labeling studies with various type III secretory systems revealed that the injectisome proteins form a pore spanning the cytoplasmic and outer membranes of the bacteria and project a needle-like structure from the cell surface (Blocker. A., et al., Mol. Microbiol., 39, 652-663, (2001), Kimbrough, T. G. and S. I. Miller, Proc Natl Acad Sci USA, 97, 11008-11013, (2000), Kubori, T., et al., Science, 280, 602-605, (1998), Sukhan, A., et al., J Bacteriol, 183, 1159-1167, (2001)). The translocator proteins appear to interact with host macrophages and polymorphonuclear neutrophils (PMNs), forming a pore-like structure in the host cell membrane (Neyt, C. and G. R. Cornelis, Mol Microbiol, 33, 971-981, (1999)). The assembled secretion apparatus then allows the effector Yops to be translocated across the bacterial cell membranes and injected into the host cell, where they function by interfering with various immune response pathways (Bleves, S. and G. R. Cornelis, Microbes Infect., 2, 1451-1460, (2000), Cornelis, G. R., Nat. Rev. Mol. Cell. Biol., 3, 742-752, (2002)). The yadA gene is also present on the pYV plasmid, encoding the YadA adhesin with the ability to bind and adhere to eukaryotic cells (Eitel, J. and P. Dersch, Infect Immun, 70, 4880-91, (2002), Skurnik, M., et al., Infect Immun, 62, 1252-61, (1994)). This protein only appears to be functional in the enteropathogenic Yersinia, as a frameshift mutation in the Y. pestis yadA gene renders it non-functional (Hu, P., et al., J Bacteriol, 180, 5192-5202, (1998)).

The involvement of iron in Yersinia infections has long been established. For example, iron-overloaded patients such as those afflicted with f-thalassemia are highly susceptible to Yersinia infections (Farmakis, D., et al., Med. Sci. Monit., 9, RA 19-22, (2003)). Furthermore, virulence could be restored in specific avirulent Y. pestis mutants by the addition of heme or heme-containing compounds (Burrows, T. W. and S. Jackson, Br. J. Exp. Pathol., 37, 577-583, (1956)). These early observations with Yersinia and other bacteria led researchers to study some of the microbial mechanisms of iron uptake. In mammalian hosts, available iron is extremely limited; intracellular iron is complexed with storage proteins, and extracellular iron is bound by the host proteins transferrin and lactoferrin. These iron-restricted conditions limit the growth of microbial invaders, thus acting as a defense barrier to infection. Many pathogens have evolved the ability to scavenge iron under these iron-poor conditions, effectively "stealing" iron from transferrin or heme-containing compounds. One of the most common mechanisms utilized by bacteria is the synthesis and secretion of siderophores, small molecules with a high affinity for iron (Andrews, S. C., et al., FEMS Microbiol. Rev., 27, 215-237, (2003)). The iron-siderophore complexes are bound by outer membrane receptors on the bacterial cell surface, and through the concerted action of outer membrane, periplasmic, and ABC transporter proteins, iron is transported into the cell. Other outer membrane receptors can directly bind heme and heme-containing compounds, scavenging the iron from these molecules. The role of several Yersinia iron uptake systems has been elucidated, while many more putative systems have been identified but not characterized.

Although Yersinia can use various siderophores produced by other bacteria and fungi to obtain iron, yersiniabactin is the only Yersinia-produced siderophore that has been detected (Baumler, A., et al., Zentralbl. Bakteriol., 278, 416-424, (1993), Rabsch, W. and G. Winkelmann, Biol Met, 4, 244-250, (1991). Reissbrodt, R. and W. Rabsch, Zentralbl Bakteriol Mikrobiol Hyg [A], 268, 306-317, (1988)). The yersiniabactin system is encoded by the ybt genes present on the chromosomal high-pathogenicity island (HPI), a locus that is associated with highly pathogenic strains of Yersinia (de Almeida, A. M., et al., Microb. Pathog., 14, 9-21, (1993), Rakin, A., et al., J Bacteriol, 177, 2292-2298, (1995)). The ybt genes encode proteins involved in the synthesis and secretion of the siderophore yersiniabactin (ybtS, irp1, irp2, ybtE, ybtT), as well as the cytoplasmic (ybtP, ybrQ) and outer membrane proteins (psnlfyuA) required for uptake of the iron-yersiniabactin complexes (Carniel, E., Microbes Infect., 3, 561-569, (2001)). Mutations in genes for yersiniabactin synthesis and/or uptake resulted in reduced Yersinia virulence in mouse models of infection (Bearden. S. W., et al., Infect. Immun., 65, 1659-1668, (1997), Brem, D., et al., Microbiology, 147, 1115-1127, (2001), Rakin, A., et al., Mol Microbiol, 13, 253-263, (1994)), indicating that this system is an important virulence factor in Yersinia pathogenesis. The nucleotide sequence of the ybt genes are at least 97% identical between the three pathogenic Yersinia species (Carniel, E., Microbes Infect., 3, 561-569, (2001), Chain, P. S., et al., Proc. Natl. Acad. Sci. USA, 101, 13826-13831, (2004)), and the Y. pestis and Y. pseudotuberculosis ybt systems were demonstrated to be interchangeable (Perry, R. D., et al., Microbiology, 145 (Pt 5), 1181-1190, (1999)). These analyses indicated that the functions of these homologs are likely conserved among the three species. Furthermore, the HPI has been discovered in various pathogenic species including some strains of E. coli, Citrobacter, and Klebsiella (Bach, S., et al., FEMS Microbiol. Lett., 183, 289-294, (2000)). The Ybt proteins expressed by these organisms are quite similar, indeed, antibodies raised against several of the Yersinia Ybt proteins recognized the corresponding proteins from the other pathogens (Bach, S., et al., FEMS Microbiol. Lett., 183, 289-294, (2000), Karch, H., et al., Infect Immun, 67, 5994-6001, (1999)). These results suggest that the acquisition of the ybt system is relatively recent among these pathogens and may have contributed to the invasive phenotypes associated with many of these serotypes.

Several additional ybt-independent iron uptake systems have been detected in Yersinia species based on mutation analysis, homology to known iron acquisition proteins, or the presence of iron-responsive regulatory elements. One such regulatory element is the "Fur box," a nucleotide sequence that binds the regulatory protein Fur when it is complexed with iron. The binding of Fe-Fur to a Fur box represses transcription of downstream promoters, and when iron becomes limiting, apo-Fur dissociates from DNA and transcription is derepressed. Fur and its homologs have been found in most species of bacteria, and regulate many genes in addition to iron uptake systems in diverse organisms (Campoy, S., et al., Microbiology, 148, 1039-1048, (2002), Horsburgh, M. J., et al., Infect Immun, 69, 3744-3754, (2001), Sebastian, S., et al., J Bacteriol, 184, 3965-3974, (2002), Stojiljkovic, I., et al., J Mol Biol, 236, 531-545, (1994)). Analysis of the Y. pestis genome identified many genes with Fur boxes upstream of their respective promoters, most of which encoded proteins with homology to known iron uptake systems (Panina, E. M., et al., Nucleic Acids Res, 29, 5195-5206, (2001)). Although few of these genes have been studied for function, several appear to encode iron-siderophore receptor proteins (omrA, irgA, itrA, ihaB, fauA) and iron ABC transporters (irsTUS, itpPTS). Since Yersinia can utilize siderophores produced by other organisms, these proteins may be responsible for the "siderophore piracy" observed with Yersinia. Such methods of iron acquisition are common among bacterial pathogens.

Several studies have elucidated the functions of other putative iron uptake systems. For example, the Hmu system of Y. pestis was demonstrated to acquire iron through the uptake of heme and heme-containing compounds (Hornung, J. M., et al., Mol Microbiol, 20, 725-39, (1996)). Although the ability to use heme as an iron source seems advantageous for a pathogen, the Y. pestis hmu mutant was fully virulent in a mouse model of infection (Thompson, J. M., et al., Infect Immun, 67, 3879-92, (1999)). A second putative heme-uptake system was identified in Y. pestis on the basis of sequence homology. The has genes of Y. pestis are homologs of the hemophore-dependent heme acquisition genes of *Pseudomonas* and *Serratia* (Rossi, M. S., et al., Infect Immun, 69, 6707-6717, (2001)). In these organisms, a hemophore (HasA) is secreted that binds heme and delivers it to bacterial surface receptors (HasR) to transport heme into the cell. The *Y. pestis* HasA protein was determined to be Fur-regulated, secreted, and capable of binding heme. However, a mutation in these genes had no effect on virulence in the mouse, even when a double mutant was tested (Rossi, M. S., et al., infect Immun, 69, 6707-6717, (2001)). Therefore, the roles of the putative heme uptake systems in pathogenesis remain elusive, and may indicate that heme uptake is more important during infection of non-murine hosts.

The functions of two putative iron ABC transport systems have also been studied in *Yersinia*. The Yfe system can transport iron and manganese in *Y. pestis*, and yfe mutants demonstrated reduced virulence in mouse models of infection (Bearden, S. W. and R. D. Perry, Mol. Microbiol., 32, 403-414, (1999)). The second putative iron ABC transporter proteins are encoded by the yfu genes, identified by the presence of an upstream Fur box (Gong, S., et al., Infect. Immun., 69, 2829-2837, (2001)). When expressed in *E. coli*, the yfu genes restored growth in iron-poor media; however, comparable studies in *Y. pestis* failed to determine a role for Yfu in iron acquisition, and the yfu-mutant showed no defect in mouse virulence (Gong, S., et al., Infect. Immun., 69, 2829-2837, (2001)).

SUMMARY OF THE INVENTION

The present invention provides a composition including two isolated polypeptides having molecular weights of 83 kDa, 70 kDa, 66 kDa, or a combination thereof, and two isolated polypeptides having molecular weights of 40 kDa, 38 kDa, or 37 kDa, or a combination thereof, wherein molecular weight is determined by electrophoresis on a sodium dodecyl sulfate-polyacrylamide gel. The polypeptides having a molecular weight of 83 kDa, 70 kDa, or 66 kDa are isolatable from a *Yersinia enterocolitica* when incubated in media containing an iron chelator and not isolatable when grown in the media without the iron chelator. In some aspects, the composition may include two different 83 kDa polypeptides isolatable from a *Y. enterocolitica* when incubated in media comprising an iron chelator. The composition protects a mouse against challenge with *Y. enterocolitica* ATCC strain 27729. The composition can further include a pharmaceutically acceptable carrier. The polypeptides may be isolatable, or in some aspects isolated from *Y. enterocolitica* is ATCC strain 27729. The composition may further include an isolated polypeptide having a molecular weight of 268 kDa, 92 kDa, 79 kDa, 54 kDa, 45 kDa, 31 kDa, 28 kDa, or a combination thereof, and isolatable from a *Y. enterocolitica* when grown in the media without the iron chelator.

The present invention also provides a composition including two isolated polypeptides having molecular weights of 83 kDa, 70 kDa, 66 kDa, or a combination thereof, and two isolated polypeptides having molecular weights of 268 kDa, 79 kDa, or 45 kDa, or a combination thereof, wherein molecular weight is determined by electrophoresis on a sodium dodecyl sulfate-polyacrylamide gel. The polypeptides having a molecular weight of 83 kDa, 70 kDa, or 66 kDa are isolatable from a *Yersinia enterocolitica* when incubated in media comprising an iron chelator and not isolatable when grown in the media without the iron chelator. The composition protects a mouse against challenge with *Y. enterocolitica* ATCC strain 27729. The composition can further include a pharmaceutically acceptable carrier. The polypeptides may be isolatable, or in some aspects isolated from *Y. enterocolitica* is ATCC strain 27729.

The present invention further provides a composition including isolated polypeptides having molecular weights of 268 kDa, 92 kDa, 83 kDa 0.79 kDa, 70 kDa, 66 kDa, 54 kDa, 45 kDa, 40 kDa, 38 kDa, 37 kDa, 31 kDa, and 28 kDa, wherein molecular weight is determined by electrophoresis on a sodium dodecyl sulfate-polyacrylamide gel. The polypeptides are isolatable from a *Yersinia enterocolitica*, and the composition protects a mouse against challenge with *Y. enterocolitica* ATCC strain 27729. The polypeptides may be isolatable, or in some aspects isolated from *Y. enterocolitica* is ATCC strain 27729.

The present invention provides a composition including two isolated polypeptides having molecular weights of 94 kDa, 88 kDa, 77 kDa, 73 kDa, or 64 kDa, or a combination thereof, and two isolated polypeptides having molecular weights of 46 kDa, 37 kDa, or a combination thereof, wherein molecular weight is determined by electrophoresis on a sodium dodecyl sulfate-polyacrylamide gel. The polypeptides having a molecular weight of 94 kDa, 88 kDa, 77 kDa, 73 kDa, or 64 kDa are isolatable from a *Yersinia pestis* when incubated in media comprising an iron chelator and not isolatable when grown in the media without the iron chelator. The composition protects a mouse against challenge with *Y. pestis* strain KIM6+. The composition can further include a pharmaceutically acceptable carrier. The polypeptides may be isolatable, or in some aspects isolated from *Y. enterocolitica* is ATCC strain 27729. The composition may further include an isolated polypeptide having a molecular weight of 254 kDa, 46 kDa, 37 kDa, 36 kDa, 31 kDa, 28 kDa, or 20 kDa, and isolatable from a *Y. pestis* when grown in the media without the iron chelator. The polypeptides may be isolatable, or in some aspects isolated from *Y. pestis* strain KIM6+.

The present invention also provides a composition including two isolated polypeptides having molecular weights of 94 kDa, 88 kDa, 77 kDa, 73 kDa, or 64 kDa, or a combination thereof, and two isolated polypeptides having molecular weights of 254 kDa, 46 kDa, 37 kDa, 36 kDa, 31 kDa, 28 kDa, 20 kDa, or a combination thereof, wherein molecular weight is determined by electrophoresis on a sodium dodecyl sulfate-polyacrylamide gel. The polypeptides having a molecular weight of 94 kDa, 88 kDa, 77 kDa, 73 kDa, or 64 kDa, are isolatable from a *Yersinia pestis* when incubated in media comprising an iron chelator and not isolatable when grown in the media without the iron chelator. The composition protects a mouse against challenge with *Y. pestis* strain KIM6+. The composition can further include a pharmaceutically acceptable carrier. The polypeptides may be isolatable, or in some aspects isolated from *Y. pestis* strain KIM6+.

The present invention further provides a composition including isolated polypeptides having molecular weights of 254 kDa, 104 kDa, 99 kDa, 94 kDa, 88 kDa, 77 kDa, 73 kDa, 64 kDa, 60 kDa, 46 kDa, 44 kDa, 37 kDa, 36 kDa, 31 kDa, 28 kDa, and 20 kDa wherein molecular weight is determined by electrophoresis on a sodium dodecyl sulfate-polyacrylamide gel. The polypeptides are isolatable from a *Yersinia pestis*, and the composition protects a mouse against challenge with *Y. pestis* strain KIM6+. The polypeptides may be isolatable, or in some aspects isolated from *Y. pestis* strain KIM6+.

The present invention provides a method for treating in infection in a subject including administering an effective amount of a composition of the present invention to a subject having or at risk of having an infection caused by a *Yersinia* spp. The subject may be an animal, such as a fish or a mammal, such as a human. The *Yersinia* spp. may be, for example, *Y. enterocolitica* or *Y. pestis*, or *Y. ruckeri*.

The present invention also provides a method for treating a symptom in a subject including administering an effective amount of a composition of the present invention to a subject having an infection caused by a *Yersinia* spp. The subject may be an animal, such as a fish or a mammal, such as a human. The *Yersinia* spp. may be, for example, *Y. enterocolitica* or *Y. pestis*, or *Y. ruckeri*. The symptom may be, for example, diarrhea, enteritis, plague, red mouth disease, or a combination thereof.

The present invention further provides for treating in infection in a subject including administering an effective amount of a composition to a subject having or at risk of having an infection caused by a *Yersinia* spp., wherein the composition includes antibody that specifically binds a polypeptide of the present invention. The antibody may be polyclonal or monoclonal. In one example, the antibody specifically binds two isolated polypeptides having molecular weights of 83 kDa, 70 kDa, 66 kDa, or a combination, thereof, wherein the polypeptides are isolatable from a *Yersinia enterocolitica* when incubated in media comprising an iron chelator and not isolatable when grown in the media without the iron chelator. In another example, the antibody specifically binds two isolated polypeptides having molecular weights of 94 kDa, 88 kDa, 77 kDa, 73 kDa, or 64 kDa, or a combination thereof, wherein the polypeptides are isolatable from a *Yersinia pestis* when incubated in media comprising an iron chelator and not isolatable when grown in the media without the iron chelator.

The present invention also provides a method for treating a symptom in a subject including administering an effective amount of a composition to a subject having an infection caused by a *Yersinia* spp., wherein the composition includes antibody that specifically binds a polypeptide of the present invention. The antibody may be polyclonal or monoclonal. In one example, the antibody specifically binds two isolated polypeptides having molecular weights of 83 kDa, 70 kDa, 66 kDa, or a combination thereof, wherein molecular weight is determined by electrophoresis on a sodium dodecyl sulfate-polyacrylamide gel, wherein the polypeptides are isolatable from a *Yersinia enterocolitica* when incubated in media comprising an iron chelator and not isolatable when grown in the media without the iron chelator. In another example, the antibody specifically binds two isolated polypeptides having molecular weights of 94 kDa, 88 kDa, 77 kDa, 73 kDa, or 64 kDa, or a combination thereof, wherein the polypeptides are isolatable from a *Yersinia pestis* when incubated in media comprising an iron chelator and not isolatable when grown in the media without the iron chelator.

The present invention further provides kits for detecting antibody that specifically binds a polypeptide of the present invention. The kit includes an isolated polypeptide of the present invention, and a reagent that detects an antibody that specifically binds the polypeptide. The polypeptide and the reagent are typically present in separate containers. In one example, the polypeptide may have a molecular weight of 83 kDa, 70 kDa, or 66 kDa, or a combination thereof, wherein the polypeptide is isolatable from a *Yersinia enterocolitica* when incubated in media comprising an iron chelator and not isolatable when grown in the media without the iron chelator. In another example, the polypeptide may have a molecular weight of 94 kDa, 88 kDa, 77 kDa, 73 kDa, or 64 kDa, or a combination thereof, wherein the polypeptide is isolatable from a *Yersinia pestis* when incubated in media comprising an iron chelator and not isolatable when grown in the media without the iron chelator.

BRIEF DESCRIPTION OF THE FIGURES

FIG. 1. Detergent-insoluble protein-enriched extracts of *Y. enterocolitica* ATCC strain 27729 and *Y. pestis* strain KIM6+ resolved by electrophoresis on a 10% sodium dodecyl sulfate-polyacrylamide gel. The numbers to the left of the gel image denote the molecular weights in kDa of the standards shown in Lane 1. Lane 1, molecular weight standards; Lane 2, *Y. pestis* strain KIM6+ grown in media supplemented with 300 μM $FeCl_3$; Lane 3, *Y. pestis* strain KIM6+ grown in media supplemented with 160 μM 2,2-diprydyl; Lane 4, *Y. enterocolitica* ATCC strain 27729 grown in media supplemented with 160 μM 2,2-diprydyl; Lane 5, *Y. enterocolitica* ATCC strain 27729 grown in media supplemented with 300 μM $FeCl_3$.

FIG. 2. Survival of vaccinated and non-vaccinated mice following challenge with *Y. enterocolitica*. Chart showing survival analysis of mice following immunization with membrane proteins derived from *Y. enterocolitica* strain 27729 grown under iron-limiting conditions and subsequent live challenge with strain 27729. Mortality was recorded for 7 days following challenge.

FIG. 3. Nucleotide sequences of SEQ ID NOs: 1-23.

DETAILED DESCRIPTION OF PREFERRED EMBODIMENTS OF THE INVENTION

The present invention provides polypeptides and compositions including polypeptides. As used herein, "polypeptide" refers to a polymer of amino acids linked by peptide bonds. Thus, for example, the terms peptide, oligopeptide, protein, and enzyme are included within the definition of polypeptide. This term also includes post-expression modifications of the polypeptide, for example, glycosylations, acetylations, phosphorylations, and the like. The term polypeptide does not connote a specific length of a polymer of amino acids. A polypeptide may be isolatable directly from a natural source, or can be prepared with the aid of recombinant, enzymatic, or chemical techniques. In the case of a polypeptide that is naturally occurring, such a polypeptide is typically isolated. An "isolated" polypeptide is one that has been removed from its natural environment. For instance, an isolated polypeptide is a polypeptide that has been removed from the cytoplasm or from the outer membrane of a cell, and many of the polypeptides, nucleic acids, and other cellular material of its natural environment are no longer present. An "isolatable" polypeptide is a polypeptide that could be isolated from a particular source. A "purified" polypeptide is one that is at least 60% free, preferably at least 75% free, and most preferably at least 90% free from other components with which they are naturally associated. Polypeptides that are produced outside the organism in which they naturally occur, e.g., through chemical or recombinant means, are considered to be isolated and purified by definition, since they were never present in a natural environment. As used herein, a "polypeptide fragment" refers to a portion of a polypeptide that results from digestion of a polypeptide with a protease. Unless otherwise specified, "a," "an," "the," and "at least one" are used interchangeably and mean one or more than one. The terms "comprises" and variations thereof do not have a limiting meaning where these terms appear in the description and claims.

A polypeptide of the present invention may be characterized by molecular weight, mass fingerprint, or the combination thereof. The molecular weight of a polypeptide, typically expressed in kilodaltons (kDa), can be determined using routine methods including, for instance, gel filtration, gel electrophoresis including sodium dodecyl sulfate (SDS) polyacrylamide gel electrophoresis (PAGE), capillary electrophoresis, mass spectrometry, and liquid chromatography including HPLC. Preferably, molecular weight is determined by resolving a polypeptide using an SDS polyacrylamide gel having a stacking gel of about 4% and a resolving gel of about 10% under reducing and denaturing conditions. Unless indicated otherwise, molecular weight refers to molecular weight as determined by SDS-PAGE. As used herein, a "mass fingerprint" refers to a population of polypeptide fragments obtained from a polypeptide after digestion with a protease. Typically, the polypeptide fragments resulting from a digestion are analyzed using a mass spectrometric method. Each polypeptide fragment is characterized by a mass, or by a mass (m) to charge (z) ratio, which is referred to as an "m/z ratio" or an "m/z value". Methods for generating a mass fingerprint of a polypeptide are routine. An example of such a method is disclosed in Example 9.

Polypeptides of the present invention may be metal regulated polypeptides. As used herein, a "metal regulated polypeptide" is a polypeptide that is expressed by a microbe at a greater level when the microbe is grown in low metal conditions compared to growth of the same microbe in high metal conditions. Low metal and high metal conditions are described herein. For instance, one class of metal regulated polypeptide produced by Yersinia spp. is not expressed at detectable levels during growth of the microbe in high metal conditions but is expressed at detectable levels during growth in low metal conditions. Examples of such metal regulated polypeptides isolatable from Yersinia enterocolitica have molecular weights of 83 kDa, 70 kDa, or 66 kDa. In some aspects, Y. enterocolitica may produce two different polypeptides each having a molecular weight of 83 kDa and each expressed at detectable levels during growth of the microbe in low metal conditions and not expressed at detectable levels during growth in high metal conditions. Examples of such metal regulated polypeptides isolatable from Yersinia pestis have molecular weights of 94 kDa, 88 kDa, 77 kDa, 73 kDa, or 64 kDa.

Another type of metal regulated polypeptide produced by Yersinia spp. is expressed at detectable levels during growth of the microbe in high metal conditions but significantly more of the polypeptide is expressed during growth in low metal conditions. The expression of such polypeptides is referred to herein as "enhanced" during growth in low metal conditions. Typically, the expression of a polypeptide during growth in low metal conditions is at least 10% or at least 50% greater than the expression of the polypeptide during growth in high metal conditions. Examples of metal regulated polypeptides showing enhanced expression and isolatable from Y. enterocolitica have molecular weights of 268 kDa, 79 kDa, or 45 kDa. Examples of metal regulated polypeptides showing enhanced expression and isolatable from Y. pestis have molecular weights of 254 kDa, 46 kDa, 37 kDa, 36 kDa, 31 kDa, 28 kDa, or 20 kDa. In some aspects, Y. pestis may produce two different polypeptides each having a molecular weight of 31 kDa and each showing enhanced expression.

The expression of some polypeptides of the present invention is not significantly influenced by the presence of a metal. Examples of such polypeptides isolatable from Y. enterocolitica have molecular weights of 92 kDa, 54 kDa, 40 kDa, 38 kDa, 37 kDa, 31 kDa, or 28 kDa. In some aspects, Y. enterocolitica may produce two different polypeptides each having a molecular weight of 31 kDa and each not significantly influenced by the presence of a metal. Examples of such polypeptides isolatable from Y. pestis have molecular weights of 104 kDa, 99 kDa, 60 kDa, or 44 kDa.

Whether a polypeptide is a metal regulated polypeptide or not can be determined by methods useful for comparing the presence of polypeptides, including, for example, gel filtration, gel electrophoresis including sodium dodecyl sulfate-polyacrylamide gel electrophoresis (SDS-PAGE), capillary electrophoresis, mass spectrometry, and liquid chromatography including HPLC. Separate cultures of a microbe are grown under high metal conditions and under low metal conditions, polypeptides of the present invention are isolated as described herein, and the polypeptides present in each culture are resolved and compared. Typically, an equal amount of polypeptides from each culture is used. Preferably, the polypeptides are resolved using an SDS polyacrylamide gel having a stacking gel of about 4% and a resolving gel of about 10% under reducing and denaturing conditions. For instance, 30 micrograms (μg) of total polypeptide from each culture may be used and loaded into wells of a gel. After running the gel and staining the polypeptides with Coomasie Brilliant Blue, the two lanes can be compared. When determining whether a polypeptide is or is not expressed at a detectable level, 30 μg of total polypeptide from a culture is resolved on an SDS-PAGE gel and stained with Coomasie Brilliant Blue using methods known in the art. A polypeptide that can be visualized by eye is considered to be expressed at a detectable level, while a polypeptide that cannot be visualized by eye is considered to be not expressed at a detectable level.

Polypeptides of the present invention may have immunogenic activity. "Immunogenic activity" refers to the ability of a polypeptide to elicit an immunological response in an animal. An immunological response to a polypeptide is the development in an animal of a cellular and/or antibody-mediated immune response to the polypeptide. Usually, an immunological response includes but is not limited to one or more of the following effects: the production of antibodies, B cells, helper T cells, suppressor T cells, and/or cytotoxic T cells, directed to an epitope or epitopes of the polypeptide. "Epitope" refers to the site on an antigen to which specific B cells and/or T cells respond so that antibody is produced. The immunogenic activity may be protective. "Protective immunogenic activity" refers to the ability of a polypeptide to elicit an immunological response in an animal that prevents or inhibits infection by Yersinia spp., for instance, Y. enterocolitica or Y. pestis. Whether a polypeptide has protective immunogenic activity can be determined by methods known in the art, for instance as described in example 4 or example 7. For example, a polypeptide of the present invention, or combination of polypeptides of the present invention, protect a rodent such as a mouse against challenge with a Yersinia spp. A polypeptide of the present invention may have seroreactive activity. "Seroactive activity" refers to the ability of a candidate polypeptide to react with antibody present in convalescent serum from an animal infected with a Yersinia spp., preferably Y. enterocolitica or Y. pestis. Polypeptides of the present invention may have immunoregulatory activity. "Immunoregulatory activity" refers to the ability of a polypeptide to act in a nonspecific manner to enhance an immune response to a particular antigen. Methods for determining whether a polypeptide has immunoregulatory activity are known in the art.

A polypeptide of the present invention has the characteristics of a polypeptide expressed by a reference microbe. The characteristics include both molecular weight and mass fingerprint. The reference microbe can be *Y. enterocolitica, Y. pseudotuberculosis, Y. pestis, Y. ruckeri, Y. rohdei, Y. aldovae, Y. bercovieri, Y. frederiksenii, Y. intermedia, Y. kristensenii*, or *Y. moolaretti*, preferably *Y. enterocolitica*, for instance, *Y. enterocolitica* ATCC strain 27729, or *Y. pestis*, for instance, *Y. pestis* strain KIM6+(Gong et al., Infect. Immun., 69:2829-2837 (2001)).

When the reference microbe is *Y. enterocolitica*, for instance. *Y. enterocolitica* ATCC strain 27729, a candidate polypeptide is considered to be a polypeptide of the present invention if it has a molecular weight of 268 kDa, 83 kDa, 79 kDa, 70 kDa, 66 kDa, or 45 kDa, and has a mass fingerprint that is similar to the mass fingerprint of a metal regulated polypeptide expressed by the reference microbe and having a molecular weight of 268 kDa, 83 kDa, 79 kDa, 70 kDa, 66 kDa, or 45 kDa, respectively. Preferably, such polypeptides are metal regulated. For instance, a candidate polypeptide is a polypeptide of the present invention if it has a molecular weight of 83 kDa and has a mass fingerprint similar to the mass fingerprint of one of the metal regulated 83 kDa polypeptides produced by the reference strain *Y. enterocolitica* ATCC strain 27729. A candidate polypeptide is also considered to be a polypeptide of the present invention if it has a molecular weight of 92 kDa, 54 kDa, 40 kDa, 38 kDa, 37 kDa, 31 kDa, or 28 kDa and has a mass fingerprint that is similar to the mass fingerprint of a polypeptide expressed by the reference microbe and having a molecular weight of 92 kDa, 54 kDa, 40 kDa, 38 kDa, 37 kDa, 31 kDa, or 28 kDa, respectively.

When the reference microbe is *Y. pestis*, for instance, *Y. pestis* strain KIM6+, a candidate polypeptide is considered to be a polypeptide of the present invention if it has a molecular weight of 254 kDa, 94 kDa, 88 kDa, 77 kDa, 73 kDa, 64 kDa, 46 kDa, 37 kDa, 36 kDa, 31 kDa, 28 kDa, or 20 kDa, and has a mass fingerprint that is similar to the mass fingerprint of a metal regulated polypeptide expressed by the reference microbe and having a molecular weight of 254 kDa, 94 kDa, 88 kDa, 77 kDa, 73 kDa, 64 kDa, 46 kDa, 37 kDa, 36 kDa, 31 kDa, 28 kDa, or 20 kDa, respectively. Preferably, such polypeptides are metal regulated. For instance, a candidate polypeptide is a polypeptide of the present invention if it has a molecular weight of 94 kDa and has a mass fingerprint similar to the mass fingerprint of one of the metal regulated 94 kDa polypeptides produced by the reference strain *Y. pestis* strain KIM6+. A candidate polypeptide is also considered to be a polypeptide of the present invention if it has a molecular weight of 104 kDa, 99 kDa, 60 kDa, or 44 kDa and has a mass fingerprint that is similar to the mass fingerprint of a polypeptide expressed by the reference microbe and having a molecular weight of 104 kDa, 99 kDa, 60 kDa, or 44 kDa, respectively.

The polypeptides expressed by a reference microbe and referred to above by molecular weight can be obtained by growth of the reference microbe under low metal conditions and the subsequent isolation of a polypeptide by the processes disclosed herein. A candidate polypeptide is isolatable from a microbe, preferably a gram negative microbe, more preferably, a member of the family Enterobacteriaceae preferably, a member of the genus *Yersinia*, such as *Y. enterocolitica, Y. pseudotuberculosis*, or *Y. pestis*. A candidate polypeptide may also be produced using recombinant, enzymatic, or chemical techniques.

A candidate polypeptide may be evaluated by mass spectrometric analysis to determine whether the candidate polypeptide has a mass fingerprint similar to one of the polypeptides expressed by a reference microbe and referred to above by molecular weight. Typically, the candidate polypeptide is isolated, for instance by resolving the candidate polypeptide by gel electrophoresis and excising the portion of the gel containing the candidate polypeptide. Any gel electrophoresis method that separates polypeptides based on differing characteristics can be used, including 1 dimensional or 2 dimensional gel electrophoresis, as well as liquid chromatographic separation based on, for instance, hydrophobicity, pi, or size. The candidate polypeptide is fragmented, for instance by digestion with a protease. Preferably, the protease cleaves the peptide bond on the carboxy-terminal side of the amino acid lysine and the amino acid arginine, except when the amino acid following the lysine or the arginine is a proline. An example of such a protease is trypsin. Methods for digesting a polypeptide with trypsin are routine and known in the an. An example of such a method is disclosed in Example 9.

Methods for the mass spectrometric analysis of polypeptides are routine and known in the art and include, but are not limited to, matrix assisted laser desorption/ionization time of flight mass spectroscopy (MALDI-TOF MS). Typically, a mixture containing the polypeptide fragments obtained from a candidate polypeptide is mixed with a matrix that functions to transform the laser energy to the sample and produce ionized, preferably monoisotopic, polypeptide fragments. Examples of matrices that can be used include, for instance, sinapinic acid or cyano-4-hydroxycinnamic acid. An example of a method for the analysis of polypeptides by MALDI-TOF MS is described in Example 9. The ionized polypeptide fragments are separated according to their m/z ratio, and detected to yield a spectrum of m/z ratio versus intensity. The spectrum includes m/z values that represent the polypeptide fragments derived from the candidate polypeptide. For any given polypeptide, the amount of each polypeptide fragment resulting from a trypsin digestion should be equimolar. However, it is known that trypsin digestion is not always 100% efficient, for instance, some sites are more efficiently cleaved. Thus, when MALDI-TOF MS is used to determine m/z values, the intensity of each m/z value is typically not identical. Generally, a spectrum has a background level of noise present across most of the x-axis (i.e., the axis having the values of the m/z ratios). This background level of noise varies depending on the running conditions and the machine used, and is easily identified by visual inspection of the spectrum. An m/z value is generally considered to represent a polypeptide fragment when the intensity is at least 2 times greater, 3 times greater, or 4 times greater than the background level of noise. The spectrum usually includes other mfz values that are artifacts resulting from, for instance, incomplete digestion, over digestion, other polypeptides that may be present in the mixture, or the protease used to digest the polypeptide including m/z values resulting from autolysis of the protease. This method of digesting a polypeptide with a protease is recognized by the art as resulting in a mass fingerprint of great specificity that can be used to accurately characterize the polypeptide and distinguish it from other polypeptides.

In this aspect of the invention, when a candidate polypeptide is analyzed by mass spectroscopy, preferably both the candidate polypeptide and the polypeptide from the reference microbe are prepared and analyzed together, thereby decreasing any potential artifacts resulting from differences in sample handling and running conditions. Preferably, all reagents used to prepare and analyze the two polypeptides are the same. For instance, the polypeptide from the reference microbe and the candidate polypeptide are isolated under substantially the same conditions, fragmented under substantially the same conditions, and analyzed by MALDI-TOF MS on the same machine under substantially the same conditions. A mass fingerprint of a candidate polypeptide is considered to be similar to the mass fingerprint of a polypeptide from a reference microbe when at least 80%, at least 90%, at least 95%, or substantially all of the m/z values present in the spectrum of the reference microbe polypeptide and above the background level of noise are also present in the spectrum of the candidate polypeptide.

In another aspect, a polypeptide is considered to be a polypeptide of the present invention if it has a molecular weight of a reference polypeptide described in Table 1 or Table 2 and has a mass fingerprint that includes the population of polypeptide fragments of the reference polypeptide as listed in Table 1 or Table 2. For instance, a polypeptide of the present invention includes a polypeptide of 83 kDa and a mass fingerprint that includes polypeptide fragments having masses of 686.37, 975.45, 1000.53, 1015.46, 1140.65, 1169.68, 1170.64, 1197.57, 1342.55, 1356.74, 1394.67, 1452.73, 1476.72, 1520.76, 1692.77, 1715.75, 1828.79, 1960.91, 2013.02, 2018.95, 2040.97, 2163.05, 2225.03, 2416.19, and 3174.44, or a mass fingerprint that includes polypeptide fragments having masses of 1001.49, 1103.57, 1139.57, 1154.51, 1170.49, 1208.59, 1213.67, 1337.70, 1452.86, 1567.84, 1633.85, 1650.82, 1659.91, 1708.77, 1748.95, 1849.92, 1986.98, 2103.95, 2111.03, 2163.11, 2386.19, 2452.09, 2537.34, and 3422.66. The mass fingerprint of a candidate polypeptide can be determined by a mass spectrometric method, for instance by MALDI-TOF MS. The mass fingerprint of a candidate polypeptide will generally have additional polypeptide fragments and therefore additional m/z values other than those listed for a polypeptide in Table 1 or Table 2. Preferably, when the candidate polypeptide is being compared to a polypeptide in Table 1 or Table 2, the candidate polypeptide is obtained from a *Y. pestis*, *Y. pseudotuberculosis*, or *Y. enterocolitica*, more preferably, *Y. enterocolitica* or *Y. pestis*. A candidate polypeptide can be obtained by growth of a microbe under low metal conditions and the subsequent isolation of a polypeptide by the processes described herein.

It is well known in the art that modifications of amino acids can be accidentally introduced during sample handling, such as oxidation, and formation of carbamidomethyl derivatives. Further, these types of modifications alter the m/z value of a polypeptide fragment. For instance, if a polypeptide fragment contains a methoinine that is oxidized the m/z value will be increased by 16 relative to the same fragment that does not contain the oxidized methionine. Accordingly, those polypeptide fragments in Tables 1 and 2 having the notation "oxidation (M)" have an m/z value that is increased by 16 relative to the same fragment that does not contain the oxidized methionine. It is understood that the polypeptide fragments of Table 1 and Table 2 can be modified during sample handling.

TABLE 1

Characteristics of polypeotides obtained from *Y. enterocolitica*.

| polypeptide designation | approximate molecular weight in kilodaltons (kDa)[1] | mass of polypeptide fragments resulting from trypsin digest[2] | predicted amino acid sequence of the polypeptide fragment (SEQ ID Numbers listed in parenthesis) |
|---|---|---|---|
| Lw545 | 268 | 928.45 | FHQLDNR (SEQ ID No: 24) |
| | | 1139.57 | VNFTAGVGGYR (SEQ ID No: 25) |
| | | 1311.65 | NSVSIGHESLNR (SEQ ID No: 26) |
| | | 1439.69 | ASTSDTGVAVGFNSK (SEQ ID No: 27) |
| | | 1525.73 | SAETLASANVYADSK (SEQ ID No: 28) |
| | | 1554.69 | EAFDLSNDALDMAK + Oxidation (M) (SEQ ID No: 29) |
| | | 1580.77 | SAEVLGIANNYTDSK (SEQ ID No: 30) |
| | | 1595.78 | ALGDSAVTYGAGSTAQK (SEQ ID No: 31) |
| | | 1682.78 | EAFDLSNDALDMAKK + Oxidation (M) (SEQ ID No: 32) |
| | | 2109.18 | AAVAVGAGSIATGVNSVAIGPLSK (SEQ ID No: 33) |

TABLE 1-continued

Characteristics of polypeotides obtained from *Y. enterocolitica*.

| polypeptide designation | approximate molecular weight in kilodaltons (kDa)[1] | mass of polypeptide fragments resulting from trypsin digest[2] | predicted amino acid sequence of the polypeptide fragment (SEQ ID Numbers listed in parenthesis) |
|---|---|---|---|
| Lw391A | 83 | 686.37 | DIGNIR (SEQ ID No: 34) |
| | | 975.45 | FFVSYQW (SEQ ID No: 35) |
| | | 1000.53 | VNGQDVTLR (SEQ ID No: 36) |
| | | 1015.46 | ASYFDTNAK (SEQ ID No: 37) |
| | | 1140.65 | DLPVSILAGTR (SEQ ID No: 38) |
| | | 1169.68 | QGVLTLVDGIR (SEQ ID No: 39) |
| | | 1170.64 | NIPGLTVTGSGR (SEQ ID No: 40) |
| | | 1197.57 | YYNNSALEPK (SEQ ID No: 41) |
| | | 1342.55 | APTMGEMYNDSK (SEQ ID No: 42) |
| | | 1356.74 | IDQIQSLSANLR (SEQ ID No: 43) |
| | | 1394.67 | TDDVDGILSFGTR (SEQ ID No: 44) |
| | | 1452.73 | GMTTTVVLGNAFDK (SEQ ID No: 45) |
| | | 1476.72 | IADTMVVTATGNER (SEQ ID No: 46) |
| | | 1520.76 | FGSGWLQDEITLR (SEQ ID No: 47) |
| | | 1692.77 | NPQTSAASSTNLMTDR (SEQ ID No: 48) |
| | | 1715.75 | FNDLMMAEDDLQFK (SEQ ID No: 49) |
| | | 1828.79 | GSSEGYADVDADKWSSR (SEQ ID No: 50) |
| | | 1960.91 | QEQTPSGATESFPQADIR (SEQ ID No: 51) |
| | | 2013.02 | QGTDTGHLNSTFLDPALVK (SEQ ID No: 52) |
| | | 2018.95 | QSDGFNAPNDETISNVLAK (SEQ ID No: 53) |
| | | 2040.97 | VYSAAATGDKSFGLGASAFGR (SEQ ID No: 54) |
| | | 2163.05 | LFTDSFASHLLTYGTEAYK (SEQ ID No: 55) |
| | | 2225.03 | VSSSGTPQAGYGVNDFYVSYK (SEQ ID No: 56) |

TABLE 1-continued

Characteristics of polypeotides obtained from *Y. enterocolitica*.

| polypeptide designation | approximate molecular weight in kilodaltons (kDa)[1] | mass of polypeptide fragments resulting from trypsin digest[2] | predicted amino acid sequence of the polypeptide fragment (SEQ ID Numbers listed in parenthesis) |
|---|---|---|---|
| | | 2416.19 | GAVSVTPTDWLMLFGSYAQAFR (SEQ ID No: 57) |
| | | 3174.44 | SSFEAPMMVTVVEADTPTSETATSATDMLR (SEQ ID No: 58) |
| Lw391B | 83 | 1001.49 | NDASVQNVR (SEQ ID No: 59) |
| | | 1103.57 | IGFLGQQDAR (SEQ ID No: 60) |
| | | 1139.57 | VNLGYAANYR (SEQ ID No: 61) |
| | | 1154.51 | GYGNPSQNYR (SEQ ID No: 62) |
| | | 1170.49 | YGDDDQFGVR (SEQ ID No: 63) |
| | | 1208.59 | GHFDTGPITHK (SEQ ID No: 64) |
| | | 1213.67 | LLASATWLDPK (SEQ ID No: 65) |
| | | 1337.70 | NVPFNVIGYTSK (SEQ ID No: 66) |
| | | 1452.86 | LKPWTRLDLGVR (SEQ ID No: 67) |
| | | 1567.84 | VSLYANHIEALGPGK (SEQ ID No: 68) |
| | | 1633.85 | GIELNVFGEPVFGTR (SEQ ID No: 69) |
| | | 1650.82 | TNDTITVVGAQETFR (SEQ ID No: 70) |
| | | 1659.91 | VTPIYGIMVKPWEK (SEQ ID No: 71) |
| | | 1708.77 | NFDSGVPNSAGSLDAMK (SEQ ID No: 72) |
| | | 1748.95 | LYVPYVADSVAGLGGIR (SEQ ID No: 73) |
| | | 1849.92 | VTVDYGSASQVGGALDVGR (SEQ ID No: 74) |
| | | 1986.98 | AGGNPLIPTYLDGQVANGGR (SEQ ID No: 75) |
| | | 2103.95 | SEYDVSQNWTVYGSVGASR (SEQ ID No: 76) |
| | | 2111.03 | GYNLDGDDISFGGLFGVLPR (SEQ ID No: 77) |
| | | 2163.11 | SGSQYANEANTLKLKPWTR (SEQ ID No: 78) |
| | | 2386.19 | GANAFINGISPSGSGVGGMINLEPK (SEQ ID No: 79) |

TABLE 1-continued

Characteristics of polypeotides obtained from *Y. enterocolitica*.

| polypeptide designation | approximate molecular weight in kilodaltons (kDa)[1] | mass of polypeptide fragments resulting from trypsin digest[2] | predicted amino acid sequence of the polypeptide fragment (SEQ ID Numbers listed in parenthesis) |
|---|---|---|---|
| | | 2452.09 | NEETGQYGAPMLTNNNGDATISR (SEQ ID No: 80) |
| | | 2537.34 | SAPYQYNGKPVVNAGQIPGIIHSK (SEQ ID No: 81) |
| | | 3422.66 | YGGTLALFEITRPTGMVDPATNVYGFYGEQR (SEQ ID No: 82) |
| Lw392 | 79 | 836.44 | YDTVALR (SEQ ID No: 83) |
| | | 1017.59 | VLLGVDFQK (SEQ ID No: 84) |
| | | 1070.48 | FDDVWSPR (SEQ ID No: 85) |
| | | 1085.50 | SVQATVGYDF (SEQ ID No: 86) |
| | | 1131.59 | ADLGTWAASLK (SEQ ID No: 87) |
| | | 1188.55 | QWADDANTLR (SEQ ID No: 88) |
| | | 1214.63 | VNSQGLELEAR (SEQ ID No: 89) |
| | | 1235.65 | AVPATYYVPAGK (SEQ ID No: 90) |
| | | 1255.66 | LSVIAGYTYNR (SEQ ID No: 91) |
| | | 1263.65 | VPSYTLGDASVR (SEQ ID No: 92) |
| | | 1360.66 | RPQFTSEGHFR (SEQ ID No: 93) |
| | | 1496.67 | GPFDGESNHNVFK (SEQ ID No: 94) |
| | | 1501.79 | GAFVQLNVNNIADK (SEQ ID No: 95) |
| | | 1614.75 | WQQIYSYEFSHK (SEQ ID No: 96) |
| | | 1652.77 | GFFDGESNHNVFKR (SEQ ID No: 97) |
| | | 1717.82 | GFHGGDVNNTFLDGLR (SEQ ID No: 98) |
| | | 1770.85 | RWQQIYSYEFSHK (SEQ ID No: 99) |
| | | 1819.86 | AGHEADLPTSGYTATTTK (SEQ ID No: 100) |
| | | 1827.01 | TDQPLILTAQSVSVVTR (SEQ ID No: 101) |
| | | 2004.92 | DPSGGYHSAVPADGSIYGQK (SEQ ID No: 102) |

TABLE 1-continued

Characteristics of polypeotides obtained from *Y. enterocolitica*.

| polypeptide designation | approximate molecular weight in kilodaltons (kDa)[1] | mass of polypeptide fragments resulting from trypsin digest[2] | predicted amino acid sequence of the polypeptide fragment (SEQ ID Numbers listed in parenthesis) |
|---|---|---|---|
| | | 2066.02 | GPSSALYGQSIPGGVVMMTSK (SEQ ID No: 103) |
| | | 2119.91 | KYVAACYSTSYCYWGAER (SEQ ID No: 104) |
| | | 2299.22 | YAIAPSLLWQPDENTSLLLR (SEQ ID No: 105) |
| | | 2307.15 | LLSDGGSYNVLQVDPWFLER (SEQ ID No: 106) |
| | | 2782.23 | QNASYTHSNTQLEQVYQGGWNSDR (SEQ ID No: 107) |
| | | 2911.35 | LTAGNNNTQVAAFDYTDAISEHWAFR (SEQ ID No: 108) |
| | | 3023.42 | RYEQSGVYLQDEMTLDNWHLNLSGR (SEQ ID No: 109) |
| | | 3286.53 | QQMDDQNVATVNQALNYTPGVFTGFSGGATR (SEQ ID No: 110) |
| Lw393 | 70 | 713.42 | VPFVPR (SEQ ID No: 111) |
| | | 759.42 | TVGINR (SEQ ID No: 112) |
| | | 806.41 | YGALMPR (SEQ ID No: 113) |
| | | 819.42 | FDIGGGVR (SEQ ID No: 114) |
| | | 919.48 | GPQGTLYGK (SEQ ID No: 115) |
| | | 1023.50 | GYIEGGVSSR (SEQ ID No: 116) |
| | | 1051.53 | SINYELGTR (SEQ ID No: 117) |
| | | 1186.57 | WNQDVQELR (SEQ ID No. 118) |
| | | 1199.60 | TVDMVFGLYR (SEQ ID No: 119) |
| | | 1394.68 | YGAGSSVNGVIDTR (SEQ ID No: 120) |
| | | 1436.66 | LSLSDGSPDPYMR (SEQ ID No: 121) |
| | | 1479.70 | ATQDAYVGWNDIK (SEQ ID No: 122) |
| | | 1540.80 | INISVHVDNLFDR (SEQ ID No: 123) |
| | | 1545.80 | TFPSGSLIVNMPQR (SEQ ID No: 124) |
| | | 1564.76 | KLSLSDGSPDPYMR (SEQ ID No: 125) |

TABLE 1-continued

Characteristics of polypeotides obtained from *Y. enterocolitica*.

| polypeptide designation | approximate molecular weight in kilodaltons (kDa)[1] | mass of polypeptide fragments resulting from trypsin digest[2] | predicted amino acid sequence of the polypeptide fragment (SEQ ID Numbers listed in parenthesis) |
|---|---|---|---|
| | | 1667.72 | SEFTNDSELYHGNR (SEQ ID No: 126) |
| | | 1730.85 | FAPGWSWDINGNVIR (SEQ ID No: 127) |
| | | 1789.81 | LAPDDQPWEMGFAASR (SEQ ID No: 128) |
| | | 1904.85 | TYGYMNGSSAVAQVNMGR (SEQ ID No: 129) |
| | | 1981.02 | SAQGGIINIVTQQPDSTPR (SEQ ID No: 130) |
| | | 1982.93 | QGTYATLDSSLGWQATER (SEQ ID No: 131) |
| | | 1995.94 | DMQLYSGPVGMQTLSNAGK (SEQ ID No: 132) |
| | | 2009.89 | SSTQYHGSMLGNPFGDQGK (SEQ ID No: 133) |
| | | 2027.02 | LAVNLVGPHYFDGDNQLR (SEQ ID No: 134) |
| | | 2058.99 | LRLAPDDQPWEMGFAASR (SEQ ID No: 135) |
| | | 2132.93 | QVDDGDMINPATGSDDLGGTR (SEQ ID No: 136) |
| | | 2162.17 | FNLSGPIQDGLLYGSVTLLR (SEQ ID No: 137) |
| | | 2274.20 | VLPGLNIENSGNMLFSTISLR (SEQ ID No: 138) |
| | | 2363.13 | SEFTNDSELYHGNRVPFVPR (SEQ ID No: 139) |
| | | 2377.30 | SKFNLSGPIQDGLLYGSVTLLR (SEQ ID No: 140) |
| | | 2383.07 | SNDDQVLGQLSAGYMLTDDWR (SEQ ID No: 141) |
| | | 2563.22 | SASANNVSSTVVSAPELSDAGVTASDK (SEQ ID No: 142) |
| | | 2657.23 | YTTDDWVFNLISAWQQQHYSR (SEQ ID No: 143) |
| | | 2833.50 | IAQGYKPSGYNIVPTAGLDAKPFVAEK (SEQ ID No: 144) |
| | | 2929.46 | SASANNVSSTVVSAPELSDAGVTASDKLPR (SEQ ID No: 145) |
| Lw550 | 66 | 867.49 | VSGLLSHR (SEQ ID No: 146) |
| | | 881.42 | TSEYLNR (SEQ ID No: 147) |
| | | 883.43 | EWHGTVR (SEQ ID No: 148) |

TABLE 1-continued

Characteristics of polypeotides obtained from *Y. enterocolitica*.

| polypeptide designation | approximate molecular weight in kilodaltons (kDa)[1] | mass of polypeptide fragments resulting from trypsin digest[2] | predicted amino acid sequence of the polypeptide fragment (SEQ ID Numbers listed in parenthesis) |
|---|---|---|---|
| | | 1020.59 | YTLILVDGK (SEQ ID No: 149) |
| | | 1086.57 | RVDIEVNDK (SEQ ID No: 150) |
| | | 1167.61 | VGKEWHGTVR (SEQ ID No: 151) |
| | | 1176.69 | YTLILVDGKR (SEQ ID No: 152) |
| | | 1207.63 | LMGGVYNVLDK (SEQ ID No: 153) |
| | | 1345.72 | IQDSAASISVVTR (SEQ ID No: 154) |
| | | 1748.72 | MDQDENYGTHWTPR (SEQ ID No: 155) |
| | | 1753.77 | NEFDFDIGHYVQDR (SEQ ID No: 156) |
| | | 1850.95 | DVPGVVVTGGGSHSDISIR (SEQ ID No: 157) |
| | | 2520.27 | GTRPNSDGSGIEQGWLPPLAAIER (SEQ ID No: 158) |
| | | 2606.16 | NNYAITHHGYYDFGNSTSYVQR (SEQ ID No: 159) |
| | | 2942.50 | AYTDITDALKDVPGVVVTGGGSHSDISIR (SEQ ID No: 160) |
| | | 3085.41 | NGAATFTLTPDDKNEFDFDIGHYVQDR (SEQ ID No: 161) |
| Lw552 | 45 | 1139.57 | VNFTAGVGGYR (SEQ ID No: 162) |
| | | 1208.61 | SSQALAIGSGYR (SEQ ID No: 163) |
| | | 1311.65 | NSVSIGHESLNR (SEQ ID No: 164) |
| | | 1439.69 | ASTSDTGVAVGFNSK (SEQ ID No: 165) |
| | | 1500.74 | TTLETAEEHTNKK (SEQ ID No: 166) |
| | | 1525.73 | SAETLASANVYADSK (SEQ ID No: 167) |
| | | 1580.77 | SAEVLGIANNYTDSK (SEQ ID No: 168) |
| | | 1595.78 | ALGDSAVTYGAGSTAQK (SEQ ID No: 169) |
| Lw555 | 37 | 704.42 | LGFAGLK (SEQ ID No: 170) |
| | | 880.43 | ADAYSGGLK (SEQ ID No: 171) |

TABLE 1-continued

Characteristics of polypeotides obtained from *Y. enterocolitica*.

| polypeptide designation | approximate molecular weight in kilodaltons (kDa)[1] | mass of polypeptide fragments resulting from trypsin digest[2] | predicted amino acid sequence of the polypeptide fragment (SEQ ID Numbers listed in parenthesis) |
|---|---|---|---|
| | | 970.38 | DGDQSYMR (SEQ ID No: 172) |
| | | 121.57 | DGNKLDLYGK (SEQ ID No: 173) |
| | | 1279.54 | AEDQDQGNPTR (SEQ ID No: 174) |
| | | 1294.58 | VDGLHYFSDDK (SEQ ID No: 175) |
| | | 1334.67 | INLLDENEPTK (SEQ ID No: 176) |
| | | 1509.71 | VDGLHYFSDDKSK (SEQ ID No: 177) |
| | | 1907.96 | NAGINTDDIVAVGLVYQF (SEQ ID No: 178) |
| | | 2245.12 | NTNFFGLVDGLNFALQYQGK (SEQ ID No: 179) |
| | | 2324.11 | YDANNVYLAATYAQTYNLTR (SEQ ID No: 180) |
| | | 2642.22 | GETQISDQLTGYGQWEYQANLNK (SEQ ID No: 181) |
| | | 2984.54 | AQNIELVAQYQFDFGLRPSVAYLQSK (SEQ ID No: 182) |
| | | 3087.49 | FGLKGETQISDQLTGYGQWEYQANLNK (SEQ ID No: 183) |
| Lw557 | 31 | 863.51 | TVYLQIK (SEQ ID No: 184) |
| | | 1403.71 | NTSDKNMLGLAPK + Oxidation (M) (SEQ ID No: 185) |
| | | 1615.81 | FEEAQPVLEDQLAK (SEQ ID No: 186) |
| | | 1779.83 | TQMSETIWLEPSSQK + Oxidation (M) (SEQ ID No: 187) |
| | | 1875.92 | VQTSTQTGNKHQYQTR (SEQ ID No: 188) |
| | | 2070.10 | VNLKFEEAQPVLEDQLAK (SEQ ID No: 189) |
| | | 2378.15 | GYTVTSSPEDAHYWIQANVLK (SEQ ID No: 190) |

[1]Molecular weight as determined by SDS-PAGE.
[2]The mass of a polypeptide fragment can be converted to m/z value by adding 1 to the mass. Each mass includes a range of plus or minus 1 Da or plus or minus 300 ppm.

TABLE 2

Characteristics of polypeptides obtained from Y. pestis.

| polypeptide designation | approximate molecular weight in kilodaltons (kDa)[1] | mass of polypeptide fragments resulting from trypsin digest[2] | predicted amino acid sequence of the polypeptide fragment |
|---|---|---|---|
| Lw529 | 104 | 643.43 | ALISLK (SEQ ID No: 191) |
| | | 684.36 | SIYFR (SEQ ID No: 192) |
| | | 770.49 | ILIGEVK (SEQ ID No: 193) |
| | | 840.46 | NPVARER (SEQ ID No: 194) |
| | | 898.55 | AVQDIILK (SEQ ID No: 195) |
| | | 961.55 | YPLISELK (SEQ ID No: 196) |
| | | 1136.61 | NGIIFSPHPR (SEQ ID No: 197) |
| | | 1276.63 | EAGVQEADFLAK (SEQ ID No: 198) |
| | | 1292.62 | NFEEAVEKAEK (SEQ ID No: 199) |
| | | 1385.65 | VVDESEPFAHEK (SEQ ID No: 200) |
| | | 1409.76 | NGGLNAAIVGQPATK (SEQ ID No: 201) |
| | | 1421.84 | AAALAAADARIPLAK (SEQ ID No: 202) |
| | | 1497.82 | AVTNVAELNELVAR (SEQ ID No: 203) |
| | | 1566.75 | QTAFSQYDRPQAR (SEQ ID No: 204) |
| | | 1678.39 | LLKEFLPASYNEGAK (SEQ ID No: 205) |
| | | 1683.82 | YAEIADHLGLSAPGDR (SEQ ID No: 206) |
| | | 1725.93 | GSLPIALEEVATDGAKR (SEQ ID No: 207) |
| | | 1872.90 | EYANFSQEQVDKIFR (SEQ ID No: 208) |
| | | 1990.01 | NHFASEYIYNAYKDEK (SEQ ID No: 209) |
| | | 2020.06 | ILINTPASQGGIGDLYKFK (SEQ ID No: 210) |
| | | 2182.01 | EYVEEFDREEEVAAATAPK (SEQ ID No: 211) |
| | | 2584.21 | YNANDNPTKQTAFSQYDRPQAR (SEQ ID No: 212) |
| | | 2842.48 | AAYSSGKPAIGVGAGNTPVVVDETADIKR (SEQ ID No: 213) |

TABLE 2-continued

Characteristics of polypeptides obtained from Y. pestis.

| polypeptide designation | approximate molecular weight in kilodaltons (kDa)[1] | mass of polypeptide fragments resulting from trypsin digest[2] | predicted amino acid sequence of the polypeptide fragment |
|---|---|---|---|
| Lw530 | 99 | 1190.64 | ILFYTGVNHK (SEQ ID No: 214) |
| | | 1513.80 | YRNIGISAHIDAGK (SEQ ID No: 215) |
| | | 1590.77 | HSDDKEPFSALAFK (SEQ ID No: 216) |
| | | 1596.83 | IATDPFVGNLTFFR (SEQ ID No: 217) |
| | | 1636.82 | YLGGEELTEEEIKK (SEQ ID No: 218) |
| | | 1670.86 | MEFPEPVISVAVEPK (SEQ ID No: 219) |
| | | 1713.93 | EFIPAVDKGIQEQLK (SEQ ID No: 220) |
| | | 1718.96 | LGANPVPLQLAIGAEEK (SEQ ID No: 221) |
| | | 1750.91 | VYSGIVNSGDTVLNSVK (SEQ ID No: 222) |
| | | 1819.92 | EFNVEANVGKPQVAYR (SEQ ID No: 223) |
| | | 1863.01 | EEIKEVHAGDIAAAIGLK (SEQ ID No: 224) |
| | | 1966.91 | LHYGSYHDVDSSELAFK (SEQ ID No: 225) |
| | | 2122.10 | VYSGIVNSGDTVLNSVKSQR (SEQ ID No: 226) |
| Lw531 | 94 | 961.44 | NRDEWSR (SEQ ID No: 227) |
| | | 1167.49 | YEYGMFSQK + Oxidation (M) (SEQ ID No: 228) |
| | | 1257.64 | VSVIDENNGRR (SEQ ID No: 229) |
| | | 1371.63 | VLYPDDSTYSGR (SEQ ID No: 230) |
| | | 1383.64 | EENDPGLGNGGLGR (SEQ ID No: 231) |
| | | 1408.71 | IIDAPDNNWVPR (SEQ ID No: 232) |
| | | 1520.82 | NLDYPSFLLALQK (SEQ ID No: 233) |
| | | 1668.86 | EYADEIWHIKPIR (SEQ ID No: 234) |
| | | 1685.79 | SYVDTQEQVDALYR (SEQ ID No: 235) |
| | | 1713.78 | GYGIRYEYGMFSQK + Oxidation (M) (SEQ ID No: 236) |

TABLE 2-continued

Characteristics of polypeptides obtained from Y. pestis.

| polypeptide designation | approximate molecular weight in kilodaltons (kDa)[1] | mass of polypeptide fragments resulting from trypsin digest[2] | predicted amino acid sequence of the polypeptide fragment |
|---|---|---|---|
| | | 1716.81 | TLLNIANMGYFSSDR + Oxidation (M) (SEQ ID No: 237) |
| | | 1796.92 | TSPFSYTSPVVSVDALK (SEQ ID No: 238) |
| | | 1832.92 | LVEEQYPDDKELLSR (SEQ ID No: 239) |
| | | 1844.91 | KTLLNIANMGYFSSDR + Oxidation (M) (SEQ ID No: 240) |
| | | 2218.12 | IAIHLNDTHPVLSIPEMMR + Oxidation (M) (SEQ ID No: 241) |
| | | 2426.09 | FNQGDYFAAVEDKNHSENVSR (SEQ ID No: 242) |
| Lw532 | 88 | 888.51 | YIQAAVPK (SEQ ID No: 243) |
| | | 926.46 | FNINYTR (SEQ ID No: 244) |
| | | 945.53 | SGFLIPNAK (SEQ ID No: 245) |
| | | 960.54 | IGFNIELR (SEQ ID No: 246) |
| | | 1171.60 | AQYLYVPYR (SEQ ID No: 247) |
| | | 1176.57 | GLQWQNEFR (SEQ ID No: 248) |
| | | 1289.64 | ITGWNAQGQTSK (SEQ ID No: 249) |
| | | 1332.67 | RGLQWQNEFR (SEQ ID No: 250) |
| | | 1357.66 | EEQVVEVWNAR (SEQ ID No: 251) |
| | | 1403.74 | IASANQVSTGLTSR (SEQ ID No: 252) |
| | | 1418.68 | FTSVNPTNPEASR (SEQ ID No: 253) |
| | | 1507.73 | IYTGPDGTDKNATR (SEQ ID No: 254) |
| | | 1578.78 | FNVSVGQIYYFSR (SEQ ID No: 255) |
| | | 1672.80 | QFQVFTAAGNSNAYR (SEQ ID No: 256) |
| | | 1735.83 | TVTATGDVNYDDPQIK (SEQ ID No: 257) |
| | | 2400.17 | LLATHYQQDIPASFADNASNPK (SEQ ID No: 258) |
| | | 2665.28 | VYNPDYQQGISQVGTTASWPIADR (SEQ ID No: 259) |

TABLE 2-continued

Characteristics of polypeptides obtained from Y. pestis.

| polypeptide designation | approximate molecular weight in kilodaltons (kDa)[1] | mass of polypeptide fragments resulting from trypsin digest[2] | predicted amino acid sequence of the polypeptide fragment |
|---|---|---|---|
| Lw533 | 77 | 686.37 | DIGNIR (SEQ ID No: 260) |
| | | 784.49 | RIEIVR (SEQ ID No: 261) |
| | | 858.41 | VSYFDTK (SEQ ID No: 262) |
| | | 952.50 | AKDYISTR (SEQ ID No: 263) |
| | | 1140.65 | DLPVSILAGTR (SEQ ID No: 264) |
| | | 1155.66 | QGVLTLVDGVR (SEQ ID No: 265) |
| | | 1170.64 | QVPGLTVTGSGR (SEQ ID No: 266) |
| | | 1197.57 | YYNNSAIEPK (SEQ ID No: 267) |
| | | 1402.71 | EQTTEGVKLENR (SEQ ID No: 268) |
| | | 1408.68 | TDDLDGILSPGTR (SEQ ID No: 269) |
| | | 1482.73 | TALFNWDLAYNR (SEQ ID No: 270) |
| | | 1522.71 | EYYTPQGIPQDGR (SEQ ID No: 271) |
| | | 1550.77 | FSSGWLQDEITLR (SEQ ID No: 272) |
| | | 1617.74 | HSTDTMVVTATGNER (SEQ ID No: 273) |
| | | 1674.78 | QEQTPGGATESFPQAK (SEQ ID No: 274) |
| | | 1745.84 | KHSTDTMVVTATGNER (SEQ ID No: 275) |
| | | 1787.92 | GTWQIDSIQSLSANLR (SEQ ID No: 276) |
| | | 1819.96 | IRFSSGWLQDEITLR (SEQ ID No: 277) |
| | | 1851.87 | VDMQAMTTTSVNIDQAK (SEQ ID No: 278) |
| | | 1940.75 | YDNVSGSSDGYADVDADK (SEQ ID No: 279) |
| | | 2013.02 | QGTDTGHLNSTFLDPALVK (SEQ ID No: 280) |
| | | 2017.97 | QSNGFNAPNDETISNVLAK (SEQ ID No: 281) |
| | | 2056.96 | VYSSAATGDHSFGLGASAFGR (SEQ ID No: 282) |

TABLE 2-continued

Characteristics of polypeptides obtained from Y. pestis.

| polypeptide designation | approximate molecular weight in kilodaltons (kDa)[1] | mass of polypeptide fragments resulting from trypsin digest[2] | predicted amino acid sequence of the polypeptide fragment |
|---|---|---|---|
| | | 2168.01 | VSSSTPQAGYGVNDFYVSYK (SEQ ID No: 283) |
| | | 2169.10 | LFIESPASHLLTYGTETYK (SEQ ID No: 284) |
| | | 2426.25 | TRLFIESPASHLLTYGTETYK (SEQ ID No: 285) |
| | | 2457.00 | YDNYSGSSDGYADVDADKWSSR (SEQ ID No: 286) |
| | | 2828.33 | VSSSTPQAGYGVNDFYVSYKGQEAFK (SEQ ID No: 287) |
| Lw534 | 73 | 628.39 | IEVIR (SEQ ID No: 288) |
| | | 748.43 | GTIFRR (SEQ ID No: 289) |
| | | 909.42 | GGYEDTLR (SEQ ID No: 290) |
| | | 930.51 | TGGLDISIR (SEQ ID No: 291) |
| | | 1291.71 | LLDSLALTYGAR (SEQ ID No: 292) |
| | | 1370.81 | LLKNTNIILDSK (SEQ ID No: 293) |
| | | 1440.70 | FTQNYANLSAANK (SEQ ID No: 294) |
| | | 1478.71 | YDNSANQLGTIGAR (SEQ ID No: 295) |
| | | 1586.83 | EAAASISVISQNELR (SEQ ID No: 296) |
| | | 1604.86 | GMPSAYTLILVDGIR (SEQ ID No: 297) |
| | | 1640.87 | LITNASVPQGSGLAGEK (SEQ ID No: 298) |
| | | 1654.77 | YEYQTTFGGHISPR (SEQ ID No: 299) |
| | | 1705.82 | DASRVESSNTGVELSR (SSQ ID No: 300) |
| | | 1707.83 | AYLVWDAQDNWTVK (SEQ ID No: 301) |
| | | 1757.91 | LNWNINEQLSTWLK (SEQ ID No: 302) |
| | | 1796.97 | LITNASVPQGSGLAGEKR (SEQ ID No: 303) |
| | | 1856.01 | IREAAASISVISQNELR (SEQ ID No: 303) |
| | | 1912.94 | INSVSIDNTTSTYTNVGK (SEQ ID No: 304) |

TABLE 2-continued

Characteristics of polypeptides obtained from Y. pestis.

| polypeptide designation | approximate molecular weight in kilodaltons (kDa)[1] | mass of polypeptide fragments resulting from trypsin digest[2] | predicted amino acid sequence of the polypeptide fragment |
|---|---|---|---|
| | | 2004.03 | DVTLNGAVNNLLDKDFTR (SEQ ID No: 305) |
| | | 2072.02 | FSFYSSGPAVEDQLGLSLR (SEQ ID No: 306) |
| | | 2155.08 | NKINSVSIDNTTSTYTNVGK (SEQ ID No: 307) |
| | | 2301.07 | LDFGTWNSSLSYNQTENIGR (SEQ ID No: 308) |
| | | 2395.11 | NYNDLAQALSDVEGVDVNSSTGK (SEQ ID No: 309) |
| | | 2484.12 | AWASSATLEHTFQENTAFGDSSK (SEQ ID No: 310) |
| | | 2557.36 | VVYNNLGSEFKPFSVLNLGVAYK (SEQ ID No: 311) |
| | | 2557.36 | VVYNNLGSSFKPFSVLNTGVAYK (SEQ ID No: 312) |
| | | 2675.42 | TPTLAQLHNGISGVTGQGTITTIGNPK (SEQ ID No: 313)) |
| | | 2983.33 | DGIVLANNGDEFAQDAWSLFSEDEWR (SEQ ID No: 314) |
| | | 3161.51 | THIFAVGNGTTTAGDVFTSSQSTAGYVVPGR (SEQ ID No: 315) |
| | | 3184.52 | ITLGNDNRLDFGTWNSSLSYNQTENIGR (SEQ ID No: 316) |
| | | 3424.79 | GGVSTGYKTPTLAQLHNGISGVTGQGTITTIGNPK (SEQ ID No: 317) |
| | | 3471.62 | LEPESSVNTEVGVYYENETGFGANVTLFHNR (SSQ ID No: 318) |
| Lw535 | 64 | 713.42 | VPFVPR (SEQ ID No: 319) |
| | | 759.42 | TVGINTR (SEQ ID No: 320) |
| | | 773.40 | AATLGDAR (SEQ ID No: 321) |
| | | 806.41 | YGALMPR (SEQ ID No: 322) |
| | | 919.48 | GPQGTLYGK (SEQ ID No: 323) |
| | | 1023.50 | GYIEGGVSSR (SEQ ID No: 324) |
| | | 1051.53 | SINYELGTR (SEQ ID No: 325) |
| | | 1102.55 | ADATGVELEAK (SEQ ID No: 326) |
| | | 1164.56 | DMQLYSGPVR (SEQ ID No: 327) |

TABLE 2-continued

Characteristics of polypeptides obtained from *Y. pestis*.

| polypeptide designation | approximate molecular weight in kilodaltons (kDa)[1] | mass of polypeptide fragments resulting from trypsin digest[2] | predicted amino acid sequence of the polypeptide fragment |
|---|---|---|---|
| | | 1186.57 | WNQDVQELR (SEQ ID No: 328) |
| | | 1199.60 | TVDMVFGLYR (SEQ ID No: 329) |
| | | 1281.67 | TVGINTRIDFF (SEQ ID No: 330) |
| | | 1394.68 | YGAGSSVNGVIDTR (SEQ ID No: 331) |
| | | 1444.73 | ADATGVELEAKWR (SEQ ID No: 332) |
| | | 1479.70 | ATQDAYVGWNDIK (SEQ ID No: 333) |
| | | 1545.80 | TFPSGSLIVNMPQR (SEQ ID No: 334) |
| | | 1667.72 | SEFTNDSELYHGNR (SEQ ID No: 335) |
| | | 1692.82 | ATQDAYVGWNDIKGR (SEQ ID No: 336) |
| | | 1730.85 | FAPGWSWDINGNVIR (SEQ ID No: 337) |
| | | 1789.81 | LAPDDQPWEMGFAASR (SEQ ID No: 338) |
| | | 1904.85 | TYGYMNGSSAVAQVNMGR (SEQ ID No: 339) |
| | | 1968.90 | ECTRATQDAYVGWNDIK (SEQ ID No: 340) |
| | | 1981.02 | SAQGGIINIVTQQPDSTPR (SEQ ID No: 341) |
| | | 2009.89 | SSTQYHGSMLGNPFGDQGK (SEQ ID No: 342) |
| | | 2027.02 | LAVNLVGPHYFDGDNQLR (SEQ ID No: 343) |
| | | 2058.99 | YETADVTLQAATFYTHTK (SEQ ID No: 344) |
| | | 2162.17 | FNLSGPIQDGLLYGSVTLLR (SEQ ID No: 345) |
| | | 2363.13 | SEFTNDSELYHGNRVPFVPR (SEQ ID No: 346) |
| | | 2377.30 | SKFNLSGPIQDGLLYGSVTLLR (SEQ ID No: 347) |
| | | 2819.49 | VAQGYKPSGYNIVPTAGLDAKPFVAEK (SEQ ID No: 348) |
| | | 2929.46 | SASANNVSSTVVSAPELSDAGVTASDKLPR (SEQ ID No: 349) |

TABLE 2-continued

Characteristics of polypeptides obtained from Y. pestis.

| polypeptide designation | approximate molecular weight in kilodaltons (kDa)[1] | mass of polypeptide fragments resulting from trypsin digest[2] | predicted amino acid sequence of the polypeptide fragment |
|---|---|---|---|
| Lw536 | 60 | 1010.51 | VEDALHATR (SEQ ID No: 350) |
| | | 1186.65 | VAAVKAPGFGDR (SEQ ID No: 351) |
| | | 1230.66 | TTLEDLGQAKR (SEQ ID No: 352) |
| | | 1237.65 | ASVEDALHATR (SEQ ID No. 353) |
| | | 1290.65 | VGAATEVEMKEK (SEQ ID No: 354) |
| | | 1566.87 | AAVEEGVVAGGGVALIR (SEQ ID No: 355) |
| | | 1604.88 | NVVLDKSFGSPTITK (SEQ ID No: 356) |
| | | 1620.85 | SFGSPTITKDGVSVAR (SEQ ID No: 357) |
| | | 1668.75 | QQIEDATSDYDKEK (SEQ ID No: 358) |
| | | 2020.03 | AAHAIAGLKGDNEDQNVGIK (SEQ ID No: 359) |
| | | 2396.29 | VVINKDTTIIIDGVGDEAAIQGR (SEQ ID No: 360) |
| Lw537 | 46 | 872.51 | NLSLLSAR (SEQ ID No: 361) |
| | | 1000.53 | QTVTTPRAQ (SEQ ID No: 362) |
| | | 1179.55 | AAADRDAAYEK (SEQ ID No: 363) |
| | | 1257.63 | NNLDNALESLR (SEQ ID No: 364) |
| | | 1299.71 | LSQDLAREQIK (SEQ ID No: 365) |
| | | 1306.65 | DAAYEKINEVR (SEQ ID No: 366) |
| | | 1324.65 | AIDSLSYTEAQK (SEQ ID No: 367) |
| | | 1367.75 | TQRPDAVNNLLK (SEQ ID No: 368) |
| | | 1394.76 | YNYLINQLNIK (SEQ ID No: 369) |
| | | 1435.73 | ASYDTVLAAEVAAR (SEQ ID No: 370) |
| | | 1608.93 | LKTQRPDAVNNLLK (SEQ ID No: 371) |

TABLE 2-continued

Characteristics of polypeptides obtained from *Y. pestis*.

| polypeptide designation | approximate molecular weight in kilodaltons (kDa)[1] | mass of polypeptide fragments resulting from trypsin digest[2] | predicted amino acid sequence of the polypeptide fragment |
|---|---|---|---|
| | | 1615.87 | FNVGLVAITDVQNAR (SEQ ID No: 372) |
| | | 1779.96 | TILDVLTATTNLYQSK (SEQ ID No: 373) |
| | | 1951.01 | QITGVYYPELASLNVER (SEQ ID No: 374) |
| | | 1957.97 | AIDSLSYTEAQKQSVYR (SEQ ID No: 375) |
| | | 2018.98 | QAQYNFVGASELLESAHR (SEQ ID No: 376) |
| | | 2098.10 | SPLLPQLGLSAGYTHANGFR (SEQ ID No: 377) |
| | | 2177.16 | QQLADARYNYLINQLNIK (SEQ ID No: 378) |
| | | 2709.43 | INEVRSPLLPQLGLSAGYTHANGFR (SEQ ID No: 379) |
| Lw538 | 44 | 775.40 | HTPFFK (SEQ ID No: 380) |
| | | 836.49 | EHILLGR (SEQ ID No: 381) |
| | | 904.49 | FAIREGGR (SEQ ID No: 382) |
| | | 1026.58 | AGENVGVLLR (SEQ ID No: 383) |
| | | 1072.60 | GTVVTGRVER (SEQ ID No: 384) |
| | | 1199.66 | EGGRTVGAGVVAK (SEQ ID No: 385) |
| | | 1231.57 | ALEGEAEWEAK (SEQ ID No: 386) |
| | | 1232.61 | GYRPQFYFR (SEQ ID No: 387) |
| | | 1289.62 | DEGGRHTPPFK (SEQ ID No: 388) |
| | | 1375.63 | AFDQIDNAPEEK (SEQ ID No: 389) |
| | | 1602.76 | AFDQIDNAPEEKAR (SEQ ID No: 390) |
| | | 1613.89 | VGEEVEIVGIKDTVK (SEQ ID No: 391) |
| | | 1709.94 | LLDEGRAGENVGVLLR (SEQ ID No: 392) |
| | | 1772.87 | GITINTSHVEYDTPAR (SEQ ID No: 393) |

TABLE 2-continued

Characteristics of polypeptides obtained from Y. pestis.

| polypeptide designation | approximate molecular weight in kilodaltons (kDa)[1] | mass of polypeptide fragments resulting from trypsin digest[2] | predicted amino acid sequence of the polypeptide fragment |
|---|---|---|---|
| | | 1794.95 | TKPHVNYGTIGHVDHGK (SEQ ID No: 394) |
| | | 1904.95 | ELLSAYDFPGDDLPVVR (SEQ ID No: 395) |
| | | 1977.01 | IIELAGYLDSYIPEPER (SEQ ID No: 396) |
| | | 2000.01 | ARGITINTSHVEYDTPAR (SEQ ID No: 397) |
| Lw683 | 37 | 690.4064 | VGFAGLK (SEQ ID No: 398) |
| | | 893.4606 | ANAYTGGLK (SEQ ID No: 399) |
| | | 910.4330 | GNGMLTYR (SEQ ID No: 400) |
| | | 1049.5617 | RANAYTGGLK (SEQ ID No: 401) |
| | | 1114.4931 | SSDAAFGFADK (SEQ ID No: 402) |
| | | 1119.4906 | NMSTYVDYK (SEQ ID No: 403) |
| | | 1121.4697 | NGSSSETNNGR (SEQ ID No: 404) |
| | | 1197.5084 | NLDGDQSYMR (SEQ ID No: 405) |
| | | 1262.5567 | FADYGSLDYGR (SEQ ID No: 406) |
| | | 1307.6146 | IDGLHYFSDNK (SEQ ID No: 407) |
| | | 1319.7085 | INLLDKNDFTK (SEQ ID No: 408) |
| | | 1422.6739 | TTAQNDLQYGQGK (SEQ ID No: 409) |
| | | 1436.6976 | YVDIGATYFFNK (SEQ ID No: 410) |
| | | 1490.6022 | AENEDGNHDSFTR (SEQ ID No: 411) |
| | | 1533.8038 | GKDIGIYGDQDLLK (SEQ ID No: 412) |
| | | 1578.7750 | TTAQNDLQYGQGKR (SEQ ID No: 413) |
| | | 2245.1167 | NTNFFGLVDGLNFALQYQGK (SEQ ID No: 414) |
| | | 2367.1131 | YDANNVYLAANYTQTYNLTR (SEQ ID No: 415) |

TABLE 2-continued

Characteristics of polypeptides obtained from *Y. pestis.*

| polypeptide designation | approximate molecular weight in kilodaltons (kDa)[1] | mass of polypeptide fragments resulting from trypsin digest[2] | predicted amino acid sequence of the polypeptide fragment |
|---|---|---|---|
| | | 2487.1124 | IDGLHYFSDNKNLDGDQSYMR (SEQ ID No: 416) |
| | | 2684.2718 | GETQITDQLTGYGQWEYQVNLNK (SEQ ID No: 417) |
| | | 2979.5242 | AHNIEVVAQYQFDFGLRPSVAYLQSK (SEQ ID No: 418) |
| | | 3292.4764 | GVADQNGDGYGMSLSYDLGWGVSASAAMASSLR (SEQ ID No: 419) |
| Lw541 | 31 | 1019.58 | ALASNILYR (SEQ ID No: 420) |
| | | 1074.51 | SDPGAAFPWK (SEQ ID No: 421) |
| | | 1202.61 | KSDPGAAFPWK (SEQ ID No: 422) |
| | | 1247.61 | IFNLVDENER (SEQ ID No: 423) |
| | | 1321.58 | MYNIDYNSFR (SEQ ID No: 424) |
| | | 1403.64 | AWHAGVSYWDGR (SEQ ID No: 425) |
| | | 1786.80 | ALYDAGIGAWYDDETK (SEQ ID No: 426) |
| | | 1990.03 | FPDITPVNVVGHSDIAPGR (SEQ ID No: 427) |
| | | 2090.99 | YGYDTSGAVSEVGYNQLIR (SEQ ID No: 428) |
| | | 2118.12 | FPDITPVNVVGHSDIAPGRK (SEQ ID No: 429) |
| Lw542 | 31 | 1142.58 | SDPGPLFPWK (SEQ ID No: 430) |
| | | 1298.68 | SDPGPLFPWKR (SEQ ID No: 431) |
| | | 1307.76 | AIALQLVPEAQR (SEQ ID No: 432) |
| | | 1340.64 | AWHAGVSSWQGR (SEQ ID No: 433) |
| | | 1370.68 | IPQNGQLDTETR (SEQ ID No: 434) |
| | | 1578.77 | GTYQIDTHYPSVAK (SEQ ID No: 435) |
| | | 1779.95 | GAASVAVIQQALAAYGYK (SEQ ID No: 436) |
| | | 1789.94 | FLVLHYTAVGDAESLR (SEQ ID No: 437) |

TABLE 2-continued

Characteristics of polypeptides obtained from Y. pestis.

| polypeptide designation | approximate molecular weight in kilodaltons (kDa)[1] | mass of polypeptide fragments res

TABLE 3

| Molecular weight of reference polypeptide (kDa)[1] | NCBI sequence identifier of polypeptide identified by the computer algorithm as having best match to mass fingerprint of reference polypeptide | SEQ ID NO: |
|---|---|---|
| 268 | 23630568, adhesin YadA | 1 |
| 83 | 282049, hemin receptor precursor | 2 |
| 83 | 49114, ferrichrome receptor FcuA | 3 |
| 79 | 565634, ferrioxamine receptor | 4 |
| 70 | 517386, FyuA precursor | 5 |
| 66 | 77958488, Outer membrane receptor for ferrienterochelin and colicins | 6 |
| 45 | 23630568, adhesin YadA | 7 |
| 37 | 77956419, Outer membrane protein (porin) | 8 |
| 31 | 48605, YlpA protein | 9 |

[1]Molecular weight as determined by SDS-PAGE.

TABLE 4

| Molecular weight of reference polypeptide (kDa)[1] | NCBI sequence identifier of polypeptide identified by the computer algorithm as having best match to mass fingerprint of reference polypeptide | SEQ ID NO: |
|---|---|---|
| 104 | 22125915, CoA-linked acetaldehyde dehydrogenase | 10 |
| 99 | 51597993, elongation factor G | 11 |
| 94 | 15981846, glycogen phosphorylase | 12 |
| 88 | 45443416, organic solvent tolerance protein precursor | 13 |
| 77 | 22124457, TonB-dependent outer membrane receptor | 14 |
| 73 | 51595142, putative exogenous ferric siderophore receptor; Iha adhesin | 15 |
| 64 | 22126288, pesticin/yersiniabactin outer membrane receptor | 16 |
| 60 | 51594757, chaperonin GroEL | 17 |
| 46 | 22127390, outer membrane channel precursor protein | 18 |
| 44 | 51597992, elongation factor Tu | 19 |
| 37 | 77633559, Outer membrane protein (porin) | 20 |
| 31 | 22125738, putative regulator | 21 |
| 31 | 22125770, putative regulator | 22 |
| 20 | 22125223, outer membrane protein X | 23 |

[1]Molecular weight as determined by SDS-PAGE.

Typically, a candidate amino acid sequence having structural similarity to a reference amino acid sequence has immunogenic activity, protective immunogenic activity, seroactive activity, immunoregulatory activity, or a combination thereof.

The polypeptides expressed by a reference microbe and referred to above by molecular weight can be obtained by growth of the reference microbe under low metal conditions and the subsequent isolation of a polypeptide by the processes disclosed herein. A candidate polypeptide is isolatable from a microbe, preferably a gram negative microbe, more preferably, a member of the family Enterobacteriaceae preferably, a member of the genus Yersinia, such as Y. enterocolitica, Y. pseudotuberculosis, or Y. pestis. A candidate polypeptide may also be produced using recombinant, enzymatic, or chemical techniques.

Also provided by the present invention are whole cell preparations of a microbe, where the microbe expresses one or more of the polypeptides of the present invention. The cells present in a whole cell preparation are preferably inactivated such that the cells cannot replicate, but the immunogenic activity of the polypeptides of the present invention expressed by the microbe is maintained. Typically, the cells are killed by exposure to agents such as glutaraldehyde, formalin, or formaldehyde.

A composition of the present invention may include at least one polypeptide described herein, or a number of polypeptides that is an integer greater than 1 (e.g., at least 2, at least 3, at least 4. In some aspects, a composition may include at least 2 metal regulated polypeptides and at least two polypeptides whose expression is not significantly influenced by the presence of a metal. For example, when the polypeptides are isolatable from *Y. enterocolitica*, a composition can include 2, 3, 4, 5, or more isolated metal regulated polypeptides having molecular weights of 268 kDa, 83 kDa, 79 kDa, 70 kDa, 66 kDa, 45 kDa, or any subset or combination thereof, and two isolated polypeptides having a molecular weight of 92 kDa, 54 kDa, 40 kDa, 38 kDa, 37 kDa, 31 kDa, 28 kDa, or any subset or combination thereof. In another example, when the polypeptides are isolatable from *Y. pestis*, a composition can include 2, 3, 4, 5, or more isolated metal regulated polypeptides having molecular weights of 254 kDa, 94 kDa, 88 kDa, 77 kDa, 73 kDa, 64 kDa, 31 kDa, 28 kDa, 20 kDa, or any subset or combination thereof, and two isolated polypeptides having molecular weights of 104 kDa, 99 kDa, 60 kDa, 44 kDa, 46 kDa, 37 kDa, 36 kDa, or any subset or combination thereof. A composition can include polypeptides isolatable from 1 microbe, or can be isolatable from a combination of 2 or more microbes. For instance, a composition can include polypeptides isolatable from 2 or more *Yersinia* spp., from 2 or more *Y. enterocolitica* strains, or from a *Yersinia* spp. and a different microbe that is not a member of the genus *Yersinia*. The present invention also provides compositions including a whole cell preparation of one or more *Yersinia* spp.

Optionally, a polypeptide of the present invention can be covalently bound or conjugated to a carrier polypeptide to improve the immunological properties of the polypeptide. Useful carrier polypeptides are known in the art. For example, a polypeptide of the present invention could be coupled to known *Yersinia* outer membrane immunogens such as the F1 antigen or the V antigen. Likewise, polysaccharide components could be conjugated to the proteins of the present invention to enhance the protective effect of the compositions. The chemical coupling of polypeptides of the present invention can be carried out using known and routine methods. For instance, various homobifunctional and/or heterobifunctional cross-linker reagents such as bis (sulfosuccinimidyl) suberate, bis(diazobenzidine), dimethyl adipimidate, dimethyl pimelimidate, dimethyl superimidate, disuccinimidyl suberate, glutaraldehyde, m-maleimidobenzoyl-N-hydroxysuccinimide, sulfo-m-maleimidobenzoyl-N-hydroxysuccinimide, sulfosuccinimidyl 4-(N-maleimidomethyl) cyclohexane-1-carboxylate, sulfosuccinimidyl 4-(p-maleimido-phenyl) butyrate and (1-ethyl-3-(dimethylaminopropyl) carbodiimide can be used (see, for instance, Harlow and Lane, Antibodies, A Laboratory Manual, generally and Chapter 5, Cold Spring Harbor Laboratory, Cold Spring Harbor, New York, N.Y. (1988)).

Preferably, such compositions of the present invention include low concentrations of lipopolysaccharide (LPS). LPS is a component of the outer membrane of most gram negative microbes (see, for instance. Nikaido and Vaara, Outer Membrane. In: *Escherichia coli* and *Salmonella typhimurium*, Cellular and Molecular Biology, Neidhardt et al., (eds.) American Society for Microbiology, Washington, D.C., pp. 7-22 (1987), and typically includes polysaccharides (0-specific chain, the outer and inner core) and the lipid A region. The lipid A component of LPS is the most biologically active component of the LPS structure and together induce a wide spectrum of pathophysiological effects in mammals. The most dramatic effects are fever, disseminated intravascular coagulation, complement activation, hypotensive shock, and death. The non-specific immunostimulatory activity of LPS can enhance the formation of a granuloma at the site of administration of compositions that include LPS.

The concentration of LPS can be determined using routine methods known in the art. Such methods typically include measurement of dye binding by LPS (see, for instance, Keler and Nowotny, *Analyt. Biochem.*, 156, 189 (1986)) or the use of a *Limulus* amebocyte lysate (LAL) test (see, for instance, Endotoxins and Their Detection With the *Limulus* Amebocyte Lystate Test, Alan R. Liss, Inc., 150 Fifth Avenue, New York, N.Y. (1982)). There are four basic commercially available methods that are typically used with an LAL test: the gel-clot test; the turbidimetric (spectrophotometric) test; the colorimetric test; and the chromogenic test. An example of a gel-clot assay is available under the tradename E-TOX-ATE (Sigma Chemical Co., St. Louis, Mo.; see Sigma Technical Bulletin No. 210), and PYROTELL (Associates of Cape Cod, Inc., East Falmouth, Mass.). Typically, assay conditions include contacting the composition with a preparation containing a lysate of the circulating amebocytes of the horseshoe crab, *Limulus polyphemus*. When exposed to LPS, the lysate increases in opacity as well as viscosity and may gel. About 0.1 milliliter of the composition is added to lysate. Typically, the pH of the composition is between 6 and 8, preferably, between 6.8 and 7.5. The mixture of composition and lysate is incubated for about 1 hour undisturbed at about 37° C.. After incubation, the mixture is observed to determine if there was gelation of the mixture. Gelation indicates the presence of endotoxin. To determine the amount of endotoxin present in the composition, dilutions of a standardized solution of endotoxin are made and tested at the same time that the composition is tested. Standardized solutions of endotoxin are commercially available from, for instance, Sigma Chemical (Catalog No. 210-SE). U.S. Pharmacopeia (Rockville, Md., Catalog No. 235503), and Associates of Cape Cod. Inc., (Catalog No. E0005). In general, when a composition of the present invention is prepared by isolating polypeptides from a microbe by a method as described herein (e.g., a method that includes disrupting and solubilizing the cells, and collecting the insoluble polypeptides), the amount of LPS in a composition of the present invention is less than the amount of LPS present in a mixture of the same amount of the microbe that has been disrupted under the same conditions but not solubilized. Typically, the level of LPS in a composition of the present invention is decreased by, in increasing order of preference, at least 50%, at least 60%, at least 70%; at least 80%, or at least 90% relative to the level of LPS in a composition prepared by disrupting, but not solubilizing, the same microbe.

The compositions of the present invention optionally further include a pharmaceutically acceptable carrier. "Pharmaceutically acceptable" refers to a diluent, carrier, excipient, salt, etc, that is compatible with the other ingredients of the composition, and not deleterious to the recipient thereof. Typically, the composition includes a pharmaceutically acceptable carrier when the composition is used as described herein. The compositions of the present invention may be formulated in pharmaceutical preparations in a variety of forms adapted to the chosen route of administration, including routes suitable for stimulating an immune response to an antigen. Thus, a composition of the present invention can be administered via known routes including, for example, oral; parental including intradermal, transcutaneous and subcutaneous, intramuscular, intravenous, intraperitoneal, etc., and topically, such as, intranasal, intrapulmonary, intramammary, intravaginal, intrauterine, intradermal, transcutaneous and rectally etc. It is foreseen that a composition can be administered to a mucosal surface, such as by administration to the nasal or respiratory mucosa (e.g. spray or aerosol), to stimulate mucosal immunity, such as production of secretory IgA antibodies, throughout the animal's body.

A composition of the present invention can also be administered via a sustained or delayed release implant. Implants suitable for use according to the invention are known and include, for example, those disclosed in Emery and Straub (WO 01/37810 (2001)), and Emery et al., (WO 96/01620 (1996)). Implants can be produced at sizes small enough to be administered by aerosol or spray. Implants also include nanospheres and microspheres.

A composition of the present invention may be administered in an amount sufficient to treat certain conditions as described herein. The amount of polypeptides or whole cells present in a composition of the present invention can vary. For instance, the dosage of polypeptides can be between 0.01 micrograms (μg) and 300 mg, typically between 0.1 mg and 10 mg. When the composition is a whole cell preparation, the cells can be present at a concentration of, for instance, $10^2$ bacteria/ml, $10^3$ bacteria/ml, $10^4$ bacteria/ml, $10^5$ bacteria/ml, $10^6$ bacteria/ml, $10^7$ bacteria/ml, $10^8$ bacteria/ml, or $10^9$ bacteria/ml. For an injectable composition (e.g. subcutaneous, intramuscular, etc.) the polypeptides may be present in the composition in an amount such that the total volume of the composition administered is 0.5 ml to 5.0 ml, typically 1.0-2.0 mi. When the composition is a whole cell preparation, the cells are preferably present in the composition in an amount that the total volume of the composition administered is 0.5 ml to 5.0 ml, typically 1.0-2.0 mi. The amount administered will vary depending on various factors including, but not limited to, the specific polypeptides chosen, the weight, physical condition and age of the animal, and the route of administration. Thus, the absolute weight of the polypeptide included in a given unit dosage form can vary widely, and depends upon factors such as the species, age, weight and physical condition of the animal, as well as the method of administration. Such factors can be determined by one of skill in the art. Other examples of dosages suitable for the invention are disclosed in Emery et al., (U.S. Pat. No. 6,027,736).

The formulations may be conveniently presented in unit dosage form and may be prepared by methods well known in the art of pharmacy. All methods of preparing a composition including a pharmaceutically acceptable carrier include the step of bringing the active compound (e.g., a polypeptide or whole cell of the present invention) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations.

A composition including a pharmaceutically acceptable carrier can also include an adjuvant. An "adjuvant" refers to an agent that can act in a nonspecific manner to enhance an immune response to a particular antigen, thus potentially reducing the quantity of antigen necessary in any given immunizing composition, and/or the frequency of injection necessary in order to generate an adequate immune response to the antigen of interest. Adjuvants may include, for example, IL-1, IL-2, emulsifiers, muramyl dipeptides, dimethyldiocradecylammonium bromide (DDA), avridine, aluminum hydroxide, oils, saponins, alpha-tocopherol, polysaccharides, emulsified paraffins (including, for instance, those available from under the tradename EMULSIGEN from MVP Laboratories, Ralston, Nebr.). ISA-70, RIBI and other substances known in the art. It is expected that polypeptides of the present invention will have immunoregulatory activity, and that such polypeptides may be used as adjuvants that directly act as T and/or B cell activators or act on specific cell types that enhance the synthesis of various cytokines or activate intracellular signaling pathways. Such polypeptides are expected to augment the immune response to increase the protective index of the existing composition.

In another embodiment, a composition of the invention including a pharmaceutically acceptable carrier can include a biological response modifier, such as, for example, IL-2. IL-4 and/or IL-6. TNF, IFN-alpha. IFN-gamma, and other cytokines that effect immune cells. An immunizing composition can also include other components known in the art such as an antibiotic, a preservative, an anti-oxidant, or a chelating agent.

The present invention also provides methods for obtaining the polypeptides described herein. The polypeptides and whole cells of the present invention are isolatable from a *Yersinia* spp. Preferred examples include *Y. enterocolitica, Y. pestis*, and *Y. pseudotuberculosis*. Microbes useful for obtaining polypeptides of the present invention and making whole cell preparations are readily available. In addition, such microbes are readily isolatable by techniques routine and known in the art. The microbes may be derived from an infected animal as a field isolate, and used to obtain polypeptides and/or whole cell preparations of the present invention, or stored for future use, for example, in a frozen repository at −20° C. to −95° C., in bacteriological media containing 20% glycerol, and other like media.

When a polypeptide of the present invention is to be obtained from a microbe, the microbe can be incubated under low metal conditions. As used herein, the phrase "low metal conditions" refers to an environment, typically bacteriological media, which contains amounts of a free metal that cause a microbe to express or enhance expression of metal regulated polypeptides. As used herein, the phrase "high metal conditions" refers to an environment that contains amounts of a free metal that cause a microbe to either not express one or more of the metal regulated polypeptides described herein at a detectable level, or to decrease expression of such a polypeptide. Metals are those present in the periodic table under Groups 1 through 17 (IUPAC notation; also referred to as Groups I-A, II-A, III-B, IV-B, V-B, VI-B, VII-B, VIII, I-B, II-B, III-A, IV-A, V-A, VI-A, and VII-A, respectively, under CAS notation). Preferably, metals are those in Groups 2 through 12, more preferably, Groups 3-12. Even more preferably, the metal is iron, zinc, copper, magnesium, nickel, cobalt, manganese, molybdenum, or selenium, most preferably, iron.

Low metal conditions are generally the result of the addition of a metal chelating compound to a bacteriological medium, or the use of bacteriological media formulated to contain low amounts of a metal. High metal conditions are generally present when a chelator is not present in the medium, a metal is added to the medium, or the combination thereof. Examples of metal chelators include natural and synthetic compounds. Examples of natural compounds include plant phenolic compounds, such as flavenoids, Examples of flavenoids include the copper chelators catechin and naringenin, and the iron chelators myricetin and quercetin. Examples of synthetic copper chelators include, for instance, tetrathiomolybdate, and examples of synthetic zinc chelators include, for instance, N,N, N',N'-Tetrakis (2-pyridylmethyl)-ethylene diamine. Examples of synthetic iron chelators include 2,2'-dipyridyl (also referred to in the art as α,α'-bipyridyl), 8-hydroxyquinoline, ethylenediamine-di-O-hydroxyphenylacetic acid (EDDHA), desferrioxamine methanesulphonate (desferol), transferrin, lactoferrin, ovotransferrin, biological siderophores, such as, the catecholates and hydroxamates, and citrate. Preferably, 2,2'-dipyridyl is used for the chelation of iron. Typically, 2,2'-dipyridyl is added to the media at a concentration of at least 0.0025 micrograms/milliliter (μg/ml), at least 0.025 μg/ml, or at least 0.25 μg/ml, and generally no greater than 10 μg/ml, no greater than 20 μg/ml, or no greater than 30 μg/ml.

It is expected that a *Yersinia* spp. with a mutation in a fur gene will result in the constitutive expression of many, if not all, of the iron regulated polypeptides of the present invention. The production of a fur mutation in a *Yersinia* spp. can be produced using routine methods including, for instance, transposon, chemical, or site-directed mutagenesis useful for generating gene knock-out mutations in gram negative bacteria.

The medium used to incubate the microbe and the volume of media used to incubate the microbe can vary. When a microbe is being evaluated for the ability to produce one or more of the polypeptides described herein, the microbe can be grown in a suitable volume, for instance, 10 milliliters to 1 liter of medium. When a microbe is being grown to obtain polypeptides for use in, for instance, administration to animals, the microbe may be grown in a fermentor to allow the isolation of larger amounts of polypeptides. Methods for growing microbes in a fermentor are routine and known in the art. The conditions used for growing a microbe preferably include a metal chelator, more preferably an iron chelator, for instance 2,2'-dipyridyl, a pH of between 6.5 and 7.5, preferably between 6.9 and 7.1, and a temperature of 37° C.

In some aspects of the invention, a microbe may be harvested after growth. Harvesting includes concentrating the microbe into a smaller volume and suspending in a media different than the growth media. Methods for concentrating a microbe are routine and known in the art, and include, for example, filtration or centrifugation. Typically, the concentrated microbe is suspended in decreasing amounts of buffer. Preferably, the final buffer includes a cation chelator, preferably, ethylenediaminetetraacetic acid (EDTA). An example of a buffer that can be used contains Tris-base (7.3 grams/liter) and EDTA (0.9 grams/liter), at a pH of 8.5. Optionally, the final buffer also minimizes proteolytic degradation. This can be accomplished by having the final buffer at a pH of greater than 8.0, preferably, at least 8.5, and/or including one or more proteinase inhibitors (e.g., phenylmethanesulfonyl fluoride). Optionally and preferably, the concentrated microbe is frozen at −20° C. or below until disrupted.

When the microbe is to be used as a whole cell preparation, the harvested cells may be processed using routine and known methods to inactivate the cells. Alternatively, when a microbe is to be used to prepare polypeptides of the present invention, the microbe may be disrupted using chemical, physical, or mechanical methods routine and known in the art, including, for example, french press, sonication, or homogenization. Preferably, homogenization is used. An example of a suitable device useful for homogenization is a model C500 Avestin Homogenizer, (Avestin Inc, Ottawa Canada). As used herein, "disruption" refers to the breaking up of the cell. Disruption of a microbe can be measured by methods that are routine and known in the art, including, for instance, changes in optical density. Typically, a microbe is subjected to disruption until the percent transmittance is increased by 20% when a 1:100 dilution is measured. The temperature during disruption is typically kept low, preferably at 4° C., to further minimize proteolytic degradation.

The disrupted microbe is solubilized in a detergent, for instance, an anionic, zwitterionic, nonionic, or cationic detergent. Preferably, the detergent is sarcosine, more preferably, sodium lauroyl sarcosinate. As used herein, the term "solubilize" refers to dissolving cellular materials (e.g., polypeptides, nucleic acids, carbohydrates) into the aqueous phase of the buffer in which the microbe was disrupted, and the formation of aggregates of insoluble cellular materials. The conditions for solubilization preferably result in the aggregation of polypeptides of the present invention into insoluble aggregates that are large enough to allow easy isolation by, for instance, centrifugation.

Significant decreases in LPS are typically observed when the disrupted microbe is solubilized in higher levels of sarcosine, solubilized for longer periods, or the combination thereof. Preferably, the sarcosine is added such that the final ratio of sarcosine to gram weight of disrupted microbe is between 1.0 gram sarcosine per 4.5 grams pellet mass and 6.0 grams sarcosine per 4.5 grams pellet mass, preferably, 4.5 gram sarcosine per 4.5 grams pellet mass. The solubilization of the microbe may be measured by methods that are routine and known in the art, including, for instance, changes in optical density. Typically, the solubilization is allowed to occur for at least 24 hours, preferably, at least 48 hours, more preferably, at least 72 hours, most preferably, at least 96 hours. The temperature during disruption is typically kept low, preferably at 4° C.

The insoluble aggregates that include one or more of the polypeptides of the present invention may be isolated by methods that are routine and known in the art. Preferably, the insoluble aggregates are isolated by centrifugation. Typically, centrifugation of polypeptides that are insoluble in detergents requires centrifugal forces of at least 50,000×g, typically 100,000×g. The use of such centrifugal forces requires the use of ultracentrifuges, and scale-up to process large volumes of sample is often difficult and not economical with these types of centrifuges. The methods described herein provide for the production of insoluble aggregates large enough to allow the use of significantly lower centrifugal forces (for instance, 46,000×g). Methods for processing large volumes at these lower centrifugal forces are available and known in the art. Thus, the insoluble aggregates can be isolated at a significantly lower cost. Examples of suitable devices useful for centrifugation of large volumes include T-1 Sharpies, (Alfa Laval Separations, Warminster, Pa.) and Hitachi Himac CC40 high speed centrifuges (Hitachi-Koki Co, Tokyo. Japan).

Optionally and preferably, the sarcosine is removed from the isolated polypeptides. Methods for removing sarcosine from the isolated polypeptides are known in the art, and include, for instance, diafiltration, precipitation, hydrophobic chromatography, ion-exchange chromatography, or affinity chromatography, and ultra filtration and washing the polypeptides in alcohol by diafiltration. After isolation, the polypeptides suspended in buffer and stored at low temperature, for instance, −20° C. or below.

Polypeptides of the present invention may also be obtained from members of the genus Yersinia using methods that are known in the art. The isolation of the polypeptides may be accomplished as described in, for instance, Emery et al., (U.S. Pat. No. 5,830,479) and Emery et al., (U.S. Patent Application US 20030036639 A1).

In those aspects of the present invention where a whole cell preparation is to be made, methods known in the art can be used. For instance, after growth a microbe can be killed with the addition of an agent such as glutaraldehyde, formalin, or formaldehyde, at a concentration sufficient to inactivate the cells in the culture. For instance, formalin can be added at a concentration of 3% (vol:vol). After a period of time sufficient to inactivate the cells, the cells can be harvested by, for instance, diafiltration and/or centrifugation, and washed.

An aspect of the present invention is further directed to methods of using the compositions of the present invention. The methods include administering to an animal an effective amount of a composition of the present invention. The animal can be, for instance, avian (including, for instance, chickens or turkeys), bovine (including, for instance, cattle), caprine (including, for instance, goats), ovine (including, for instance, sheep), porcine (including, for instance, swine), bison (including, for instance, buffalo), a companion animal (including, for instance, cats, dogs, and horses), members of the family Cervidae (including, for instance, deer, elk, moose, caribou, and reindeer), piscine (including, for instance, salmon or trout), crustacean (including, for instance, lobster, crab, or shrimp), members of the family Muridae (including, for instance, rats or mice), or human.

In some aspects, the methods may further include additional administrations (e.g., one or more booster administrations) of the composition to the animal to enhance or stimulate a secondary immune response. A booster can be administered at a time after the first administration, for instance, 1 to 8 weeks, preferably 2 to 4 weeks, after the first administration of the composition. Subsequent boosters can be administered one, two, three, four, or more times annually. Without intending to be limited by theory, it is expected that in some aspects of the present invention annual boosters will not be necessary, as an animal will be challenged in the field by exposure to microbes expressing polypeptides present in the compositions having epitopes that are identical to or structurally related to epitopes present on polypeptides of the composition administered to the animal.

In one aspect, the invention is directed to methods for making antibody, such as inducing the production of antibody in an animal, or by recombinant techniques. The antibody produced includes antibody that specifically binds at least one polypeptide present in the composition. In this aspect of the invention, an "effective amount" is an amount effective to result in the production of antibody in the animal. Methods for determining whether an animal has produced antibodies that specifically bind polypeptides present in a composition of the present invention can be determined as described herein. The present invention further includes antibody that specifically bind to a polypeptide of the present invention, and compositions including such antibodies.

The method may be used to produce antibody that specifically binds polypeptides expressed by a microbe other than the microbe from which the polypeptides of the composition were isolated. As used herein, an antibody that can "specifically bind" a polypeptide is an antibody that interacts with the epitope of the antigen that induced the synthesis of the antibody, or interacts with a structurally related epitope. At least some of the polypeptides present in the compositions of the present invention typically include epitopes that are conserved in the polypeptides of different species of microbes. Accordingly, antibody produced using a composition derived from one microbe is expected to bind to polypeptides expressed by other microbes and provide broad spectrum protection against gram negative organisms. Examples of gram negative microbes to which the antibody may specifically bind are enteropathogens, for instance, members of the family Enterobacteriaceae, preferably, members of the genus *Yersinia*.

The present invention is also directed to the use of such antibody to target a microbe expressing a polypeptide of the present invention or a polypeptide having an epitope structurally related to an epitope present on a polypeptide of the present invention. A compound can be covalently bound to an antibody, where the compound can be, for instance, a toxin. Likewise, such compounds can be covalently bound to a bacterial siderophore, such as yersiniabactin, to target the microbe. The chemical coupling or conjugation of an antibody of the present invention or a portion thereof (such as an Fab fragment) can be carried out using known and routine methods.

In one aspect the invention is also directed to treating an infection in an animal caused by a gram negative microbe, preferably by a member of the genus *Yersinia*. As used herein, the term "infection" refers to the presence of a gram negative microbe, preferably, a member of the genus *Yersinia*, in an animal's body, which may or may not be clinically apparent. An animal with an infection by member of the genus *Yersinia* that is not clinically apparent is often referred to as an asymptomatic carrier. The method includes administering an effective amount of the composition of the present invention to an animal having an infection caused by a member of the genus *Yersinia*, and determining whether the *Yersinia* spp. causing the infection has decreased. Methods for determining whether an infection is caused by a member of the genus *Yersinia* are routine and known in the art.

In another aspect, the present invention is directed to methods for treating one or more symptoms of certain conditions in animals such as sheep, cattle, goats, pigs, dogs, birds, rodents and deer that may be caused by infection by a member of the genus *Yersinia*. Examples of conditions caused by *Yersinia* spp. infections include, for instance, diarrhea or enteritis in bovine, ovine, and porcine animals and humans, plague-like illnesses in domestic cats and humans, abortion in cattle and sheep, epididymitis-orchitis in rams, and multiple abscess formation in sheep. Yet another aspect of the present invention is directed at treating cold water diseases of fish such as enteric red mouth disease in juvenile fish, particularly in intensive aquaculture of trout and salmon. Treatment of symptoms associated with these conditions can be prophylactic or, alternatively, can be initiated after the development of a condition described herein. As used herein, the term "symptom" refers to objective evidence in a subject of a condition caused by infection by a member of the genus *Yersinia* spp. Symptoms associated with conditions referred to herein and the evaluation of such symptoms are routine and known in the art. Treatment that is prophylactic, for instance, initiated before a subject manifests symptoms of a condition caused by a microbe, is referred to herein as treatment of a subject that is "at risk" of developing the condition. Typically, an animal "at risk" of developing a condition is an animal present in an area where the condition has been diagnosed and/or is likely to be exposed to a *Yersinia* spp. causing the condition. Accordingly, administration of a composition can be performed before, during, or after the occurrence of the conditions described herein. Treatment initiated after the development of a condition may result in decreasing the severity of the symptoms of one of the conditions, or completely removing the symptoms. In this aspect of the invention, an "effective amount" is an amount effective to prevent the manifestation of symptoms of a disease, decrease the severity of the symptoms of a disease, and/or completely remove the symptoms.

The present invention is also directed to decreasing the colonization by gram negative bacteria, for instance blocking the attachment sites by gram negative bacteria, to tissues of the skeletal system (for instance, bones, cartilage, tendons and ligaments), muscular system, (for instance, skeletal and smooth muscles), circulatory system (for instance, heart, blood vessels, capillaries and blood), nervous system (for instance, brain, spinal cord, and peripheral nerves), respiratory system (for instance, nose, trachea lungs, bronchi, bronchioceles, alveoli), digestive system (for instance, mouth, salivary glands oesophagus liver stomach large and small intestine), excretory system (for instance, kidneys, ureters, bladder and urethra), endocrine system (for instance, hypothalamus, pituitary, thyroid, pancreas and adrenal glands), reproductive system (for instance, ovaries, oviduct, uterus, vagina, mammary glands, testes, and seminal vesicles), lymphatic/immune systems (for instance, lymph, lymph nodes and vessels, mononuclear or white blood cells, such as macrophages, neutrophils, monocytes, cosinophils, basophils, lymphocytes t- and b-cells), and specific cell lineages (for instance, precursor cells, epithelial cells, stem cells), and the like. Preferably, the gram negative bacteria is a member of the genus *Yersinia*. The method includes administering an effective amount of a composition of the present invention to an animal colonized by, or at risk of being colonized by a member of the genus *Yersinia*. In this aspect of the invention, an "effective amount" is an amount effective to decrease colonization of the animal by the microbe. Methods for evaluating the colonization of an animal by a microbe are routine and known in the art. For instance, colonization of an animal's intestinal tract by a microbe can be determined by measuring the presence of the microbe in the animal's feces. It is expected that decreasing the colonization of an animal by a microbe will reduce transmission of the microbe to humans.

A composition of the invention can be used to provide for active or passive immunization against bacterial infection. Generally, the composition can be administered to an animal to provide active immunization. However, the composition can also be used to induce production of immune products, such as antibodies, which can be collected from the producing animal and administered to another animal to provide passive immunity. Immune components, such as antibodies, can be collected to prepare antibody compositions from serum, plasma, blood, colostrum, etc. for passive immunization therapies. Antibody compositions comprising monoclonal antibodies and/or anti-idiotypes can also be prepared using known methods. Such antibody compositions include chimeric antibodies and humanized antibodies. Chimeric antibodies include human-derived constant regions of both heavy and light chains and murine-derived variable regions that are antigen-specific (Morrison et al., Proc. Natl. Acad. Sci. USA, 1984, 81(21):6851-5; LoBuglio et al., Proc. Natl. Acad. Sci. USA, 1989, 86(11):4220-4; Boulianne et al., Nature, 1984, 312(5995):643-6.). Humanized antibodies substitute the murine constant and framework (FR) (of the variable region) with the human counterparts (Jones et al., Nature, 1986, 321(6069):522-5; Riechmann et al., Nature, 1988, 332(6162):323-7; Verhoeyen et al., Science, 1988, 239(4847): 1534-6; Queen et al., Proc. Natl. Acad. Sci.

USA, 1989, 86(24): 10029-33; Daugherty et al., Nucleic Acids Res., 1991, 19(9): 2471-6.). Alternatively, certain mouse strains can be used that have been genetically engineered to produce antibodies that are almost completely of human origin; following immunization the B cells of these mice are harvested and immortalized for the production of human monoclonal antibodies (Bruggeman and Taussig, Curr. Opin. Biotechnol., 1997, 8(4):455-8; Lonberg and Huszar. Int. Rev. Immunol., 1995; 13(1):65-93; Lonberg et al., Nature, 1994, 368:856-9; Taylor et al., Nucleic Acids Res., 1992, 20:6287-95.). Passive antibody compositions and fragments thereof, e.g., scFv, Fab, F(ab)$_2$ or Fv or other modified forms thereof, may be administered to a recipient in the form of serum, plasma, blood, colostrum, and the like. However, the antibodies may also be isolated from serum, plasma, blood, colostrum, and the like, using known methods for later use in a concentrated or reconstituted form such as, for instance, lavage solutions, impregnated dressings and/or topical agents and the like. Passive immunizing preparations may be particularly advantageous for treatment of acute systemic illness, or passive immunization of young animals that failed to receive adequate levels of passive immunity through maternal colostrum. Antibodies useful for passive immunization may be useful to conjugate to various drugs or antibiotics that could be directly targeted to bacteria expressing during a systemic or localized infection a polypeptide of the present invention or a polypeptide having an epitope structurally related to an epitope present on a polypeptide of the present invention.

Animal models, in particular mouse models, are available for experimentally evaluating the compositions of the present invention (see, for instance, Alpar, H. O., et al., Adv. Drug Deliv. Rev., 51, 173-201, (2001), Brem, D., et al., Microbiology, 147, 1115-1127, (2001), Carter, P. B. and F. M. Collins, Infect. Immun., 9, 851-857, (1974), Collyn, F., et al., Infect. Immun., 72.4784-9470, (2004), Di Genaro, M. S., et al., Microbiol. Inununol., 42, 781-788, (1998), Grosfeld, H., et al., Infect Immun, 71, 374-383, (2003), Jones, S. M., et al., Vaccine, 19, 358-366, (2001), Karlyshev, A. V., et al., Infect Immun, 69, 7810-7819, (2001), Leary, S. E., et al., Microb Pathog, 23, 167-179, (1997), Noll, A., et al., Eur J Immunol, 29, 986-996, (1999), Pelludat, C., et al., Infect Immun, 70, 1832-1841, (2002), Sabhnani. L, et al., FEMS Immunol Med Microbiol, 38, 215-29, (2003), and Williamson, E. D., et al., Vaccine, 19, 566-571, (2000)). These mouse models are commonly accepted models for the study of human disease caused by members of the genus *Yersinia*, and additionally have served as accepted models in the development and initial testing of vaccines aimed at preventing human illnesses by *Yersinia* spp.

Another aspect of the present invention provides methods for detecting antibody that specifically binds polypeptides of the present invention. These methods are useful in, for instance, detecting whether an animal has antibody that specifically bind polypeptides of the present invention, and diagnosing whether an animal may have a condition caused by a microbe expressing polypeptides described herein, or expressing polypeptides that share epitopes with the polypeptides described herein. Such diagnostic systems may be in kit form. The methods include contacting an antibody with a preparation that includes polypeptides of the present invention to result in a mixture. The antibody may be present in a biological sample, for instance, blood, milk, or colostrum. The method further includes incubating the mixture under conditions to allow the antibody to specifically bind the polypeptide to form a polypeptide:antibody complex. As used herein, the term "polypeptide:antibody complex" refers to the complex that results when an antibody specifically binds to a polypeptide. The preparation that includes the polypeptides of the present invention may also include reagents, for instance a buffer, that provide conditions appropriate for the formation of the polypeptide:antibody complex. The polypeptide:antibody complex is then detected. The detection of antibodies is known in the art and can include, for instance, immunofluorescence and peroxidase. The methods for detecting the presence of antibodies that specifically bind to polypeptides of the present invention can be used in various formats that have been used to detect antibody, including radioimmunoassay and enzyme-linked immunosorbent assay.

The present invention also provides a kit for detecting antibody that specifically binds polypeptides of the present invention. The antibody detected may be obtained from an animal suspected to have an infection caused by a gram negative microbe, more preferably, a member of the family Enterobacteriaceae preferably, a member of the genus *Yersinia*, such as *Y. enterocolitica, Y. pseudotuberculosis*, or *Y. pestis*. The kit includes at least one of the polypeptides of the present invention, or a number of polypeptides that is an integer greater than 1 (e.g., at least 2, at least 3, etc.), in a suitable packaging material in an amount sufficient for at least one assay. Optionally, other reagents such as buffers and solutions needed to practice the invention are also included. For instance, a kit may also include a reagent to permit detection of an antibody that specifically binds to a polypeptide of the present invention, such as a detectably labeled secondary antibody designed to specifically bind to an antibody obtained from an animal. Instructions for use of the packaged polypeptides are also typically included. As used herein, the phrase "packaging material" refers to one or more physical structures used to house the contents of the kit. The packaging material is constructed by well known methods, generally to provide a sterile, contaminant-free environment. The packaging material may have a label which indicates that the polypeptides can be used for detecting antibody that specifically binds polypeptides of the present invention. In addition, the packaging material contains instructions indicating how the materials within the kit are employed to detect the antibody. As used herein, the term "package" refers to a container such as glass, plastic, paper, foil, and the like, capable of holding within fixed limits the polypeptides, and other reagents, for instance a secondary antibody. Thus, for example, a package can be a microtiter plate well to which microgram quantities of polypeptides have been affixed. A package can also contain a secondary antibody. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The present invention is illustrated by the following examples. It is to be understood that the particular examples, materials, amounts, and procedures are to be interpreted broadly in accordance with the scope and spirit of the invention as set forth herein.

EXAMPLES

Example 1

Production and Isolation of Metal Regulated Proteins

The compositions used in the following examples were prepared using the proteins derived from *Y. enterocolitica*

ATCC strain 27729 and *Y. pestis* strain KIM6+(obtained from R. D. Perry, University of Kentucky). The two strains were each inoculated from frozen stocks into 25 ml tryptic soy broth (TSB) containing 160 µM 2,2-diprydyl or 300 µM FeCl$_3$, and incubated at 37° C. while shaking at 400 rpm. Following 12 hours of incubation, 5 ml of each culture was transferred into 500 ml of pre-incubated (37° C.) media containing 160 µM 2,2-diprydyl or 300 µM FeCl$_3$ and incubated at 37° C. while stirring at 100 rpm. After 8 hours of incubation, the cultures were centrifuged at 10,000×g for 20 minutes. The bacterial pellets were resuspended in 100 ml of sterile physiological saline and centrifuged at 10,000×g for 10 minutes to remove any contaminating media proteins. The bacterial pellets were then resuspended in 40 ml of Tris-buffered saline pH 7.2 (TBS) and disrupted by sonication for 1.5 minutes at 4° C. using a Branson 450 equipped with a half inch disruption horn (Branson, Danbury Conn.). The disrupted bacterial suspensions were clarified by centrifugation at 32,000×g for 12 minutes. The supernatants were collected and solubilized by the addition of sodium lauroyl sarcosinate (4% vol/vol) at 4° C. for 24 hours. The detergent-insoluble protein-enriched fractions were collected by centrifugation at 32,000×g for 2.5 hours at 4° C. The protein pellets were resuspended in 200 µl Tris-buffer (pH 7.2) and stored at −90° C. A sample of each extract was resolved on a 10% SDS-PAGE gel per standard methods and visualized by Coomassie Blue staining (FIG. 3).

Example 2

Preparation of the Immunizing Compositions Derived from *Y. enterocolitica*

The proteins made from *Y. enterocolitica* as described in Example 1 were used to prepare a composition for administration to animals. The composition contained polypeptides having molecular weights of 268 kDa, 92 kDa, 83 kDa, 79 kDa, 70 kDa, 66 kDa, 54 kDa, 45 kDa, 40 kDa, 38 kDa, 37 kDa, 31 kDa, or 28 kDa. The polypeptides having molecular weights of 83 kDa, 70 kDa, and 66 kDa were expressed only under iron limited conditions, and the expression of polypeptides having molecular weights of 268 kDa, 79 kDa, and 45 kDa was enhanced under iron limited conditions.

A stock vaccine was prepared from the composition by emulsifying the aqueous protein suspension (500 μg total protein/ml) into the commercial adjuvant, EMULSIGEN, (MVP Laboratories, Ralston, Nebr.) using an IKA Ultra Turrax T-50 homogenizing vessel (IKA, Cincinnati, Ohio). The vaccine was administered to mice to give a final dose of 50 μg total protein in a 0.1 ml injectable volume with an adjuvant concentration of 22.5% vol/vol. A placebo was prepared by replacing the antigen with physiological saline in the above formulation and emulsifying the suspension into EMULSIGEN to give an adjuvant concentration of 22.5%.

Example 3

Preparation of Challenge Organism

When used as a challenge, the *Y. enterocolitica* ATCC strain 27729 was prepared as follows. Briefly, the isolate from a frozen stock was streaked onto a blood agar plate and incubated at 37° C. for 18 hours. A single colony was subcultured into 50 ml Tryptic Soy Broth (Difco) containing 25 μg/ml 2, 2' dipyridyl. The culture was incubated at 37° C. for 6 hours while rotating at 200 rpm, at which point the culture was centrifuged at 10,000×g for 10 minutes at 4° C. to pellet the bacteria. The bacterial pellet was washed twice by centrifugation in physiological saline at 4° C. The final pellet was resuspended in 25 ml of physiological saline and used for challenge. Just prior to challenge, 1 ml of the above bacterial suspension was serially diluted ten fold to enumerate the number of CFU/mouse dose.

Example 4

Mouse Vaccination and Challenge Study to Evaluate Protection Against Intravenous Challenge The efficacy of the *Y. enterocolitica* composition was evaluated using a live virulent challenge in mice. Twenty CF-1 mice (Harlan Breeding Laboratories, Indianapolis, Ind.) were divided into two groups of 10 mice per group. Mice in the control group were vaccinated with the placebo, while mice in the second group were immunized with 50 μg of the composition obtained as described in Example 1. Immunizations of 0.1 cc were administered intraperitoneally two times at 14 day intervals. Fourteen days after the second vaccination, a challenge dose of strain 27729 (9.4×10 CFU/mouse) was administered to all mice in the lateral tail vein. Mortality was recorded for 7 days following challenge.

Of the 10 placebo-vaccinated mice, 10 (100%) died within 168 hours of challenge, while none of the vaccinated mice died within the same time period. Furthermore, all of the vaccinated mice survived for the remainder of the study, which was terminated at 20 days post-challenge. A Kaplan-Meier survival analysis and logrank test (see FIG. 1) indicated that immunization provided statistically significant ($p<0.0001$–) protection against challenge. These results suggest that proteins from *Y. enterocolitica* grown under iron-restricted conditions constitute effective antigens in the intravenous mouse model of infection.

Example 5

Western Blot Analysis of *Y. enterocolitica* Proteins with Hyperimmunized and Convalescent Mouse Polyclonal Serum Western blot analysis was used to evaluate the immunoreactive proteins derived from *Y. enterocolitica* against hyperimmunized mouse polyclonal serum and convalescent sera. Hyperimmunizzed mouse polyclonal serum was obtained after vaccinating with the composition described in example 2, and convalescent sera was obtained from vaccinated/challenged mice that survived the trial described in example 4. The composition contained polypeptides having molecular weights of 268 kDa, 92 kDa, 79 kDa, 70 kDa, 66 kDa, 54 kDa, 52 kDa, 41 kDa, 38 kDa, 37 kDa, 31 kDa, 28 kDa, and two proteins having molecular weights of 83 kDa. The polypeptides having molecular weights of 83 kDa, 70 kDa, and 66 kDa were expressed only under iron limited conditions.

To obtain hyper-immunized serum, mice were immunized two times at 14 day intervals as described in Example 4. The hyperimmunized polyclonal serum was collected from mice 14 days following the second immunization. Convalescent serum derived from vaccinated/challenged mice was obtained 14 days after challenge. The proteins derived from *Y. enterocolitica* strain 27729 were first size fractionated on SDS-PAGE (4% stacker/10% resolving gel) using 30 ug total protein as described in example 1. Band migration was visualized using broad range kaleidoscope standards (Bio-Rad) to aid in the electroblot transfer while biotinylated broad range standards were used as molecular weight references on the blot. For western blot analysis, proteins were electroblotted from the SDS-PAGE gel onto trans-blot nitrocellulose membranes (BioRad) overnight, at 4° C. at 50 Volts, in Towbin buffer (25 mM Tris, 192 mM glycine, and 20% methanol) using a BioRad Trans-Blot transfer cell. The nitrocellulose membrane was blocked by standard methods using 3.0% fish gelatin (BioRad). The hyperimmunized polyclonal serum and convalescent sera was diluted 1/25000 in Tris-buffered saline containing 1.0% fish gelatin, 0.05% tween 20 and 0.2% sodium azide (antibody buffer). The nitrocellulose membrane was incubated with the primary antibody solution overnight. The membrane was then washed two times in Tris-Buffered Saline containing 0.05% tween 20 (TTBS) and transferred to antibody buffer containing a 1/10,000 dilution of goat anti-mouse antibody conjugated to alkaline phosphatase (BioRad) and a 1/3,000 dilution of avidin conjugated to alkaline phosphatase (BioRad). The membrane was incubated at 37° C. for 2 hours on a shaker, and subsequently washed in TTBS four times to remove unbound conjugate. The blot was resolved, for 30 minutes at 37° C. on a shaker, in substrate solution containing alkaline phosphate color reagent A and B in 1×AP color development buffer (BioRad).

Western blot analysis was used as a tool to potentially identify proteins derived from the composition as described in example 1 as immuno-reactive with antibodies derived from the hyperimmunized and/or convalescent sera. Western blot analysis revealed a number of immuno-reactive proteins. The hyperimmunized sera contained antibodies that reacted with proteins at the 268 kDa, 92 kDa, 83 kDa, 79 kDa, 70 kDa, 66 kDa, 54 kDa, 52 kDa, 41 kDa, 38 kDa, 37 kDa, 31 kDa and 28 kDa. Similarly, the convalescent sera showed identical banding patterns at the 268 kDa, 92 kDa, 83 kDa, 79 kDa, 70 kDa, 66 kDa, 54 kDa, 52 kDa, 41 kDa, 38 kDa, 37 kDa, 31 kDa and 28 kDa. In addition, three immuno-reactive proteins were seen at the 52 kDa, 40 kDa and 20 kDa regions that were not seen on the SDS-PAGE gel initially, nor were they seen in the western blot analysis using the hyperimmunized sera. It is interesting to speculate that these three proteins were at too low of concentration to be visualized on the SDS-PAGE gel, but may be highly immunogenic resulting in greater band intensity after priming the immune system that resulted in an enhanced band intensity of these proteins after challenge.

The Western Blot analysis of the vaccine composition revealed differences in band intensities of the immuno-reactive proteins between both the hyperimmunized and convalescent sera. These differences could be the result of different immunogenic properties of individual proteins and how the immune system recognizes each individual protein within the composition. In addition, the amount and ratio of proteins within the composition can also influence the immunological status of each protein which can influence the immunological response of the animal to individual proteins within the composition. Nevertheless, each protein within the composition reacted immunologically as examined by Western Blot Analysis, thus the immunological response of the mouse upon vaccination, recognized and responded mounting an antibody response to each individual protein within the composition. Taken together, the results as described in example 4 illustrate that the protein composition was extremely efficacious providing a 100% protection in challenged mice compared to the non-vaccinated mice having 100% mortality.

Example 6

Western Blot Analysis of *Y. pestis* Proteins with Hyperimmunized Serum Prepared Against Proteins of *Y. enterocolitica*

Western blot analysis was used to evaluate the immuno-reactive proteins derived from *Y. pestis* against hyperimmunized sera prepared against the composition derived from *Y. enterocolitica* as described in example 5. The composition contained polypeptides having molecular weights of 254 kDa, 104 kDa, 99 kDa, 94 kDa, 88 kDa, 77 kDa, 73 kDa, 64 kDa, 60 kDa, 46 kDa, 44 kDa, 37 kDa 36 kDa, 31 kDa 28 kDa and 20 kDa. The polypeptides having molecular weights of 94 kDa, 88 kDa, 77 kDa, 73 kDa, and 64 kDa were expressed only under iron limited conditions. The proteins derived from *Y. pestis* strain KIM6+ was first size fractionated on SDS-PAGE (4% stacker/10% resolving gel) as previously described in example 5 using 30 ug total protein. Western blot analysis was run under identical conditions as described in example 5 except for the following modification; the convalescent sera was not tested against the membrane proteins of *Y. pestis*. The results showed proteins at approximately the 254 kDa, 94 kDa, 88 kDa, 46 kDa, 44 kDa, 37 kDa, 36 kDa and 20 kDa regions to be immuno-reactive with antibodies derived from the hyperimmunized serum prepared against membrane proteins of *Y. enterocolitica*.

Example 7

Mouse Vaccination and Challenge Study to Evaluate Protection Against Intravenous and Pneumonic *Y. pestis* Challenge Eighty-eight female Swiss-Webster (Harlan Laboratories) weighing 16-22 grams are equally distributed into 4 groups (22 mice/group), designated 1 through 4. The animals are housed in a HEPA-filtered, micro-vent positive air supply animal caging system (BSL3 facility). Food and water are supplied ad libitum.

Proteins from *Y. pestis* strain KIM6+ are prepared as described above in example 1, and formulated as a vaccine using aluminum hydroxide as the adjuvant (Rehydagel-HPA, Rheis NJ) at a final concentration of 20% vol/vol and 500 µg total protein/ml. The placebo is prepared by replacing the antigen with PBS while maintaining the same adjuvant concentration. Mice in Groups 1 and 3 are vaccinated intraperitoneally two times at 14 day intervals with 0.1 ml of vaccine containing 50 µg total protein, while mice in Groups 2 and 4 are immunized with the placebo by an identical schedule.

*Y. pestis* strain CO92 is used for challenge, and is prepared in a BSL3 containment facility. Fourteen days after the second vaccination, mice in Groups 1 and 2 are challenged intravenously in the lateral tail vein with 0.1 ml strain CO92 ($10^3$ CFU or approximately 100 $LD_{50}$ per mouse). Mice in groups 3 and 4 are subjected to an aerosolized challenge dose of *Y. pestis* CO92 diluted in physiological saline to achieve an approximate concentration of 100 $LD_{50}$ CFU per mouse for 30 minutes in an airtight chamber. The aerosolized $LD_{50}$ for strain CO92 in Swiss Webster mice is determined by small pilot studies prior to the proposed challenge experiments. Mortality is recorded for 21 days after challenge.

Example 8

Fish Vaccination and Challenge Study to Evaluate Protection Against *Y. ruckeri* Challenge Two groups of 20 rainbow trout, designated as groups 1 and 2 weighing approximately 2 grams are maintained in two separate 60 liter tanks at a temperature of 18° C. Fish are fed twice daily with a commercial trout feed (Ziegler Brothers, Gardners, Pa.). Fish in group 1 are vaccinated with a composition derived from *Y. ruckeri* using the same method as described in example 1. The extracted proteins derived from *Y. ruckeri* are used to prepare a vaccine composition for administration to fish. A stock vaccine is prepared from the composition by emulsifying the aqueous protein suspension into a water-in-oil emulsion containing Drakeol 6 mineral oil and Arlacel A as an emulsifier. The vaccine is administered intraperitoneally to give a final dose of 25 ug total protein in a 0.1 cc injectable volume using 0.1 cc. A placebo is prepared by replacing the antigen with physiological saline in the above formulation and is given to the fish in group 2 (controls). Fish are given a second vaccination 28 days after the first vaccination. Fourteen days after the second vaccination all fish are intraperitoneally challenged.

A virulent isolate of *Y. ruckeri* is used for challenge. The challenge isolate is cultured in Tryticase Soy Broth (TSB) containing 160 μM 2,2-diprydyl and grown for 12 hours of incubation at 37° C. The culture is washed once in physiological saline by centrifugation at 10,000×g and resuspended in saline. The culture is adjusted to $5.0\times10^7$ CFU per ml. Each trout is intraperitoneally inoculated with 0.1 cc of the corresponding bacteria at a final challenge dose of $5.0\times10^6$ CFU. Mortality was recorded daily for 14 days after challenge. All dead fish are removed from the tank and the livers are removed and plated to enumerate the presence of the challenge organism. Efficacy is measured as a degree of livability comparing vaccinates to non-vaccinated controls.

Example 9

Characterization of Metal Regulated Proteins of *Y. enterocolitica* ATCC Strain 27729 and *Y. pestis* Strain KIM6+

The proteins of the composition prepared as described in example 1 from *Y. enterocolitica* ATCC strain 27729 and *Y. pestis* strain KIM6+ were characterized using matrix assisted laser desorption/ionization time-of-flight spectrometry (MALDI-TOF MS). Samples of each composition were was resolved using a 10% sodium dodecyl sulfate-polyacrylamide gel. After the proteins of a composition had been resolved, the gel was stained with coomasic brilliant blue to visualize the proteins.

Materials and Methods

Excision and Washing.

The gel was washed for 10 minutes with water twice. Each protein band of interest was excised by cutting as close to the protein band as possible to reduce the amount of gel present in the sample. Each gel slice was cut into Ix mm cubes and placed in 1.5 ml tube. The gel pieces were washed with water for 15 minutes. All the solvent volumes used in the wash steps were approximately equal to twice the volume of the gel slice. The gel slice was next washed with water/acetonitrile (1:1) for 15 minutes. The water/acetonitrile mixture was removed, and acetonitrile was added to cover until the gel pieces turned a sticky white, at which time the acetonitrile was removed. The gel pieces were rehydrated in 100 mM $NH_4HCO_3$, and after 5 minutes, a volume of acetonitrile equal to twice the volume of the gel pieces was added. This was incubated for 15 minutes, the liquid removed, and the gel pieces dried in a Speed Vac.

Reduction & Alkylation.

The dried gel pieces were rehydrated in 10 mM DTT and 100 mM $NH_4HCO_3$, and incubated for 45 minutes at 56° C. After allowing the tubes to cool to room temperature, the liquid was removed and the same volume of a mixture of 55 mM iodoacetamide and 100 mM $NH_4HCO_3$ was immediately added. This was incubated for 30 minutes at room temperature in the dark. The liquid was removed, acetonitrile was added to cover until the gel pieces turned a sticky white, at which time the acetonitrile was removed. The gel pieces were rehydrated in 100 mM $NH_4HCO_3$, and after 5 minutes, a volume of acetonitrile equal to twice the volume of the gel pieces was added. This was incubated for 15 minutes, the liquid removed, and the gel pieces dried in a Speed vac. If residual coomassie still remained, the wash with 100 mM $NH_4HCO_3$/acetonitrile was repeated.

In-Gel Digestion.

Gel pieces were completely dried down in a Speed Vac. The pieces were rehydrated in digestion buffer (50 mM $NH_4HCO_3$, 5 mM $CaCl_2$, 12.5 nanograms per microliter (ng/μl) trypsin) at 4° C. Enough buffer was added to cover the gel pieces, and more was added as needed. The gel pieces were incubated on ice for 45 minutes, and the supernatant removed and replaced with 5-2 μl of same buffer without trypsin. This was incubated at 37° C. overnight in an air incubator.

Extraction of Peptides.

A sufficient volume of 25 mM $NH_4HCO_3$ was added to cover gel pieces, and incubated for 15 minutes (typically in a bath sonicator). The same volume of acetonitrile was added and incubated for 15 minutes (in a bath sonicator if possible), and the supernatant was recovered. The extraction was repeated twice, using 5% formic acid instead of $NH_4HCO_3$. A sufficient volume of 5% formic acid was added to cover gel pieces, and incubated for 15 minutes (typically in a bath sonicator). The same volume of acetonitrile was added and incubated for 15 minutes (typically in a bath sonicator), and the supernatant was recovered. The extracts were pooled, and 10 mM DTT was added to a final concentration of 1 mM DTT. The sample was dried in a SpeedVac to a final volume of approximately 5 μl.

Desalting of Peptides.

The samples were desalted using ZIPTIP pipette tips (C18, Millipore, Billerica, Mass.) as suggested by the manufacturer. Briefly, a sample was reconstituted in reconstitution solution (5:95 acetonitrile:$H_2O$, 0.1%-0.5% trifluoroacetic acid), centrifuged, and the pH checked to verify that it was less than 3. A ZIPTIP was hydrated by aspirating 10 μl of solution 1 (50:50 acetonitrile:$H_2O$, 0.1% trifluoroacetic acid) and discarding the aspirated aliquots. This was followed by aspirating 10 μl of solution 2 (0.1% trifluoroacetic acid in deionized $H_2O$) and discarding the aspirated aliquots. The sample was loaded into the tip by aspirating 10 μl of the sample slowly into the tip, expelling it into the sample tube, and repeating this 5 to 6 times. Ten microliters of solution 2 was aspirated into the tip, the solution discarded by expelling, and this process was repeated 5-7 times to wash. The peptides were eluted by aspirating 2.5 μl of ice cold solution 3 (60:40, acetonitrile:$H_2O$, 0.1% trofluoroacetic acid), expelling, and then re-aspirating the same aliquot in and out of the tip 3 times. After the solution has been expelled from the tip, the tube is capped and stored on ice.

Mass Spectrometric Peptide Mapping.

The peptides were suspended in 10 µl to 30 µl of 5% formic acid, and analyzed by MALDI-TOF MS (Bruker Daltonics Inc., Billerica, Mass.). The mass spectrum of the peptide fragments was determined as suggested by the manufacturer. Briefly, a sample containing the peptides resulting from a tryptic digest were mixed with matrix cyano-4-hydroxycinnamic acid, transferred to a target, and allowed to dry. The dried sample was placed in the mass spectrometer, irradiated, and the time of flight of each ion detected and used to determine a peptide mass fingerprint for each protein present in the composition. Known polypeptides (human angiotensin II, monoisotopic mass $MH^+$ 1046.5 (Sigma Chemical Co.), and adenocorticotropin hormone fragment 18-39, $MH^+$ 2465.2 (Sigma Chemical Co.)) were used to standardize the machine.

Data Analysis.

The experimentally observed masses for the peptides in each mass spectrum were compared to the expected masses of resulting from known proteins using the Peptide Mass Fingerprint search method of the Mascot search engine (Matrix Science Ltd., London, UK, and www.matrixscience.com, see Perkins et al., Electrophoresis 20, 3551-3567 (1999)). The search parameters included: database, NCBInr; taxonomy, bacteria (eubacteria); type of search, peptide mass fingerprint; enzyme, trypsin; fixed modifications, none; variable modifications, none or oxidized methionine; mass values, monoisotopic; protein mass, unrestricted; peptide mass tolerance, ±1 Da or ±1 330 ppm; peptide charge state, Mr; max missed cleavages, 1; number of queries, 25.

Results

The result of this search was a mass fingerprint for protein present in the composition (Tables 5 and 6).

TABLE 5

Experimental data from MALDI-TOF MS analysis of proteins isolated from *Y. enterocolitica* ATCC strain 27729.

| Polypeptide Designation | Approximate molecular weight in kilodaltons (kDa)[1] | m/z value of polypeptide fragments resulting from trypsin digestion[2] |
|---|---|---|
| Lw545 | 268 | 929.46 |
| | | 1140.47 |
| | | 1312.57 |
| | | 1440.69 |
| | | 1526.68 |
| | | 1555.66 |
| | | 1581.70 |
| | | 1596.67 |
| | | 1683.69 |
| | | 2110.21 |
| Lw391A (±1 Da) | 83 | 687.5 |
| | | 976.4 |
| | | 1001.6 |
| | | 1016.5 |
| | | 1141.6 |
| | | 1170.7 |
| | | 1171.7 |
| | | 1198.5 |
| | | 1344.5 |
| | | 1357.7 |
| | | 1395.6 |
| | | 1453.7 |
| | | 1477.7 |
| | | 1521.7 |
| | | 1693.8 |
| | | 1716.8 |
| | | 1829.8 |

TABLE 5-continued

Experimental data from MALDI-TOF MS analysis of proteins isolated from *Y. enterocolitica* ATCC strain 27729.

| Polypeptide Designation | Approximate molecular weight in kilodaltons (kDa)[1] | m/z value of polypeptide fragments resulting from trypsin digestion[2] |
|---|---|---|
| | | 1962.0 |
| | | 2014.1 |
| | | 2020.0 |
| | | 2042.0 |
| | | 2164.1 |
| | | 2226.1 |
| | | 2417.3 |
| | | 3175.5 |
| Lw391B (±1 Da) | 83 | 1001.6 |
| | | 1104.6 |
| | | 1140.6 |
| | | 1155.5 |
| | | 1171.7 |
| | | 1209.5 |
| | | 1214.7 |
| | | 1338.6 |
| | | 1453.7 |
| | | 1568.8 |
| | | 1634.9 |
| | | 1651.8 |
| | | 1660.9 |
| | | 1709.8 |
| | | 1750.0 |
| | | 1851.0 |
| | | 1988.1 |
| | | 2105.1 |
| | | 2112.1 |
| | | 2164.1 |
| | | 2387.2 |
| | | 2453.1 |
| | | 2538.4 |
| | | 3423.7 |
| Lw392 (±1 Da | 79 | 837.5 |
| | | 1018.6 |
| | | 1071.5 |
| | | 1086.5 |
| | | 1132.7 |
| | | 1189.5 |
| | | 1215.6 |
| | | 1236.6 |
| | | 1256.6 |
| | | 1264.6 |
| | | 1361.6 |
| | | 1497.7 |
| | | 1502.8 |
| | | 1615.7 |
| | | 1653.8 |
| | | 1718.9 |
| | | 1770.9 |
| | | 1820.9 |
| | | 1828.1 |
| | | 2006.0 |
| | | 2067.1 |
| | | 2120.9 |
| | | 2300.3 |
| | | 2308.2 |
| | | 2783.3 |
| | | 2912.4 |
| | | 3024.5 |
| | | 3287.6 |
| Lw393 (±1 Da) | 70 | 714.6 |
| | | 760.5 |
| | | 807.5 |
| | | 820.5 |
| | | 920.5 |
| | | 1024.6 |
| | | 1052.6 |
| | | 1187.6 |
| | | 1200.6 |
| | | 1395.7 |
| | | 1437.7 |
| | | 1480.7 |
| | | 1541.9 |

TABLE 5-continued

Experimental data from MALDI-TOF MS analysis of proteins isolated from *Y. enterocolitica* ATCC strain 27729.

| Polypeptide Designation | Approximate molecular weight in kilodaltons (kDa)[1] | m/z value of polypeptide fragments resulting from trypsin digestion[2] |
|---|---|---|
| | | 1546.9 |
| | | 1565.8 |
| | | 1668.8 |
| | | 1732.0 |
| | | 1790.9 |
| | | 1906.0 |
| | | 1982.2 |
| | | 1984.1 |
| | | 1997.1 |
| | | 2011.1 |
| | | 2028.2 |
| | | 2060.2 |
| | | 2134.1 |
| | | 2163.3 |
| | | 2275.4 |
| | | 2364.3 |
| | | 2378.5 |
| | | 2384.3 |
| | | 2564.4 |
| | | 2658.4 |
| | | 2834.7 |
| | | 2930.7 |
| Lw550 | 66 | 868.6500 |
| | | 882.5700 |
| | | 884.5900 |
| | | 1021.7000 |
| | | 1087.7100 |
| | | 1168.7300 |
| | | 1177.8200 |
| | | 1208.6800 |
| | | 1346.8700 |
| | | 1750.0100 |
| | | 1755.0500 |
| | | 1852.2800 |
| | | 2521.8100 |
| | | 2607.6700 |
| | | 2944.1000 |
| | | 3087.0800 |
| Lw552 | 45 | 1140.5500 |
| | | 1209.5400 |
| | | 1312.5800 |
| | | 1440.6400 |
| | | 1501.6900 |
| | | 1526.6200 |
| | | 1581.6800 |
| | | 1596.6800 |
| Lw555 | 37 | 705.3700 |
| | | 881.2400 |
| | | 971.1700 |
| | | 1122.3100 |
| | | 1280.1900 |
| | | 1295.2200 |
| | | 1335.2900 |
| | | 1510.3000 |
| | | 1908.5300 |
| | | 2245.7300 |
| | | 2324.7100 |
| | | 2642.7500 |
| | | 2985.0200 |
| | | 3087.9700 |
| Lw557 | 31 | 864.49 |
| | | 1404.50 |
| | | 1616.68 |
| | | 1780.68 |
| | | 1876.82 |
| | | 2071.04 |
| | | 2379.08 |

[1]Molecular weight, in kilodaltons, of polypeptide obtained from *Y. enterocolitica* ATCC strain 27729.
[2]m/z, mass (m) to charge (z) ratio.

TABLE 6

Experimental data from MALDI-TOF MS analysis of proteins isolated from *Y. pestis* strain KIM6+.

| Polypeptide Designation | Approximate molecular weight in kilodaltons (kDa)[1] | m/z value of polypeptide fragments resulting from trypsin digestion[2] |
|---|---|---|
| Lw529 | 104 | 644.50 |
| | | 685.40 |
| | | 771.40 |
| | | 841.40 |
| | | 899.50 |
| | | 962.40 |
| | | 1137.40 |
| | | 1277.40 |
| | | 1293.40 |
| | | 1386.40 |
| | | 1410.50 |
| | | 1422.60 |
| | | 1498.60 |
| | | 1567.50 |
| | | 1679.70 |
| | | 1684.60 |
| | | 1726.70 |
| | | 1873.70 |
| | | 1991.70 |
| | | 2020.80 |
| | | 2182.80 |
| | | 2584.90 |
| | | 2843.20 |
| Lw530 | 99 | 1191.40 |
| | | 1514.50 |
| | | 1591.50 |
| | | 1597.50 |
| | | 1637.50 |
| | | 1671.50 |
| | | 1714.60 |
| | | 1719.60 |
| | | 1751.60 |
| | | 1820.60 |
| | | 1863.70 |
| | | 1967.60 |
| | | 2122.60 |
| Lw531 | 94 | 962.20 |
| | | 1168.20 |
| | | 1258.30 |
| | | 1372.30 |
| | | 1384.30 |
| | | 1409.30 |
| | | 1521.40 |
| | | 1669.50 |
| | | 1686.40 |
| | | 1714.40 |
| | | 1717.40 |
| | | 1797.50 |
| | | 1833.50 |
| | | 1845.50 |
| | | 2218.60 |
| | | 2426.60 |
| Lw532 | 88 | 889.30 |
| | | 927.30 |
| | | 946.40 |
| | | 961.40 |
| | | 1172.40 |
| | | 1177.40 |
| | | 1290.40 |
| | | 1333.50 |
| | | 1358.40 |
| | | 1404.50 |
| | | 1419.50 |
| | | 1508.50 |
| | | 1579.60 |
| | | 1673.60 |
| | | 1736.60 |
| | | 2401.00 |
| | | 2666.00 |
| Lw533 | 77 | 687.40 |
| | | 785.40 |
| | | 859.30 |
| | | 953.40 |

TABLE 6-continued

Experimental data from MALDI-TOF MS analysis of proteins isolated from *Y. pestis* strain KIM6+.

| Polypeptide Designation | Approximate molecular weight in kilodaltons (kDa)[1] | m/z value of pol

TABLE 6-continued

Experimental data from MALDI-TOF MS analysis of proteins isolated from *Y. pestis* strain KIM6+.

| Polypeptide Designation | Approximate molecular weight in kilodaltons (kDa)[1] | m/z value of polypeptide fragments resulting from trypsin digestion[2] |
|---|---|---|
|  |  | 1437.31 |
|  |  | 1491.23 |
|  |  | 1534.41 |
|  |  | 1579.39 |
|  |  | 2245.71 |
|  |  | 2367.68 |
|  |  | 2487.63 |
|  |  | 2684.79 |
|  |  | 2980.02 |
|  |  | 3292.91 |
| Lw541 | 31 | 1020.84 |
|  |  | 1075.77 |
|  |  | 1203.86 |
|  |  | 1248.88 |
|  |  | 1322.87 |
|  |  | 1404.95 |
|  |  | 1788.29 |
|  |  | 1991.60 |
|  |  | 2092.61 |
|  |  | 2119.74 |
| Lw542 | 31 | 1143.91 |
|  |  | 1299.97 |
|  |  | 1309.09 |
|  |  | 1341.97 |
|  |  | 1372.04 |
|  |  | 1580.12 |
|  |  | 1781.45 |
|  |  | 1791.43 |
|  |  | 1954.57 |
|  |  | 2191.78 |
|  |  | 2632.11 |
| Lw544 | 20 | 807.40 |
|  |  | 1114.43 |
|  |  | 1210.48 |
|  |  | 1244.46 |
|  |  | 1259.51 |
|  |  | 1270.49 |
|  |  | 1357.49 |
|  |  | 1790.90 |
|  |  | 2003.91 |
|  |  | 2989.45 |

[1]Molecular weight, in kilodaltons, of polypeptide obtained from *Y. pestis* strain KIM6+.
[2]m/z, mass (m) to charge (z) ratio.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A composition comprising:
   a *Yersinia* spp. microbe comprising polypeptides expressed by the *Yersinia* spp. when incubated in media comprising an iron chelator and not expressed at detectable levels when the *Yersinia* spp. is grown in the media without the iron chelator; and
   an adjuvant.

2. The composition of claim 1 wherein the *Yersinia* spp. comprises *Y. pestis*.

3. The composition of claim 2 wherein the *Y. pestis* comprises *Y. pestis* strain KIM6+.

4. The composition of claim 2 wherein the polypeptides comprise:
   a first polypeptide having a molecular weight of 94 kDa as determined by electrophoresis on a sodium dodecyl sulfate-polyacrylamide gel;
   a second polypeptide having a molecular weight of 88 kDa as determined by electrophoresis on a sodium dodecyl sulfate-polyacrylamide gel;
   a third polypeptide having a molecular weight of 77 kDa as determined by electrophoresis on a sodium dodecyl sulfate-polyacrylamide gel;
   a fourth polypeptide having a molecular weight of 73 kDa as determined by electrophoresis on a sodium dodecyl sulfate-polyacrylamide gel; and
   a fifth polypeptide having a molecular weight of 64 kDa as determined by electrophoresis on a sodium dodecyl sulfate-polyacrylamide gel.

5. The composition of claim 4 wherein:
   the 94 kDa polypeptide comprises the amino acid sequences of SEQ ID NO:227, SEQ ID NO:229, SEQ ID NO:228, SEQ ID NO:230, SEQ ID NO:231, SEQ ID NO:232, SEQ ID NO:233, SEQ ID NO:234, SEQ ID NO:235, SEQ ID NO:237, SEQ ID NO:238, SEQ ID NO:239, SEQ ID NO:241, and SEQ ID NO:242;
   the 88 kDa polypeptide comprises the amino acid sequences of SEQ ID NO:243, SEQ ID NO:244, SEQ ID NO:245, SEQ ID NO:246, SEQ ID NO:247, SEQ ID NO:248, SEQ ID NO:249, SEQ ID NO:251, SEQ ID NO:252, SEQ ID NO:253, SEQ ID NO:254, SEQ ID NO:255, SEQ ID NO:256, SEQ ID NO:257, SEQ ID NO:258, and SEQ ID NO:259;
   the 77 kDa polypeptide comprises the amino acid sequences of SEQ ID NO:261, SEQ ID NO:262, SEQ ID NO:264, SEQ ID NO:265, SEQ ID NO:266, SEQ ID NO:267, SEQ ID NO:268, SEQ ID NO:269, SEQ ID NO:270, SEQ ID NO:271, SEQ ID NO:272, SEQ ID NO:273, SEQ ID NO:274, SEQ ID NO:276, SEQ ID NO:278, SEQ ID NO:279, SEQ ID NO:280, SEQ ID NO:281, SEQ ID NO:282, SEQ ID NO:283, and SEQ ID NO:284;
   the 73 kDa polypeptide comprises the amino acid sequences of SEQ ID NO:288, SEQ ID NO:289, SEQ ID NO:290, SEQ ID NO:291, SEQ ID NO:202, SEQ ID NO:293, SEQ ID NO:294, SEQ ID NO:295, SEQ ID NO:296, SEQ ID NO:297, SEQ ID NO:298, SEQ ID NO:299, SEQ ID NO:300, SEQ ID NO:301, SEQ ID NO:302, SEQ ID NO:304, SEQ ID NO:305, SEQ ID NO:306, SEQ ID NO:308, SEQ ID NO:309, SEQ ID NO:310, SEQ ID NO:311, SEQ ID NO:313, SEQ ID NO:314, SEQ ID NO:315, and SEQ ID NO:318; and
   the 64 kDa polypeptide comprises the amino acid sequences of SEQ ID NO:319, SEQ ID NO:320, SEQ ID NO:321, SEQ ID NO:322, SEQ ID NO:323, SEQ ID NO:324, SEQ ID NO:325, SEQ ID NO:326, SEQ ID NO:327, SEQ ID NO:328, SEQ ID NO:329, SEQ ID NO:331, SEQ ID NO:333, SEQ ID NO:334, SEQ ID NO:335, SEQ ID NO:337, SEQ ID NO:338, SEQ ID NO:339, SEQ ID NO:341, SEQ ID NO:342, SEQ ID NO:343, SEQ ID NO:344, SEQ ID NO:345, SEQ ID NO:348, and SEQ ID NO:349.

6. A composition comprising:
   isolated polypeptides having molecular weights of 94 kDa, 88 kDa, 77 kDa, 73 kDa, and 64 kDa, wherein molecular weight is determined by electrophoresis on a sodium dodecyl sulfate-polyacrylamide gel, wherein the polypeptides having a molecular weight of 94 kDa, 88 kDa, 77 kDa, 73 kDa, and 64 kDa are expressed by a *Yersinia pestis* at a greater level when incubated in media comprising an iron chelator than when grown in the media without the iron chelator; wherein:

the 94 kDa polypeptide comprises the amino acid sequences of SEQ ID NO:227, SEQ ID NO:229, SEQ ID NO:228, SEQ ID NO:230, SEQ ID NO:231, SEQ ID NO:232, SEQ ID NO:233, SEQ ID NO:234, SEQ ID NO:235, SEQ ID NO:237, SEQ ID NO:238, SEQ ID NO:239, SEQ ID NO:241, and SEQ ID NO:242;

the 88 kDa polypeptide comprises the amino acid sequences of SEQ ID NO:243, SEQ ID NO:244, SEQ ID NO:245, SEQ ID NO:246, SEQ ID NO:247, SEQ ID NO:248, SEQ ID NO:249, SEQ ID NO:251, SEQ ID NO:252, SEQ ID NO:253, SEQ ID NO:254, SEQ ID NO:255, SEQ ID NO:256, SEQ ID NO:257, SEQ ID NO:258, and SEQ ID NO:259;

the 77 kDa polypeptide comprises the amino acid sequences of SEQ ID NO:261, SEQ ID NO:262, SEQ ID NO:264, SEQ ID NO:265, SEQ ID NO:266, SEQ ID NO:267, SEQ ID NO:268, SEQ ID NO:269, SEQ ID NO:270, SEQ ID NO:271, SEQ ID NO:272, SEQ ID NO:273, SEQ ID NO:274, SEQ ID NO:276, SEQ ID NO:278, SEQ ID NO:279, SEQ ID NO:280, SEQ ID NO:281, SEQ ID NO:282, SEQ ID NO:283, and SEQ ID NO:284;

the 73 kDa polypeptide comprises the amino acid sequences of SEQ ID NO:288, SEQ ID NO:289, SEQ ID NO:290, SEQ ID NO:291, SEQ ID NO:202, SEQ ID NO:293, SEQ ID NO:294, SEQ ID NO:295, SEQ ID NO:296, SEQ ID NO:297, SEQ ID NO:298, SEQ ID NO:299, SEQ ID NO:300, SEQ ID NO:301, SEQ ID NO:302, SEQ ID NO:304, SEQ ID NO:305, SEQ ID NO:306, SEQ ID NO:308, SEQ ID NO:309, SEQ ID NO:310, SEQ ID NO:311, SEQ ID NO:313, SEQ ID NO:314, SEQ ID NO:315, and SEQ ID NO:318; and the 64 kDa polypeptide comprises the amino acid sequences of SEQ ID NO:319, SEQ ID NO:320, SEQ ID NO:321, SEQ ID NO:322, SEQ ID NO:323, SEQ ID NO:324, SEQ ID NO:325, SEQ ID NO:326, SEQ ID NO:327, SEQ ID NO:328, SEQ ID NO:329, SEQ ID NO:331, SEQ ID NO:333, SEQ ID NO:334, SEQ ID NO:335, SEQ ID NO:337, SEQ ID NO:338, SEQ ID NO:339, SEQ ID NO:341, SEQ ID NO:342, SEQ ID NO:343, SEQ ID NO:344, SEQ ID NO:345, SEQ ID NO:348, and SEQ ID NO:349; and an adjuvant.

7. The composition of claim 2 further comprising a pharmaceutically acceptable carrier.

8. The composition of claim 1 wherein the *Yersinia* spp. comprises *Y. enterocolitica*.

9. The composition of claim 8 wherein the *Yersinia* spp. comprises *Y. enterocolitica* ATCC strain 27729.

10. The composition of claim 8 wherein the polypeptides comprise:

a first polypeptide having a molecular weight of 83 kDa as determined by electrophoresis on a sodium dodecyl sulfate-polyacrylamide gel;

a second polypeptide having a molecular weight of 70 kDa as determined by electrophoresis on a sodium dodecyl sulfate-polyacrylamide gel; and a third polypeptide having a molecular weight of 66 kDa as determined by electrophoresis on a sodium dodecyl sulfate-polyacrylamide gel.

11. The composition of claim 10 wherein:

the 83 kDa polypeptide comprises the amino acid sequences of SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, and SEQ ID NO:58, or the amino acid sequences of SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:79, SEQ ID NO:80, SEQ ID NO:81, SEQ ID NO:82 and one selected from the group consisting of: SEQ ID NO:67 and SEQ ID NO:78;

the 70 kDa polypeptide comprises the amino acid sequences of SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:122, SEQ ID NO:123, SEQ ID NO:124, SEQ ID NO:125, SEQ ID NO:127, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:138, SEQ ID NO:139, SEQ ID NO:140, SEQ ID NO:141, SEQ ID NO:143, SEQ ID NO:144, and SEQ ID NO:145; and the 66 kDa polypeptide comprises the amino acid sequences of SEQ ID NO:146, SEQ ID NO:147, SEQ ID NO:150 SEQ ID NO:151, SEQ ID NO:152, SEQ ID NO:153, SEQ ID NO:154, SEQ ID NO:155, SEQ ID NO:158, SEQ ID NO:159, SEQ ID NO:160, and SEQ ID NO:161.

12. The composition of claim 1 wherein the *Yersinia* spp. microbe is inactivated.

\* \* \* \* \*